US009018230B2

(12) United States Patent
Mano et al.

(10) Patent No.: US 9,018,230 B2
(45) Date of Patent: Apr. 28, 2015

(54) IDENTIFICATION, ASSESSMENT, AND THERAPY OF CANCERS WITH INNATE OR ACQUIRED RESISTANCE TO ALK INHIBITORS

(75) Inventors: Hiroyuki Mano, Tokyo (JP); Young L. Choi, Tokyo (JP); Manabu Soda, Tochigi (JP)

(73) Assignee: Jichi Medical University, Tochigi (JP)

( * ) Notice: Subject to any disclaimer, the term of this patent is extended or adjusted under 35 U.S.C. 154(b) by 0 days.

(21) Appl. No.: 13/576,508

(22) PCT Filed: Feb. 4, 2011

(86) PCT No.: PCT/IB2011/000382
§ 371 (c)(1),
(2), (4) Date: Oct. 12, 2012

(87) PCT Pub. No.: WO2011/095894
PCT Pub. Date: Aug. 11, 2011

(65) Prior Publication Data
US 2013/0203810 A1 Aug. 8, 2013

Related U.S. Application Data

(60) Provisional application No. 61/337,465, filed on Feb. 4, 2010.

(51) Int. Cl.
*C12Q 1/68* (2006.01)
*C12Q 1/48* (2006.01)
*G01N 33/574* (2006.01)

(52) U.S. Cl.
CPC .............. *C12Q 1/485* (2013.01); *C12Q 1/6886* (2013.01); *C12Q 2600/106* (2013.01); *C12Q 2600/136* (2013.01); *C12Q 2600/156* (2013.01); *G01N 33/57484* (2013.01); *G01N 2333/9121* (2013.01)

(58) Field of Classification Search
CPC ........... A61K 2039/505; C12Q 1/6886; C12Q 2600/156; C12Q 1/485; C07K 16/30
See application file for complete search history.

(56) References Cited

U.S. PATENT DOCUMENTS

2009/0156475 A1* 6/2009 Rikova et al. .................... 514/12
2011/0206691 A1* 8/2011 Mosse et al. ............... 424/158.1

FOREIGN PATENT DOCUMENTS

| CN | 101466721 A | 6/2009 |
| WO | WO-2008/127248 A1 | 10/2008 |
| WO | WO-2009/103061 A2 | 8/2009 |
| WO | WO-2010/132888 A2 | 11/2010 |

OTHER PUBLICATIONS

Wood et al. ("Targeted ALK inhibition of therapy for neuroblastoma."; Submitted Oct. 2009 to the EMBL/GenBank/DDJB databases.).*
Choi, Y. L. et al., "EML4-ALK Mutations in Lung Cancer That Confer Resistance to ALK Inhibitors", *New England Journal of Medicine*, 363(18):1734-1739 (USA, Oct. 28 2010).
McDermott, U. et al., "Genomic Alterations of Anaplastic Lymphoma Kinase May Sensitize tumors to Anaplastic Lympohma Kinase Inhibitors", *Cancer Research*, 68(9):3389-3395 (American Association for Cancer Research, USA, May 1, 2008).
Supplementary European Search Report from corresponding European application EP 11739469 dated Jun. 10, 2013.
Choi et al., "Identification of Novel Isoforms of the EML4-ALK transforming Gene in Non-Small cell Lung Cancer," Cancer Research, 68(13):4971-4976 (2008).
Lu et al., "ALK Mutants in the Kinase Domain Exhibit Altered Kinase Activity and Differential Sensitivity to Small Molecule ALK Inhibitors," Biochemistry, 48(16):3600-3609 (2009).
Soda et al., "Identification of the transforming EML4-ALK fusion gene in non-small-cell lung cancer," Nature, 448:561-566 (2007).
International Search Report dated Dec. 16, 2011 from PCT/IB2011/000382.
Christensen, J. G. et al., "Cytoreductive antitumor activity of PF-2341066, a novel inhibitor of anaplastic lymphoma kinase and c-Met, in experimental models of anaplastic large-cell lymphoma", *Mol. Cancer Ther.*, 6(12):3314-3322 (American Assoc. of Cancer Research, 2007).
Office Action from corresponding Taiwanese application 100103831 dated Sep. 13, 2013.
Wood, A.C., "Inhibition of ALK mutated neuroblastomas by the selective inhibitor PF-02341066.", ASCO University, from http://meetinglibrary.asco.org/content/35242-65 (2009).
Wood, A.C., "Tyrosine-protein kinase receptor—D1MAM2 (D1MAM2_Human)", UniProtKB, from http://www.uniprot.org/uniprot/D1MAM2 (Feb. 10 2000).
Examination Report from EP 11739469.2 dated Feb. 28, 2014.

* cited by examiner

*Primary Examiner* — Misook Yu
*Assistant Examiner* — Nelson B Moseley, II
(74) *Attorney, Agent, or Firm* — Dana M. Gordon; Foley Hoag LLP

(57) ABSTRACT

Described herein are compositions, kits, and methods for determining whether subjects having cancer(s) positive for ALK mutations are likely to respond to treatment with an ALK inhibitor and/or whether a patient having such cancer(s) is likely to have a relatively slower disease progression. Further described are methods for prognosing a time course of disease in a subject having such cancer.

13 Claims, 4 Drawing Sheets

A

B

C

IDENTIFICATION, ASSESSMENT, AND THERAPY OF CANCERS WITH INNATE OR ACQUIRED RESISTANCE TO ALK INHIBITORS

RELATED APPLICATIONS

This application is the U.S. National Stage Application of International Application No. PCT/IB2011/000382, filed Feb. 4, 2011, which claims the benefit of priority to U.S. Provisional Patent Application Ser. No. 61/337,465, filed Feb. 4, 2010; the entire contents of each of which application are expressly incorporated herein by reference.

BACKGROUND OF THE INVENTION

Tyrosine kinases are a class of enzymes that catalyze phosphorylation of tyrosine residues of protein substrates via a transfer of the terminal phosphate of adenosine triphosphate. In many contexts, tyrosine kinases play critical roles in signal transduction for a number of cell functions, including cell proliferation, carcinogenesis, and cell differentiation.

EML4-ALK is a fusion-type protein tyrosine kinase that is present in ~5% of non-small cell lung cancer (NSCLC) cases and which is generated as a result of a small inversion within the short arm of human chromosome 2 (Soda™, M. et al. (2007) *Nature* 448:561-566; Mano, H. (2008) *Cancer Sci.* 99:2349-2355). EML4-ALK undergoes constitutive dimerization as a result of interaction between the coiled-coil domain within the EML4 region of each monomer and thereby acquires pronounced oncogenic activity. Transgenic mice that express EML4-ALK, specifically in lung epithelial cells, develop hundreds of adenocarcinoma nodules in both lungs soon after birth, and oral administration of a specific inhibitor of ALK tyrosine kinase activity rapidly eradicates such nodules from the lungs (Soda, M. et al. (2008) *Proc. Natl. Acad. Sci. USA* 105:19893-19897). These observations reveal the essential role of EML4-ALK in the carcinogenesis of NSCLC harboring this fusion kinase, and they further support the feasibility of molecularly targeted therapy with ALK inhibitors for this cancer. For example, clinical trials of an inhibitor, PF-02341066, of the tyrosine kinase activity of both ALK and MET are under way for the treatment of EML4-ALK-positive NSCLC, and their interim results are promising (Kwak, E. L. et al. (2009) *J. Clin. Oncol.* 27(suppl):15s (abstract 3509)). A subset of EML4-ALK-positive tumors, however, do not respond to the inhibitor, with unknown molecular basis of treatment failure.

In addition to PF-02341066, other tyrosine kinase inhibitors (TKIs) have been shown to possess pronounced therapeutic activity in cancer patients. Imatinib mesylate, a TKI for ABL1 and KIT, for instance, markedly improves the outcome of individuals with chronic myeloid leukemia positive for the BCR-ABL1 fusion kinase or with a gastrointestinal stromal tumor positive for activated KIT (Druker, B. J. et al. (2001) *N. Engl. J. Med.* 344:1031-1037; Heinrich, M. C. et al. (2008) *J. Clin. Oncol.* 26:5360-5367). Furthermore, gefitinib and erlotinib, both of which are TKIs for the epidermal growth factor receptor (EGFR), are effective in the treatment of NSCLC associated with EGFR activation (Mok, T. S. et al. (2009) *J. Clin. Oncol.* 27:5080-2087; Mok, T. S. et al. (2009) *N. Engl. J. Med.* 361:947-957). Unfortunately, a subset of target tumors are either refractory to corresponding TKIs from the start of treatment or become resistant after an initial response. Secondary mutations in the target kinases that directly or allosterically affect the shape of the ATP-binding pocket, resulting in hindrance of TKI binding, have been detected in some cases of treatment failure (Deininger, M. et al. (2005) *Blood* 105:2640-2653; Kobayashi, S. et al. (2005) *N. Engl. J. Med.* 352:786-792; Pao, W. et al. (2005) *PLoS Med.* 2:e73; Shah, N. P. et al. (2002) *Cancer Cell* 2:117-125). Accordingly, there is an immediate need to identify mutations conferring resistance upon tyrosine kinases, such as EML4-ALK, in order to better develop compositions, kits, and methods for identifying, assessing, preventing, and treating disorders related to their aberrant expression and/or activity.

SUMMARY OF THE INVENTION

The present invention provides, at least, composition, methods, and kits for the identification, assessment and treatment of cancer based upon the identification of novel anaplastic lymphoma kinase (ALK) mutation(s) conferring resistance to known ALK inhibitors. Such ALK mutations are also clinically relevant for the identification of pharmaceutical compositions that are able to fit into the abnormal ATP-binding pocket of generated by the novel ALK mutation(s) and inhibit ALK activity.

In one aspect, the present invention provides a method for identifying a subject having cancer or at risk for developing cancer as having an increased risk of unresponsiveness to treatment with an ALK inhibitor, comprising collecting a sample from the patient and analyzing the sample to detect the presence of one or more mutant ALK polynucleotide molecules, wherein the presence of the one or more mutant ALK polynucleotide molecules indicates that the subject has an increased risk of unresponsiveness to treatment with the ALK inhibitor.

In another aspect, the present invention provides a method for identifying a subject having cancer or at risk for developing cancer as having an increased risk of unresponsiveness to treatment with an ALK inhibitor, comprising collecting a sample from the patient and analyzing the sample to detect the expression level, structure, and/or activity of one or more mutant ALK polypeptides, wherein the presence of the one or more mutant ALK polypeptides indicates that the subject has an increased risk of unresponsiveness to treatment with the ALK inhibitor.

In some embodiments of any aspect of the present invention, the subject has not previously been treated with an ALK inhibitor, or has been previously treated with an ALK inhibitor and has developed at least partial resistance to the ALK inhibitor (e.g., PF-02341066, PDD, 2-methyl-11-(2-methylpropyl)-4-oxo-4,5,6,11,12,13-hexahydro-2H-indazolo[5,4-a]pyrrolo[3,4-c]carbazol-8-yl[4-(dimethylamino)benzyl]carbamate, (1S,2S,3R,4R)-3-({5-chloro-2-[(1-ethyl-2,3,4,5-tetrahydro-6-methoxy-2-oxo-1H-1-benz azepin-7-yl)amino]-4-pyrimidinyl}amino)bicyclo[2.2.1]hept-5-ene-2-carboxamide, and NVP-TAE684). In other embodiments, the cancer is selected from the group consisting of anaplastic large cell lymphoma, neuroblastoma, breast cancer, colorectal cancer, inflammatory myofibroblastic tumors, and non-small cell lung cancers. In still other embodiments, the sample is selected from the group consisting of sputum, bronchoalveolar lavage, pleural effusion, tissue, whole blood, serum, plasma, buccal scrape, saliva, cerebrospinal fluid, urine, stool, circulating tumor cells, circulating nucleic acids, and bone marrow. In yet other embodiments, the sample comprises cells or tissue. In some embodiments the tissue is a tumor or cancer tissue. In other embodiments, the one or more mutant ALK polynucleotide molecules or polypeptides are selected from the group consisting of the mutant ALK polynucleotide molecules or polypeptides listed in Table 1. In still other embodiments, the one or more ALK mutations are assessed by a nucleic acid hybridization assay. In yet other embodiments, the one or more ALK mutations are assessed by polymerase chain reaction. In other embodiments, the expression level of the one or more ALK polypeptides is detected using a reagent which specifically binds to one or more ALK polypeptides (e.g., antibody, an antibody derivative, and an antibody fragment). In still other embodiments, the amount, structure and/or activity of the one or more mutant ALK polypeptides is compared to a control sample. In yet other embodiments, the one or more ALK mutations are assessed at a first point in time and at least one subsequent point in time. In other embodiments, the sample comprises germline or somatic genomic DNA.

In still another aspect, the present invention provides a method of treating a patient having cancer, or at risk for developing cancer, comprising collecting a sample from the patient, analyzing the sample to detect the presence of one or more mutant ALK polynucleotide molecules set forth in Table 1, and administering to said patient a therapeutically effective amount of an ALK inhibitor. In some embodiments, the ALK inhibitor is selected from the group consisting of PF-02341066, PDD, 2-methyl-11-(2-methylpropyl)-4-oxo-4,5,6,11,12,13-hexahydro-2H-indazolo[5,4-c]pyrrolo[3,4-c] carbazol-8-yl[4-(dimethylamino)benzyl]carbamate, (1S,2S, 3R,4R)-3-({5-chloro-2-[(1-ethyl-2,3,4,5-tetrahydro-6-methoxy-2-oxo-1H-1-benzazepin-7-yl)amino]-4-pyrimidinyl}amino)bicyclo[2.2.1]hept-5-ene-2-carboxamide, and NVP-TAE684. In other embodiments, the subject has not previously been treated with an ALK inhibitor, or has been previously treated with an ALK inhibitor and has developed at least partial resistance to the ALK inhibitor.

In yet another aspect, the present invention provides a kit for determining the chemosensitivity of a cancer patient to treatment with an ALK inhibitor, comprising: a reagent that specifically binds to one or more mutant ALK polynucleotide molecules or polypeptides; and instructions for use. In some embodiments, the kit further comprises an ALK inhibitor. In other embodiments, the reagent comprises one or more polynucleotide probes, each of which comprises a polynucleotide sequence which is complementary to a nucleotide sequence listed in Table 1 or complementary to a nucleotide sequence encoding a polypeptide listed in Table 1 (e.g., oligonucleotides, cDNA molecules, RNA molecules, and synthetic gene probes comprising nucleobases). In still other embodiments, the probes comprise polynucleotides from about 50 to $10^7$ nucleotides in length. In yet other embodiments, the reagent comprises an antibody, and antibody derivative, and an antibody fragment to a polypeptide encoded by one or more polynucleotide sequences listed in Table 1.

In another aspect, the present invention provides a method of determining whether a test compound modulates activity of one or more mutant ALK polypeptides comprising contacting mammalian cells transfected with a construct encoding the one or more mutant ALK polypeptides with the test compound and assessing the mammalian cells for activity of the one or more mutant ALK polypeptides, wherein significantly modulated activity in the presence of the test compound relative to a control experiment identifies the test compound as a modulator of the one or more mutant ALK polypeptides. In some embodiments, the one or more mutant ALK polynucleotide molecules or polypeptides are selected from the group consisting of the mutant ALK polynucleotide molecules or polypeptides listed in Table 1. In other embodiments, the control comprises mammalian cells expressing a wild type ALK polypeptide selected from the group consisting of polypeptides listed in Table 1. In still other embodiments, activity of the one or more mutant ALK polypeptides is selected from the group consisting of ATP binding, tyrosine kinase activity, cancer cell proliferation, tumor growth, tumor number, apoptosis, and tumor metastasis. In yet other embodiments, the control experiment comprises mammalian cells expressing the one or more mutant ALK polypeptides in the absence of the test compound as determined by, for example, activity of the one or more mutant ALK polypeptides (e.g., ATP binding, tyrosine kinase activity, cancer cell proliferation, tumor growth, tumor number, apoptosis, and tumor metastasis).

BRIEF DESCRIPTION OF THE FIGURES

FIG. 1A shows a schematic representation of the EML4-ALK protein. Positions of two de novo mutations in the kinase domain are shown, and those of PCR primers for amplification of kinase-domain or fusion cDNAs are indicated by the closed and open arrows above, respectively. FIG. 1B shows the results of deep sequencing of ALK kinase-domain cDNAs. PCR products of ~1000 bp from the NSCLC cell line H2228 or from specimen IDs J-#1, J-#12, J-#113, J-#127 or LK-#33 were sequenced with the GAII system. The numbers for total read coverage (Total) and mismatched reads (Mismatch) are shown at each position of the kinase-domain cDNAs with blue and red diamonds, respectively. Insets show magnified views for the 5' region of the cDNAs for J-#1 and J-#113 (depicted by green rectangles). FIG. 1C shows electrophoretograms for the ALK cDNA clones surrounding G4374 and C4493 positions. PCR was performed with cDNAs prepared from sputum obtained before treatment (Initial) and from the cells in pleural effusion obtained after relapse (Relapse). Substituted A nucleotides are shown in red.

FIG. 4A shows the number of BA/F3 cells expressing EML4-ALK (wild type), EML4-ALK(C1156Y), EML4-ALK(L1196M), or the double mutant EML4-ALK (C1156Y/L1196M) counted after incubation of $5\times10^5$ cells for 48 h with the indicated concentrations of PF-02341066. The percentage of viable cells is shown relative to BA/F3 cells expressing the wild-type EML4-ALK. Data are means±s.d. from three separate experiments. FIG. 4B shows the effect of PF-02341066 on tyrosine phosphorylation of wild type or mutant forms of EML4-ALK. BA/F3 cells expressing FLAG-tagged wild-type EML4-ALK or its mutants were exposed to the indicated concentrations of PF-02341066 for 15 h, after which EML4-ALK was immunoprecipitated from cell lysates and subjected to immunoblot analysis with antibodies specific for Tyr$^{1604}$-phosphorylated ALK or for the FLAG epitope (ALK). Cells expressing an inactive mutant of EML4-ALK (KM) were examined as a negative control. FIG. 4C shows an in vitro kinase assay for FLAG-tagged wild-type EML4-ALK or its mutants immunoprecipitated from BA/F3 cells (not exposed to an ALK inhibitor). The immunoprecipitates were incubated with [γ-$^{32}$P]ATP, a synthetic peptide, and the indicated concentrations of PF-02341066. Phosphorylation of the peptide substrate immunoprecipitates were separately subjected to immunoblot analysis with antibodies to FLAG (lower panel).

DETAILED DESCRIPTION OF THE INVENTION

Figure 1:
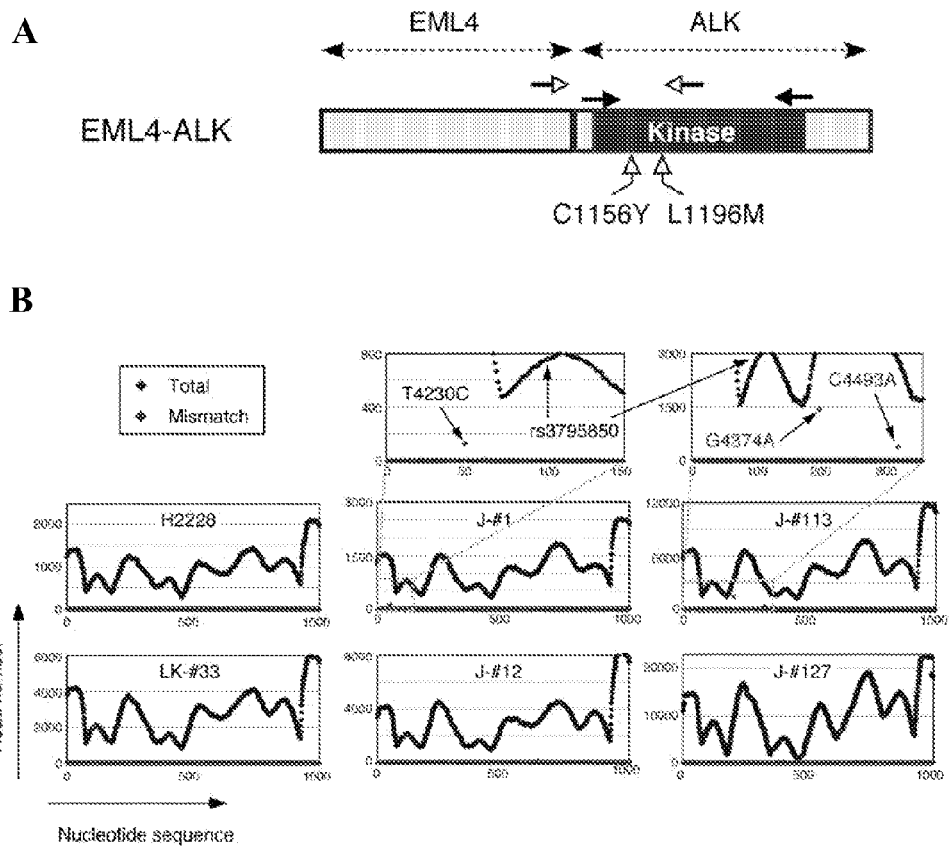
FIG. 1 depicts novel ALK mutations of the present invention associated with resistance to ALK tyrosine kinase inhibitors.
Figure 1:
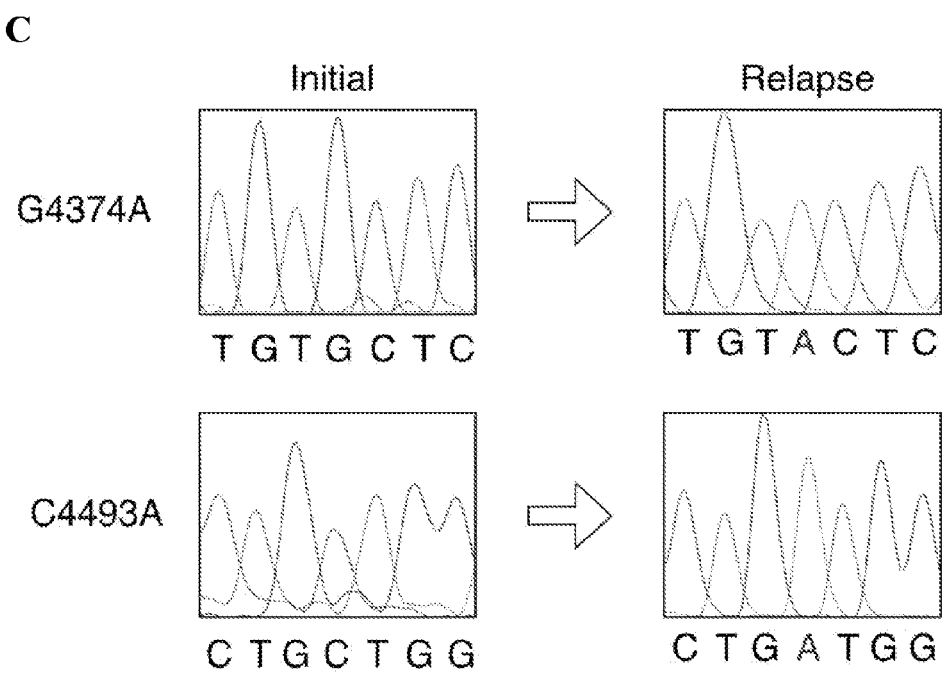

The present invention is based, at least in part, on the identification of specific regions of the genome, including for example, Anaplastic Lymphoma Kinase (ALK) mutations, associated with predicting efficacy of ALK inhibitors in treating cancer. In particular, novel ALK gene mutations (e.g., EML4-ALK polypeptide encoding mutations) have been identified herein that can lead to polypeptides at least partially resistant to therapy with ALK inhibitors. The present invention further provides methods for identifying such specific genomic regions using techniques known in the art, including, but not limited to, oligonucleotide-based microarrays (Brennan, et al. (2004) *Cancer Res.* 64(14):4744-8; Lucito, et al. (2003) *Genome Res.* 13:2291-2305; Bignell et al. (2004) *Genome Res.* 14:287-295; Zhao, et al (2004) *Cancer Research,* 64(9):3060-71), and other methods as described herein including, for example, polymerase chain reaction (PCR)— and direct sequencing-based methods. The present invention further provides diagnostic kits for use in the methods.

Various aspects of the present invention are described in further detail in the following subsections.

I. Definitions

The articles "a" and "an" are used herein to refer to one or to more than one (i.e., to at least one) of the grammatical object of the article. By way of example, "an element" means one element or more than one element.

The term "altered amount" of a marker or "altered level" of a marker refers to increased or decreased copy number of a marker or chromosomal region, such as ALK gene mutations and/or gene products (e.g., the markers set forth in Table 1), and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The term "altered level of expression" of ALK gene mutations and/or gene products (e.g., the markers set forth in Table 1) refers to an expression level or copy number of a marker in a test sample such as a sample derived from a patient suffering from cancer, that is greater or less than the standard error of the assay employed to assess expression or copy number, and may be at least twice, at least twice three, at least twice four, at least twice five, or at least twice ten or more times the expression level or copy number of the ALK gene mutations and/or gene products (e.g., the markers set forth in Table 1) in a control sample (e.g., a sample from a healthy subject not having the associated disease), or the average expression level or copy number of the ALK gene mutations and/or gene products (e.g., the markers set forth in Table 1) in several control samples. The altered level of expression is greater or less than the standard error of the assay employed to assess expression or copy number, and is at least twice, at least three, at least four, at least five, at least ten or more times the expression level or copy number of the ALK gene mutations and/or gene products (e.g., the markers set forth in Table 1) in a control sample (e.g., a sample from a healthy subject not having the associated disease), or the average expression level or copy number of the ALK gene mutations and/or gene products (e.g., the markers set forth in Table 1) in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker.

The term "altered structure" of a marker refers to the presence of mutations or mutations within the marker gene or maker protein, e.g., mutations which affect expression or activity of the marker, as compared to the normal or wild-type gene or protein. For example, mutations include, but are not limited to inter- and intra-chromosomal rearrangement, substitutions, deletions, and insertion mutations. Mutations may be present in the coding or non-coding region of the marker.

"Anaplastic lymphoma kinase" and "ALK" are used interchangeably herein and refer to native anaplastic lymphoma kinase, and certain variants and mutations thereof, derived from any source (e.g., rodents, humans, and other mammals). In some embodiments, ALK protein is represented by NCBI RefSeq identification number NP_004295. Unless indicated otherwise, the terms refer to the human protein. The gene encoding ALK may also be referred to herein as "ALK". In some embodiments, ALK nucleotide sequences are represented by NCBI Ref Seq identification number NM_004304.3 and GenBank accession number 29029631, relevant sequences therein (e.g., the coding, 5' UTR, 3'UTR, transcription start, translation start, transcription stop, translation stop, etc. sequences) of which can readily be identified by a skilled artisan.

In addition, "Anaplastic lymphoma kinase" and "ALK" are also used herein to include ALK fusion kinases and variants thereof, which are well known to a skilled artisan. Such ALK fusion kinases and variants thereof comprise ALK kinase activity and can harbor mutations as described herein rendering the ALK kinase activity resistant to ALK inhibitors. Representative examples include EML4-ALK Variant 1 (AB274722.1; BAF73611.1), EML4-ALK Variant 2 (AB275889.1; BAF73612.1), EML4-ALK Variant 3a (AB374361.1; BAG55003.1), EML4-ALK Variant 3b (AB374362.1; BAG55004.1), EML4-ALK Variant 4 (AB374363.1; BAG75147.1), EML4-ALK Variant 5a (AB374364.1; BAG75148.1), EML4-ALK Variant 5b (AB374365.1; BAG75149.1), EML4-ALK Variant 6 (AB462411.1; BAH57335.1), EML4-ALK Variant 7 (AB462412.1; BAH57336.1), KIF5B-ALK (AB462413.1; BAH57337.1), NPM-ALK, TPM3-ALK, TFGXL-ALK, TFGL-ALK, TFGS-ALK, ATIC-ALK, CLTC-ALK, MSN-ALK, TPM4-ALK, MYH9-ALK, RANBP2-ALK, ALO17-ALK, and CARS-ALK (see, for example, Pulford et al., (2004) *J. Cell. Physiol.* 199:330-358, which is herein incorporated by reference in its entirety). In addition, a skilled artisan will understand that ALK kinase variants can arise depending upon the particular fusion event between an ALK kinase and its fusion partner (e.g., EML4 can fuse at least exon 2, 6a, 6b, 13, 14, and/or 15, as described, for example, in Horn and Pao, (2009) *J. Clin. Oncol.* 27:4247-4253, which is herein incorporated by reference in its entirety). For example, representative ALK sequences are provided herein as follows:

TABLE 1

```
Wild Type ALK cD10, Sequence (NM_004304.3; GI:29029631):

1 ggggcggca gcggtggtag cagctggtac ctcccgccgc ctctgttcgg agggtcgcgg
  61 ggcaccgagg tgctttccgg ccgccctctg gtcggccacc caaagccgcg ggcgctgatg
 121 atgggtgagg aggggcggc aagatttcgg gcgccctgc cctgaacgcc ctcagctgct
 181 gccgccgggg ccgctccagt gcctgcgaac tctgaggagc cgaggcgccg gtgagagcaa
 241 ggacgctgca aacttgcgca gcgcgggggc tgggattcac gcccagaagt tcagcaggca
 301 gacagtccga agccttcccg cagcggagag atagcttgag ggtgcgcaag acggcagcct
 361 ccgccctcgg ttcccgccca gacgggcag aagagcttgg aggagccaaa aggaacgcaa
 421 aaggcggcca ggacagcgtg cagcagctgg gagccgccgt tctcagcctt aaaagttgca
 481 gagattggag gctgccccga gaggggacag accccagctc cgactgcggg gggcaggaga
 541 ggacggtacc caactgccac ctcccttcaa ccatagtagt tcctctgtac cgagcgcagc
 601 gagctacaga cgggggcgg gcactcggcg cggagagcgg gaggctcaag gtcccagcca
 661 gtgagcccag tgtgcttgag tgtctctgga ctcgcccctg agcttccagg tctgtttcat
 721 ttagactcct gctcgcctcc gtgcagttgg gggaaagcaa gagacttgcg cgcacgcaca
 781 gtcctctgga gatcaggtgg aaggagccgc tgggtaccaa ggactgttca gagcctcttc
 841 ccatctcggg gagagcgaag ggtgaggcg gccccggaga gcagtgtaaa cggcctcctc
 901 cggcgggatg ggagccatcg ggctcctgtg gctcctgccg ctgctgcttt ccacggcagc
 961 tgtgggctcc gggatgggga ccggccagcg cgcgggctcc ccagctgcgg ggccgccgct
1021 gcagccccgg gagccactca gctactcgcg cctgcagagg aagagtctgg cagttgactt
1081 cgtggtgccc tcgctcttcc gtgtctacgc ccgggaccta ctgctgccac catcctcctc
1141 ggagctgaag gctggcaggc ccgaggcccg cggctcgcta gctctggact gcgccccgct
1201 gctcaggttg ctgggccgg cgccgggggt ctcctggacc gccggttcac cagcccggc
1261 agaggccccgg acgctgtcca gggtgctgaa gggcggctcc gtgcgcaagc tccggcgtgc
1321 caagcagttg gtgctggagc tgggcgagga ggcgatcttg gagggttgcg tcgggccccc
1381 cggggaggcg gctgtggggc tgctccagtt caatctcagc gagctgttca gttggtggat
1441 tcgccaaggc gaaggcgac tgaggatccg cctgatgccc gagaagaagg cgtcggaagt
1501 gggcagagag ggaaggctgt ccgcggcaat tcgcgcctcc cagccccgcc ttctcttcca
1561 gatcttcggg actggtcata gctccttgga atcaccaaca aacatgcctt ctccttctcc
1621 tgattatttt acatggaatc tcacctggat aatgaaagac tccttccctt tcctgtctca
1681 tcgcagccga tatggtctgg agtgcagctt tgacttcccc tgtgagctgg agtattcccc
1741 tccactgcat gacctcagga accagagctg gtcctggcgc cgcatcccct ccgaggaggc
1801 ctcccagatg gacttgctgg atgggcctgg ggcagagcgt tctaaggaga tgcccagagg
1861 ctcctttctc cttctcaaca cctcagctga ctccaagcac accatcctga gtccgtggat
1921 gaggagcagc agtgagcact gcacactggc cgtctcggtg cacaggcacc tgcagccctc
1981 tggaaggtac attgcccagc tgctgcccca caacgaggct gcaagagaga tcctcctgat
2041 gcccactcca gggaagcatg gttggacagt gctccaggga agaatcgggc gtccagacaa
2101 cccatttcga gtggccctgg aatacatctc cagtggaaac cgcagctttg ctgcagtgga
2161 cttctttgcc ctgaagaact gcagtgaagg aacatcccca ggctccaaga tggccctgca
2221 gagctccttc acttgttgga atgggacagt cctccagctt gggcaggcct gtgacttcca
2281 ccaggactgt gcccagggag aagatgagag ccagatgtgc cggaaactgc ctgtgggttt
2341 ttactgcaac tttgaagatg gcttctgttg ctggacccaa ggcacactgt cacccccacac
2401 tcctcaatgg caggtcagga ccctaaagga tgcccggttc caggaccacc aagaccatgc
2461 tctattgctc agtaccactg atgtccccgc ttctgaaagt gctacagtga ccagtgctac
2521 gtttcctgca ccgatcaaga gctctccatg tgagctccga atgtcctggc tcattcgtgg
2581 agtcttgagg ggaaacgtgt ccttggtgct agtggagaac aaaaccggga aggagcaagg
2641 caggatggtc tggcatgtcg ccgcctatga aggcttgagc ctgtggcagt ggatggtgtt
2701 gcctctcctc gatgtgtctg acaggttctg gctgcagatg gtcgcatggt ggggacaagg
2761 atccagagcc atcgtggctt ttgacaatat ctccatcagc ctggactgct acctcaccat
2821 tagcggagag gacaagatcc tgcagaatac agcacccaaa tcaagaaacc tgtttgagag
2881 aaacccaaac aaggagctga acccgggga aaattcacca agacagaccc ccatctttga
2941 ccctacagtt cattggctgt tcaccacatg tggggccagc gggccccatg gccccaccca
3001 ggcacagtgc aacaacgcct accagaactc caacctgagc gtggaggtgg ggagcgaggg
3061 ccccctgaaa ggcatccaga tctggaaggt gccagccacc gacacctaca gcatctcgg
3121 ctacgagct gctggcggga aaggcggaa gaacaccatg atgcggtccc acgcgtgtc
3181 tgtgctgggc atcttcaacc tggagaagga tgacatgctg tacatcctgg ttgggcagca
3241 gggagaggac gcctgcccca gtacaaacca gttaatccag aaagtctgca ttggagagaa
3301 caatgtgata gaagaagaaa tccgtgtgaa cagaagcgtg catgagtggg caggaggcgg
3361 aggaggaggg ggtgaagcca cctacgtatt taagatgaag gatggagtgc cggtgccct
3421 gatcattgca gccggaggtg gtggcagggc ctacgggcc aagacagaca cgttccaccc
3481 agagagactg gagaataact cctcggttct agggctaaac ggcaattccg gagccgcagg
3541 tggtggaggt ggctgaatg ataacacttc cttgctctgg gccggaaat ctttgcagga
3601 gggtgccacc ggagacatt cctgccccca ggccatgaag aagtgggggt gggagacaag
3661 aggggtttc ggaggggtg gagggggtg ctcctcaggt ggaggagcg gaggatatat
3721 aggcggcaat gcagcctcaa acaatgaccc cgaaatggat ggggaagatg gggtttcctt
3781 catcagtcca ctgggcatcc tgtacacccc agcttaaaa gtgatggaag gccacggga
3841 agtgaatatt aagcattatc taaactgcag tcactgtgag gtagacgaat gtcacatgga
```

TABLE 1 -continued

```
3901 ccctgaaagc cacaaggtca tctgcttctg tgaccacggg acggtgctgg ctgaggatgg
3961 cgtctcctgc attgtgtcac ccaccccgga gccacacctg ccactctcgc tgatcctctc
4021 tgtggtgacc tctgccctcg tggccgccct ggtcctggct ttctccggca tcatgattgt
4081 gtaccgccgg aagcaccagg agctgcaagc catgcagatg gagctgcaga gccctgagta
4141 caagctgagc aagctccgca cctcgaccat catgaccgac tacaaccca actactgctt
4201 tgctggcaag acctcctcca tcagtgacct gaaggaggtg ccgcggaaaa acatcaccct
4261 cattcggggt ctgggccatg gcgcctttgg ggaggtgtat gaaggccagg tgtccggaat
4321 gcccaacgac ccaagccccc tgcaagtggc tgtgaagacg ctgcctgaag tgtgctctga
4381 acaggacgaa ctgatttcc tcatggaagc cctgatcatc agcaaattca accaccagaa
4441 cattgttcgc tgcattgggg tgagcctgca atccctgccc cggttcatcc tgctggagct
4501 catggcgggg ggagacctca agtccttcct ccgagagacc cgcctcgcc cgagccagcc
4561 ctcctccctg gccatgctgg accttctgca cgtggctcgg gacattgcct gtggctgtca
4621 gtatttggag gaaaaccact tcatccaccg agacattgct gccagaaact gcctcttgac
4681 ctgtccaggc cctggaagag tggccaagat tggagacttc gggatggccc gagacatcta
4741 cagggcgagc tactatagaa agggaggctg tgccatgctg ccagttaagt ggatgccccc
4801 agaggccttc atggaaggaa tattcacttc taaaacagac acatggtcct ttggagtgct
4861 gctatgggaa atcttttctc ttggatatat gccatacccc agcaaaagca accaggaagt
4921 tctggagttt gtcaccagtg gaggccggat ggacccaccc aagaactgcc ctggcctgt
4981 ataccggata atgactcagt gctggcaaca tcagcctgaa gacaggccca actttgccat
5041 cattttggag aggattgaat actgcaccca ggacccggat gtaatcaaca ccgctttgcc
5101 gatagaatat ggtccacttg tggaagagga agagaaagtg cctgtgaggc ccaaggaccc
5161 tgagggggtt cctcctctcc tggtctctca acaggcaaaa cgggaggagg agcgcagccc
5221 agctgcccca ccacctctgc ctaccacctc ctctggcaag gctgcaaaga aacccacagc
5281 tgcagagatc tctgttcgag tccctagagg gccggccgtg gaagggggac acgtgaatat
5341 ggcattctct cagtccaacc ctccttcgga gttgcacaag gtccacggat ccagaaacaa
5401 gcccaccagc ttgtggaacc caacgtacgg ctcctggttt acagagaaac ccaccaaaaa
5461 gaataatcct atagcaaaga aggagccaca cgacagggt aacctgggc tggagggaag
5521 ctgtactgtc ccacctaacg ttgcaactgg gagacttccg ggggcctcac tgctcctaga
5581 gccctcttcg ctgactgcca atatgaagga ggtacctctg ttcaggctac gtcacttccc
5641 ttgtgggaat gtcaattacg gctaccagca cagggcttg cccttagaag ccgctactgc
5701 ccctgggagct ggtcattacg aggataccat tctgaaaagc aagaatagca tgaaccagcc
5761 tgggccctga gctcggtcgc acactcactt ctcttccttg ggatccctaa gaccgtggag
5821 gagagagagg caatggctcc ttcacaaacc agagaccaaa tgtcacgttt tgttttgtgc
5881 caacctattt tgaagtacca ccaaaaaagc tgtatttga aaatgcttta gaaaggtttt
5941 gagcatgggt tcatccctat ctttcgaaag aagaaaatat cataaaaatg agtgataaat
6001 acaaggccca gatgtggttg cataaggttt ttatgcatgt ttgttgtata cttccttatg
6061 cttctttcaa attgtgtgtg ctctgcttca atgtagtcag aattagctgc ttctatgttt
6121 catagttggg gtcatagatg tttccttgcc ttgttgatgt ggacatgagc catttgaggg
6181 gagagggaac ggaaataaag gagttatttg taatgactaa aa
```

Wild Type cDNA sequence TGC (4373 to 4375) codon mutation(s) encoding an amino acid other than cysteine or a corresponding mutation in a homolog thereof
Wild Type cDNA sequence CTG (4493 to 4495) codon mutation(s) encoding an amino acid other than leucine or a corresponding mutation in a homolog thereof
Wild Type cDNA sequence G4374A mutation or a corresponding mutation in a homolog thereof
Wild Type cDNA sequence C4493A mutation or a corresponding mutation in a homolog thereof Wild Type ALK Protein Sequence (NP 004295.2; GI:29029632):

```
   1 mgaigllwll plllstaavg sgmgtgqrag spaagpplqp replsysrlq rkslavdfvv
  61 pslfrvyard lllppsssel kagrpeargs laldcapllr llgpapgvsw tagspapaea
 121 rtlsrvlkgg svrklrrakq lvlelgeeai legcvgppge aavgllqfnl selfswwirq
 181 gegrlrirlm pekkasevgr egrlsaaira sqprllfqif gtghsslesp tnmpspspdy
 241 ftwnltwimk dsfpflshrs ryglecsfdf pceleysppl hdlrnqswsw rripseeasq
 301 mdlldgpgae rskemprgsf lllntsadsk htilspwmrs ssehctlays vhrhlqpsgr
 361 yiaqllphne aareillmpt pgkhgwtvlq grigrpdnpf rvaleyissg nrslsavdff
 421 alkncsegts pgskmalqss ftcwngtvlq lgqacdfhqd caqgedesqm crklpvgfyc
 481 nfedgfcgwt qgtlsphtpq wqvrtlkdar fqdhqdhall lsttdvpase satvtsatfp
 541 apikssspcel rmswlirgvl rgnvslvlve nktgkeqgrm vwhvaayegl slwqwmvlpl
 601 ldvsdrfwlq mvawwgqgsr aivafdnisi sldcyltisg edkilqntap ksrnlfernp
 661 nkelkpgens prqtpifdpt vhwlfttcga sgphgptqaq cnnayqnsnl svevgsegpl
 721 kgiqiwkvpa tdtysisgyg aaggkggknt mmrshgvsvl gifnlekddm lyilvgqqge
 781 dacpstnqli qkvcigennv ieeeirvnrs vhewagggg gggatyvfkm kdgvpvplii
 841 aaggggrayg aktdtfhper lennssvlgl ngnsgaaggg ggwndntsll wagkslqega
 901 tgghscpqam kkwgwetrgg fgggggcss ggggggyigg naasnndpem dgedgvsfis
 961 plgilytpal kvmeghgevn ikhylncshc evdechmdpe shkvicfcdh gtvlaedgvs
1021 civspteph lplslilsvv tsalvaalvl afsgimivyr rkhgelqamq melqspeykl
1081 sklrtstimt dynpnycfag ktssisdlke vprknitlir glghgafgev yegqvsgmpn
1141 dpsplqvavk tlpevcseqd eldflmeali iskfnhqniv rcigvslqsl prfillelma
1201 ggdlksflre trprpsqpss lamldllhva rdiacgcqyl eenhfihrdi aarncllltcp
1261 gpgrvakigd fgmardiyra syyrkggcam lpvkwmppea fmegiftskt dtwsfgvllw
1321 eifslgympy psksnqevle fvtsggrmdp kncpgpvyr imtqcwqhqp edrpnfaiil
1381 erieyctqdp dvintalpie ygplveeeek vpvrpkdpeg vppllvsqqa kreeerspaa
1441 ppplpttssg kaakkptaae isvrvprgpa vegghvnmaf sqsnppselh kvhgsrnkpt
1501 slwnptygsw ftekptkknn piakkephdr gnlglegsct vppnvatgrl pgasllleps
1561 sltanmkevp lfrlrhfpcg nvnygyqqqg lpleaatapg aghyedtilk sknsmnqpgp
```

Wild Type protein sequence Cys1156Xaa mutation wherein Xaa is an amino

TABLE 1 -continued acid other than cysteine or a corresponding mutation in a homolog
thereof
Wild Type protein sequence Leu1196Xaa mutation wherein Xaa is an amino
acid other than leucine or a corresponding mutation in a homolog
thereof
Wild Type protein sequence Cys1156Tyr mutation or a corresponding
mutation in a homolog thereof
Wild Type protein sequence Leu1196Met mutation or a corresponding
mutation in a homolog thereof EML4-ALK Variant 1 cDNA Sequence (AB274722.1; GI:152002652)

```
   1 ggcggcgcgg cgcggcgctc gcggctgctg cctgggaggg aggccgggca ggcggctgag
  61 cggcgcggct ctcaacgtga cggggaagtg gttcggcgg ccgcggctta ctacccagg
 121 gcgaacggac ggacgacgga ggcgggagcc ggtagccgag ccgggcgacc tagagaacga
 181 gcgggtcagg ctcagcgtcg gccactctgt cggtccgctg aatgaagtgc ccgcccctct
 241 gagcccggag cccggcgctt tccccgcaag atggacggtt tcgccggcag tctcgatgat
 301 agtatttctg ctgcaagtac ttctgatgtt caagatcgcc tgtcagctct tgagtcacga
 361 gttcagcaac aagaagatga aatcactgtg ctaaaggcgg ctttggctga tgttttgagg
 421 cgtcttgcaa tctctgaaga tcatgtggcc tcagtgaaaa aatcagtctc aagtaaaggc
 481 caaccaagcc ctcgagcagt tattcccatg tcctgtataa ccaatggaag tggtgcaaac
 541 agaaaaccaa gtcataccag tgctgtctca attgcaggaa aagaaactct ttcatctgct
 601 gctaaaagtg gtacagaaaa aaagaaagaa aaaccacaag gacagagaga aaaaaagag
 661 gaatctcatt ctaatgatca aagtccacaa attcgagcat caccttctcc ccagccctct
 721 tcacaacctc tccaaataca cagacaaact ccagaaagca agaatgctac tcccaccaaa
 781 agcataaaac gaccatcacc agctgaaaag tcacataatt cttgggaaaa ttcagatgat
 841 agccgtaata aattgtcgaa ataccttca cacccaaat taataccaaa agttaccaaa
 901 actgcagaca agcataaaga tgtcatcatc aaccaagaag gagaatatat taaaatgttt
 961 atgcgcggtc ggcaattac catgttcatt ccttccgatg ttgacaacta tgatgacatc
1021 agaacggaac tgcctcctga gaagctcaaa ctggagtgga catatggtta tcgaggaaag
1081 gactgtagag ctaatgttta ccttcttccg accggggaaa tagtttattt cattgcatca
1141 gtagtagtac tatttaatta tgaggagaga actcagcgac actacctggg ccatacagac
1201 tgtgtgaaat gccttgctat acatcctgac aaaattagga ttgcaactgg acagatagct
1261 ggcgtggata aagatggaag gcctctacaa ccccacgtca gagtgtggga ttctgttact
1321 ctatccacac tgcagattat tggacttggc acttttgagc gtggagtagg atgcctggat
1381 ttttcaaaag cagattcagg tgttcattta tgtgttattg atgactccaa tgagcatatg
1441 cttactgtat gggactggca gaagaaagca aaaggagcag aaataaagac aacaaatgaa
1501 gttgttttgg ctgtggagtt tcacccaaca gatgcaaata ccataattac atgcggtaaa
1561 tctcatattt tcttctggac ctggagcggc aattcactaa caagaaaaca gggaattttt
1621 gggaaatatg aaaagccaaa atttgtgcag tgtttagcat tcttgggaa tggagatgtt
1681 cttactggag actcaggtgg agtcatgctt atatggagca aaactactgt agagcccaca
1741 cctgggaaag gacctaaagt gtaccgccgg aagcaccagg agctgcaagc catgcagatg
1801 gagctgcaga gccctgagta caagctgagc aagctccgcc cctcgaccat catgaccgac
1861 tacaacccca actactgctt tgctggcaag acctcctcca tcagtgacct gaaggaggtg
1921 ccgcggaaaa acatcaccct cattcggggt ctgggccatg gagcctttgg ggaggtgtat
1981 gaaggccagg tgtccggaat gcccaacgac ccaagccccc tgcaagtggc tgtgaagacg
2041 ctgcctgaag tgtgctctga acaggacgaa ctggatttcc tcatggaagc cctgatcatc
2101 agcaaattca accaccagaa cattgttcgc tgcattgggg tgagcctgca atccctgccc
2161 cggttcatcc tgctggagct catggcgggg ggagacctca gtccttcct ccgagagacc
2221 cgccctcgcc cgagccagcc ctcctccctg gccatgctgg accttctgca cgtggctcgg
2281 gacattgcct gtggctgtca gtatttggag aaaaccact tcatccaccg agacattgct
2341 gccagaaact gcctcttgac ctgtccaggc cctggaagag tggccaagat tggagacttc
2401 gggatgcccc gagacatcta cagggcgagc tactatagaa agggaggctg tgccatgctg
2461 ccagttaagt ggatgccccc agaggccttc atggaaggaa tattcacttc taaaacagac
2521 acatggtcct ttggagtgct gctatgggaa atctttttctc ttggatatat gccataccc
2581 agcaaaagca accaggaagt tctggagttt gtcaccagtg gaggccggat ggacccaccc
2641 aagaactgcc ctgggcctgt ataccggata atgactcagt gctggcaaca tcagcctgaa
2701 gacaggccca actttgccat cattttggag aggattgaat actgcaccca ggacccggat
2761 gtaatcaaca ccgctttgcc gatagaatat ggtccacttg tggaagagga agagaaagtg
2821 cctgtgagge ccaaggaccc tgaggggggtt cctcctctcc tggtctctca acaggcaaaa
2881 cgggaggagg agcgcagccc agctgcccca ccacctctgc ctaccacctc ctctggcaag
2941 gctgcaaaga accccacagc tgcagaggtc tctgttcgag tccctagagg gccggccgtg
3001 gaaggggac acgtgaatat ggcattctct cagtccaacc ctccttcgga gttgcacagg
3061 gtccacggat ccagaaacaa gcccaccagc ttgtgaacc caacgtacgg ctcctggttt
3121 acagagaaac ccaccaaaaa gaataatcct atagcaaaga aggagccaca cgagaggggt
3181 aacctggggc tggaggaag ctgtactgtc ccacctaacg ttgcaactgg agacttccg
3241 ggggcctcac tgctcctaga gccctcttcg ctgactgcca atatgaagga ggtacctctg
3301 ttcaggctac gtcacttccc ttgtgggaat gtcaattacg gctaccagca acagggcttg
3361 cccttagaag ccgctactgc ccctggagct ggtcattacg aggataccat tctgaaaagc
3421 aagaatagca tgaaccagcc tgggcctga gctcggtcac acactcactt ctcttccttg
3481 ggatccctaa gaccgtggag gagagagagg caatcaatgg ctccttcaca aaccagagac
3541 caaatgtcac gttttgtttt gtgccaacct attttgaagt accaccaaaa aagctgtatt
3601 ttgaaaatgc tttagaaagg ttttgagcat gggttcatcc tattcttttcg aaagaagaaa
3661 atatcataaa aatgagtgat aaatacaagg cccagatgtg gttgcataag gttttttatgc
3721 atgtttgttg tatacttcct tatgcttctt ttaaattgtg tgtgctctgc ttcaatgtag
3781 tcagaattag ctgcttctat gtttcatagt tggggtcata gatgtttcct tgccttgttg
3841 atgtggacat gagccatttg aggggagagg gaacggaaat aaaggagtta tttgtaatga
3901 aaaaaaaaaa aaaaaaaaaa aaaaaa
```

TABLE 1 -continued

EML4-ALK Variant 1 Protein Sequence (BAF73611.1; GI:152002653)

```
   1 mdgfagsldd sisaastsdv qdrlsalesr vqqqedeitv lkaaladvlr rlaisedhva
  61 svkksysskg qpspravipm scitngsgan rkpshtsays iagketlssa aksgtekkke
 121 kpggqrekke eshsndqspq iraspspqps sqplqihrqt peshnatptk sikrpspaek
 181 shnswensdd srnklskips tpklipkvtk tadkhkdvii nqegeyikmf mrgrpitmfi
 241 psdvdnyddi rtelppeklk lewaygyrgk dcranvyllp tgeivyfias vvvlfnyeer
 301 tqrhylghtd cvkclaihpd kiriatgqia gvdkdgrplq phvrvwdsvt lstlqiiglg
 361 tfergvgcld fskadsgvhl cviddsnehm ltvwdwqkka kgaeikttne vvlavefhpt
 421 dantiitcgk shiffwtwsg nsltrkqgif gkyekpkfvq claflgngdv ltgdsggvml
 481 iwskttvept pgkgpkvyrr khgelqamqm elqspeykls klrtstimtd ynpnycfagk
 541 tssisdlkev prknitlirg lghgafgevy egqvsgmpnd psplqvavkt lpevcseqde
 601 ldflmealii skfnhqnivr cigvslqslp rfillelmag gdlksflret rprpsqpssl
 661 amldllhvar diacgcqyle enhfihrdia arnclltcpg pgrvakigdf gmardiyras
 721 yyrkggcaml pvkwmppeaf megiftsktd twsfgvllwe ifslgympyp sksnqevlef
 781 vtsggrmdpp kncpgpvyri mtqcwqhqpe drpnfaiile rieyctqdpd vintalpiey
 841 gplveeeekv pvrpkdpegv ppllvsqqak reeerspaap pplpttssgk aakkptaaev
 901 svrvprgpav egghvnmafs qsnppselhr vhgsrnkpts lwnptygswf tekptkknnp
 961 iakkepherg nlglegsctv ppnvatgrlp gaslllepss ltanmkevpl frlrhfpcgn
1021 vnygyqqqgl pleaatapga ghyedtilks knsmnqpgp
```

EML4-ALK Variant 2 cDNA Sequence (AB275889.1; GI:152002654)

```
   1 ggcggcgcgg cgcggcgctc gcggctgctg cctgggaggg aggccgggca ggcggctgag
  61 cggcgcggct ctcaacgtga cggggaagtg gttcgggcgg ccgcggctta ctaccccagg
 121 gcgaacggac ggacgacgga ggcgggagcc ggtagccgag ccgggcgacc tagagaacga
 181 gcgggtcagg ctcagcgtcg gccactctgt cggtccgctg aatgaagtgc ccgcccctct
 241 gagcccggag cccggcgctt tccccgcaag atggacggtt tcgccggcag tctcgatgat
 301 agtatttctg ctgcaagtac ttctgatgtt caagatcgcc tgtcagctct tgagtcacga
 361 gttcagcaac aagaagatga aatcactgtg ctaaaggcgg ctttggctga tgttttgagg
 421 cgtcttgcaa tctctgaaga tcatgtggcc tcagtgaaaa atcagtctc aagtaaaggc
 481 caaccaagcc ctcgagcagt tattcccatg tcctgtataa ccaatggaag tggtgcaaac
 541 agaaaaccaa gtcataccag tgctgtctca attgcaggaa aagaaactct ttcatctgct
 601 gctaaaagtg gtacagaaaa aaagaaagaa aaaccacaag gacagagaga aaaaaaagag
 661 gaatctcatt ctaatgatca aagtccacaa attcgagcat caccttctcc ccagccctct
 721 tcacaacctc tccaaataca cagacaaact ccagaaagca agaatgctac tcccaccaaa
 781 agcataaaac gaccatcacc agctgaaaag tcacataatt cttgggaaaa ttcagatgat
 841 agccgtaata aattgtcgaa ataccttca acacccaaat taataccaaa agttaccaaa
 901 actgcagaca agcataaaga tgtcatcatc aaccaagaag gagaatatat taaaatgttt
 961 atgcgcggtc ggccaattac catgttcatt ccttccgatg ttgacaacta tgatgacatc
1021 agaacggaac tgcctcctga gaagctcaaa ctggagtggg catatggtta tcgaggaaag
1081 gactgtagag ctaatgttta ccttcttccg accggggaaa tagtttattt cattgcatca
1141 gtagtagtac tatttaatta tgaggagaga actcagcgac actacctggg ccatacagac
1201 tgtgtgaaat gccttgctat acatcctgac aaaattagga ttgcaactgg acagatagct
1261 ggcgtggata aagatggaag gcctctacaa ccccacgtca gagtgtggga ttctgttact
1321 ctatccacac tgcagattat tggacttggc acttttgagc gtggagtagg atgcctggat
1381 ttttcaaaag cagattcagg tgttcattta tgtgttattg atgactccaa tgagcatatg
1441 cttactgtat gggactggca gaagaaagca aaggagcag aaataaagac aacaaatgaa
1501 gttgttttgg ctgtggagtt tcacccaaca gatgcaaata ccataattac atgcggtaaa
1561 tctcatattt tcttctggac ctggagcggc aattcactaa caagaaaaca gggaattttt
1621 gggaaatatg aaaagccaaa atttgtgcag tgtttagcat tcttggggaa tggagatgtt
1681 cttactggag actcaggtgg agtcatgctt atatggagca aaactactgt agagcccaca
1741 cctgggaaag gacctaaagg tgtatatcaa atcagcaaac aaatcaaagc tcatggtgc
1801 agtgtgttca cactttgtca gatgagaaat gggatgttat taactggagg agggaaagac
1861 agaaaaataa ttctgtggga tcatgatctg aatcctgaaa gagaaataga ggttcctgat
1921 cagtatggca aatcagagc tgtagcagaa ggaaaggcag atcaatttt agtaggcaca
1981 tcacgaaact ttattttacg aggaacattt aatgatggct tccaaataga agtacagggt
2041 catacagatg agctttgggg tcttgccaca catcccttca aagattttgct cttgacatgt
2101 gctcaggaca ggcaggtgtg cctgtggaac tcaatgaaac acaggctgga atggaccagg
2161 ctggtagatg aaccaggaca ctgtgcagat tttcatccaa gtggcacagt ggtggccata
2221 ggaacgcact caggcaggtg gtttgttctg gatgcagaaa ccagagatct agtttctatc
2281 cacacagacg ggaatgaaca gctctctgtg atgcgctact caatagatgg taccttcctg
2341 gctgtaggat ctcatgacaa ctttatttac ctctatgtag tctctgaaaa tggaagaaaa
2401 tatagcagat atgaaggtg cactggacat tccagctaca tcacacacct tgactggtcc
2461 ccagacaaca gtatataat gtctaactcg ggagactatg aaatattgta cttgtaccgc
2521 cggaagcacc aggagctgca agccatgcag atggagctgc agagccctga gtacaagctg
2581 agcaagctcc gcacctcgac catcatgacc gactacaacc caactactg ctttgctggc
2641 aagacctcct ccatcagtga cctgaaggag gtgccgcgga aaacatcac cctcattcgg
2701 ggtctggccc atgagccttt ggggaggtg tatgaaggcc aggtgtccgg aatgcccaac
2761 gacccaagcc ccctgcaagt ggctgtgaag acgctgcctg aagtgtgctc tgaacaggac
2821 gaactggatt tcctcatgga agccctgatc atcagcaaat tcaaccacca gaacattgtt
2881 cgctgcattg gggtgagcct gcaatccctg ccccggttca tcctgctgga gctcatggcg
2941 gggggagacc tcaagtcctt cctccgagag acccgccctc gcccgagcca gccctcctcc
3001 ctgccatgc tggacctttt gcacgtggct cggatcgctt gtggctg tcagtatttg
3061 gaggaaaacc acttcatcca ccgagacatt gctgccagaa actgcctctt gacctgtcca
3121 ggccctggaa gagtggccaa gattggagac ttcgggatgg cccgagacat ctacagggcg
3181 agctactata gaaagggagg ctgtgccatg ctgccagtta gtggatgcc cccagaggcc
3241 ttcatggaag gaatattcac ttctaaaaca gacacatggt cctttggagt gctgctatgg
3301 gaaatctttt ctccttggata tatgccatac cccagcaaaa gcaaccagga agttctggag
```

TABLE 1 -continued

```
3361 tttgtcacca gtggaggccg gatggaccca cccaagaact gccctgggcc tgtataccgg
3421 ataatgactc agtgctggca acatcagcct gaagacaggc ccaactttgc catcattttg
3481 gagaggattg aatactgcac ccaggacccg gatgtaatca acaccgcttt gccgatagaa
3541 tatggtccac ttgtggaaga ggaagagaaa gtgcctgtga ggcccaagga ccctgagggg
3601 gttcctcctc tcctggtctc tcaacaggca aaacgggagg aggagcgcag cccagctgcc
3661 ccaccacctc tgcctaccac ctcctctggc aaggctgcaa agaaacccac agctgcagag
3721 gtctctgttc gagtccctag agggccggcc gtggaagggg acacgtgaa tatggcattc
3781 tctcagtcca acccctcctt cggagttgca cagggtcacg gatccagaaa caagcccacc
3841 agcttgtgga acccaacgta cggctcctgg tttacagaga aacccaccaa aaagaataat
3901 cctatagcaa agaaggagcc acacgagagg ggtaacctgg ggctggaggg aagctgtact
3961 gtcccaccta acgttgcaac tgggagactt ccggggggcct cactgctcct agagccctct
4021 tcgctgactg ccaatatgaa ggaggtacct ctgttcaggc tacgtcactt cccttgtggg
4081 aatgtcaatt acggctacca gcaacagggc ttgcccttag aagccgctac tgccccctgga
4141 gctggtcatt acgaggatac cattctgaaa agcaagaata gcatgaacca gcctgggccc
4201 tgagctcggt cacacactca cttctcttcc tgggatccc taagaccgtg gaggagagag
4261 aggcaatcaa tggctccttc acaaaccaga gaccaaatgt cacgttttgt tttgtgccaa
4321 cctattttga agtaccacca aaaaagctgt attttgaaaa tgcttttagaa aggttttgga
4381 catgggttca tcctattctt tcgaaagaag aaaatatcat aaaaatgagt gataaataca
4441 aggcccagat gtggttgcat aaggttttta tgcatgtttg ttgtatactt ccttatgctt
4501 cttttaaatt gtgtgtgctc tgcttcaatg tagtcagaat tagctgcttc tatgtttcat
4561 agttggggtc atagatgttt cctttgcctt ttgatgtgga catgagccat ttgaggggag
4621 agggaacgga aataaaggag ttatttgtaa tgaaaaaaaa aaaaaaaaa aaaaaaaaa
```

EML4-ALK Variant 2 Protein Sequence (BAF73612.1; GI:152002655)

```
    1 mdgfagsldd sisaaststdv qdrlsalesr vqqqedeitv lkaaladvlr rlaisedhva
   61 svkksysskg qpspravipm scitngsgan rkpshtsays iagketlssa aksgtekkke
  121 kpqggqrekke eshsndqspq iraspspqps sqplqihrqt peskhnatptk sikrpspaek
  181 shnswensdd srnklskips tpklipkvtk tadkhkdvii nqegeyikmf mrgrpitmfi
  241 psdvdnyddi rtelppeklk lewaygyrgk dcranvyllp tgeivyfias vvvlfnyeer
  301 tqrhylghtd cvkclaihpd kiriatgqia gvdkdgrplq phvrvwdsvt lstlqiiglg
  361 tfergvgcld fskadsgvhl cviddsnehm ltvwdwqkka kgaeikttne vvlavefhpt
  421 dantiitcgk shiffwtwsg nsltrkqgif gkyekpkfvq claflgngdv ltgdsggvml
  481 iwskttvept pgkgpkgvyq iskqikandg svfticqmrn gmlltgggkd rkiilwdhdl
  541 npereievpd qygtiravae gkadqflvgt srnfilrgtf ndgfqievqg htdelwglat
  601 hpfkdlllltc aqdrqvclwn smehrlewtr lvdepghcad fhpsgtvvai gthsgrwfvl
  661 daetrdlvsi htdgneqlsv mrysidgtfl avgshdnfiy lyvvsengrk ysrygrctgh
  721 ssyithldws pdnkyimsns gdyeilylyr rkhcielqamq melqspeykl sklrtstimt
  781 dynpnycfag ktssisdlke vprknitlir glghgafgev yegqvsgmpn dpsplqvavk
  841 tlpevcseqd eldflmeali iskfnhqniv rcigvslqsl prfillelma ggdlksflre
  901 trprpsqpss lamldllhva rdiacgcqyl eenhfihrdi aarnclltcp gpgrvakigd
  961 fgmardiyra syyrkggcam lpvkwmppea fmegiftskt dtwsfgvllw eifslgympy
 1021 psksnqevle fvtsggrmdp pkncpgpvyr imtqcwqhqp edrpnfaiil erieyctqdp
 1081 dvintalpie ygplveeeek vpvrpkdpeg vppllvsqqa kreeerspaa ppplpttssg
 1141 kaakkptaae vsvrvprgpa vegghvnmaf sqsnppselh rvhgsrnkpt slwnptygsw
 1201 ftekptkknn piakkepher gnlglegsct vppnvatgrl pgaslleps sltanmkevp
 1261 lfrlrhfpcg nvnygyqqqg lpleaatapg aghyedtilk sknsmnqpgp
```

EML4-ALK Variant 3a Nucleic Acid Sequence (AB374361.1; GI:194072592)

```
    1 actctgtcgg tccgctgaat gaagtgcccg cccctctaag cccggagccc ggcgctttcc
   61 ccgcaagatg gacggtttcg ccggcagtct cgatgatagt attctgctg caagtacttc
  121 tgatgttcaa gatcgcctgt cagctcttga gtcacgagtt cagcaacaag aagatgaaat
  181 cactgtgcta aaggcggctt tggctgatgt tttgaggcgt cttgcaatct ctgaagatca
  241 tgtggcctca gtgaaaaat cagtctcaag taaaggccaa ccaagccctc gagcagttat
  301 tcccatgtcc tgtataacca atggaagtgg tgcaaacaga aaaccaagtc ataccagtgc
  361 tgtctcaatt gcaggaaaag aaactctttc atctgctgct aaaagtggta cagaaaaaaa
  421 gaaagaaaaa ccacaaggac agagagaaaa aaaagaggaa tctcattcta atgatcaaag
  481 tccacaaatt cgagcatcca cttctcccca gccctcctcc aaatacacag
  541 acaaactcca gaaagcaaga atgctactcc caccaaaagc ataaacgac catcaccagc
  601 tgaaagtcca cataattctt gggaaaattc agatgatagc cgtaataaat tgtcgaaaat
  661 accttcaaca cccaaattaa taccaaaagt taccaaaact gcagacaagc ataagatgt
  721 catcatcaac caagtgtacc gccggaagca ccaggagctg aaggccatgc agatggagct
  781 gcagagccct gagtacaagc tgagcaagct ccgcacctcg accatcatga ccgactacaa
  841 ccccaactac tgctttgctg caagacctc tccatcagt gacctgaagg aggtgccgcg
  901 gaaaaacatc ccctcattc ggggtctggg ccatggagcc tttggggagg tgtatgaagg
  961 ccaggtgtcc ggaatgccca acgacccaag cccctgcaa gtggctgtga agacgctgcc
 1021 tgaagtgtgc tctgaacagg acgaactgga tttcctcatg gaagccctga tcatcagcaa
 1081 attcaaccac cagaacattg ttcgctgcat tggggtgagc ctgcaatccc tgccccggtt
 1141 catcctgctg gagctcatgg cgggggagga cctcaagtcc ttcctccgag acccgccc
 1201 tcgcccgagc cagcccctcct ccctggccat gctggacctt ctgcacgtgg ctcgggacat
 1261 tgcctgtggc tgtcagtatt tggaggaaaa ccacttcatc caccgagacg ttgctgccag
 1321 aaactgcctc ttgacctgtc cagggccctgg aagagtggcc aagattggag acttcgggat
 1381 ggcccgagac atctacaggg cgagctacta tagaaaggga ggctgtgcca tgctgccagt
 1441 taagtggatg ccccagagg ccttcatgga aggaatattc acttctaaaa cagacacatg
 1501 gtcctttggg gtgctgctat gggaaatctt ttctctttga tatgccat accccagcaa
 1561 aagcaaccag gaagttctgg agtttgtcac cagtggaggc cggatgacc cacccaagaa
 1621 ctgccctggg cctgtatacc ggataatgac tcagtgctgg caacatcagc tgaagacag
 1681 gcccaacttt gccatcattt tggagaggat tgaatactgc acccaggacc cggatgtaat
 1741 caacaccgct ttgccgatag aatatggtcc acttgtggaa gaggaagaga aagtgcctgt
```

TABLE 1 -continued

```
1801 gaggcccaag gaccctgagg gggttcctcc tctcctggtc tctcaacagg caaaacggga
1861 ggaggagcgc agcccagctg ccccaccacc tctgcctacc acctcctctg gcaaggctgc
1921 aaagaaaccc acagctgcag aggtctctgt tcgagtccct agagggccgg ccgtggaagg
1981 gggacacgtg aatatggcat tctctcagtc caaccctcct tcggagttgc acagggtcca
2041 cggatccaga aacaagccca ccagcttgtg gaacccaacg tacggctcct ggttacaga
2101 gaaacccacc aaaaagaata atcctatagc aaagaaggag ccacacgaga ggggtaacct
2161 ggggctggag ggaagctgta ctgtcccacc taacgttgca actgggagac ttccgggggc
2221 ctcactgctc ctagagccct cttcgctgac tgccaatatg aaggaggtac ctctgttcag
2281 gctacgtcac ttcccttgtg ggaatgtcaa ttacggctac cagcaacagg gcttgccctt
2341 agaagccgct actgccctg gagctggtca ttacgaggat accattctga aaagcaagaa
2401 tagcatgaac cagcctgggc cctgagctcg gtcgcacact cacttctctt ccttgggatc
2461 cctaagaccg tgg
```

EML4-ALK Variant 3a Protein Sequence (BAG55003.1; GI:194072593)

```
  1 mdgfagsldd sisaastsdv qdrlsalesr vqqqedeitv lkaaladvlr rlaisedhva
 61 svkksysskg qpspravipm scitngsgan rkpshtsays iagketlssa aksgtekkke
121 kpqgqrekke eshsndqspq iraspspqps sqplqihrqt pesknatptk sikrpspaek
181 shnswensdd srnklskips tpklipkvtk tadkhkdvii nqvyrrkhqe lqamqmelqs
241 peyklsklrt stimtdynpn ycfagktssi sdlkevprkn itlirglghg afgevyegqv
301 sgmpndpspl qvavktlpev cseqdeldfl mealiiskfn hqnivrcigv slqslprfil
361 lelmaggdlk sflretrprp sqpsslamld llhvardiac gcqyleenhf ihrdiaarnc
421 lltcpgpgry akigdfgmar diyrasyyrk ggcamlpvkw mppeafmegi ftsktdtwsf
481 gvllweifsl gympypsksn qevlefvtsg grmdppkncp gpvyrimtqc wqhqpedrpn
541 faiileriey ctqdpdvint alpieygplv eeeekvprp kdpegvppll vsqqakreee
601 rspaappplp tssgkaakk ptaaevsvry prgpaveggh vnmafsqsnp pselhrvhgs
661 rnkptslwnp tygswftekp tkknnpiakk ephergnlgl egsctvppnv atgrlpgasl
721 llepssltan mkevplfrlr hfpcgnvnyg yqqqglplea atapgaghye dtilksknsm
781 nqpgp
```

EML4-ALK Variant 3b Nucleic Acid Sequence (AB374362.1; GI:194072594)

```
  1 actctgtcgg tccgctgaat gaagtgcccg cccctctaag cccggagccc ggcgctttcc
 61 ccgcaagatg gacggtttcg ccggcagtct cgatgatagt atttctgctg caagtacttc
121 tgatgttcaa gatcgcctgt cagctcttga gtcacgagtt cagcaacaag aagatgaaat
181 cactgtgcta aaggcggctt tggctgatgt ttttgaggcgt cttgcaatct ctgaagatca
241 tgtggcctca gtgaaaaaat cagtctcaag taaaggccaa ccaagccctc gagcagttat
301 tcccatgtcc tgtataacca atggaagtgg tgcaaacaga aaccaagtc ataccagtgc
361 tgtctcaatt gcaggaaaag aaactctttc atctgctgct aaaagtggta cagaaaaaaa
421 gaaagaaaaa ccacaaggac agagagaaaa aaaagaggaa tctcattcta atgatcaaag
481 tccacaaatt cgagcatcac cttctcccca gccctcttca caacctctcc aaatacacag
541 acaaactcca gaaagcaaga atgctactcc caccaaaagc ataaaacgac catcaccagc
601 tgaaaagtca cataattctt gggaaaattc agatgatagc cgtaataaat tgtcgaaaat
661 accttcaaca cccaaattaa taccaaaagt taccaaaact gcagacaagc ataaagatgt
721 catcatcaac caagcaaaaa tgtcaactcg cgaaaaaaac agccaagtgt accgccggaa
781 gcaccaggag ctgcaagcca tgcagatgga gctgcagagc cctgagtaca agctgagcaa
841 gctccgcacc tcgaccatca tgaccgacta caaccccaac tactgctttg ctggcaagac
901 ctcctccatc agtgacctga aggaggtgcc gcggaaaaac atcaccctca ttcggggtct
961 gggccatgga gcctttgggg aggtgtatga aggccaggtg tccggaatgc caacgaccc
1021 aagcccctg caagtggctg tgaagacgct gcctgaagtg tgctctgaac aggacgaact
1081 ggatttcctc atggaagccc tgatcatcag caaattcaac caccagaaca ttgttcgctg
1141 cattggggtg agcctgcaat ccctgccccg gttcatcctg ctggagctca tggcggggga
1201 agacctcaag tccttcctcc gagagacccg ccctcgcccg agccagccct cctccctggc
1261 catgctggac ctttctgcacg tggctcggga cattgcctgt ggctgtcagt atttggagga
1321 aaaccacttc atccaccgag acattgctgc cagaaactgc ctcttgacct gtccaggccc
1381 tggaagagtg gccaagattg gagacttcgg gatggcccga gacatctaca gggcgagcta
1441 ctatagaaag ggaggctgtg ccatgctgcc agttaagtgg atgccccag aggccttcat
1501 ggaaggaata ttcacttcta aaacagacac atggtccttt ggagtgctgc tatgggaaat
1561 cttttctctt ggatatatgc catacccag caaaagcaac caggaagttc tggagtttgt
1621 caccagtgga ggccgatgga acccacccaa gaactgccct gggcctgtat accggataat
1681 gactcagtgc tggcaacatc agcctgaaga caggcccaac tttgccatca ttttggagag
1741 gattgaatac tgcacccagg acccggatgt aatcaacacc gctttgccga tagaatatgg
1801 tccacttgtg gaagaggaag agaaagtgcc tgtgaggccc aaggaccctg aggggttcc
1861 tcctctcctg gtctctcaac aggcaaaacg ggaggaggag cgcagcccag ctgccccacc
1921 acctctgcct accacctcct ctggcaaggc tgcaaagaaa cccacagctg cagaggtctc
1981 tgttcgagtc cctagagggc cggccgtgga agggggacac gtgaatatgg cattctctca
2041 gtccaaccct ccttcggagt tgcacagggt ccaccggagc acatcatt tgaaaagcaa
2101 gtggaaccca acgtacgggt cctggtttac agagaaaccc accaaaaaga ataatcctat
2161 agcaaagaag gagccacacg agaggggtaa cctggggctg gagggaagct gtactgtccc
2221 acctaacgtt gcaactggga gacttccggg ggcctcactg ctcctagagc cctcttcgct
2281 gactgccaat atgaaggagg tacctctgtt caggctacgt cacttccctt gtgggaatgt
2341 caattacggc taccagcaac agggcttgcc cttagaagcc gctactgccc ctggagctgg
2401 tcattacgag gataccattc tgaaaagcaa gaatagcatg aaccagcctg ggccctgagc
2461 tcggtcgcac actcacttct cttccttggg atccctaaga ccgtgg
```

EML4-ALK Variant 3b Protein Sequence (BAG55004.1; GI:194072595)

```
  1 mdgfagsldd sisaastsdv qdrlsalesr vqqqedeitv lkaaladvlr rlaisedhva
 61 svkksysskg gpspravipm scitngsgan rkpshtsays iagketlssa aksgtekkke
121 kpqgqrekke eshsndqspq iraspspqps sqplqihrqt pesknatptk sikrpspaek
```

TABLE 1 -continued

```
181 shnswensdd srnklskips tpklipkvtk tadkhkdvii nqakmstrek nsqvyrrkhq
241 elqamqmelq speyklsklr tstimtdynp nycfagktss isdlkevprk nitlirglgh
301 gafgevyegq vsgmpndpsp lqvavktlpe vcseqdeldf lmealiiskf nhgnivrcig
361 vslqslprfi llelmaggdl ksflretrpr psqpsslaml dllhvardia cgcqyleenh
421 fihrdiaarn clltcpgpgr vakigdfgma rdiyrasyyr kggcamlpvk wmppeafmeg
481 iftsktdtws fgvllweifs lgympypsks nqevlefvts ggrmdppknc pgpvyrimtq
541 cwqhqpedrp nfaiilerie yctqdpdvin talpieygpl veeeekvpvr pkdpegvppl
601 lvsqqakree erspaappppl pttssgkaak kptaaevsvr vprgpavegg hvnmafsgsn
661 ppselhrvhg srnkptslwn ptygswftek ptkknnpiak kephergnlg legsctvppn
721 vatgrlpgas lllepsslta nmkevplfrl rhfpcgnvny gyqqqglple aatapgaghy
781 edtilkskns mnqpgp
```

EML4-ALK Variant 4 Nucleic Acid Sequence (AB374363.1; GI:209837703)

```
   1 actctgtcgg tccgctgaat gaagtgcccg cccctctaag cccggagccc ggcgctttcc
  61 ccgcaagatg gacggtttcg ccggcagtct cgatgatagt atttctgctg caagtacttc
 121 tgatgttcaa gatcgcctgt cagctcttga gtcacgagtt cagcaacaag aagatgaaat
 181 cactgtgcta aaggcggctt tggctgatgt tttgaggcgt cttgcaatct ctgaagatca
 241 tgtggcctca gtgaaaaaat cagtctcaag taaaggccaa ccaagccctc gagcagttat
 301 tcccatgtcc tgtataacca atggaagtgg tgcaaacaga aaaccaagtc ataccagtgc
 361 tgtctcaatt gcaggaaaag aaactctttc atctgctgct aaaagtggta cagaaaaaaa
 421 gaaagaaaaa ccacaaggac agagagaaaa aaaagaggaa tctcattcta atgatcaaag
 481 tccacaaatt cgagcatcac cttctcccca gccctcttca caacctctcc aaatacacag
 541 acaaactcca gaaagcaaga atgctactcc caccaaaagc ataaacgac catcaccagc
 601 tgaaagtcaa cataattctt gggaaaattc agatgatagc cgtaataaat tgtcgaaaat
 661 accttcaaca cccaaattaa taccaaaagt taccaaaact gcagacaagc ataaagatgt
 721 catcatcaac caagaaggag aatatattaa aatgttatg cgcggtcggc caattaccat
 781 gttcattcct tccgatgttg acaactatga tgacatcaga acggaactgc ctcctgagaa
 841 gctcaaactg gagtgggcat atggttatcg aggaaaggac tgtagagcta atgtttacct
 901 tcttccgacc ggggaaatag ttatttcat tgcatcagta gtagtactat ttaattatga
 961 ggagagaact cagcgacact acctgggcca tacagactgt gtgaaatgcc ttgctataca
1021 tcctgacaaa attaggattg caactggaca gatagctggc gtggataaag atggaaggcc
1081 tctacaaccc cacgtcagag tgtgggattc tgttactcta tccacactgc agattattgg
1141 acttggcact tttgagcgtg gagtaggatg cctggatttt tcaaaagcag attcaggttgt
1201 tcatttatgt gttattgatg actccaatga gcatatgctt actgtatggg actggcagag
1261 gaaagcaaaa ggagcagaaa taaagacaac aaatgaagtt gttttggctg tggagtttca
1321 cccaacagat gcaaatacca taattacatg cggtaaatct catattttct tctggacctg
1381 gagcggcaat tcactaacaa gaaaacaggg aaatttttgg aaatatgaaa gccaaaatt
1441 tgtgcagtgt ttagcattct tggggaatgg agatgttctt actggagact caggtggagt
1501 catgcttata tggagcaaaa ctactgtaga gcccacacct gggaaggac ctaaaggtgt
1561 atatcaaatc agcaaacaaa tcaaagctca tgatggcagt gtgttcacac tttgtcagat
1621 gagaaatggg atgttattaa ctggagggag gaaagacaaa aaataattc tgtgggatca
1681 tgatctgaat cctgaaagag aaatagagat atgctggatg agccctgagt acaagctgag
1741 caagctccgc acctcgacca tcatgaccga ctacaaccccc aactactgct tgctggcaa
1801 gacctcctcc atcagtgacc tgaaggaggt gccgcgaaa aacatcaccc tcattcgggg
1861 tctgggccat ggagccttttg gtgaggtgta tgaaggccag gtgtccggaa tgcccaacga
1921 cccaagcccc ctgcaagtgg ctgtgaagac gctgcctgaa gtgtgctctg aacaggacga
1981 actggatttc ctcatggaag ccctgatcat cagcaaattc aaccaccaga cattgttcg
2041 ctgcattggg gtgagcctgc aatccctgcc ccggttcatc ctgctggagc tcatggcggg
2101 gggagacctc aagtccttcc tccgagagac ccgcccctcgc ctgagccagc cctcctccct
2161 ggccatgctg gacttctgc acgtggctcg ggacattgcc tgtggctgtc agtatttgga
2221 ggaaaaccac ttcatccacc gagacattgc tgccagaaac tgcctcttga cctgtccagg
2281 ccctggaaga gtgccaaga ttggagactt cgggatggcc cgagacatct acagggcgag
2341 ctactataga aagggaggct gtgccatgct gccagttaag tggatgccc cagaggcctt
2401 catggaagga atattcactt ctaaaacaga cacatggtcc tttggagtgc tgctatggga
2461 aatcttttct cttggatata tgccataccc cagcaaaagc aaccaagaag ttctggagtt
2521 tgtcaccagt ggaggccgga tggacccacc caagaactgc cctgggcctg tataccggat
2581 aatgactcag tgctggcaac atcagcctga agacaggccc aactttgcca tcatttggaa
2641 gaggattgaa tactgcaccc aggaccggga tgtaatcaac accgctttgc cgatagaata
2701 tggtccactt gtggaagagg aagagaaagt gcctgtgagg cccaaggacc ctgaggggt
2761 tcctcctctc ctggtctctc aacaggcaaa acgggaggag gagcgcagcc cagctgcccc
2821 accacctctg cctaccacct cctctggcaa ggctgcaaag aaacccacag ctgcaggt
2881 ctctgttcga gtccctagag ggccggccgt ggaagggga cacgtgaata tggcattctc
2941 tcagtccaac cctccttcgg agttgcacag ggtccacgga tccagaaaca gcccaccag
3001 cttgtgaac ccaacgtacg gctcctggtt tacagaaaa cccaccaaaa agaataatcc
3061 tatagcaaag aaggagccac acgagagggg taacctgggg ctgagggaa gctgtactgt
3121 cccacctaac gttcaactg ggagacttcc ggggcctca ctgctcctag agccctcttc
3181 gctgactgcc aatatgaagg aggtacctct gttcaggcta cgtcacttcc cttgtgggaa
3241 tgtcaattac ggctaccagc aacagggctt gccttagaa gccgctactg cccctggagc
3301 tggtcattac gaggatacca ttctgaaaag caagaatagc atgaaccagc ctgggccctg
3361 agctcggtcg cacactcact tctcttcctt gggatcccta agaccgtgg
```

EML4-ALK Variant 4 Protein Sequence (BAG75147.1; GI:209837704)

```
   1 mdgfagsldd sisaastsdv qdrlsalesr vqqqedeitv lkaaladvlr rlaisedhva
  61 svkksysskg qpspravipm scitngsgan rkpshtsays iagketlssa aksgtekkke
 121 kpqgqrekke eshsndqspq iraspspqps sqplqihrqt peknatptk sikrpspaek
 181 shnswensdd srnklskips tpklipkvtk tadkhkdvii nqegeyikmf mrgrpitmfi
 241 psdvdnyddi rtelppeklk lewaygyrgk dcranvyllp tgeivyfias vvvlfnyeer
 301 tqrhylghtd cvkclaihpd kiriatgqia gvdkdgrplq phvrvwdsvt lstlqiiglg
```

TABLE 1 -continued

```
 361 tfergvgcld fskadsgvhl cviddsnehm ltvwdwqrka kgaeikttne vvlavefhpt
 421 dantiitcgk shiffwtwsg nsltrkqgif gkyekpkfvq claflgngdv ltgdsggvml
 481 iwskttvept pgkgpkgvyq iskqikandg svfticqmrn gmlltgggkd rkiilwdhdl
 541 npereieicw mspeyklskl rtstimtdyn pnycfagkts sisdlkevpr knitlirglg
 601 hgafgevyeg qvsgmpndps plqvavktlp evcseqdeld flmealiisk fnhqnivrci
 661 gvslqslprf illelmaggd lksflretrp rpsqpsslam ldllhvardi acgcqyleen
 721 hfihrdiaar nclltcpgpg rvakigdfgm ardiyrasyy rkggcamlpv kwmppeafme
 781 giftsktdtw sfgvllweif slgympypsk snqevlefvt sggrmdppkn cpgpvyrimt
 841 qcwqhqpedr pnfaiileri eyctqdpdvi ntalpieygp lveeeekvpv rpkdpegvpp
 901 llvsqqakre eerspaappp lpttssgkaa kkptaaevsv rvprgpaveg ghvnmafsqs
 961 nppselhrvh gsrnkptslw nptygswfte kptkknnpia kkephergnl glegsctvpp
1021 nvatgrlpga slllepsslt anmkevplfr lrhfpcgnvn ygyqqqglpl eaatapgagh
1081 yedtilkskn smnqpgp
```

EML4-ALK Variant 5a Nucleic Acid Sequence (AB374364.1; GI:209837705)

```
    1 actctgtcgg tccgctgaat gaagtgcccg cccctctaag cccggagccc ggcgctttcc
   61 ccgcaagatg gacggtttcg ccggcagtct cgatgatagt atttctgctg caagtacttc
  121 tgatgttcaa gatcgcctgt cagctcttga gtcacgagtt cagcaacaag aagatgaaat
  181 cactgtgcta aaggcggctt tggctgatgt tttgaggcgt cttgcaatct ctgaagatca
  241 tgtggcctca gtgaaaaaat cagtctcaag taaagtgtac cgccggaagc accaggagct
  301 gcaagccatg cagatggagc tgcagagccc tgagtacaag ctgagcaagc tccgcacctc
  361 gaccatcatg accgactaca accccaacta ctgctttgct ggcaagacct cctccatcag
  421 tgacctgaag gaggtgccgc ggaaaaacat cacccctcat tcggggtctgg gccatggagc
  481 ctttggggag gtgtatgaag gccaggtgtc cggaatgccc aacgacccaa gcccctgca
  541 agtggctgtg aagacgctgc ctgaagtgtg ctctgaacag gacgaactgg atttcctcat
  601 ggaagccctg atcatcagca aattcaacca ccagaacatt gttcgctgca ttggggtgag
  661 cctgcaatcc ctgccccggt tcatcctgct ggagctcatg gcggggggag acctcaagtc
  721 cttcctccga gagacccgcc ctcgcccgag ccagccctcc tccctggcca tgctggacct
  781 tctgcacgtg gctcgggaca ttgcctgtgg ctgtcagtat tggaggaaa accacttcat
  841 ccaccgagac attgctgcca gaactgcct cttgacctgt ccaggccctg gaagagtggc
  901 caagattgga gacttcggga tggcccgaga catctacagg gcgagctact atagaaaggg
  961 aggctgtgcc atgctgccag ttaagtggat gccccagag gccttcatgg aaggaatatt
 1021 cacttctaaa acagacacat ggtccttttga agtgctgtca tgggaaatct ttttctcttgg
 1081 atatatgcca taccccagca aaagcaacca ggaagttctg gagtttgtca ccagtggagg
 1141 ccggatggac ccaccccaaga actgcccctgg gcctgtatac cggataatga ctcagtgctg
 1201 gcaacatcag cctgaagaca ggcccaactt tgccatcatt ttggagagga ttgaatactg
 1261 cacccaggac ccggatgtaa tcaacaccgc tttgccgata gaatatggtc cacttgtgga
 1321 agaggaagag aaagtgcctg tgaggcccaa ggacccgag ggggttcctc ctctcctggt
 1381 ctctcaaacg gcaaaacggg aggaggagcg cagcccagct gccccaccac ctctgcctac
 1441 cacctcctct ggcaaggctg caaagaaacc cacagctgca gaggtctctg ttcgagtccc
 1501 tagagggccg gccgtggaag ggggacacgt gaatatggca ttctctcagt ccaaccctcc
 1561 ttcggagttg cacagggtcc acggatccag aaacaagccc accagcttgt ggaacccaac
 1621 gtacggctcc tggtttacag agaaacccac caaaaagaat aatcctatag caaagaagga
 1681 gccacacgag agggggtaacc tggggctgga gggaagctgt actgtcccac ctaacgttgc
 1741 aactggagga cttccggggg cctcactgct cctagagccc tcttcgctga ctgccaatat
 1801 gaaggaggta cctctgttca ggctacgtca cttcccttgt gggaatgtca attacggcta
 1861 ccagcaacag ggcttgccct tagaagccgc tactgcccct ggagctggtc attacgagga
 1921 taccattctg aaaagcaaga atagcatgaa ccagcctggg ccctgagctc ggtcgcacac
 1981 tcacttctct tccttgggat ccctaagacc gtgg
```

EML4-ALK Variant 5a Protein Sequence (BAG75148.1; GI:209837706)

```
    1 mdgfagsldd sisaastsdv qdrlsalesr vqqqedeitv lkaaladvlr rlaisedhva
   61 svkksysskv yrrkhqelqa mqmelqspey klsklrtsti mtdynpnycf agktssisdl
  121 kevprknitl irglghgafg evyegqvsgm pndpsplqva vktlpevcse qdeldflmea
  181 liiskfnhqn ivrcigvslq slprfillel maggdlksfl retrprpsqp sslamldllh
  241 vardiacgcq yleenhfihr diaarncllt cpgpgrvaki gdfgmardiy rasyyrkggc
  301 amlpvkwmpp eafmegifts ktdtwsfgvl lweifslgym pypsksnqev lefvtsggrm
  361 dppkncpgpv yrimtqcwqh qpedrpnfai ilerieyctq dpdvintalp ieygplveee
  421 ekvpvrpkdp egvppllvsq qakreeersp aappplptts sgkaakkpta aevsvrvprg
  481 pavegghvnm afsqsnppse lhrvhgsrnk ptslwnptyg swftekptkk nnpiakkeph
  541 ergnlglegs ctvppnvatg rlpgaslllE psslTanmke vplfrlrhfp cgnvnygyqq
  601 qglpleaata pgaghyedti lksknsmnqp gp
```

EML4-ALK Variant 5b Protein Sequence (AB374365.1; GI:209837707)

```
    1 actctgtcgg tccgctgaat gaagtgcccg cccctctaag cccggagccc ggcgctttcc
   61 ccgcaagatg gacggtttcg ccggcagtct cgatgatagt atttctgctg caagtacttc
  121 tgatgttcaa gatcgcctgt cagctcttga gtcacgagtt cagcaacaag aagatgaaat
  181 cactgtgcta aaggcggctt tggctgatgt tttgaggcgt cttgcaatct ctgaagatca
  241 tgtggcctca gtgaaaaaat cagtctcaag taaaggttca gagctcaggg gaggatatgg
  301 agatccaggg aggcttcctg taggaagtgg cctgtgtagt gcttcaaggg ccaggctgcc
  361 aggccatgtt gcagctgacc acccacctgc agtgtaccgc ggaagcacc aggagctgca
  421 agccatgcag atggagctgc agagccctga gtacaagctg agcaagctcc gcacctcgac
  481 catcatgacc gactacaacc ccaactactg ctttgctggc aagacctcct ccatcagtga
  541 cctgaaggag gtgccgcgga aaaacatcac ccctcattcg ggtctgggcc atggagcctt
  601 tggggaggtgt atgaaggcc aggtgtccgg aatgcccaac gacccaagcc cctgcaagt
  661 ggctgtgaag acgctgcctg aagtgtgctc tgaacaggac gaactggatt tcctcatgga
  721 agccctgatc atcagcaaat tcaaccacca gaacattgtt cgctgcattg gggtgagcct
```

TABLE 1 -continued

```
 781 gcaatccctg ccccggttca tcctgctgga gctcatggcg gggggagacc tcaagtcctt
 841 cctccgagag acccgccctc gcccgagcca gccctcctcc ctggccatgc tggaccttct
 901 gcacgtggct cgggacattg cctgtggctg tcagtatttg gaggaaaacc acttcatcca
 961 ccgagacatt gctgccagaa actgcctctt gacctgtcca ggccctggaa gagtggccaa
1021 gattggagac ttcgggatgg cccgagacat ctacagggcg agctactata gaaaggagg
1081 ctgtgccatg ctgccagtta agtggatgcc cccagaggcc ttcatggaag gaatattcac
1141 ttctaaaaca gacacatggt cctttggagt gctgctatgg gaaatctttt ctcttggata
1201 tatgccatac cccagcaaaa gcaaccagga agttctggag tttgtcacca gtggaggccg
1261 gatggaccca cccaagaact gccctgggcc tgtataccgg ataatgactc agtgctggca
1321 acatcagcct gaagacaggc caaactttgc catcattttg gagaggattg aatactgcac
1381 ccaggacccg gatgtaatca acaccgcttt gccgatagaa tatggtccac ttgtggaaga
1441 ggaagagaaa gtgcctgtga ggcccaagga ccctgagggg gttcctcctc tcctggtctc
1501 tcaacaggca aaacgggagg aggagcgcag cccagctgcc ccaccacctc tgcctaccac
1561 ctcctctggc aaggctgcaa agaaacccac agctgcagag gtctctgttc gagtccctag
1621 agggccggcc gtgaaggggg acacgtgaa tatggcattc tctcagtcca accctccttc
1681 ggagttgcac agggtccacg gatccagaaa caagcccacc agcttgtgga acccaacgta
1741 cggctcctgg tttacagaga aacccaccaa aagaataat cctatagcaa agaaggagcc
1801 acacgagagg ggtaacctgg ggctggaggg aagctgtact gtcccaccta acgttgcaac
1861 tgggagactt ccgggggcct cactgctcct agagccctct tcgctgactg ccaatatgaa
1921 ggaggtacct ctgttcaggc tacgtcactt ccctgtgggg aatgtcaatt acggctacca
1981 gcaacagggc ttgcccttag aagccgctac tgcccctgga gctggtcatt acgaggatac
2041 cattctgaaa agcaagaata gcatgaacca gcctgggccc tgagctcggt cgcacactca
2101 cttctcttcc ttgggatccc taagaccgtg g
```

EML4-ALK Variant 5b Protein Sequence (BAG75149.1; GI:209837708)

```
  1 mdgfagsldd sisaastsdv qdrlsalesr vqqqedeitv lkaaladvlr rlaisedhva
 61 svkksysskg selrggygdp grlpvgsglc sasrarlpgh vaadhppavy rrkhqelqam
121 qmelqspeyk lsklrtstim tdynpnycfa gktssisdlk evprknitli rglghgafge
181 vyegqvsgmp ndpsplqvav ktlpevcseq deldflmeal iiskfnhqni vrcigvslqs
241 lprfillelm aggdlksflr etrprpsqps slamldllhv ardiacgcqy leenhfihrd
301 iaarnclltc pgpgrvakig dfgmardiyr asyyrkggca mlpvkwmppe afmegiftsk
361 tdtwsfgvll weifslgymp ypsksnqevl efvtsggrmd ppkncpgpvy rimtqcwqhq
421 pedrpnfaii lerieyctqd pdvintalpi eygplveeee kvpvrpkdpe gvppllvsqq
481 akreeerspa appplpttss gkaakkptaa evsvrvprgp aveggvhvnma fsqsnppsel
541 hrvhgsrnkp tslwnptygs wftekptkkn npiakkephe rgnlglegsc tvppnvatgr
601 lpgaslllep ssltanmkev plfrlrhfpc gnvnygyqqq glpleaatap gaghyedtil
661 ksknsmnqpg p
```

EML4-ALK Variant 6 Nucleic Acid Sequence (AB462411.1; GI:227452648)

```
   1 tactctgtcg gtccgctgaa tgaagtgccc gccctctaa gcccggagcc cggcgctttc
  61 cccgcaagat ggacggtttc gccggcagtc tcgatgatag tatttctgct gcaagtactt
 121 ctgatgttca agatcgcctg tcagctcttg agtcacgagt tcagcaacaa gaagatgaaa
 181 tcactgtgct aaaggcggct ttggctgatg ttttgaggcg tcttgcaatc tctgaagatc
 241 atgtggcctc agtgaaaaaa tcagtctcaa gtaaaggcca accaagccct cgagcagtta
 301 ttcccatgtc ctgtataacc aatgaagtg tgcaaacag aaaaccaagt cataccagtg
 361 ctgtctcaat tgcaggaaaa gaaactcttt catctgctgc taaaagtggt acagaaaaaa
 421 agaaagaaaa accacaagga cagagagaaa aaaagagga tctcattct aatgatcaaa
 481 gtccacaaat tcgagcatca cctttctccc agccctcttc acaacctctc caaatacaca
 541 gacaaactcc agaaagcaag aatgctactc ccaccaaaag cataaaacga ccatcaccag
 601 ctgaaaagtc acataattct tgggaaaatt cagatgatag ccgtaataaa ttgtcgaaaa
 661 taccttcaac ccccaaatta ataccaaaag ttaccaaaac tgcagacaag cataaagatg
 721 tcatcatcaa ccaagaagga gaatatatta aaatgtttat gcgcggtcgg ccaattacca
 781 tgttcattcc ttccgatgtt gacaactatg atgacatcag aacggaactg cctcctgaga
 841 agctcaaact ggagtgggca tatggttatc gaggaaagga ctgtagagct aatgtttacc
 901 ttcttccgac cggggaaata gtttatttca ttgcatcagt agtagtacta tttaattatg
 961 aggagagaac tcagcgacac tacctgggcc atacagactg tgtgaaatgc cttgctatac
1021 atcctgacaa aatttaggatt gcaactggac agatagctgg cgtggataaa gatggaaggc
1081 ctctacaacc ccacgtcaga gtgtgggatt ctgttactct atccacactg cagattattg
1141 gacttggcac ttttgagcgt ggagtaggat gcctggattt tcaaaagca gattcaggtg
1201 ttcatttatg tgttattgat gactccaatg agcatatgct tactgtatgg gactggcaga
1261 ggaaagcaaa aggagcagaa ataaagacaa caaatgaagt tgtttttggct gtggagtttc
1321 acccaacaga tgcaaatacc ataattacat gcgtaaatc tcatatttc ttctggacct
1381 ggagcggcaa ttcactaaca agaaaacagg gaattttttgg gaaatatgaa aagccaaaat
1441 ttgtgcagtg tttagcattc ttggggaatg gagatgttct tactggagac tcaggtggag
1501 tcatgcttat atggaagcaa actactgtag agcccacacg tgggaaagga cctaaaggaa
1561 gtggcctgtg tagtgcttca agggccaggc tgcaggcca tgttgcagct gaccacccac
1621 ctgcagtgta ccgccggaag caccaggagc tgcaagccat gcagatggag ctgcagagcc
1681 ctgagtacaa gctgagcaag ctccgcacct cgaccatcat gaccgactac aaccccaact
1741 actgctttgc tggcaagacc tcctccatca gtgacctgaa ggaggtgccg cggaaaaaca
1801 tcacctcat tcggggtctg ggccatggag cctttgggga ggtgtatgaa ggcaggtgt
1861 ccggaatgcc caacgaccca gcccctgc aagtggctgt gaagacgctg cctgaagtgt
1921 gctctgaaca ggacgaactg gatttcctca tggaagccct gatcatcagc aaattcaacc
1981 accagaacat tgttcgctgc attggggtga gcctgcaatc cctgccccgt ttcatcctgc
2041 tggagctcat ggcggggga gacctcaagt ccttcctccg agagacccgg cctcgcccga
2101 gccagccctc ctcctggcc atgctggacc ttctgcacgt ggctcgggac attgctgtg
2161 gctgtcagta tttggaggaa aaccacttca tccaccgaga cattgctgcc agaaactgcc
2221 tcttgacctg tccaggccct ggaagagtgg ccaagattgg agcttcggg atggcccgag
2281 acatctacag ggcgagctac tatagaaagg gaggctgtgc catgctgcca gttaagtgga
```

TABLE 1 -continued

```
2341 tgcccccaga ggccttcatg gaaggaatat tcacttctaa aacagacaca tggtcctttg
2401 gagtgctgct atgggaaatc ttttctcttg gatatatgcc atacccagc aaaagcaacc
2461 aggaagttct ggagtttgtc accagtggag gccggatgga cccacccaag aactgccctg
2521 ggcctgtata ccggataatg actcagtgct ggcaacatca gctgaagac aggccaact
2581 ttgccatcat tttggagagg attgaatact gcacccagga cccggatgta atcaacaccg
2641 ctttgccgat agaatatggt ccacttgtgt aagaggaaga gaaagtgcct gtgaggccca
2701 aggaccctga gggggttcct cctctcctgg tctctcaaca ggcaaaacgg gaggaggagc
2761 gcagcccagc tgccccacca cctctgccta ccacctcctc tggcaaggct gcaaagaaac
2821 ccacagctgc agaggtctct gttcgagtcc ctagagggc ggcgtggaa ggggacacg
2881 tgaatatggc attctctcag tccaaccctc cttcggagtt gcacagggtc cacggatcca
2941 gaaacaagcc caccagcttg tggaacccaa cgtacggctc ctggtttaca gagaaaccca
3001 ccaaaaagaa taatcctata gcaaagaagg agccacacga gaggggtaac ctggggctgg
3061 agggaagctg tactgtccca cctaacgttg caactgggag acttccgggg gcctcactgc
3121 tcctagagcc ctcttcgctg actgccaata tgaaggaggt acctctgttc aggctacgtc
3181 acttcccttg tgggaatgtc aattacggct ccagcaacaa gggcttgccc ttagaagccg
3241 ctactgcccc tggagctggt cattacgagg ataccattct gaaaagcaag aatagcatga
3301 accagcctgg gccctgagct cggtcgcaca ctcacttctc ttccttggga tccctaagac
3361 cgtgg
```

EML4-ALK Variant 6 Protein Sequence (BAH57335.1; GI:227452649)

```
   1 mdgfagsldd sisaastsdv qdrlsalesr vqqqedeitv lkaaladvlr rlaisedhva
  61 svkksysskg qpspravipm scitngsgan rkpshtsays iagketlssa aksgtekkke
 121 kpqgqrekke eshsndqspq iraspspqps sqplqihrqt pesknatptk sikrpspaek
 181 shnswensdd srnklskips tpklipkvtk tadkhkdvii nqegeyikmf mrgrpitmfi
 241 psdvdnyddi rtelppeklk lewaygyrgk dcranvyllp tgeivyfias vvvlfnyeer
 301 tqrhylghtd cvkclaihpd kiriatgqia gvdkdgrplq phvrvwdsvt lstlqiiglg
 361 tfergvgcld fskadsgvhl cviddsnehm ltvwdwqrka kgaeikttne vvlavefhpt
 421 dantiitcgk shiffwtwsg nsltrkqgif gkyekpkfvq claflgngdv ltgdsggvml
 481 iwskttvept pgkgpkgsgl csasrarlpg hvaadhppav yrrkhqelqa mqmelqspey
 541 klsklrtsti mtdynpnycf agktssisdl kevprknitl irglghgafg evyegqvsgm
 601 pndpsplqva vktlpevcse qdeldflmea liiskfnhqn ivrcigvslq slprfillel
 661 maggdlksfl retrprpsqp sslamldllh vardiacgcq yleenhfihr diaarncllt
 721 cpgpgrvaki gdfgmardiy rasyyrkggc amlpvkwmpp eafmegifts ktdtwsfgvl
 781 lweifslgym pypsksnqev lefvtsggrm dppkncpgpv yrimtqcwqh qpedrpnfai
 841 ilerieyctq dpdvintalp ieygplveee ekvpvrpkdp egvppllvsq qakreeeersp
 901 aappplptts sgkaakkpta aevsvrvprg pavegghvnm afsqsnppse lhrvhgsrnk
 961 ptslwnptyg swftekptkk nnpiakkeph ergnlglegs ctvppnvatg rlpgasllle
1021 pssltanmke vplfrlrhfp cgnvnygyqq qglpleaata pgaghyedti lksknsmnqp
1081 gp
```

EML4-ALK Variant 7 Nucleic Acid Sequence (AB462412.1; GI:227452650)

```
   1 tactctgtcg gtccgctgaa tgaagtgccc gccctctaa gcccggagcc cggcgctttc
  61 cccgcaagat ggacggtttc gccggcagtc tcgatgatag tatttctgct gcaagtactt
 121 ctgatgttca agatcgcctc tcagctcttg agtcacgagt tcagcaacaa gaagatgaaa
 181 tcactgtgct aaaggcggct ttggctgatg ttttgaggcg tcttgcaatc tctgaagatc
 241 atgtggcctc agtgaaaaaa tcagtctcaa gtaaaggcca accaagccct cgagcagtta
 301 ttcccatgtc ctgtataacc aatggaagtg gtgcaaacag aaaaccaagt cataccagtg
 361 ctgtctcaat tgcaggaaaa gaaactcttt catctgctgc taaaagtggt acagaaaaaa
 421 agaaagaaaa accaagga cagagagaaa aaaagagga atctcattct aatgatcaaa
 481 gtccacaaat tcgagcatca ccttctcccc agccctcttc acaacctctc caaatacaca
 541 gacaaactcc agaaagcaag aatgctactc ccaccaaaag cataaaacga ccatcaccag
 601 ctgaaaagtc acataattct tgggaaaatt cagatgatag ccgtaataaa ttgtcgaaaa
 661 taccttcaac acccaaatta ataccaaaag ttaccaaaac tgcagacaag cataaagatg
 721 tcatcatcaa ccaagaagga gaatatatta aatgtttat gcgcggtcgg ccaattacca
 781 tgttcattcc ttccgatgtt gacaactatg atgacatcag aacggaactg cctcctgaga
 841 agctcaaact ggagtgggca tatggttatc gaggaaagga ctgtagagct aatgtttacc
 901 ttcttccgac cggggaaata gtttatttca ttgcatcagt agtagtacta tttaattatg
 961 aggagagaac tcagcgacac tacctgggcc atacagactg tgtgaaatgc cttgctatac
1021 atcctgacaa aattaggatt gcaactggac agatagctgg cgtggataaa gatggaaggc
1081 ctctacaacc ccacgtcaga gtgtgggatt ctgttactct atccacactg cagattattg
1141 gacttggcac ttttgagcgt ggagtaggat gcctggattt tcaaaagca gattcaggtg
1201 ttcatttatg tgttattgat gactccaatg agcatatgct tactgtatgg gactggcaga
1261 ggaaagcaaa aggagcagaa ataaagacaa caatgaagt tgtttggct gtggagtttc
1321 acccaacaga tgcaaatacc ataattcat gcggtaaatc tcatttttc ttctggacct
1381 ggagcggcaa ttcactaaca agaaaacagg gaatttttgg gaaatatgaa aagccaaaat
1441 ttgtgcagtg tttagcattc ttggggaatg gagatgttct tactgagac tcaggtggag
1501 tcatgcttat atggagcaaa actactgtag agcccacacc tgggaaagga cctaaaggtg
1561 tatatcaaat cagcaaacaa atcaaagctc atgatggcag tgtgttcaca ctttgtcaga
1621 tgaaaatgg gatgttatta actggaggag ggaaagacaa aaaaataatt ctgtgggatc
1681 atgatctgaa tcctgaaaga gaaatagagc accaggagct gcaagccatg cagatggagc
1741 tgcagagccc tgagtacaag ctgagcaagc tccgcacctc gaccatcatg accgactaca
1801 accccaacta ctgctttgct ggcaagacct cctccatcag tgacctgaag gaggtgccgc
1861 ggaaaaacat caccctcatt cggggtctgg gccatggagc ctttggggag gtgtatgaag
1921 gccaggtgtc cggaatgccc aacgacccaa gcccctcca gttggctgtg aagacgctgc
1981 ctgaagtgtg ctctgaacag gacgaactgg attcctcat ggaagccctg atcatcagca
2041 aattcaacca ccagaacatt gttcgctgca ttggggtgag cctgcaatcc ctgccccggt
2101 tcatcctgct ggagctcatg gcgggggag acctcaagtc cttcctccga gagacccgcc
2161 ctcgcccgag ccagccctcc tcctggccca tgctggacct tctgcacgtg gctcgggaca
```

TABLE 1 -continued

```
2221 ttgcctgtgg ctgtcagtat ttggaggaaa accacttcat ccaccgagac attgctgcca
2281 gaaactgcct cttgacctgt ccaggccctg gaagagtggc caagattgga gacttcggga
2341 tggcccgaga catctacagg gcgagctact atagaaaggg aggctgtgcc atgctgccag
2401 ttaagtggat gcccccagag gccttcatgg aaggaatatt cacttctaaa acagacacat
2461 ggtcctttgg agtgctgcta tgggaaatct tttctcttgg atatatgcca taccccagca
2521 aaagcaacca ggaagttctg gagtttgtca ccagtggagg ccggatggac ccacccaaga
2581 actgccctgg gcctgtatac cggataatga ctcagtgctg gcaacatcag cctgaagaca
2641 ggcccaactt tgccatcatt ttggagagga ttgaatactg cacccaggac ccggatgtaa
2701 tcaacaccgc tttgccgata gaatatggtc cacttgttga agaggaagag aaagtgcctg
2761 tgaggcccaa ggaccctgag ggggttcctc ctctcctggt ctctcaacag caaaacggg
2821 aggaggagcg cagcccagct gccccaccac ctctgcctac cacctcctct ggcaaggctg
2881 caaagaaacc cacagctgca gaggtctctg ttcgagtccc tagagggccg gccgtggaag
2941 gggacacgt gaatatgcca ttctctcagt ccaaccctcc ttcggagttg cacaagtcc
3001 acggatccag aaacaagccc accagcttgt ggaacccaac gtacggctcc tggtttacag
3061 agaaacccac caaaaagaat aatcctatag caaagaagga gccacacgac agggtaacc
3121 tggggctgga gggaagctgt actgtccac taacgttgc aactgggaga cttccggggg
3181 cctcactgct cctagagccc tcttcgctga ctgccaatat gaaggaggta cctctgttca
3241 ggctacgtca cttcccttgt gggaatgtca attacggcta ccagcaacag ggcttgccct
3301 tagaagccgc tactgcccct ggagctggtc attacgagga taccattctg aaaagcaaga
3361 atagcatgaa ccagcctggg ccctgagctc ggtcgcacac tcacttctct tccttgggat
3421 ccctaagacc gtgga
```

EML4-ALK Variant 7 Protein Sequence (BAH57336.1; GI:227452651)

```
   1 mdgfagsldd sisaastsdv qdrlsalesr vqqqedeitv lkaaladvlr rlaisedhva
  61 svkksysskg qpspravipm scitngsgan rkpshtsays iagketlssa aksgtekkke
 121 kpggqrekke eshsndqspq iraspspqps sqplqihrqt pesknatptk sikrpspaek
 181 shnswensdd srnklskips tpklipkvtk tadkhkdvii nqegeyikmf mrgrpitmfi
 241 psdvdnyddi rtelppeklk lewaygyrgk dcranvyllp tgeivyfias vvvlfnyeer
 301 tqrhylghtd cvkclaihpd kiriatgkia gvdkdgrplq phvrvwdsvt lstlqiiglg
 361 tfergvgcld fskadsgvhl cviddsnehm ltvwdwqrka kgaeikttne vvlavefhpt
 421 dantiitcgk shiffwtwsg nsltrkqgif gkyekpkfvq claflgngdv ltgdsggvml
 481 iwsktttvept pgkgpkgvyq iskqikandg svfticqmrn gmlltgggkd rkiilwdhdl
 541 npereiehqe lqamqmelqs peyklsklrt stimtdynpn ycfagktssi sdlkevprkn
 601 itlirglghg afgevyegqv sgmpndpspl qvavktlpev cseqdeldfl mealiiskfn
 661 hqnivrcigv slqslprfil lelmaggdlk sflretrprp sqpsslamld llhvardiac
 721 gcqyleenhf ihrdiaarnc lltcpgpgry akigdfgmar diyrasyyrk ggcamlpvkw
 781 mppeafmegi ftsktdtwsf gvllweifsl gympypskns qevleftvsg grmdppkncp
 841 gpvyrimtqc wqhqpedrpn faiilleriey ctqdpdvint alpieygplv eeeekvpvrp
 901 kdpegvppll vsqqakreee rspaappplp tssgkaakk ptaaevsvry prgpaveggh
 961 vnmafsqsnp pselhkvhgs rnkptslwnp tygswftekp tkknnpiakk ephdrgnlgl
1021 egsctvppnv atgrlpgasl llepssltan mkevplfrlr hfpcgnvnyg yqqqglplea
1081 atapgaghye dtilksknsm nqpgp
```

KIF5B-ALK Nucleic Acid Sequence (AB462413.1; GI:227452652)

```
   1 tgcgagaaag atggcggacc tggccgagtg caacatcaaa gtgatgtgtc gcttcagacc
  61 tctcaacgag tctgaagtga accgcggcga caagtacatc gccaagtttc agggagaaga
 121 cacggtcgtg atcgcgtcca agcctatgc atttgatcgg gtgttccagt caagcacatc
 181 tcaagacgaa gtgtataatg actgtgcaaa gaagattgtt aaagatgtac ttgaaggata
 241 taatggaaca atatttgcat atggacaaac atcctctggg aagacacaca caatggaggg
 301 taaacttcat gatccagaag gcatgggaat tattccaaga atagtgcaag atattttaa
 361 ttatatttac tccatggatg aaaatttgga atttcatatt aaggtttcat attttgaaat
 421 atatttggat aagataaggg acctgttaga tgtttcaaag accaaccttt cagttcatga
 481 agacaaaaac cgagttccct atgtaaaggg gtgcacagag cgttttgtat gtagtccaga
 541 tgaagttatg gataccatag atgaaggaaa atccaacaga catgtagcag ttacaaatat
 601 gaatgaacat agctctagga gtcacagtat atttcttatt aatgtcaaac aagagaacac
 661 acaaacggaa caaaagctga gtgaaaaact ttatctggtt gatttagctg gtagtgaaaa
 721 ggttagtaaa actggagctg aaggtgctgt gctggatgaa gctaaaaaca tcaacaagtc
 781 actttctgct cttggaaatg ttatttctgc tttggctgag ggtagtacat atgttccata
 841 tcgagatagt aaaatgacaa gaatccttca agattcatta ggtggcaact gtagaaccac
 901 tattgtaatt tgctgctctc catcatcata caatgagtct gaaacaaaat ctacactctc
 961 atttggccaa agggccaaaa caattaagaa cacagtttgt gtcaatgtgg agttaactgc
1021 agaacagtgg aaaagaagt atgaaaaaga aaaagaaaaa aataagatcc tgcggaacac
1081 tattcagtgg cttgaaaatg agctcaacag atggcgtaat ggggagacgg tgcctattga
1141 tgaacagttt gacaaagaga agccaacttg gaagctttc acagtggata agatattac
1201 tcttaccaat gataaaccag caaccgcaat tggagttata gaaatttta ctgatgctga
1261 aagaagaaag tgtgaagaag aaattgctaa attatacaaa cagcttgatg acaaggatga
1321 agaaattaac cagcaaagtc aactggtaga gaaactgaag acgcaaatgt ggatcagga
1381 ggagcttttg gcatctacca gaagggatca agacaatatg caagctgagc tgaatcgcct
1441 tcaagcagaa aatgatgcct ctaaagaaga agtgaaagaa gttttacagg ccctagaaga
1501 acttgctgtc aattatgatc agaagtctca ggaagttgaa gacaaaacta aggaatga
1561 attgcttagt gatgaattga atcagaaatc ggcaacttta gcgagtatag atgctgagct
1621 tcagaaactt aaggaaatga ccaaccacca gaaaaacga gcagctgaga tgatggcatc
1681 tttactaaaa gaccttcag aaataggaat tgctgtggga aataatgatg taaagcagcc
1741 tgagggaact ggcatgatag atgaagagtt cactgttgca agactctaca ttagcaaaat
1801 gaagtcagaa gtaaaaacca tggtgaaacg ttgcaagcag ttagaagca cacaaactga
1861 gagcaacaaa aaatggaag aaatgaaaa ggagttagca gcatgtcagc ttcgtatctc
1921 tcaacatgaa gccaaaatca agtcattgac tgaataccctt caaaatgtgg aacaaaagaa
1981 aagacagttg gaggaatctg tcgatgccct cagtgaagaa ctagtccagc ttcgagcaca
```

TABLE 1 -continued

```
2041 agagaaagtc catgaaatgg aaaaggagca cttaaataag gttcagactg caaatgaagt
2101 taagcaagct gttgaacagc agatccagag ccatagagaa actcatcaaa aacagatcag
2161 tagtttgaga gatgaagtag aagcaaaagc aaaacttatt actgatcttc aagaccaaaa
2221 ccagaaaatg atgttagagc aggaacgtct aagagtagaa catgagaagt tgaaagccac
2281 agatcaggaa aagagcagaa aactacatga acttacggtt atgcaagata gacgagaaca
2341 agcaagacaa gacttgaagg gtttggaaga gacagtggca aaagaacttc agactttaca
2401 caacctgcgc aaactctttg ttcaggacct ggctacaaga gttaaaagag tgctgagat
2461 tgattctgat gacaccggag gcagcgctgc tcagaagcaa aaaatctcct ttcttgaaaa
2521 taatccttgaa cagctcacta aagtgcacaa acagttggta cgtgataatg cgatctccg
2581 ctgtgaactt cctaagttgg aaaagcgact tcgagctaca gctgagagag tgaaagcttt
2641 ggaatcagca ctgaaagaag ctaaagaaaa tgcatctcgt gatcgcaaac gctatcagca
2701 agaagtagat cgcataaagg aagcagtcag gtcaaagaat atggccagaa gagggcattc
2761 tgcacagatt gtgtaccgcc ggaagcacca ggagctgcaa gccatgcaga cgctgctga
2821 gagccctgag tacaagctga gcaagctccg cacctcgacc atcatgaccg actacaaccc
2881 caactactgc tttgctggca agacctcctc catcagtgac ctgaaggagg tgccgcggaa
2941 aaacatcacc ctcattcggg gtctgggcca tggcgccttt ggggaggtgt atgaaggcca
3001 ggtgtccgga atgcccaacg acccaagccc cctgcaagtg gctgtgaaga cgctgcctga
3061 agtgtgctct gaacaggacg aactggattt cctcatggaa gccctgatca tcagcaaatt
3121 caaccaccag aacattgttc gctgcattgg ggtgagcctg caatccctgc cccggttcat
3181 cctgctggag ctcatggcgg ggggagacct caagtccttc ctccgagaga cccgcctcg
3241 cccgagccag ccctcctccc tggccatgct ggaccttctg cacgtggctc gggacattgc
3301 ctgtggctgt cagtatttgg aggaaaacca cttcatccac cgagacattg ctgccagaaa
3361 ctgcctcttg acctgtccag gccctggaag agtggcaaga attggagact cgggatggc
3421 ccgagacatc tacagggcga gctactatag aaagggaggc tgtgccatgc tgccagttaa
3481 gtggatgccc ccagaggcct tcatggaagg aatattcact tctaaaacag acacatggtc
3541 ctttggagtg ctgctatggg aaatctttc tcttggatat atgccatacc ccagcaaaag
3601 caaccaggaa gttctggagt tgtcaccag tggaggccgg atggaccac ccaagaactg
3661 ccctgggcct gtataccgga taatgactca gtgctggcaa catcagcctg aagacaggcc
3721 caactttgcc atcattttgg agaggattga atactgcact caggacccgg atgtaatcaa
3781 caccgctttg ccgatagaat atggtccact tgtggaagag gaagagaaag tgcctgtgag
3841 gcccaaggac cctgaggggg ttcctcctct cctggtctct caacaggcaa aacgggagga
3901 ggagcgcagc ccagctgccc caccacctct gcctaccacc tcctctggca aggctgcaaa
3961 gaaacccaca gctgcagagg tctctgttcg agtccctaga gggccggccg tggaaggggg
4021 acacgtgaat atggcattct ctcagtccaa ccctccttcg gagttgcaca aggtcacagg
4081 atccagaaac aagcccacca gcttgtgaa cccaacgtac ggctcctggt ttacagagaa
4141 acccaccaaa aagaataatc ctatagcaaa gaaggagcca cacgcaggg gtaacctggg
4201 gctggaggga agctgtactg tcccacctaa cgttgcaact gggagacttc cgggggcctc
4261 actgctccta gagcccctctt cgctgactgc caatatgaag gaggtacctc tgttcaggct
4321 acgtcacttc ccttgtggga atgtcaatta cggctaccaa caacagggct tgcccttaga
4381 agccgctact gcccctggag ctggtcatta cgaggatacc attctgaaaa gcaagaatag
4441 catgaaccag cctgggccct gagctcggtc gcacactca
```

KIF5B-ALK Protein Sequence (BAH57337.1; GI:227452653)

```
   1 madlaecnik vmcrfrpine sevnrgdkyi akfqgedtvv iaskpyafdr vfqsstsqeq
  61 vyndcakkiv kdvlegyngt ifaygqtssg kthtmegklh dpegmgiipr ivqdifnyiy
 121 smdenlefhi kvsyfeiyld kirdlldvsk tnlsvhedkn rvpyvkgcte rfvcspdevm
 181 dtidegksnr hvavtnmneh ssrshsifli nvkqentqte qklsgklylv dlagseksvk
 241 tgaegavlde akninkslsa lgnvisalae gstyvpyrds kmtrilqdsl ggncrttivi
 301 ccspssynes etkstllfgq raktikntvc vnveltaeqw kkkyekekek nkilrntiqw
 361 lenelnrwrn getvpideqf dkekanleaf tvdkditltn dkpataigvi gnftdaerrk
 421 ceeeiaklyk qlddkdeein qqsqlveklk tqmldgeell astrrdqnlm qaelnrlqae
 481 ndaskeevke vlqaleelav nydqksqeve dktkeyells delnqksatl asidaelqkl
 541 kemtnhqkkr aaemmaslk dlaeigiavg nndvkqpegt gmideeftva rlyiskmkse
 601 vktmvkrckq lestqtesnk kmeenekela acqlrisqhe akiksLteyl qnveqkkrql
 661 eesvdalsee lvqlragekv hemekehlnk vqtanevkqa veqqiqshre thqkqisslr
 721 deveakakli tdlqdqnqkm mleqerlrve heklkatdqe ksrklheltv mqdrreqarq
 781 dlkgleetva kelqtlhnlr klfvqdlatr vkksaeidsd dtggsaaqkq kisflennle
 841 qltkvhkqlv rdnadlrcel pklekrlrat aervkalesa lkeakenasr drkryqqevd
 901 rikeavrskn marrghsaqi vyrrkhqelq amqmelqspe yklsklrtst imtdynpnyc
 961 fagktssisd lkevprknit lirglghgaf gevyegqvsg mpndpsplqv avktlpevcs
1021 eqdeldflme aliiskfnhq nivrcigvsl qslprfille lmaggdlksf lretrprpsq
1081 psslamldll hvardiacgc qyleenhfih rdiaarncll tcpgpgrvak igdfgmardi
1141 yrasyyrkgg camlpvkwmp peafmegift sktdtwsfgv llweifslgy mpypsksnqe
1201 vlefvtsggr mdppkncpgp vyrimtqcwq hqpedrpnfa iilerieyct qdpdvintal
1261 pieygplvee eekvprpkd pegvppllvs qqakreeers paappplptt ssgkaakkpt
1321 aaevsvrvpr gpavegghvn mafsqsnpps elhkvhgsrn kptslwnpty gswftekptk
1381 knnpiakkep hdrgnlgleg sctvppnvat grlpgaslll epssltanmk evplfrlrhf
1441 pcgnvnygyq qqglpleaat apgaghyedt ilksknsmnq pgp
```

NPM-ALK Sequence (t(2;5)(p23;q35 chromosomal translocation)*
TPM3-ALK Sequence (t(1;2)(p25;p23) chromosomal translocation)*

TFGXL-ALK Nucleic Acid Sequence (AF390893.1; GI:20269389)

```
   1 atgaacggac agttggatct aagtggggaag ctaatcatca aagctcaact tggggaggat
  61 attcggcgaa ttcctattca taatgaagat attacttatg atgaattagt gctaatgatg
 121 caacgagttt tcagaggaaa acttctgagt aatgatgaag taacaataaa gtataaagat
 181 gaagatggag atcttataac aatttttgat agttctgacc tttcctttgc aattcagtgc
 241 agtaggatac tgaaactgac attatttgtt aatgccagc caagaccct gaatcaagt
 301 caggtgaaat atctccgtcg agaactgata gaacttcgaa ataaagtgaa tcgtttattg
```

TABLE 1 -continued

```
 361 gatagcttgg aaccacctgg agaaccagga ccttccacca atattcctga aaatgatact
 421 gtggatggta gggaagaaaa gtctgcttct gattcttctg gaaaacagtc tactcaggtt
 481 atggcagcaa gtatgtctgc ttttgatcct ttaaaaaacc aagatgaaat caataaaaat
 541 gttatgtcag cgtttggctt aacagatgat caggttcag ggccacccag tgctcctgca
 601 gaagatcgtt caggaacacc cgacagcatt gcttcctcct cctcagcagc tcacccacca
 661 ggcgttcagc cacagcagcc accatataca ggagctcaga ctcaagcagg tcagattgaa
 721 gtgtaccgcc ggaagcacca ggagctgcaa gccatgcaga tggagctgca gagccctgag
 781 tacaagctga gcaagctccg cacctcgacc atcatgaccg actacaaccc caactactgc
 841 tttgctggca agaccctcct catcagtgac ctgaaggagg tgccgcggaa aaacatcacc
 901 ctcattcggg gtctgggcca tggcgccttt ggggaggtgt atgaaggcca ggtgtccgga
 961 atgcccaacg acccaagccc cctgcaagtg gctgtgaaga cgctgcctga agtgtgctct
1021 gaacaggacg aactggattt cctcatgaa gccctgatca tcagcaaatt caaccaccag
1081 aacattgttc gctgcattgg ggtgagcctg caatccctgc cccggttcat cctgctggga
1141 ctcatggcgg ggggagacct caagtccttc ctccgagaga cccgcctcg cccgagccag
1201 ccctcctccc tggccatgct ggaccttctg cacgtggctc gggacattgc ctgtggctgt
1261 cagtatttgg aggaaaacca cttcatccac cgagacattg ctgccagaaa ctgcctcttg
1321 acctgtccag gccctggaag agtggccaag atggagaat tcggatggc ccgagacatc
1381 tacagggcga gctactatag aaaggggagc tgtgccatgc tgccagttaa gtggatgccc
1441 ccagaggcct tcatggaagg aatattcact tctaaaacag acacatggtc ctttggagtg
1501 ctgctatggg aaatctttc tcttggatat atgccatacc ccagcaaaag caaccaggaa
1561 gttctggagt ttgtcaccag tggaggccgg atggacccac ccaagaactg ccctgggcct
1621 gtataccgga taatgactca gtgctggcaa catcagcctg aagacaggcc caactttgcc
1681 atcattttgg agaggattga atactgcacc caggacccgg atgtaatcaa caccgcttttg
1741 ccgatagaat atggtccact tgtggaagag aagagaaag tgcctgtgag gcccaaggac
1801 cctgaggggg ttcctcctct cctggtctct caacaggcaa aacgggagga ggagcgcagc
1861 ccagctgccc caccacctct gcctaccacc tcctctggca aggctgcaaa gaaacccaca
1921 gctgcagagg tctctgttcg agtccctaga gggccggccg tggaaggggg acacgtgaat
1981 atggcattct ctcagtccaa ccctcctcg gagttgcaca aggtccacgg atccagaaac
2041 aagcccacca gcttgtggaa cccaacgtac ggctcctggt ttacagagaa acccaccaaa
2101 aagaataatc ctatagcaaa gaaggagcca cacgacaggg gtaacctggg gctggaggga
2161 agctgtactg tcccacctaa cgttgcaact gggagactt cggggccctc actgctccta
2221 gagccctctt cgctgactgc caatatgaag gaggtacctc tgttcaggct acgtcacttc
2281 ccttgtggga atgtcaatta cggctaccag caacagggct gcccttaga agccgctact
2341 gcccctggag ctggtcatta cgaggatacc attctgaaaa gcaagaatag catgaaccag
2401 cctgggccct ga
```

TFGXL-ALK Protein Sequence (AAM17922.1; GI:20269390)*

```
  1 mngqldlsgk liikaqlged irripihned itydevlmm qrvfrgklls ndevtikykd
 61 edgdlitifd ssdlsfaiqc srilkltlfv ngqprpless qvkylrreli elrnkvnrll
121 dsleppgepg pstnipendt vdgreeksas dssgkqstqv maasmsafdp lknqdeinkn
181 vmsafgltdd qvsgppsapa edrsgtpdsi assssaahpp gvqpqqppyt gaqtqagqie
241 vyrrkhqelq amqmelqspe yklsklrtst imtdynpnyc fagktssisd lkevprknit
301 lirglghgaf gevyegqvsg mpndpsplqv avktlpevcs eqdeldflme aliiskfnhq
361 nivrcigvsl qslprfille lmaggdlksf lretrprpsq psslamldll hvardiacgc
421 qyleenhfih rdiaarncll tcpgpgrvak igdfgmardi yrasyyrkgg camlpvkwmp
481 peafmegift sktdtwsfgv llweifslgy mpypsksnqe vlefvtsggr mdppkncpgp
541 vyrimtqcwq hqpedrpnfa iilerieyct qdpdvintal pieygplvee eekvpvrpkd
601 pegvppllvs qqakreeers paappplptt ssgkaakkpt aaevsvrvpr gpaveggghvn
661 mafsqsnpps elhkvhgsrn kptslwnpty gswftekptk knnpiakkep hdrgnlgleg
721 sctvppnvat grlpgaslll epssltanmk evplfrlrhf pcgnvnygyq qqglpleeat
781 apgaghyedt ilksknsmnq pgp
```

TFGL-ALK Nucleic Acid Sequence (AF143407.1; GI:6739534)

```
  1 cctccgcaag ccgtctttct ctagagttgt atatatagaa catcctggag tccaccatga
 61 acggacagtt ggatctaagt gggaagctaa tcatcaaagc tcaacttggg gaggatattc
121 ggcgaattcc tattcataat gaagatatta cttatgatga attagtgcta atgatgcaac
181 gagttttcag aggaaaactc tgagtaatg atgaagtaac aataaagtat aaagatgaag
241 atggagatct tataacaatt tttgatagtt ctgacctttc ctttgcaatt cagtgcagta
301 ggatactgaa actgacatta tttgttaatg ccagccaag accccttgaa tcaagtcagg
361 tgaaatatct ccgtcgagaa ctgatagaac ttcgaaataa agtgaatcgt ttattggata
421 gcttggaacc acctggagaa ccaggacctt ccaccaatat tcctgaaaat gatactgtgg
481 atggtaggga agaaaagtct gcttctgatt cttctgaaaa acagtctact caggttatgg
541 cagcaagtat gtctgctttt gatccttta aaaaaccaaga tgaaatcaat aaaaatgtta
601 tgtcagcgtt tggcttaaca gatgatcagg tttcagtgta ccgccggaag caccaggagc
661 tgcaagccat gcagatggag ctgcagagcc ctgagtacaa gctgagcaag ctccggcacct
721 cgaccatcat gaccgactac aaccccaact actgctttgc tggcaagacc tcctccatca
781 gtgacctgaa ggaggtgccg cggaaaaaca tcaccctcat tcgggggtctg gccatggcg
841 cctttgggga ggtgtatgaa ggccaggtgt ccggaatgcc caacgaccca gccccctgc
901 aagtggctgt gaagacgctg cctgaagtgt gctctgaaca ggacgaactg gatttcctca
961 tggaagccct gatcatcagc aaattcaacc accagaacat tgttcgctgc attggggtga
1021 gcctgcaatc cctgccccgg ttcatcctgc tgagctcat ggcgggggga gacctcaagt
1081 ccttcctccg agacccgc cctcgccga gccagccctc ctcctggcc atgctggacc
1141 ttctgcacgt ggctcgggac attgctgtgt gctgtcagta tttggaggaa aaccacttca
1201 tccaccgaga cattgctgcc agaaactgcc tcttgacctg tccaggccct ggaagagtgg
1261 ccaagattgg agacttcggg atggcccgag acatctacag ggcgagctac tatagaaagg
1321 gaggctgtgc catgctgcca gttaagtgga tgccccaga ggccttcatg aaggaatat
1381 tcacttctaa aacagacaca tggtcctttg gagtgctgct atgggaaatc ttttctcttg
1441 gatatatgcc atacccagc aaaagcaacc aggaagttct ggagtttgtc accagtggag
```

TABLE 1 -continued

```
1501 gccggatgga cccacccaag aactgccctg ggcctgtata ccggataatg actcagtgct
1561 ggcaacatca gcctgaagac aggcccaact ttgccatcat tttggagagg attgaatact
1621 gcacccagga cccggatgta atcaacaccg ctttgccgat agaatatggt ccacttgtgg
1681 aagaggaaga gaaagtgcct gtgaggccca aggaccctga gggggttcct cctctcctgg
1741 tctctcaaca ggcaaaacgg gaggaggagc gcagcccagc tgccccacca cctctgccta
1801 ccacctcctc tggcaaggct gcaaagaaac ccacagctgc agaggtctct gttcgagtcc
1861 ctagagggcc ggccgtggaa ggggacacg tgaatatggc attctctcag tccaaccctc
1921 cttcggagtt gcacaaggtc cacggatcca gaaacaagcc caccagcttg tggaacccaa
1981 cgtacggctc ctggtttaca gagaaaccca caaaaagaa taatcctata gcaaagaagg
2041 agccacacga caggggtaac ctggggctgg agggaagctg tactgtccca cctaacgttg
2101 caactgggag acttccgggg gcctcactgc tcctagagcc ctcttcgctg actgccaata
2161 tgaaggaggt acctctgttc aggctacgtc acttcccttg tgggaatgtc aattacggct
2221 accagcaaca gggcttgccc ttagaagccg ctactgcccc tggagctggt cattacgagg
2281 ataccattct gaaaagcaag aatagcatga accagcctgg gccctgagct cggtcgcaca
2341 ctcacttctc ttccttggga tccctaagac cgtggaggag agagaggcaa tggctccttc
2401 acaaaccaga gaccaaatgt cacgttttgt tttgtgccaa cctattttga agtaccacca
2461 aaaaagctgt attttgaaaa tgctttagaa aggttttgag catgggttca tcctattctt
2521 tcgaaagaag aaaatatcat aaaaatgagt gataaataca aggcccagat gtggttgcat
2581 aaggttttta tgcatgtttg ttgtatactt ccctatgctt cttttaaatt gtgtgtgctc
2641 tgcttcaatg tagtcagaat tagctgcttc tatgtttcat agttgggtc atagatgttt
2701 ccttgccttg ttgatgtgga catgagccat ttgagggag agggaacgga aataaaggag
2761 ttatttgtaa tgactaaaa
```

TFGL-ALK Protein Sequence (AAF27292.1; GI:6739535)*

```
   1 mngqldlsgk liikaqlged irripihned itydelvlmm qrvfrgklls ndevtikykd
  61 edgdlitifd ssdlsfaiqc srilkltlfv ngqprpless qvkylrreli elrnkvnrll
 121 dsleppgepg pstnipendt vdgreeksas dssgkqstqv maasmsafdp lknqdeinkn
 181 vmsafgltdd qvsvyrrkhq elqamqmelq speyklsklr tstimtdynp nycfagktss
 241 isdlkevprk nitlirglgh gafgevyegq vsgmpndpsp lqvavktlpe vcseqdeldf
 301 lmealiiskf nhqnivrcig vslqslprfi llelmaggdl ksflretrpr psqpsslaml
 361 dllhvardia cgcqyleenh fihrdiaarn clltcpgpgr vakigdfgma rdiyrasyyr
 421 kggcamlpvk wmppeafmeg iftsktdtws fgvllweifs lgymypypsks nqevlefvts
 481 ggrmdppknc pgpvyrimtq cwqhqpedrp nfaiilerie yctqdpdvin talpieygpl
 541 veeeekvpvr pkdpegvppl lvsqqakree erspaapppl pttssgkaak kptaaevsvr
 601 vprgpavegg hvnmafsqsn ppselhkvhg srnkptslwn ptygswftek ptkknnpiak
 661 kephdrgnlg legsctvppn vatgrlpgas lllepsslta nmkevplfrl rhfpcgnvny
 721 gyqqqglple aatapgaghy edtilksksns mnqpgp
```

TFGS-ALK Nucleic Acid Sequence (AF125093.1; GI:7229260)

```
   1 cctccgcaag ccgtctttct ctagagttgt atatatagaa catcctggag tccaccatga
  61 acggacagtt ggatctaagt gggaagctaa tcatcaaagc tcaacttggg gaggatattc
 121 ggcgaattcc tattcataat gaagatatta cttatgatga attagtgcta atgatgcaac
 181 gagtttttcag aggaaaactt ctgagtaatg atgaagtaac aataaagtat aaagatgaag
 241 atggagatct tataacaatt tttgatagtt cgaccttttc ctttgcaatt cagtgcagta
 301 ggatactgaa actgacatta tttgttaatg gccagccaag accccttgaa tcaagtcagg
 361 tgaaatatct ccgtcgagaa ctgatagaac ttgaaataa agtgaatcgt ttattggata
 421 gcttggaacc acctggagaa ccaggacctt ccaccaatat tcctgaaaat gtgtaccgcc
 481 ggaagcacca ggagctgcaa gccatgcaga tggagctgca gagccctgca tacaagctgg
 541 gcaagctccg cacctcgacc atcatgaccg actacaaccc caactactgc tttgctggca
 601 agacctcctc catcagtgac ctgaaggagg tgccgcggaa aaacatcacc ctcattcggg
 661 gtctgggcca tggcgccttt ggggaggtgt atgaaggcca ggtgtccgga atgcccaacg
 721 acccaagccc cctgcaagtg gctgtgaaga cgctgcctga agtgtgctct gaacaggacg
 781 aactggattt cctcatggaa gccctgatca tcagcaaatt caaccaccag aacattgttc
 841 gctgcattgg ggtgagcctg caatcccgc cccggttcat cctgctggag ctcatggcgg
 901 ggggagacct caagtccttc ctccgagaga cccgccctcg cccgagccag ccctcctccc
 961 tggccatgct ggaccttctg cacgtggctc gggacattgc ctgtggctgt cagtatttgg
1021 aggaaaacca cttcatccac cgagacattg ctgccagaa ctgcctcttg acctgtccag
1081 gcccctgaag agtggccaag attggagact tcgggatggc ccgagacatc tacagggcga
1141 gctactatag aaagggaggc tgtgccatgc tgccagttaa gtggatgccc cagaggcct
1201 tcatggaagg aatattcact tctaaaacag acacatggtc ctttggagtg ctgctatggg
1261 aaatcttttc tcttggatat atgccatacc ccagcaaaag caaccaggaa gttctggagt
1321 ttgtcaccag tggaggccgg atgacccac caagaactg ccctgggcct gtataccggg
1381 taatgactca gtgctggcaa catcagcctg aagacaggcc caactttgcc atcattttgg
1441 agaggattga atactgcacc caggacccgg atgtaatcaa caccgctttg ccgatagaat
1501 atggtccact tgtggaagag gaagagaaag tgcctgtgag gcccaaggac cctgagggg
1561 ttcctcctct cctggtctct caacaggcaa aacgggagga ggagcgcagc cagctgccc
1621 caccacctct gcctaccacc tcctctggca aggctgcaaa gaaacccaca gctgcagagg
1681 tctctgttcg agtccctaga gggccggccg tggaagggg acacgtgaat atggcattct
1741 ctcagtccaa cccctccttcg gagttgcaca aggtccacgg atccagaaac aagccaccca
1801 gcttgtggaa cccaacgtac ggctcctggt ttacagagaa acccaccaaa aagaataatc
1861 ctatagcaaa gaaggagcca cacgacaggg gtaacctggg gctgggga agctgtactg
1921 tcccacctaa cgttgcaact gggagacttc cggggcctc actgctccta gagccctctt
1981 cgctgactgc caatatgaag gaggtacctc tgttcaggct acgtcactc ccttgtggga
2041 atgtcaatta cggctaccag caacagggct tgcccttaga agccgctact gcccctggag
2101 ctggtcatta cgaggatacc attctgaaaa gcaagaatag catgaaccag cctgggccct
2161 gagctcggtc gcacactcac ttctcttcct gggatccct aagaccgtgg aggagagaga
2221 ggcaatggct ccttcacaaa ccagagacca aatgtcacgt tttgttttgt gccaacctat
2281 tttgaagtac caccaaaaaa gctgtatttt gaaaatgctt tagaaaggtt ttgagcatgg
```

TABLE 1 -continued

```
2341 gttcatccta ttctttcgaa agaagaaaat atcataaaaa tgagtgataa atacaaggcc
2401 cagatgtggt tgcataaggt ttttatgcat gtttgttgta tacttcctta tgcttctttt
2461 aaattgtgtg tgctctgctt caatgtagtc agaattagct gcttctatgt ttcatagttg
2521 gggtcataga tgtttccttg ccttgttgat gtggacatga gccatttgag gggagaggga
2581 acggaaataa aggagttatt tgtaatgact aaaa
```

TFGS-ALK Protein Sequence (AAF42734.1; GI:7229261)*

```
   1 mngqldlsgk liikaqlged irripihned itydelvlmm qrvfrgklls ndevtikykd
  61 edgdlitifd ssdlsfaiqc srilkltlfv ngqprpless qvkylrreli elrnkvnrll
 121 dsleppgepg pstnipenvy rrkhqelqam qmelqspeyk lsklrtstim tdynpnycfa
 181 gktssisdlk evprknitli rglghgafge vyegqvsgmp ndpsplqvav ktlpevcseq
 241 deldflmeal iiskfnhqni vrcigvslqs lprfillelm aggdlksflr etrprpsqps
 301 slamldllhv ardiacgcqy leenhfihrd iaarnclltc pgpgrvakig dfgmardiyr
 361 asyyrkggca mlpvkwmppe afmegiftsk tdtwsfgvll weifslgymp ypsksnqevl
 421 efvtsggrmd ppkncpgpvy rimtcwqhqp pedrpnfaii lerieyctqd pdvintalpi
 481 eygplveeee kvpvrpkdpe gvppllvsqq akreeerspa appplpttss gkaakkptaa
 541 evsvrvprgp avegghvnma fsqsnppsel hkvhgsrnkp tslwnptygs wftekpktkkn
 601 npiakkephd rgnlglegsc tvppnvatgr lpgaslllep ssltanmkev plfrlrhfpc
 661 gnvnygyqqq glpleaatap gaghyedtil ksknsmnqpg p
```

ATIC-ALK Sequence (inv(2)(p23;q35) chromosomal translocation)*
CLTC-ALK Sequence (t(2;17)(p23;q23) chromosomal translocation)*

MSN-ALK Nucleic Acid Sequence (AF295356.1; GI:14625823)

```
   1 aactccgctg cctttgccgc caccatgccc aaaacgatca gtgtgcgtgt gaccaccatg
  61 gatgcagagc tggagtttgc catccagccc aacaccaccg ggaagcagct atttgaccag
 121 gtggtgaaaa ctattggctt gagggaagtt tggttctttg gtctgcagta ccaggacact
 181 aaaggttttct ccacctggct gaaactcaat aagaaggtga ctgcccagga tgtgcggaag
 241 gaaagcccc tgctctttaa gttccgtgcc aagttctacc ctgaggatgt gtccgaggaa
 301 ttgattcagg acatcactca gcgcctgttc tttctgcaag tgaaagaggg cattctcaat
 361 gatgatattt actgccgcc tgagaccgct gtgctgctgg cctcgtatgc tgtccagtct
 421 aagtatggcg acttcaataa ggaagtgcat aagtctggct acctggccgg agacaagttg
 481 ctcccgcaga gagtcctgga acagcacaaa ctcaacaagg accagtggga ggagcggatc
 541 caggtgtggc atgaggaaca ccgtggcatg ctcagggagg atgctgtcct ggaatatctg
 601 aagattgctc aagatctgga gatgtatggt gtgaactact tcagcatcaa gaacaagaaa
 661 ggctcagagc tgtggctggg ggtggatgcc ctgggtctca acatctatga gcagaatgac
 721 agactaactc ccaagatagg cttcccctgg agtgaaatca ggaacatctc tttcaatgat
 781 aagaaatttg tcatcaagcc cattgacaaa aaagccccgg acttcgtctt ctatgctccc
 841 cggctgcgga ttaacaagcg gatcttgcc ttgtgcatgg gaaccatga actatacatg
 901 cgccgtcgca agcctgatac cattgaggtg cagcagatga aggcacaggc ccgggaggag
 961 aagcaccaga agcagtgatgga gcgtgctatg ctggaaaatg aagaagaaga gcgtgaaatg
1021 gcagagaagg agaaagagaa gattgaacgg gagaaggagg agctgatgga gaggctgaag
1081 cagatcgagg aacagactaa gaaggctcag caagaactgg aagaacagac ccgtagggct
1141 ctggaacttg agcaggaacg gaagcgtgcc cagagcgagg ctgaaaagct ggccaaggag
1201 cgtcaagaag ctgaagaggc caaggaggcc ttgctgcagg cctcccggga ccagaaaaag
1261 actcaggaac agctggcctt ggaaatggca gagctgacag ctcgaatctc ccagctggag
1321 atggcccgac agaagaagga gagtgaggct gtggagtggc agcagaagca ggagctgcaa
1381 gccatgcaga tggagctgca gagccctgag tacaagctga gcaagctccg cacctcgacc
1441 atcatgaccg actacaaccc caactactgc tttgctggca agacctcctc catcagtgac
1501 ctgaaggagg tgccgcggaa aaacatcacc ctcattcggg gtctgggcca tggcgccttt
1561 gggggaggtgt atgaaggcca ggtgtccgga atgcccaacg acccaag
```

MSN-ALK Protein Sequence (AAK71522.1; GI:14625824)*

```
   1 mpktisvrvt tmdaelefai qpnttgkqlf dqvvktiglr evwffglqyq dtkgfstwlk
  61 lnkkvtaqdv rkespllfkf rakfypedvs eeliqditqr lfflqvkegi lnddiycppe
 121 tavllasyav qskygdfnke vhksgylagd kllpqrvleq hklnkdqwee riqvwheehr
 181 gmlredavle ylkiaqdlem ygvnyfsikn kkgselwlgv dalglniyeq ndrltpkigf
 241 pwseirnisf ndkkfvikpi dkkapdfvfy aprlrinkri lalcmgnhel ymrrrkpdti
 301 evqqmkagar eekhqkqmer amlenekkkr emaekekeki erekeelmer lkqieeqtkk
 361 aqqeleeqtr ralelegerk raqseaekla kerqeaeeak eallqasrdq kktqeqlale
 421 maeltarisq lemarqkkes eavewqqkqe lqamqmelqs peyklsklrt stimtdynpn
 481 ycfagktssi sdlkevprkn itlirglghg afgevyegqv sgmpndp
```

TPM4-ALK Minor Variant Nucleic Acid Sequence (AF362887.1; GI:14010353)
```
   1 cgagaagttg agggagaaag gcgggcccgg gaacaggctg aggctgaggt ggcctccttg
  61 aaccgtagga tccagctggt tgaagaagag ctggaccgtg ctcaggagcg tgcggaggtg
 121 tctgaactaa aatgtggtga cctggaagaa gaactcaaga atgttactaa caatctgaaa
 181 tctctggagg ctgcatctga aaagtattct gaaaaggagg acaaatatga agaagaaatt
 241 aaacttctgt ctgacaaact gaaaggagct gagacccgtg ctgaatttgc agagagaacg
 301 gttgcaaaac tggaaaagac aattgatgac ctggaagtgt acctccgggca gcaccaagag
 361 ctgcaagcca tgcagatgga gctgcagagc cctgagtaca agctgagcaa gctccgcacc
 421 ctcgac
```

TPM4-ALK Minor Variant Protein Sequence (AAK51964.1; GI:14010354)

```
   1 revegerrar eqaeaevasl nrriqlveee ldrageraev selkcgdlee elknvtnnlk
  61 sleaasekys ekedkyeeei kllsdklkea etraefaert vakletkidd levylrkhqe
 121 lqamqmelqs peyklsklrt ld
```

TABLE 1 -continued

```
TPM4-ALK Major Variant Nucleic Acid Sequence (AF362886.1; GI:14010351)

1 ctggcagagt cccgttgccg agagatggat gagcagatta gactgatgga ccagaacctg
  61 aagtgtctga gtgctgctga agaaaagtac tctcaaaaag aagataaata tgaggaagaa
 121 atcaagattc ttactgataa actcaaggag gcagagaccc gtgctgaatt tgcagagaga
 181 acggttgcaa aactggaaaa gacaattgat gacctggaag tgtaccgccg gaagcaccag
 241 gagctgcaag ccatgcagat ggagctgcag agccctgagt acaagctgag caagctccgc
 301 acctcgac TPM4-ALK Major Variant Protein Sequence (AAK51963.1; GI:14010352)

1 laesrcremd eqirlmdqnl kclsaaeeky sqkedkyeee ikiltdklke aetraefaer
  61 tvaklektid dlevyrrkhq elqamqmelq speyklsklr tst
MYH9-ALK Sequence (t(2;22)(p23;q11.2) chromosomal translocation)*
RANBP2-ALK Sequence (t(2;2)(p23;q13) or inv(2)(p23;q11-13)
chromosomal translocations)*
ALO17-ALK Sequence (t(2;17)(p23;q25) chromosomal translocation)*
CARS-ALK Sequence (t(2;11;2)(p23;p15;q31) chromosomal translocation)*
*With the exception of MSN-ALK and MYH-9, all of the
fusion proteins contain the final 563 amino acids of ALK.
MSN-ALK and MYH9 contain the final 567 and 566 amino
acids, respectively.
```

"ALK mutations" generally refer to alterations in a nucleic acid and/or amino acid sequence relative to a reference anaplastic lymphoma kinase sequence. In some embodiments, however, "ALK mutations" can refer to specific anaplastic lymphomas kinase mutations predictive of response to treatment with ALK inhibiting agents (e.g., PF-02341066 and/or PDD). For example, mutations of the cysteine amino acid at position 1156 (C1156) and/or the leucine amino acid at position 1196 (L1196) of wild type ALK protein (NP_004295) to a different amino acid are described herein to confer resistance to ALK inhibiting agents. In one embodiment, the C1156 position comprises a tyrosine amino acid and/or the L1196 position comprises a methionine amino acid. A skilled artisan will also recognize that amino acid positions corresponding to the "C1156" and "L1196" mutations of wild type ALK protein will have different numbers relative to different reference sequences (e.g., ALK homologs, ALK fusion proteins, etc.) without affecting the predictive value of response to treatment with ALK inhibiting agents (e.g., PF-02341066 and/or PDD). A skilled artisan will further recognize that there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |

| -continued GENETIC CODE | |
|---|---|
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (for example, illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid. In addition, a skilled artisan will understand how to mutate nucleotides of a specific codon so as to specifically alter an encoded amino acid based on the relevant codon chart. For example, the codon for Cys-1156 is "TGC" and that for Tyr may be "TAT" or "TAC". Thus, a single nucleotide G-to-A substitution at position 2 of the codon will encode tyrosine rather than cysteine. A skilled artisan can perform similar manipulations to design other mutations.

"Binding compound" shall refer to a binding composition, such as a small molecule, an antibody, a peptide, a peptide or non-peptide ligand, a protein, an oligonucleotide, an oligonucleotide analog, such as a peptide nucleic acid, a lectin, or any other molecular entity that is capable of specifically binding to a target protein or molecule or stable complex formation with an analyte of interest, such as a complex of proteins.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids and organic molecules having a molecular weight of up to about 1000 daltons and containing atoms selected from the group consisting of hydrogen, carbon, oxygen, nitrogen, sulfur and phosphorus.

A "biomarker" or "marker" is a gene, mRNA, or protein which may be altered, wherein said alteration is associated with cancer. The alteration may be in amount, structure, and/or activity in a cancer tissue or cancer cell, as compared to its amount, structure, and/or activity, in a normal or healthy tissue or cell (e.g., a control), and is associated with a disease state, such as cancer. For example, a marker of the present invention which is associated with cancer or predictive of responsiveness to anti-cancer therapeutics may have an altered nucleotide sequence, amino acid sequence, chromosomal translocation, intra-chromosomal inversion, copy number, expression level, protein level, protein activity, or methylation status, in a cancer tissue or cancer cell as compared to a normal, healthy tissue or cell. Furthermore, a "marker" includes a molecule whose structure is altered, e.g., mutated (contains an mutation), e.g., differs from the wild type sequence at the nucleotide or amino acid level, e.g., by substitution, deletion, or insertion, when present in a tissue or cell associated with a disease state, such as cancer.

The terms "cancer" or "tumor" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, mu chain disease, benign monoclonal gammopathy, immunocytic amyloidosis, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

"Chemotherapeutic agent" means a chemical substance, such as a cytotoxic or cytostatic agent, that is used to treat a condition, e.g., cancer.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The "copy number of a gene" or the "copy number of a marker" refers to the number of DNA sequences in a cell encoding a particular gene product. Generally, for a given gene, a mammal has two copies of each gene. The copy number can be increased, however, by gene amplification or duplication, or reduced by deletion.

A marker is "fixed" to a substrate if it is covalently or non-covalently associated with the substrate such that the substrate can be rinsed with a fluid (e.g., standard saline citrate, pH 7.4) without a substantial fraction of the marker dissociating from the substrate.

"Hazard ratio", as used herein, refers to a statistical method used to generate an estimate for relative risk. "Hazard ratio" is the ratio between the predicted hazard of one group versus another group. For example, patient populations treated with an ALK inhibiting agent versus without an ALK inhibiting agent can be assessed for whether or not the ALK inhibiting agent is effective in increasing the time to distant recurrence of disease, particularly with regard to ALK mutation status. For example, treating subjects harboring ALK mutations in cancerous tissue, as described herein, results in increased therapeutic benefit from ALK inhibiting agents relative to subjects not having said ALK mutations in cancerous tissue.

"ALK inhibiting agent" or "ALK inhibitor," as used herein, refers to a compound that can inhibit the biological activity of ALK. Biological activities can also include patient response as set forth in this application. Exemplary ALK inhibiting agents include, but are not limited to, PF-02341066, PDD, 2-methyl-11-(2-methylpropyl)-4-oxo-4,5,6,11,12,13-hexahydro-2H-indazolo[5,4-a]pyrrolo[3,4-c]carbazol-8-yl [4-(dimethylamino)benzyl]carbamate, (1S,2S,3R,4R)-3-({5-chloro-2-[(1-ethyl-2,3,4,5-tetrahydro-6-methoxy-2-oxo-1H-1-benzazepin-7-yl)amino]-4-pyrimidinyl}amino) bicyclo[2.2.1]hept-5-ene-2-carboxamide, and NVP-TAE684 (see, for example, PNAS 104:270-275, 2007; Choi, Y. L. et al. (2008) *Cancer Res.* 68:4971-2976; and *Biochemistry* 48:3600-3609, 2009, which are hereby incorporated by reference).

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantial homology," as used herein, refers to homology of at least 50%, at least 60%, at least 65%, at least 70%, at least 75%, at least 80%, at least 85%, at least 90%, at least 95% or more.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

A "marker nucleic acid" or "biomarker nucleic acid" is a nucleic acid (e.g., DNA, mRNA, cDNA) encoded by or corresponding to a marker of the present invention. For example, such marker nucleic acid molecules include DNA (e.g., genomic DNA and cDNA) comprising the entire or a partial sequence of any of the nucleic acid sequences set forth in Table 1 or the complement or hybridizing fragment of such a sequence. The marker nucleic acid molecules also include RNA comprising the entire or a partial sequence of any of the nucleic acid sequences set forth in Table 1 or the complement of such a sequence, wherein all thymidine residues are replaced with uridine residues. A "marker protein" is a protein encoded by or corresponding to a marker of the present invention. A marker protein comprises the entire or a partial sequence of a protein encoded by any of the sequences set forth in Table 1 or a fragment thereof. The terms "protein" and "polypeptide" are used interchangeably herein.

The "normal" copy number of a marker or "normal" level of expression of a marker is the level of expression, copy number of the marker, in a biological sample, e.g., a sample containing sputum, bronchoalveolar lavage, pleural effusion, tissue, whole blood, serum, plasma, buccal scrape, saliva, cerebrospinal fluid, urine, stool, and bone marrow, from a subject, e.g., a human, not afflicted with cancer.

An "overexpression" or "significantly higher level of expression, copy number, and/or activity" of ALK gene mutations and/or gene products (e.g., the markers set forth in Table 1) refers to an expression level, copy number, and/or activity in a test sample that is greater than the standard error of the assay employed to assess expression or copy number, and may be at least two, at least three, at least four, at least five, or at least ten or more times the expression level or copy number of the ALK gene mutations and/or gene products (e.g., the markers set forth in Table 1) in a control sample (e.g., a sample from a healthy subject not afflicted with cancer), or the average expression level or copy number of the ALK gene mutations and/or gene products (e.g., the markers set forth in Table 1) in several control samples.

The term "probe" refers to any molecule which is capable of selectively binding to a specifically intended target molecule, for example a marker of the present invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

"RECIST" shall mean an acronym that stands for "Response Evaluation Criteria in Solid Tumours" and is a set of published rules that define when cancer patients improve ("respond"), stay the same ("stable") or worsen ("progression") during treatments. Response as defined by RECIST criteria have been published, for example, at Journal of the National Cancer Institute, Vol. 92, No. 3, Feb. 2, 2000 and RECIST criteria may include other similar published definitions and rule sets. One skilled in the art would understand definitions that go with RECIST criteria, as used herein, such as "PR," "CR," "SD" and "PD."

"Responsiveness," to "respond" to treatment, and other forms of this verb, as used herein, refer to the reaction of a subject to treatment with an ALK inhibiting agent. As an example, a subject responds to treatment with an ALK inhibiting agent if growth of a tumor in the subject is retarded about 10%, about 20%, about 30%, about 40%, about 50%, about 60%, about 70%, about 80%, about 90% or more. In another example, a subject responds to treatment with an ALK inhibiting agent if a tumor in the subject shrinks by about 5%, about 10%, about 20%, about 30%, about 40%, about 50% or more as determined by any appropriate measure, e.g., by mass or volume. In another example, a subject responds to treatment with an ALK inhibiting agent if the subject experiences a life expectancy extended by about 5%, about 10%, about 20%, about 30%, about 40%, about 50% or more beyond the life expectancy predicted if no treatment is administered. In another example, a subject responds to treatment with an ALK inhibiting agent if the subject has an increased disease-free survival, overall survival or increased time to progression. Several methods may be used to determine if a patient responds to a treatment including the RECIST criteria, as set forth above.

"Sample," "tissue sample," "patient sample," "patient cell or tissue sample" or "specimen" each refer to a collection of similar cells obtained from a tissue of a subject or patient. The source of the tissue sample may be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample may contain compounds that are not naturally intermixed with the tissue in nature such as preservatives, anticoagulants, buffers, fixatives, nutrients, antibiotics or the like.

The amount of a marker, e.g., expression or copy number of ALK gene mutations and/or gene products (e.g., the markers set forth in Table 1), in a subject is "significantly" higher or lower than the normal amount of a marker, if the amount of the marker is greater or less, respectively, than the normal level by an amount greater than the standard error of the assay employed to assess amount, or at least two, at least three, at least four, at least five, at least ten or more times that amount. Alternately, the amount of the marker in the subject can be considered "significantly" higher or lower than the normal amount if the amount is at least about two, at least about three, at least about four, or at least about five times, higher or lower, respectively, than the normal amount of the marker.

As used herein, "significant event" shall refer to an event in a patient's disease that is important as determined by one skilled in the art. Examples of significant events include, for example, without limitation, primary diagnosis, death, recurrence, the determination that a patient's disease is metastatic, relapse of a patient's disease or the progression of a patient's disease from any one of the above noted stages to another. A significant event may be any important event used to assess OS, TTP and/or using the RECIST or other response criteria, as determined by one skilled in the art.

As used herein, the terms "subject" and "patient" are used interchangeably. As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human).

As used herein, "time course" shall refer to the amount of time between an initial event and a subsequent event. For example, with respect to a patient's cancer, time course may relate to a patient's disease and may be measured by gauging significant events in the course of the disease, wherein the first event may be diagnosis and the subsequent event may be metastasis, for example.

"Time to progression" or "TTP" refers to a time as measured from the start of the treatment to progression or a cancer or censor. Censoring may come from a study end or from a change in treatment. Time to progression can also be represented as a probability as, for example, in a Kaplein-Meier plot where time to progression may represent the probability of being progression free over a particular time, that time being the time between the start of the treatment to progression or censor.

A "transcribed polynucleotide" is a polynucleotide (e.g., an RNA, a cDNA, or an analog of one of an RNA or cDNA) which is complementary to or homologous with all or a portion of a mature RNA made by transcription of a marker of the present invention and normal post-transcriptional processing (e.g., splicing), if any, of the transcript, and reverse transcription of the transcript.

"Treat," "treatment," and other forms of this word refer to the administration of an ALK inhibiting agent to impede growth of a cancer, to cause a cancer to shrink by weight or volume, to extend the expected survival time of the subject and or time to progression of the tumor or the like.

An "underexpression" or "significantly lower level of expression, copy number, and/or activity" of ALK gene mutations and/or gene products (e.g., the markers set forth in Table 1) refers to an expression level or copy number in a test sample that is greater than the standard error of the assay employed to assess expression or copy number, for example, at least twice, at least three, at least four, at least five, or at least ten or more times less than the expression level, copy number, and/or activity of the ALK gene mutations and/or gene products (e.g., the markers set forth in Table 1) in a control sample (e.g., a sample from a healthy subject not afflicted with cancer), or the average expression level, copy number, and/or activity of the ALK gene mutations and/or gene products (e.g., the markers set forth in Table 1) in several control samples.

II. Exemplary Methods of the Invention

The present invention is based, at least in part, on the identification of specific regions of the genome, including, for example, ALK mutations, associated with predicting efficacy of ALK inhibitors in treating cancer. Analysis of ALK gene expression sequences has led to the identification of novel mutations to ALK polypeptides (e.g., biomarkers listed in Table 1, including EML4-ALK polypeptides) that can render the polypeptides at least partially resistant to therapy with ALK inhibitors. Accordingly, the presence and/or absence of one or more of such biomarkers in various methods described herein is within the scope of the present invention.

In some embodiments, methods of the present invention may be used to monitor the progression of cancer in a subject, wherein if a sample in a subject presents one or more ALK mutations (e.g., EML4-ALK mutations) identified herein during the progression of cancer, e.g., at a first point in time and a subsequent point in time, then the cancer is less likely to respond to ALK inhibitor-mediated treatment and vice versa. In yet another embodiment, between the first point in time and a subsequent point in time, the subject has undergone treatment, e.g., chemotherapy, radiation therapy, surgery, or any other therapeutic approach useful for inhibiting cancer, has completed treatment, or is in remission.

As described further herein, one or more biomarkers of the present inventions (e.g., ALK mutations, including EML4-ALK mutations) can be specifically identified by the presence in genomic (e.g., germline and/or somatic) sequence when compared to a reference sequence, such as SEQ ID NO:1. For example, the methods described herein can involve detecting biomarkers of the present invention by carrying out a target nucleic acid amplification reaction of a stretch of DNA comprising one or more mutations listed in Table 1 and analyzing the amplified target nucleic acid for the presence of the one or more mutations.

Various techniques for amplifying nucleic acid are known in the art, such as: PCR (Polymerase Chain Reaction), described in U.S. Pat. No. 4,683,195 (incorporated by reference), U.S. Pat. No. 4,683,202 (incorporated by reference) and U.S. Pat. No. 4,800,159 (incorporated by reference), and its RT-PCR alternative (Reverse Transcription PCR), particularly in its one-step format as disclosed in patent EP-B-

0.569.272, LCR (Ligase Chain Reaction), as described for example in patent application EP-A-0.201.184, RCR (Repair Chain Reaction), as described for example in international application WO-A-90/01069 (incorporated by reference), 3SR (Self Sustained Sequence Replication), as described for example in patent application WO-A-90/06995 (incorporated by reference), NASBA (Nucleic Acid Sequence-Based Amplification), as described for example instance in EP-B-0.397.269 and U.S. Pat. No. 5,466,586 (incorporated by reference) using double stranded DNA as template, and TMA (Transcription Mediated Amplification), as described for example in U.S. Pat. No. 5,399,491 (incorporated by reference).

Detection of the presence of one or more of the mutations in the amplified product can be performed in various manners that are well known in the art, such as DNA sequencing methodologies like Sanger sequencing and deep sequencing, use of restriction enzymes, allele specific amplification, Peptide Nucleic Acid (PNA)-mediated PCR, detection of conformational differences, like Single Strand Conformation Polymorphism (SSCP) and Denaturing Gradient Gel Electrophoresis (DGGE) assays with detection steps on membranes (dot blot) using labeled oligonucleotide probes, assays with detection steps in microtiter plates, like Reverse Hybridization, Oligonucleotide Ligation Assay (OLA, MLPA), First Nucleotide Change (FNC) technology, Cross-linking technology, Rapid cycle PCR and simultaneous fluorescence analysis (e.g. 5' nuclease/Taqman), and PCR followed by mini-sequencing using mass spectrometry or capillary electrophoresis III. Exemplary Isolated Nucleic Acid Molecules One aspect of the present invention pertains to isolated nucleic acid molecules that correspond to a biomarker of the present invention, including nucleic acids which encode a polypeptide corresponding to a marker of the present invention or a portion of such a polypeptide. The nucleic acid molecules of the present invention include those nucleic acid molecules which reside in ALK or ALK-related genomic (e.g., germline and/or somatic) regions identified herein and/or encode ALK or ALK-related (e.g., EML4-ALK) polypeptides. In some embodiments, the nucleic acid molecules of the present invention comprise, consist essentially of, or consist of the nucleic sequences, or fragments thereof, presented in Table 1. Isolated nucleic acid molecules of the present invention also include nucleic acid molecules sufficient for use as hybridization probes to identify nucleic acid molecules that correspond to a marker of the present invention, including nucleic acid molecules which encode a polypeptide corresponding to a marker of the present invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A nucleic acid molecule of the present invention, e.g., ALK gene mutations set forth in Table 1), can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the present invention can be amplified using cDNA, mRNA, or genomic DNA (e.g., germline and/or somatic genomic DNA) as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

In another embodiment, an isolated nucleic acid molecule of the present invention comprises a nucleic acid molecule which has a nucleotide sequence complementary to the nucleotide sequence of a nucleic acid corresponding to a marker of the present invention or to the nucleotide sequence of a nucleic acid encoding a protein which corresponds to a marker of the present invention. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 45, at least about 50, at least about 55 at least about 60, at least about 65, at least about 70, at least about 75, at least about 80, at least about 85 kb, at least about 90, at least about 95, at least about 100 or more consecutive nucleotides of a nucleic acid of the present invention.

Probes based on the sequence of a nucleic acid molecule of the present invention can be used to detect transcripts or genomic sequences corresponding to one or more markers of the present invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that are substantially homologous to the ALK gene mutations and/or gene products (e.g., the markers set forth in Table 1) such that they are at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater. In other embodiments, the invention further encompasses nucleic acid molecules that are substantially homologous to the ALK gene mutations and/or gene products (e.g., the markers set forth in Table 1) such that they differ by only or at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, at least 75, at least 80, at least 85, at least 90, at least 95, at least 100 nucleotides or any range in between.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

In another embodiment, an isolated nucleic acid molecule of the present invention is at least 7, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 550, at least 650, at least 700, at least 800, at least 900, at least 1000, at least 1200, at least 1400, at least 1600, at least 1800, at least 2000, at least 2200, at least 2400, at least 2600, at least 2800, at least 3000, at least 3500, at least 4000, at least 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60%, at least 65%, at least 70%, at least 75%, at least 80%, or at least 85% identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). Another, non-limiting example of stringent hybridization conditions are hybridization in 6× sodium chloride/sodium citrate (SSC) at about 45° C., followed by one or more washes in 0.2×SSC, 0.1% SDS at 50-65° C.

The invention also includes molecular beacon nucleic acid molecules having at least one region which is complementary to a nucleic acid molecule of the present invention, such that the molecular beacon is useful for quantitating the presence of the nucleic acid molecule of the present invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930 (incorporated by reference).

IV. Exemplary Isolated Proteins and Antibodies

One aspect of the present invention pertains to isolated proteins which correspond to individual markers of the present invention, and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein or biologically active portion thereof is recombinantly produced, it may be substantially free of culture medium, i.e., culture medium represents less than about 20%, less than about 10%, or less than about 5% of the volume of the protein preparation. When the protein is produced by chemical synthesis, it may substantially be free of chemical precursors or other chemicals, i.e., it is separated from chemical precursors or other chemicals which are involved in the synthesis of the protein. Accordingly such preparations of the protein have less than about 30%, less than about 20%, less than about 10%, less than about 5% (by dry weight) of chemical precursors or compounds other than the polypeptide of interest.

Biologically active portions of a polypeptide corresponding to a marker of the present invention include polypeptides comprising amino acid sequences sufficiently identical to or derived from the amino acid sequence of the protein corresponding to ALK gene mutations and/or gene products (e.g., the markers set forth in Table 1) of the present invention, which include fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more amino acids in length. Moreover, other biologically active portions, in which other regions of the protein are deleted, can be prepared by recombinant techniques and evaluated for one or more of the functional activities of the native form of a polypeptide of the present invention.

In certain embodiments, the polypeptide has an amino acid sequence of a protein encoded by a nucleic acid molecule listed in Table 1. Other useful proteins are substantially identical (e.g., at least 60, at least 65, at least 70, at least 75, at least 80, at least 85, at least 86, at least 87, at least 88, at least 89, at least 90, at least 91, at least 92, at least 93, at least 94, at least 95, at least 96, at least 97, at least 98, at least 99, at least 99.5% or greater) to one of these sequences and retain the functional activity of the protein (e.g., conferring resistance or sensitivity to an ALK inhibitor) of the corresponding full-length protein yet differ in amino acid sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. Another, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used (see the NCBI website on the world wide web at ncbi.nlm.nih.gov). Another non-limiting example of a mathematical algorithm utilized for the comparison of sequences is the algorithm of Myers and Miller, (1988) *Comput Appl Biosci*, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An isolated polypeptide corresponding to a marker of the present invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the present invention comprises at least 8 (or at least 10, at least 15, at least 20, or at least 30 or more) amino acid residues of the amino acid sequence of one of the polypeptides of the present invention, and encompasses an epitope of the protein such that an antibody raised against the peptide forms a specific immune complex with a marker of the present invention to which the protein corresponds. Exemplary epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the present invention pertains to antibodies directed against a polypeptide of the present invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the present invention. A molecule which specifically binds to a given polypeptide of the present invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the present invention as an immunogen. The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the present invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the present invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409 (incorporated by reference); PCT Publication No. WO 92/18619 (incorporated by reference); PCT Publication No. WO 91/17271 (incorporated by reference); PCT Publication No. WO 92/20791 (incorporated by reference); PCT Publication No. WO 92/15679 (incorporated by reference); PCT Publication No. WO 93/01288 (incorporated by reference); PCT Publication No. WO 92/01047 (incorporated by reference); PCT Publication No. WO 92/09690 (incorporated by reference); PCT Publication No. WO 90/02809 (incorporated by reference); Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the present invention. Such chimeric and humanized monoclonal antibodies can be produced by recombinant DNA techniques known in the art, for example using methods described in PCT Publication No. WO 87/02671 (incorporated by reference); European Patent Application 184,187; European Patent Application 171,496; European Patent Application 173,494; PCT Publication No. WO 86/01533 (incorporated by reference); U.S. Pat. No. 4,816,567 (incorporated by reference); European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539 (incorporated by reference); Jones et al. (1986) *Nature* 321:552-525; Verhoeyan et al. (1988) *Science* 239:1534; and Beidler et al. (1988) *J. Immunol.* 141:4053-4060.

Completely human antibodies are particularly desirable for therapeutic treatment of human subjects. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the present invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126 (incorporated by reference); U.S. Pat. No. 5,633,425 (incorporated by reference); U.S. Pat. No. 5,569,825 (incorporated by reference); U.S. Pat. No. 5,661,016 (incorporated by reference); and U.S. Pat. No. 5,545,806 (incorporated by reference). In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

An antibody directed against a polypeptide corresponding to a marker of the present invention (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g., in a tumor cell-containing body fluid) as part of a clinical testing procedure, e.g., to, for example, determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}$I, $^{131}$I, $^{35}$S or $^{3}$H.

V. Exemplary Recombinant Expression Vectors and Host Cells

Another aspect of the present invention pertains to vectors, such as expression vectors, containing a nucleic acid encoding a polypeptide corresponding to a marker of the present invention (or a portion of such a polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors of the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990). Another strategy is to alter the nucleic acid sequence of the nucleic acid to be inserted into an expression vector so that the individual codons for each amino acid may be among those utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), such as promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 (incorporated by reference) and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the present invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Exemplary selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the present invention, such as a prokaryotic or eukaryotic host cell in culture, can be used to produce a polypeptide corresponding to a marker of the present invention. Accordingly, the invention further provides methods for producing a polypeptide corresponding to a marker of the present invention using the host cells of the present invention. In one embodiment, the method comprises culturing the host cell of invention (into which a recombinant expression vector encoding a polypeptide of the present invention has been introduced) in a suitable medium such that the marker is produced. In another embodiment, the method further comprises isolating the marker polypeptide from the medium or the host cell.

The host cells of the present invention can also be used to produce nonhuman transgenic animals. For example, in one embodiment, a host cell of the present invention is a fertilized oocyte or an embryonic stem cell into which sequences encoding a polypeptide corresponding to a marker of the present invention have been introduced. Such host cells can then be used to create non-human transgenic animals in which exogenous sequences encoding a marker protein of the present invention have been introduced into their genome or homologous recombinant animals in which endogenous gene(s) encoding a polypeptide corresponding to a marker of the present invention sequences have been altered. Such animals are useful for studying the function and/or activity of the polypeptide corresponding to the marker, for identifying and/or evaluating modulators of polypeptide activity, as well as in pre-clinical testing of therapeutics or diagnostic molecules, for marker discovery or evaluation, e.g., therapeutic and diagnostic marker discovery or evaluation, or as surrogates of drug efficacy and specificity.

As used herein, a "transgenic animal" is a non-human animal, e.g., a mammal, such as a rodent, e.g., a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, such as a mammal, e.g., a mouse, in which an endogenous gene has been altered by homologous recombination between the endogenous gene and an exogenous DNA molecule introduced into a cell of the animal, e.g., an embryonic cell of the animal, prior to development of the animal. Transgenic animals also include inducible transgenic animals, such as those described in, for example, Chan I. T., et al. (2004) *J Clin Invest.* 113(4):528-38 and Chin L. et al (1999) *Nature* 400(6743):468-72.

A transgenic animal of the present invention can be created by introducing a nucleic acid encoding a polypeptide corresponding to a marker of the present invention into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the present invention to particular cells. Methods for generating transgenic animals via embryo manipulation and microinjection, particularly animals such as mice, have become conventional in the art and are described, for example, in U.S. Pat. No. 4,736,866 (incorporated by reference) and U.S. Pat. No. 4,870,009 (incorporated by reference), U.S. Pat. No. 4,873,191 (incorporated by reference) and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide corresponding to a marker of the present invention into which a deletion, addition or substitution has been introduced to thereby alter, e.g., functionally disrupt, the gene. In another embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, Cell 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354 (incorporated by reference), WO 91/01140 (incorporated by reference), WO 92/0968 (incorporated by reference), and WO 93/04169 (incorporated by reference).

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, Science 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication Nos. WO 97/07668 (incorporated by reference) and WO 97/07669 (incorporated by reference).

V. Exemplary Kits

A kit is any manufacture (e.g., a package or container) comprising at least one reagent, e.g., a probe, for specifically detecting a marker of the present invention, the manufacture being promoted, distributed, or sold as a unit for performing the methods of the present invention. When the compositions, kits, and methods of the present invention are used for carrying out the methods of the present invention, the ALK gene mutations and/or gene products (e.g., the markers set forth in Table 1) of the present invention may be selected such that a positive result is obtained in at least about 20%, at least about 40%, at least about 60%, at least about 80%, at least about 90%, at least about 95%, at least about 99% or in 100% of subjects afflicted with cancer, of the corresponding stage, grade, histological type, or benign/premaligant/malignant nature. In certain embodiments, the marker or panel of markers of the present invention may be selected such that a PPV (positive predictive value) of greater than about 10% is obtained for the general population (e.g., coupled with an assay specificity greater than 99.5%).

When a plurality of ALK gene mutations and/or gene products (e.g., the markers set forth in Table 1) of the present invention are used in the compositions, kits, and methods of the present invention, the amount, structure, and/or activity of each marker or level of expression or copy number can be compared with the normal amount, structure, and/or activity of each of the plurality of markers or level of expression or copy number, in non-cancerous samples of the same type, either in a single reaction mixture (i.e., using reagents, such as different fluorescent probes, for each marker) or in individual reaction mixtures corresponding to one or more of the ALK gene mutations and/or gene products (e.g., the markers set forth in Table 1). If a plurality of ALK gene mutations and/or gene products (e.g., the markers set forth in Table 1) is used, then 2, 3, 4, 5, 6, 7, 8, 9, 10, or more individual markers may be used or identified.

The invention includes compositions, kits, and methods for assaying cancer cells in a sample (e.g., an archived tissue sample or a sample obtained from a subject). These compositions, kits, and methods are substantially the same as those described above, except that, where necessary, the compositions, kits, and methods are adapted for use with certain types of samples.

The invention thus includes a kit for assessing the presence of cancer cells having or likely to have reduced responsiveness to ALK inhibitors (e.g., in a sample such as a subject sample). The kit may comprise one or more reagents capable of identifying ALK gene mutations and/or gene products (e.g., the markers set forth in Table 1) of the present invention, e.g., binding specifically with a nucleic acid or polypeptide corresponding to ALK gene mutations and/or gene products (e.g., the markers set forth in Table 1) of the present invention. Suitable reagents for binding with a polypeptide corresponding to a marker of the present invention include antibodies, antibody derivatives, antibody fragments, and the like. Suitable reagents for binding with a nucleic acid (e.g., a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like. In some embodiments, the kits can comprise reagents useful for performing the methods described herein, such as comprising at least one pair of primers recognizing and hybridizing to stretches of nucleic acid surrounding at least one stretch of nucleic acid comprising at least one mutation listed in Table 1 and means for detecting the amplified-target nucleic acid for the presence of said mutation.

The kit of the present invention may optionally comprise additional components useful for performing the methods of the present invention. By way of example, the kit may comprise fluids (e.g., SSC buffer) suitable for annealing complementary nucleic acids or for binding an antibody with a protein with which it specifically binds, one or more sample compartments, an instructional material which describes performance of a method of the present invention, a sample of normal cells, a sample of cancer cells, and the like.

A kit of the present invention may comprise a reagent useful for determining protein level or protein activity of a marker. In another embodiment, a kit of the present invention may comprise a reagent for determining methylation status of a marker, or may comprise a reagent for determining alteration of structure of a marker, e.g., the presence of a mutation.

VI. Predictive Medicine

The present invention also pertains to the field of predictive medicine in which diagnostic assays, pharmacogenomics, and monitoring clinical trials are used for predictive purposes to thereby treat an individual prophylactically. Accordingly, one aspect of the present invention relates to assays for determining the amount, structure, and/or activity of polypeptides or nucleic acids corresponding to one or more markers of the present invention, in order to determine whether an individual having cancer or at risk of developing cancer will be more likely to respond to ALK inhibitor-mediated therapy.

Accordingly, in one aspect, the invention is drawn to a method for determining whether a subject with a cancer is likely to respond to treatment with an ALK inhibiting agent. In another aspect, the invention is drawn to a method for predicting a time course of disease. In still another aspect, the method is drawn to a method for predicting a probability of a significant event in the time course of the disease. In certain embodiments, the method comprises detecting a biomarker or combination of biomarkers associated with responsiveness to treatment with an ALK inhibiting agent (e.g., ALK mutations) as described herein, and determining whether the subject is likely to respond to treatment with the ALK inhibiting agent.

In some embodiments, the methods involve cytogenetic screening of biological tissue sample from a patient who has been diagnosed with or is suspected of having cancer (e.g., presents with symptoms of cancer) to detect ALK mutations (e.g., those listed in Table 1).

The results of the screening method and the interpretation thereof are predictive of the patient's response to treatment with ALK inhibiting agents (e.g., PF-02341066 and/or PDD). According to the present invention, the presence of an ALK mutation is indicative that treatment with ALK inhibiting agents (e.g., PF-02341066 and/or PDD) will provide enhanced therapeutic benefit against the cancer cells relative to those of patients not having an ALK mutation.

In one embodiment, the methods of the present invention comprise contacting a DNA sample, e.g., a sample containing germline and/or somatic DNA, such as a chromosomal sample, obtained from cells isolated from the patient to polynucleotide probes that are specific for and hybridize under stringent conditions with genomic DNA in chromosomal regions associated with cytogenetic abnormalities (e.g., ALK mutations described herein) to determine the presence or absence of one or more of the abnormalities (e.g., mutations) in the cells of the patient. The results of the analysis are predictive of the patient's likely response to treatment with therapeutic agents, particularly agents that inhibit ALK (e.g., PF-02341066 and/or PDD).

In another embodiment, a time course is measured by determining the time between significant events in the course of a patient's disease, wherein the measurement is predictive of whether a patient has a long time course. In another embodiment, the significant event is the progression from primary diagnosis to death. In another embodiment, the significant event is the progression from primary diagnosis to metastatic disease. In another embodiment, the significant event is the progression from primary diagnosis to relapse. In another embodiment, the significant event is the progression from metastatic disease to death. In another embodiment, the significant event is the progression from metastatic disease to relapse. In another embodiment, the significant event is the progression from relapse to death. In certain embodiments, the time course is measured with respect to overall survival rate, time to progression and/or using the RECIST or other response criteria.

In certain embodiments, a predetermined measure is created by dividing patient samples into at least two patient subgroups. In certain embodiments, the number of subgroups is two so that the patient sample is divided into a subgroup of patients having an ALK mutation(s) and a subgroup not having an ALK mutation(s). In certain embodiments, the ALK mutation status in the subject is compared to either the subgroup having or not having an ALK mutation(s); if the patient has an ALK mutation(s), then the patient is unlikely to respond to an ALK inhibitor (e.g., PF-02341066 and/or PDD) and/or the patient is likely to have a long time course. In certain embodiments, the number of subgroups is greater than two, including, without limitation, three subgroups, four subgroups, five subgroups and six subgroups, depending on stratification of predicted ALK inhibitor efficacy as correlated with particular ALK mutations. In certain embodiments, likeliness to respond is measured with respect to overall survival rate, time to progression and/or using the RECIST criteria. In certain embodiments, the ALK inhibitor is PF-02341066 and/or PDD.

In another aspect, the invention is drawn to a method for determining whether a subject with an ALK mutation positive cancer is likely to respond to treatment with an ALK inhibiting agent (e.g., PF-02341066 and/or PDD) and/or the time course of disease is long. In another aspect, the invention is drawn to a method for predicting a time course of disease in a subject with an ALK mutation positive cancer. In another aspect, the invention is drawn to a method for predicting the probability of a significant event in a subject with an ALK mutation positive cancer.

1. Methods for Detecting ALK Mutations

Methods of evaluating ALK gene mutations and/or gene products (e.g., the markers set forth in Table 1) are well known to those of skill in the art, including hybridization-based assays. For example, one method for evaluating the copy number of encoding nucleic acid in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the presence/absence and relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal mRNA (e.g., a non-amplified portion of the same or related cell, tissue, organ, etc.) provides an estimate of the presence/absence and relative copy number of the target nucleic acid.

An alternative means for determining the copy number is in situ hybridization (e.g., Angerer (1987) Meth. Enzymol 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

Exemplary hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g., membrane or glass) bound methods or array-based approaches.

In one aspect, FISH analysis is used. Cell samples are obtained from patients according to methods well known in the art in order to be tested by an appropriate cytogenetic testing method known in the art, for example, the FISH method. In one embodiment, FISH can be performed according to the Vysis™ system (Abbott Molecular), whose manufacturer's protocols are incorporated herein by reference.

Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. No. 5,491,224 (incorporated by reference) and U.S. Pat. No. 6,277,569 (incorporated by reference) to Bittner, et al.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224 (incorporated by reference).

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell may still occur, but less of a signal may be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe. Although any probes that detect human chromosome 2p23 or ortholog thereof or any chromosomal region comprising a translocation with the ALK gene of 2p23 or ortholog thereof can be used. Suitable probes are well known in the art (e.g., available from Vysis, Inc. (Downers Grove, Ill.).

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224 (incorporated by reference).

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)- or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. In general, hybridization steps comprise adding an excess of blocking DNA to the labeled probe composition, contacting the blocked probe composition under hybridizing conditions with the chromosome region to be detected, e.g., on a slide where the DNA has been denatured, washing away unhybridized probe, and detecting the binding of the probe composition to the chromosome or chromosomal region.

Probes are hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization.

After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple band-pass filter sets to observe multiple fluorophores. See, for example, U.S. Pat. No. 5,776,688 (incorporated by reference). Alternatively, techniques such as flow cytometry can be used to examine the hybridization pattern of the chromosomal probes. FISH can be used to detect chromosome copy number or rearrangement of regions of chromosomes. These probes hybridize, or bind, to the complementary DNA and, because they are labeled with fluorescent tags, allow researchers to see the location of those sequences of DNA using a fluorescence microscope. Unlike most other techniques used to study chromosomes, which require that the cells be actively dividing, FISH can also be performed on non-dividing cells, making it a highly versatile procedure. Therefore, FISH can be performed using interphase cells, or cells in metaphase of the cell division cycle. Many of the techniques involved in FISH analysis are described in U.S. Pat. No. 5,447,841 (incorporated by reference) by Gray and Pinkel.

FISH results can be interpreted with reference to control cells that are known not to contain the specific cytogenetic abnormality the probe is designed to detect. The FISH hybridization pattern of the probe to DNA from the control cells is compared to hybridization of the same probe to the DNA from cells that are being tested or assayed for the specific cytogenetic abnormality. When a probe is designed to detect a deletion of a chromosome or chromosomal region, there normally is less hybridization of the probe to DNA from the cells being tested than from the control cells. Normally, there is absence of a probe signal in the tested cells, indicative of loss of the region of a chromosome the probe normally hybridizes to. When a probe is designed to detect a chromosomal duplication or addition, there normally is more hybridization of the probe to DNA from the cells being tested than from the control cells. Normally, there is addition of a probe signal in the tested cells, indicative of the presence of an additional chromosomal region to which the probe normally hybridizes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods of the present invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl. Acad Sci USA* 89:5321-5325 (1992) is used. Array-based CGH is described in U.S. Pat. No. 6,455,258, the contents of each of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93) may also be used to identify regions of amplification or deletion.

2. Methods for Assessing Gene Expression

Marker expression level can also be assayed. Expression of a marker of the present invention may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the target cDNA.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, polyethylene, dextran, amylases, natural and modified celluloses, polyacrylamides, gabbros, and magnetite.

In order to conduct assays with the above-mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In another embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169 (incorporated by reference); Stavrianopoulos, et al., U.S. Pat. No. 4,868,103 (incorporated by reference)). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S, and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example, through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typical. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155 (incorporated by reference)).

The isolated nucleic acid can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the present invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

The probes can be full length or less than the full length of the nucleic acid sequence encoding the protein. Shorter probes are empirically tested for specificity. Exemplary nucleic acid probes are 20 bases or longer in length (See, e.g., Sambrook et al. for methods of selecting nucleic acid probe sequences for use in nucleic acid hybridization). Visualization of the hybridized portions allows the qualitative determination of the presence or absence of cDNA.

An alternative method for determining the level of a transcript corresponding to a marker of the present invention in a sample involves the process of nucleic acid amplification, e.g., by rtPCR (the experimental embodiment set forth in Mullis, 1987, U.S. Pat. No. 4,683,202 (incorporated by reference)), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033 (incorporated by reference)) or any other nucleic acid amplification method, followed by the detection of the amplified molecules using techniques well known to those of skill in the art. Fluorogenic rtPCR may also be used in the methods of the present invention. In fluorogenic rtPCR, quantitation is based on amount of fluorescence signals, e.g., TaqMan and sybr green. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a non-cancerous sample, or between samples from different sources.

Alternatively, the expression level can be provided as a relative expression level. To determine a relative expression level of a marker, the level of expression of the marker is determined for 10 or more samples of normal versus cancer cell isolates, or even 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

In certain embodiments, the samples used in the baseline determination will be from cancer cells or normal cells of the same tissue type. The choice of the cell source is dependent on the use of the relative expression level. Using expression found in normal tissues as a mean expression score aids in validating whether the marker assayed is specific to the tissue from which the cell was derived (versus normal cells). In addition, as more data is accumulated, the mean expression value can be revised, providing improved relative expression values based on accumulated data. Expression data from normal cells provides a means for grading the severity of the cancer state.

In another embodiment, expression of a marker is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the marker, and fragments thereof cDNA can, optionally, be amplified using any of a variety of polymerase chain reaction methods prior to hybridization with the reference polynucleotide. Expression of one or more markers can likewise be detected using quantitative PCR (QPCR) to assess the level of expression of the marker(s). Alternatively, any of the many known methods of detecting mutations or variants (e.g., single nucleotide polymorphisms, deletions) of a marker of the present invention may be used to detect occurrence of a mutated marker in a subject.

In a related embodiment, a mixture of transcribed polynucleotides obtained from the sample is contacted with a substrate having fixed thereto a polynucleotide complementary to or homologous with at least a portion (e.g., at least 7, at least 10, at least 15, at least 20, at least 25, at least 30, at least 40, at least 50, at least 100, at least 500, or more nucleotide residues) of a marker of the present invention. If polynucleotides complementary to or homologous with a marker of the present invention are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, the hybridization may be performed under stringent hybridization conditions.

In another embodiment, a combination of methods to assess the expression of a marker is utilized.

Because the compositions, kits, and methods of the present invention rely on detection of a difference in expression levels or copy number of one or more markers of the present invention, in certain embodiments the level of expression or copy number of the marker is significantly greater than the minimum detection limit of the method used to assess expression or copy number in at least one of normal cells and cancerous cells.

3. Methods for Assessing Expressed Protein

The activity or level of a marker protein can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry and the like. A skilled artisan can readily adapt known protein/antibody detection methods for use in determining whether cells express a marker of the present invention.

Another agent for detecting a polypeptide of the present invention is an antibody capable of binding to a polypeptide corresponding to a marker of the present invention, e.g., an antibody with a detectable label. Antibodies can be polyclonal or monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a protein corresponding to the marker, such as the protein encoded by the open reading frame corresponding to the marker or such a protein which has undergone all or a portion of its normal post-translational modification, is used.

Immunohistochemistry or IHC refers to the process of localizing antigens (e.g. proteins) in cells of a tissue section exploiting the principle of antibodies binding specifically to antigens in biological tissues. Immunohistochemical staining is widely used in the diagnosis of abnormal cells such as those found in cancerous tumors. Specific molecular markers are characteristic of particular cellular events such as proliferation or cell death (apoptosis). IHC is also widely used in research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyse a colour-producing reaction. Alternatively, the antibody can also be tagged to a fluorophore, such as fluorescein, rhodamine, DyLight Fluor or Alexa Fluor.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

In one format, antibodies, or antibody fragments, can be used in methods such as Western blots or immunofluorescence techniques to detect the expressed proteins. In such uses, one may immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support, such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

In another embodiment, Western blot (immunoblot) analysis is used to detect and quantify the presence of a polypeptide in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a polypeptide. The anti-polypeptide antibodies specifically bind to the polypeptide on the solid support. These antibodies may be directly labeled or alternatively may be subsequently detected using labeled antibodies (e.g., labeled sheep anti-human antibodies) that specifically bind to the anti-polypeptide.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The polypeptide is detected and/or quantified using any of a number of well recognized immunological binding assays (see, e.g., U.S. Pat. No. 4,366,241 (incorporated by reference); U.S. Pat. No. 4,376,110 (incorporated by reference); U.S. Pat. No. 4,517,288 (incorporated by reference); and U.S. Pat. No. 4,837,168 (incorporated by reference)). For a review of the general immunoassays, see also Asai (1993) *Methods in Cell Biology* Volume 37: *Antibodies in Cell Biology*, Academic Press, Inc. New York; Stites & Ten (1991) *Basic and Clinical Immunology* 7th Edition.

Immunological binding assays (or immunoassays) typically utilize a "capture agent" to specifically bind to and often immobilize the analyte (polypeptide or subsequence). The capture agent is a moiety that specifically binds to the analyte. In another embodiment, the capture agent is an antibody that specifically binds a polypeptide. The antibody (anti-peptide) may be produced by any of a number of means well known to those of skill in the art.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled anti-antibody. Alternatively, the labeling agent may be a third moiety, such as another antibody, that specifically binds to the antibody/polypeptide complex.

In one embodiment, the labeling agent is a second human antibody bearing a label. Alternatively, the second antibody may lack a label, but it may, in turn, be bound by a labeled third antibody specific to antibodies of the species from which the second antibody is derived. The second can be modified with a detectable moiety, e.g., as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542).

As indicated above, immunoassays for the detection and/or quantification of a polypeptide can take a wide variety of formats well known to those of skill in the art.

Exemplary immunoassays for detecting a polypeptide may be competitive or noncompetitive. Noncompetitive immunoassays are assays in which the amount of captured analyte is directly measured. In one "sandwich" assay, for example, the capture agent (anti-peptide antibodies) can be bound directly to a solid substrate where they are immobilized. These immobilized antibodies then capture polypeptide present in the test sample. The polypeptide thus immobilized is then bound by a labeling agent, such as a second human antibody bearing a label.

In competitive assays, the amount of analyte (polypeptide) present in the sample is measured indirectly by measuring the amount of an added (exogenous) analyte (polypeptide) displaced (or competed away) from a capture agent (anti-peptide antibody) by the analyte present in the sample. In one competitive assay, a known amount of, in this case, a polypeptide is added to the sample and the sample is then contacted with a capture agent. The amount of polypeptide bound to the antibody is inversely proportional to the concentration of polypeptide present in the sample.

In another embodiment, the antibody is immobilized on a solid substrate. The amount of polypeptide bound to the antibody may be determined either by measuring the amount of polypeptide present in a polypeptide/antibody complex, or alternatively by measuring the amount of remaining uncomplexed polypeptide. The amount of polypeptide may be detected by providing a labeled polypeptide.

The assays described herein are scored (as positive or negative or quantity of polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of polypeptide.

Antibodies for use in the various immunoassays described herein, can be produced as described herein.

In another embodiment, level (activity) is assayed by measuring the enzymatic activity of the gene product. Methods of assaying the activity of an enzyme are well known to those of skill in the art.

In vivo techniques for detection of a marker protein include introducing into a subject a labeled antibody directed against the protein. For example, the antibody can be labeled with a radioactive marker whose presence and location in a subject can be detected by standard imaging techniques.

Certain markers identified by the methods of the present invention may be secreted proteins. It is a simple matter for the skilled artisan to determine whether any particular marker protein is a secreted protein. In order to make this determination, the marker protein is expressed in, for example, a mammalian cell, e.g., a human cell line, extracellular fluid is collected, and the presence or absence of the protein in the extracellular fluid is assessed (e.g., using a labeled antibody which binds specifically with the protein).

The following is an example of a method which can be used to detect secretion of a protein. About $8 \times 10^5$ 293T cells are incubated at 37° C. in wells containing growth medium (Dulbecco's modified Eagle's medium {DMEM} supplemented with 10% fetal bovine serum) under a 5% (v/v) $CO_2$, 95% air atmosphere to about 60-70% confluence. The cells are then transfected using a standard transfection mixture comprising 2 micrograms of DNA comprising an expression vector encoding the protein and 10 microliters of LipofectAMINE™ (GIBCO/BRL Catalog no. 18342-012) per well. The transfection mixture is maintained for about 5 hours, and then replaced with fresh growth medium and maintained in an air atmosphere. Each well is gently rinsed twice with DMEM which does not contain methionine or cysteine (DMEM-MC; ICN Catalog no. 16-424-54). About 1 milliliter of DMEM-MC and about 50 microcuries of Trans-$^{35}$S™ reagent (ICN Catalog no. 51006) are added to each well. The wells are maintained under the 5% $CO_2$ atmosphere described above and incubated at 37° C. for a selected period. Following incubation, 150 microliters of conditioned medium is removed and centrifuged to remove floating cells and debris. The presence of the protein in the supernatant is an indication that the protein is secreted.

It will be appreciated that subject samples, e.g., a sample containing sputum, bronchoalveolar lavage, pleural effusion, tissue, whole blood, serum, plasma, buccal scrape, saliva, cerebrospinal fluid, urine, stool, and bone marrow, may contain cells therein, particularly when the cells are cancerous, and, more particularly, when the cancer is metastasizing, and thus may be used in the methods of the present invention. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the level of expression of the marker in the sample. Thus, the compositions, kits, and methods of the present invention can be used to detect expression of markers corresponding to proteins having at least one portion which is displayed on the surface of cells which express it. It is a simple matter for the skilled artisan to determine whether the protein corresponding to any particular marker comprises a cell-surface protein. For example, immunological methods may be used to detect such proteins on whole cells, or well known computer-based sequence analysis methods (e.g., the SIGNALP program; Nielsen et al., 1997, *Protein Engineering* 10:1-6) may be used to predict the presence of at least one extracellular domain (i.e., including both secreted proteins and proteins having at least one cell-surface domain). Expression of a marker corresponding to a protein having at least one portion which is displayed on the surface of a cell which expresses it may be detected without necessarily lysing the cell (e.g., using a labeled antibody which binds specifically with a cell-surface domain of the protein).

The invention also encompasses kits for detecting the presence of a polypeptide or nucleic acid corresponding to a marker of the present invention in a biological sample, e.g., a sample containing sputum, bronchoalveolar lavage, pleural effusion, tissue, whole blood, serum, plasma, buccal scrape, saliva, cerebrospinal fluid, urine, stool, and bone marrow. Such kits can be used to determine if a subject is suffering from or is at increased risk of developing cancer. For example, the kit can comprise a labeled compound or agent capable of detecting a polypeptide or an mRNA encoding a polypeptide corresponding to a marker of the present invention in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: (1) a first antibody (e.g., attached to a solid support) which binds to a polypeptide corresponding to a marker of the present invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the present invention or (2) a pair of primers useful for amplifying a nucleic acid molecule corresponding to a marker of the present invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

4. Method for Assessing Structural Alterations

The invention also provides a method for assessing the presence of a structural alteration, e.g., mutation.

Another detection method is allele specific hybridization using probes overlapping the polymorphic site and having about 5, about 10, about 20, about 25, or about 30 nucleotides around the polymorphic region. In another embodiment of the present invention, several probes capable of hybridizing specifically to mutations are attached to a solid phase support, e.g., a "chip". Oligonucleotides can be bound to a solid support by a variety of processes, including lithography. For example a chip can hold up to 250,000 oligonucleotides (GeneChip, Affymetrix™). Mutation detection analysis using these chips comprising oligonucleotides, also termed "DNA probe arrays" is described e.g., in Cronin et al. (1996) *Human Mutation* 7:244. In one embodiment, a chip comprises all the mutations of at least one polymorphic region of a gene. The solid phase support is then contacted with a test nucleic acid and hybridization to the specific probes is detected. Accordingly, the identity of numerous mutations of one or more genes can be identified in a simple hybridization experiment. For example, the identity of the mutation of the nucleotide polymorphism in the 5' upstream regulatory element can be determined in a single hybridization experiment.

In other detection methods, it is necessary to first amplify at least a portion of a marker prior to identifying the mutation. Amplification can be performed, e.g., by PCR and/or LCR (see Wu and Wallace (1989) *Genomics* 4:560), according to methods known in the art. In one embodiment, genomic DNA of a cell is exposed to two PCR primers and amplification for a number of cycles sufficient to produce the required amount of amplified DNA. In certain embodiments, the primers are located between 150 and 350 base pairs apart.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al., (1988) *Bio/Technology* 6:1197), and self-sustained sequence replication (Guatelli et al., (1989) *Proc. Nat. Acad. Sci.* 87:1874), and nucleic acid based sequence amplification (NABSA), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of a marker and detect mutations by comparing the sequence of the sample sequence with the corresponding reference (control) sequence. Exemplary sequencing reactions include those based on techniques developed by Maxam and Gilbert (*Proc. Natl. Acad Sci USA* (1977) 74:560) or Sanger (Sanger et al. (1977) *Proc. Nat. Acad. Sci.* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 (incorporated by reference) and international patent application Publication Number WO 94/16101 (incorporated by reference), entitled DNA Sequencing by Mass Spectrometry by H. Köster; U.S. Pat. No. 5,547,835 (incorporated by reference) and international patent application Publication Number WO 94/21822 (incorporated by reference) entitled DNA Sequencing by Mass Spectrometry Via Exonuclease Degradation by H. Köster), and U.S. Pat. No. 5,605,798 (incorporated by reference) and International Patent Application No. PCT/US96/03651 (incorporated by reference) entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 (incorporated by reference) entitled "Method of DNA sequencing employing a mixed DNA-polymer chain probe" and U.S. Pat. No. 5,571,676 (incorporated by reference) entitled "Method for mismatch-directed in vitro DNA sequencing."

In some cases, the presence of a specific allele of a marker in DNA from a subject can be shown by restriction enzyme analysis. For example, a specific nucleotide polymorphism can result in a nucleotide sequence comprising a restriction site which is absent from the nucleotide sequence of another mutation.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of a marker mutation with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides are different. See, for example, Cotton et al (1988) *Proc. Natl. Acad Sci USA* 85:4397; Saleeba et al (1992) *Methods Enzymol.* 217:286-295. In another embodiment, the control or sample nucleic acid is labeled for detection.

In another embodiment, an mutation can be identified by denaturing high-performance liquid chromatography (DHPLC) (Oelher and Underhill, (1995) *Am. J. Human Gen.* 57:Suppl. A266). DHPLC uses reverse-phase ion-pairing chromatography to detect the heteroduplexes that are generated during amplification of PCR fragments from individuals who are heterozygous at a particular nucleotide locus within that fragment (Oefner and Underhill (1995) *Am. J. Human Gen.* 57:Suppl. A266). In general, PCR products are produced using PCR primers flanking the DNA of interest. DHPLC analysis is carried out and the resulting chromatograms are analyzed to identify base pair alterations or deletions based on specific chromatographic profiles (see O'Donovan et al. (1998) *Genomics* 52:44-49).

In other embodiments, alterations in electrophoretic mobility are used to identify the type of marker mutation. For example, single strand conformation polymorphism (SSCP) may be used to detect differences in electrophoretic mobility between mutant and wild type nucleic acids (Orita et al. (1989) *Proc Natl. Acad. Sci. USA* 86:2766, see also Cotton (1993) *Mutat Res* 285:125-144; and Hayashi (1992) *Genet Anal Tech Appl* 9:73-79). Single-stranded DNA fragments of sample and control nucleic acids are denatured and allowed to renature. The secondary structure of single-stranded nucleic acids varies according to sequence and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the identity of a mutation of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265: 1275).

Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163); Saiki et at (1989) *Proc. Natl. Acad. Sci. USA* 86:6230; and Wallace et al. (1979) *Nucl. Acids Res.* 6:3543). Such allele specific oligonucleotide hybridization techniques may be used for the simultaneous detection of several nucleotide changes in different polymorphic regions of marker. For example, oligonucleotides having nucleotide sequences of specific mutations are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238; Newton et al. (1989) *Nucl. Acids Res.* 17:2503). This technique is also termed "PROBE" for Probe Oligo Base Extension. In addition it may be desirable to introduce a novel restriction site in the region of the mutation to create cleavage-based detection (Gasparini et al (1992) *Mol. Cell Probes* 6:1).

In another embodiment, identification of the mutation is carried out using an oligonucleotide ligation assay (OLA), as described, e.g., in U.S. Pat. No. 4,998,617 and in Landegren, U. et al., (1988) *Science* 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., (1990) *Proc. Natl. Acad. Sci. (U.S.A.)* 87:8923-8927. In this method, PCR is used to achieve the exponential amplification of target DNA, which is then detected using OLA.

The invention further provides methods for detecting single nucleotide polymorphisms in a marker. Because single nucleotide polymorphisms constitute sites of variation flanked by regions of invariant sequence, their analysis requires no more than the determination of the identity of the single nucleotide present at the site of variation and it is unnecessary to determine a complete gene sequence for each subject. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127 (incorporated by reference)). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the present invention, a solution-based method is used for determining the identity of the nucleotide of a polymorphic site (Cohen, D. et al. French Patent 2,650,840; PCT Appln. No. WO91/02087 (incorporated by reference)). As in the Mundy method of U.S. Pat. No. 4,656,127 (incorporated by reference), a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712 (incorporated by reference)). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087 (incorporated by reference)) the method of Goelet, P. et al. is a heterogeneous phase assay, in which the primer or the target molecule is immobilized to a solid phase.

Several primer-guided nucleotide incorporation procedures for assaying polymorphic sites in DNA have been described (Komher, J. S. et al., (1989) *Nucl. Acids. Res.* 17:7779-7784; Sokolov, B. P., (1990) *Nucl. Acids Res.* 18:3671; Syvanen, A.-C., et al., (1990) *Genomics* 8:684-692; Kuppuswamy, M. N. et al., (1991) *Proc. Natl. Acad. Sci. (U.S.A.)* 88:1143-1147; Prezant, T. R. et al., (1992) *Hum. Mutat.* 1:159-164; Ugozzoli, L. et al., (1992) *GATA* 9:107-112; Nyren, P. (1993) et al., *Anal. Biochem.* 208:171-175). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. C., et al., (1993) *Amer. J. Hum. Genet.* 52:46-59).

For determining the identity of the mutation of a polymorphic region located in the coding region of a marker, yet other methods than those described above can be used. For example, identification of a mutation which encodes a mutated marker can be performed by using an antibody specifically recognizing the mutant protein in, e.g., immunohistochemistry or immunoprecipitation. Antibodies to wild-type markers or mutated forms of markers can be prepared according to methods known in the art.

Alternatively, one can also measure an activity of a marker, such as binding to a marker ligand. Binding assays are known in the art and involve, e.g., obtaining cells from a subject, and performing binding experiments with a labeled ligand, to determine whether binding to the mutated form of the protein differs from binding to the wild-type of the protein.

VI. Exemplary Screening Methods Based on ALK-Inhibition

The present invention further provides methods for identifying substances that inhibit ALK polypeptides (e.g., EML4-ALK polypeptides) to thereby inhibit cancer cell proliferation, growth, differentiation, apoptosis, and/or metastasis. The methods include contacting a test compound with an ALK polypeptide (e.g., polypeptides listed in Table 1). In some embodiments, the ALK polypeptide comprises a variant (e.g., polypeptides listed in Table 1) that increases the risk of partial or nonresponsiveness to inhibition by one or more ALK inhibitors. A compound that is an inhibitor of tumor metastasis may be identified by determining the effect of a test compound on activity of the ALK polypeptide variant (including, for example, ligand binding such as ATP binding and/or tyrosine kinase activity). In a particular example, a test compound that inhibits tyrosine kinase activity as compared to activity in the absence of the test compound identifies the test compound as an inhibitor of tumor metastasis. If the compound inhibits activity of an ALK variant, it can further be evaluated for its ability to inhibit tumor growth or metastasis.

In particular, activating tyrosine kinase mutants, including the novel biomarkers of the present invention listed in Table 1 (e.g., ALK mutants), are useful to identify compounds that can be used to treat, ameliorate, or prevent neoplasms, for example by inhibiting or preventing cancer cell proliferation, growth, differentiation, apoptosis, and/or metastasis. Screening chemical libraries for molecules which modulate, e.g., inhibit, antagonize, or agonize or mimic, are known in the art. The chemical libraries, for example, can be peptide libraries, peptidomimetic libraries, chemically synthesized libraries, recombinant, e.g., phage display libraries, and in vitro translation-based libraries, other non-peptide synthetic organic libraries.

The screening or creation, identification and selection of appropriate high affinity inhibitors of a novel biomarker of the present invention listed in Table 1 (e.g., ALK mutants) can be accomplished by a variety of methods. Broadly speaking these may include, but are not limited to, two general approaches. One approach is to use structural knowledge about the target protein to design a candidate molecule with which it will precisely interact. An example would be computer assisted molecular design, particularly based on novel structure-function information disclosed herein as FIG. 6. A second approach is to use combinatorial or other libraries of molecules, whereby a large library of molecules is screened for affinity with regard to the target enzyme, or ability to inhibit activity of the target enzyme. In a further example, a panel of antibodies may be screened for the ability to inhibit the target enzyme.

Some embodiments provided herein involve determining the ability of a given compound to inhibit a novel biomarker of the present invention listed in Table 1 (e.g., ALK mutants). Test compounds can be assessed for their probable ability to treat neoplastic lesions either directly, or indirectly by comparing their activities against compounds known to be useful for treating neoplasia. For example, the ability of test compounds to inhibit ligand binding such as ATP binding and/or tyrosine kinase activity against novel biomarkers of the present invention listed in Table 1 (e.g., ALK mutants) can be compared to that of known ALK inhibitors such as PF-02341066 and/or PDD. In one embodiment, such test compounds would have at least 100%, at least 99.9%, at least 99.8%, at least 99.7%, at least 99.6%, at least 99.5%, at least 99.4%, at least 99.3%, at least 99.2%, at least 99.1%, at least 99%, at least 98.5%, at least 98%, at least 97.5%, at least 97%, at least 96.5%, at least 96%, at least 95.5%, at least 94%, at least 93.5%, at least 93%, at least 92.5%, at least 92%, at least 91.5%, at least 91%, at least 90.5%, at least 90%, at least 89.5%, at least 89%, at least 88.5%, at least 88%, at least 87.5%, at least 87%, at least 86.5%, at least 86%, at least 85.5%, at least 85%, at least 84.5%, at least 84%, at least 83.5%, at least 83%, at least 82.5%, at least 82%, at least 81.5%, at least 81%, at least 80.5%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56%, at least 55%, at least 54%, at least 53%, at least 52%, at least 51%, at least 50%, or any range in between, of inhibition of a novel biomarker of the present invention listed in Table 1 (e.g., ALK mutants) relative to that of a known ALK inhibitor under the same assay conditions. In certain embodiments, cells can be transfected with a construct encoding a novel biomarker of the present invention listed in Table 1 (e.g., ALK mutants), contacted with a test compound that is tagged or labelled with a detectable marker and analyzed for the presence bound test compound. In certain embodiments, the transfected cells are observed to bind the test compound as compared to cells that have not been transfected with a novel biomarker of the present invention listed in Table 1 (e.g., ALK mutants), which is an indication that the test compound is binding to a novel biomarker of the present invention listed in Table 1 (e.g., ALK mutants) expressed by those cells. The binding of the compound is typically determined by any one of a wide variety of assays known in the art such as ELISA, RIA, and/or BIAcore assays.

Compounds can be screened for inhibitory or other effects on the activity of a novel biomarker of the present invention listed in Table 1 (e.g., ALK mutants) using an expressed recombinant version of the enzyme, or a homolog or ortholog isolated from another species. Alternatively, cells expressing one of these novel biomarker polypeptides can be treated with a test compound and the effect of the test compound on phosphorylation of a specific target can be determined, for instance using one of the techniques described herein. In one example, tyrosine kinase activity is determined. Methods for determining tyrosine kinase phosphorylation influencing activity (e.g., inhibition) are well known to one of skill in the art. In some examples, tyrosine kinase activity may be determined by assessing incorporation of a labeled phosphate (such as $^{32}$P-labeled phosphate) into a substrate which is capable of being phosphorylated by a novel biomarker of the present invention listed in Table 1 (e.g., ALK mutants) (e.g., a protein or a peptide fragment, especially those of downstream signaling components). In other embodiments, tyrosine kinase activity can be measured using a universal tyrosine kinase activity kit (for example, Universal Tyrosine Kinase Assay Kit (Takara Bio, Inc., Madison, Wis.); Tyrosine Kinase Assay Kit (Millipore, Billerica, Mass.)).

In another embodiment, screening methods are provided that involve further determining whether the compound reduces the growth of tumor cells, for instance, tumor cells known to express an activated tyrosine kinase mutation such as a novel biomarker of the present invention listed in Table 1 (e.g., ALK mutants). Various cell lines can be used, which may be selected based on the tissue to be tested that are well known to a skilled artisan (e.g., BA/F3 cells). For example, many cell lines are well characterized, and are used for instance by the United States National Cancer Institute (NCI) in their screening program for new anti-cancer drugs.

Significant and statistically significant tumor cell growth inhibition, such as occurs for greater than about 50% at a dose of 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4.5 µM, 4 µM, 3.5 µM, 3 µM, 2.5 µM, 2 µM, 1.5 µM, 1 µM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, 1 nM or below, is further indicative that the compound is useful for treating neoplastic lesions. An IC$_{50}$ value may be determined and used for comparative purposes. This value is the concentration of drug needed to inhibit tumor cell growth by 50% relative to the control.

These values can further be applied to other criteria. For example, in other embodiments, screening methods provided herein further involve determining whether the test compound induces apoptosis in cultures of tumor cells. Two distinct forms of cell death may be described by morphological and biochemical criteria: necrosis and apoptosis. Necrosis is accompanied by increased permeability of the plasma membrane, whereby the cells swell and the plasma membrane ruptures within minutes. Apoptosis is characterized by membrane blebbing, condensation of cytoplasm, and the activation of endogenous endonucleases.

Apoptosis occurs naturally during normal tissue turnover and during embryonic development of organs and limbs. Apoptosis also can be induced by various stimuli, including cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc.

Test compounds can be screened for induction of apoptosis using cultures of tumor cells maintained under conditions as described above. In some examples of such screening methods, treatment of cells with test compounds involves either pre- or post-confluent cultures and treatment for one to seven days at various concentrations of the test compounds. Apoptotic cells can be measured in both the attached and "floating" portions of the cultures. Both are collected by removing the supernatant, trypsinizing the attached cells, and combining both preparations following a centrifugation wash step (10 minutes, 2000 rpm). Following treatment with a test compound, cultures can be assayed for apoptosis and necrosis, for instance by florescent microscopy following labeling with acridine orange and ethidium bromide. Many methods for measuring apoptotic cells are known to those of ordinary skill in the art; for instance, one method for measuring apoptotic cell number has been described by Duke & Cohen (Curr. Prot. Immuno., Coligan et al., eds., 3.17.1-3.17.1, 1992). For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis. Apoptosis also can be quantified by measuring an increase in DNA fragmentation in cells that have been treated with test compounds. Commercial photometric enzyme immunoassays (EIA) for the quantitative in vitro determination of cytoplasmic histone-associated-DNA-fragments (mono- and oligo-nucleosomes) are available (e.g., Cell Death Detection ELISA, Boehringer Mannheim).

In additional embodiments, screening methods provided herein further include determining whether the test compound decreases tumor metastasis, for example in an animal model of metastasis. Methods for assessing tumor metastasis are known to one of skill in the art (see e.g. Khanna and Hunter, Carcinogenesis 26:513-523, 2005). One model of metastasis involves human-mouse xenografts, in which human cancer cell lines or tissues are transplanted into immunocompromised mice (such as SCID mice or nude mice). In similar methods, a cell line that has been engineered to express a novel biomarker of the present invention listed in Table 1 (e.g., ALK mutants) can be transplanted into an immunocompromised mouse. In one example, tumor cells or cell lines are injected directly into the systemic circulation. The site of injection largely defines the site to which metastases develop in these experimental systems. The most common site of tumor cell injection employed for experimental metastasis models is the lateral tail vein in mice, which results primarily in pulmonary metastases. In contrast, intrasplenic or portal vein injection of tumor cells is the most common site employed for developing metastasis in the liver and intracardiac injection of cells may result in metastases to several sites, including bone. Following injection of tumor cells or other cell lines into the circulation, development of metastases at the site of interest (such as lung) is monitored over a period of days or weeks.

Another model for assessing tumor metastasis utilizes orthotopic transplantation, wherein cancer cells are transplanted to the anatomic location or tissue from which a tumor was derived (for example by direct injection or surgical implantation of tumor fragments). Spontaneous metastases that arise from the orthotopic tumor can be assessed over a period of days or weeks. The ability of a test compound to decrease or prevent tumor metastasis may be assessed by administering a test compound to an animal following injection of tumor cells subcutaneously, intramuscularly, or into the circulation or by orthotopic transplantation. The number, size, or time of development of metastases may be assessed. A compound that inhibits tumor metastasis may decrease the number of metastases, for example by at least 10%, at least 20%, at least 30%, at least 40%, at least 50%, at least 55%, at least 60%, at least 65%, at least 70%, at least 75%, at least 80%, at least 85%, at least 90%, at least 95%, or even 100% as compared to a control sample. A compound that inhibits tumor metastasis may also decrease the size of metastases as compared to a control sample. Similarly, a compound that inhibits tumor metastasis may delay the onset of development of metastases, for example by at least one week, two weeks, one month, six months, one year, or even indefinitely.

VII. Exemplary ALK Inhibitors

The methods disclosed herein include identifying a subject as a candidate for treatment with an inhibitor of a novel biomarker of the present invention listed in Table 1 (e.g., ALK mutants) to induce tumor cell death, reduce tumor growth, or decrease risk of tumor metastasis. Inhibitors of ALK polypeptides are known to one of skill in the art. For example, PF-02341066, PDD, 2-methyl-11-(2-methylpropyl)-4-oxo-4,5,6,11,12,13-hexahydro-2H-indazolo[5,4-a]pyrrolo[3,4-c]carbazol-8-yl[4-(dimethylamino)benzyl]carbamate, (1S,2S,3R,4R)-3-({5-chloro-2-[(1-ethyl-2,3,4,5-tetrahydro-6-methoxy-2-oxo-1H-1-benzazepin-7-yl)amino]-4-pyrimidinyl}amino)bicyclo[2.2.1]hept-5-ene-2-carboxamide, and NVP-TAE684 9 see, for example, PNAS 104:270-275, 2007; Choi, Y. L. et al. (2008) *Cancer Res.* 68:4971-2976; and *Biochemistry* 48:3600-3609, 2009, which are hereby incorporated by reference).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EXEMPLIFICATION

This invention is further illustrated by the following examples which should not be construed as limiting. The contents of all references, figures, sequence listing, patents and published patent applications cited throughout this application are hereby incorporated by reference.

Example 1

Materials and Methods for Examples 2-4 a. DNA Sequencing

Oligo(dT)-primed cDNAs were generated from specimen RNAs extracted with the use of the EZ1 system (Qiagen, Valencia, Calif.) and were subjected to the polymerase chain reaction (PCR) of 30 cycles (consisting of 98° C. for 10 s and 68° C. for 1 min) with PrimeSTAR HS DNA polymerase (Takara Bio Inc., Shiga, Japan) and the primers ALK-TK-F (5'-TACAACCCCAACTACTGCTTTGCT-3') and ALK-TK-R1 (5'-AGGCACTTTCTCTTCCTCTTCCAC-3'). The PCR products corresponding to the kinase domain of ALK were then fragmented and sequenced with an Illumina Genome Analyzer II (GAII) for 76 bases from both ends by the paired-end sequencing system (Illumina, San Diego, Calif.). Raw read data were quality-filtered on the basis of the presence of the PCR primer sequences and a Q value of ≥20 for all bases. The filter-passed reads were then aligned to the ALK cDNA sequence with the use of the Bowtie algorithm (available on the world wide web at bowtie-bio.sourceforge.net/index.shtml).

For capillary sequencing with a 3130x1 Genetic Analyzer (Applied Biosystems, Foster City, Calif.), PCR products were prepared from cDNAs with the same primer set or with the combination of the EA-F-g-S (5'-CCACACCTGGGAAAG-GACCTAAAG-3') and ALK-TK-R2 (5'-CCTCCAAATACT-GACAGCCACAGG-3') primers.

b. Mutant EML4-ALK

A cDNA encoding FLAG epitope-tagged EML4-ALK variant 1 (Soda™, M. et al. (2007) Nature 448:561-566) was inserted into the pMX-iresCD8 retroviral vector (Yamashita Y. et al. (2001) J. Biol. Chem. 276:39012-39020) for simultaneous expression of FLAG-tagged EML4-ALK and mouse CD8. Nucleotide changes corresponding to the C1156Y and L1196M mutations of ALK were introduced into the plasmid individually or in combination for expression of EML4-ALK (C1156Y), EML4-ALK(L1196M), or EML4-ALK(C1156Y/L1196M). Recombinant retroviruses based on these plasmids were generated with the use of the packaging cell line, BOSC23 (Pear, W. S. et al. (1993) Proc. Natl. Acad. Sci. USA 90:8392-8396), and were used to infect the mouse interleukin-3-dependent cell line BA/F3 (Palacious, R. et al. (1985) Cell 41:727-734). The resulting CD8-positive cells were purified with the use of a miniMACS cell separation column and magnetic beads conjugated with antibodies to CD8 (both from Miltenyi Biotec, Gladbach, Germany). PF-02341066 was obtained from Selleck.

For examination of the tyrosine phosphorylation of EML4-ALK, BA/F3 cells expressing the fusion protein were exposed to ALK inhibitors for 15 h, after which EML4-ALK was immunoprecipitated from cell lysates with antibodies to FLAG (Sigma-Aldrich, St. Louis, Mo.) and subjected to immunoblot analysis with antibodies to $Tyr^{1604}$-phosphorylated ALK (Cell Signaling Technology, Danvers, Mass.). An in vitro kinase assay was performed at room temperature for 30 min as described previously (Donella-Deana, A. et al. (2005) Biochemistry 44:8533-8542) with the synthetic YFF peptide (Operon Biotechnologies, Huntsville, Ala.).

Example 2

Novel ALK Mutations Associated with Resistance to ALK Tyrosine Kinase Inhibitors The patient was a 28-year-old man without a history of smoking, and was diagnosed with lung adenocarcinoma at a clinical stage of T4N3M1 in April 2008. Given that the tumor did not harbor any EGFR mutations, the patient was treated by conventional chemotherapy, which resulted in disease progression with the formation of multiple metastases in the brain and bone. In November 2008, the presence of mRNA for EML4-ALK variant 1 in the tumor was confirmed by reverse transcription-PCR analysis of sputum as well as by fluorescence in situ hybridization analysis of a biopsy specimen. The patient was thus enrolled in a trial of PF-02341066 and experienced a marked improvement in his performance status (reduction from level 4 to 2). Although he showed a "partial response" to the treatment, his pleural effusion was not totally eradicated. After 5 months of treatment, however, the tumor abruptly started to grow again, resulting in an increase in pleural effusion and in the formation of multiple cancer nodules in both lungs. The patient was dropped from the trial in May 2009, and pleural effusion was then obtained for molecular analysis.

Given that the tumor resumed growth despite sustained administration of the ALK inhibitor, it was determined whether the tumor acquired secondary genetic changes conferring resistance to the drug. Furthermore, given that resistance to TKIs often results from acquired mutations within the target kinases, the possibility that EML4-ALK itself had undergone amino acid changes was examined.

Sputum (ID J-#1) and pleural effusion (ID J-#113) specimens were available for molecular analysis of the patient's tumor before and after treatment, respectively. Given that the proportion of tumor cells in the two specimens may have differed, a next-generation sequencer was used to perform deep sequencing of EML4-ALK cDNAs derived from these specimens. The cDNAs corresponding to the tyrosine kinase domain of ALK were thus amplified from both specimens (FIG. 1A), fragmented, and subjected to nucleotide sequencing with the GAII system. For comparison, the EML4-ALK-positive NSCLC cell line, H2228, and three other clinical specimens also positive for the fusion protein were similarly analyzed. A known single nucleotide polymorphism, rs3795850, was detected in the cDNAs from the four specimens (FIG. 1B). In addition, a T→C change at a position corresponding to nucleotide 4230 of human wild-type ALK cDNA (GenBank accession number, NM_004304) was detected at a low frequency (8.9%) in the J-#1 cDNAs. Furthermore, two novel alterations, G→A and C→A changes at positions corresponding to nucleotides 4374 and 4493 of wild-type ALK cDNA, were detected at frequencies of 41.8 and 14.0%, respectively, in the J-#113 cDNAs. There were no other recurrent alterations (present in ≥5% of reads) in the kinase-domain cDNAs derived from any of the specimens.

These nucleotide changes were subsequently confirmed using a Sanger sequencer. To exclude the possibility that the mutations had occurred in endogenous wild-type ALK rather than in EML4-ALK, PCR was also performed with a forward primer targeted to EML4 cDNA so that only the fusion cDNA would be amplified (FIG. 1A). The T4230C change was not detected among hundreds of fusion cDNAs derived from J-#1, indicating that it was an artifact that arose in the initial PCR or the GAII sequencing step.

Figure 2:
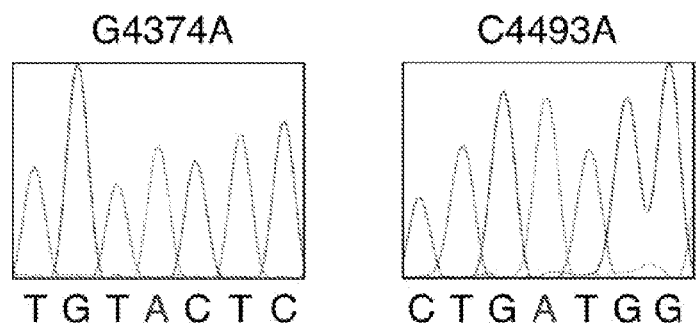
FIG. 2 depicts genomic sequences surrounding the positions corresponding to G4374 and C4493 of ALK cDNA. Genomic DNA isolated from cells in the pleural effusion of the patient was subjected to PCR for 35 cycles of 94° C. for 15 s, 60° C. for 30 s and 68° C. for 2 min, with Platinum Taq DNA polymerase (Invitrogen, Carlsbad, Calif.) and the following primers (5'-GGTAAGAAGTGGCTCACTCTTGAG-3' and 5'-CACAACAACTGCAGCAAAGACTGG-3'), and the products were ligated into the pT7Blue-2 plasmid (Takara Bio). Inserts of the plasmids were then sequenced with the 3130x1 Genetic Analyzer, resulting in the identification of PCR clones containing the G4374A (left panel) or C4493A (right panel) changes. Substituted A nucleotides are shown in red.

However, both the G4374A and C4493A changes were readily confirmed by Sanger sequencing. Among 73 fusion cDNA clones sequenced for J-#113, 34 clones (46.6%) were positive for G4374A, 11 (15.1%) were positive for C4493A, and the remainder (38.4%) were wild type (FIG. 1C). Whereas the PCR analysis covered both nucleotide positions in the same products, none of the products contained both mutations, indicating that each mutation occurred independently. Genomic fragments encompassing the G4374 or C4493 positions were also amplified by PCR and subjected to nucleotide sequencing, resulting in confirmation of each change in the tumor genome (FIG. 2).

The G4374A and C4493A substitutions result in Cys→Tyr and Leu→Met changes at the positions corresponding to amino acids 1156 and 1196, respectively, of wild-type human ALK.

Example 3

Novel ALK Mutations Confer Resistance to ALK Tyrosine Kinase Inhibitors

Figure 3:
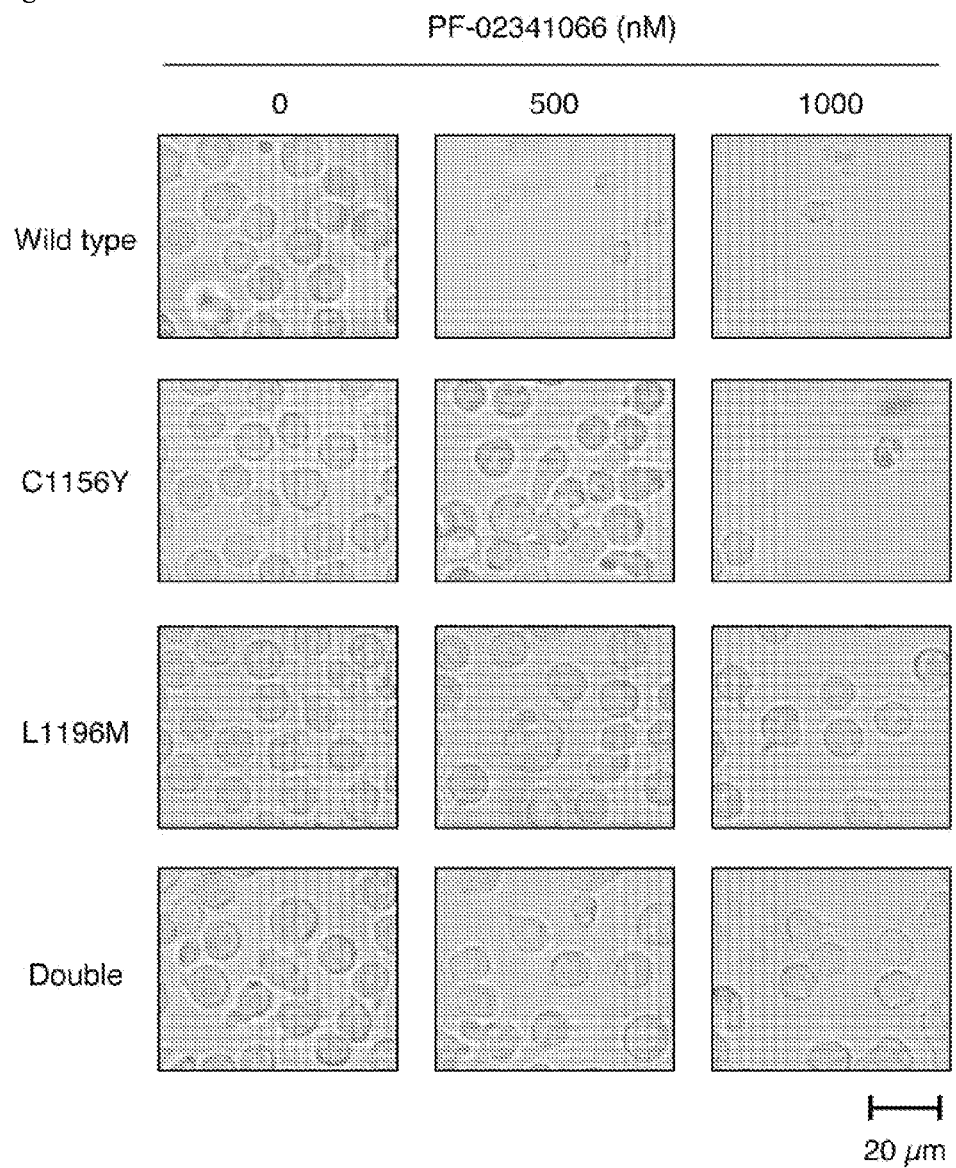
FIG. 3 depicts the results of BA/F3 cells treated with PF-02341066. BA/F3 cells expressing EML4-ALK (wild type), EML4-ALK(C1156Y), EML4-ALK(L1196M), or the double mutant EML4-ALK(C1156Y/L1196M) were incubated in the presence of the indicated concentrations of PF-02341066 for 48 h, after which cell morphology was examined by phase-contrast microscopy. Scale bar, 20 µm.
Figure 4:
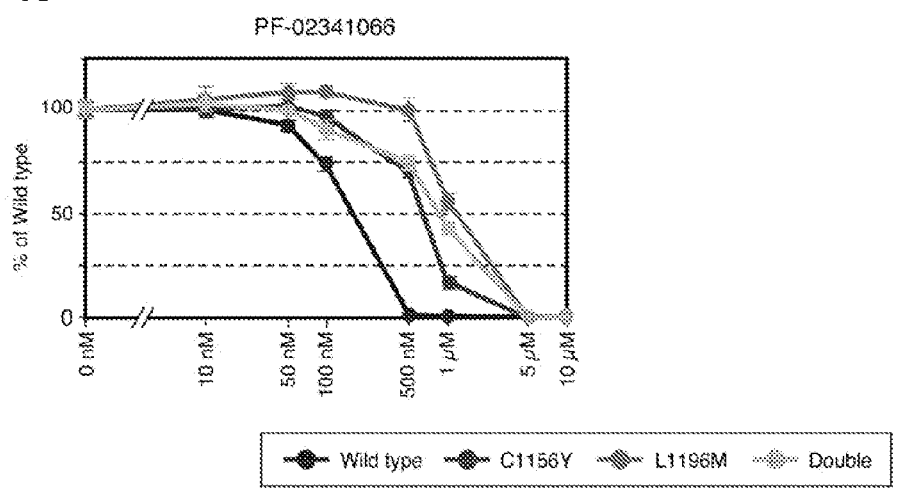
FIG. 4 depicts properties of novel ALK mutations of the present invention associated with resistance to ALK tyrosine kinase inhibitors.
Figure 4:
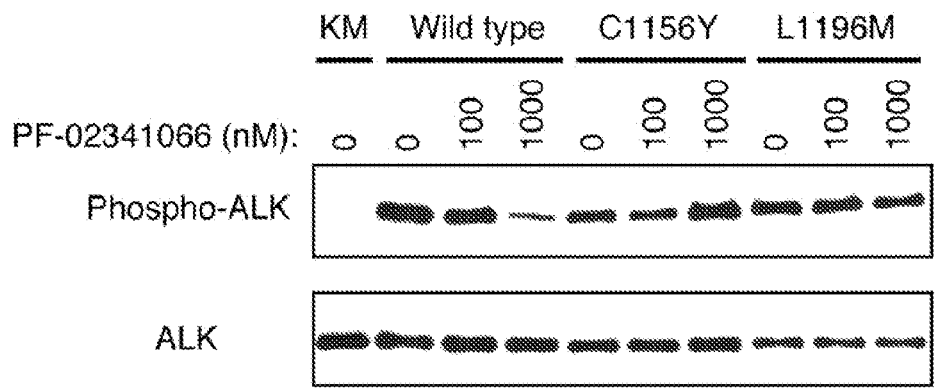
Figure 4:
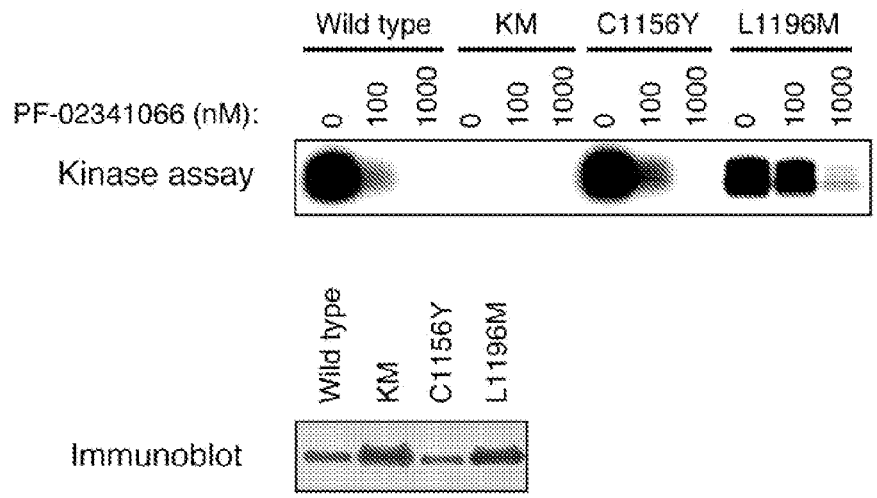

It was next examined whether such amino acid changes affect the sensitivity of EML4-ALK to ALK inhibitors. Wild-type EML4-ALK, the single mutants EML4-ALK(C1156Y) and EML4-ALK(L1196M), and the double mutant EML4-ALK(C1156Y/L1196M) were expressed individually in BA/F3 cells, and the cells were then exposed to ALK inhibitors. PF-02341066 inhibited in a concentration-dependent manner the growth of BA/F3 cells expressing wild-type EML4-ALK (FIG. 4A). In contrast, cells expressing either C1156Y or L1196M mutants manifested a markedly reduced sensitivity to this drug, with repeated experiments showing that BA/F3 cells expressing EML4-ALK(L1196M) were more resistant to PF-02341066 than were those expressing EML4-ALK(C1156Y) (FIG. 3). The presence of both mutations did not result in an additive effect on the resistance of cells to PF-02341066. These data thus showed that C1156Y and L1196M mutations each confer resistance to this drug.

Tyrosine phosphorylation of EML4-ALK was examined by immunoblot analysis with antibodies specific for ALK phosphorylated at Tyr1604. Although exposure of BA/F3 cells to PF-02341066 markedly inhibited the tyrosine phosphorylation of wild-type EML4-ALK, it had no substantial effect on that of EML4-ALK(C1156Y) or EML4-ALK (L1196M) (FIG. 4B). Consistent with these findings, an in vitro kinase assay revealed that the C1156Y and L1196M mutants of EML4-ALK were less sensitive to inhibition of enzymatic activity by PF-02341066 than was the wild-type protein (FIG. 4C). As was the case for inhibition of cell growth (FIG. 4A), the L1196M mutant was more refractory to inhibition of kinase activity by PF-02341066 than was the C1156Y mutant (FIG. 4C).

Example 4

Figure 5:
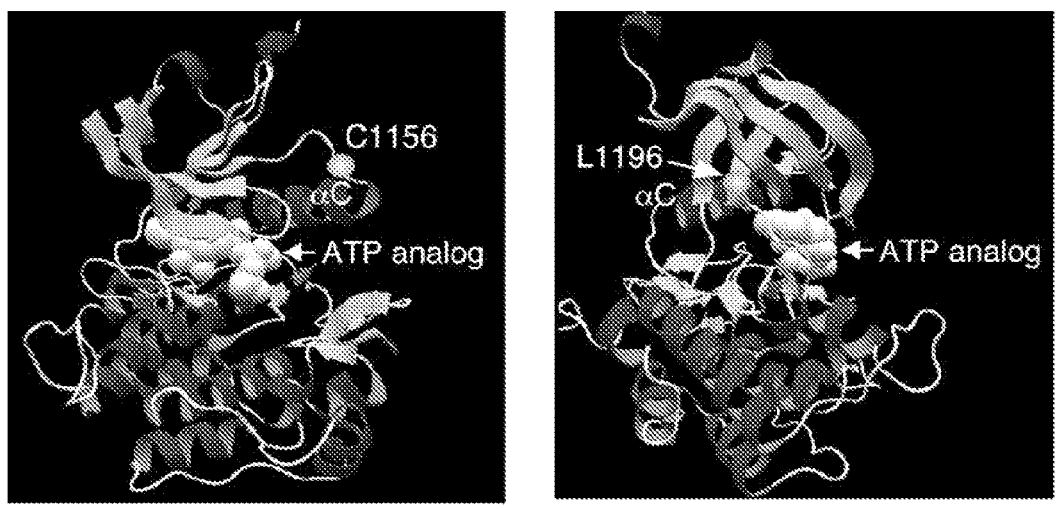
FIG. 5 depicts a three-dimensional structure model for the kinase domain of ALK. Amino acid positions of ALK were superimposed on the crystal structure of the insulin receptor with a bound ATP analog (ID "1ir3" in the Protein Data Bank of Japan, available on the world wide web at pdbj.org/index.html). The right panel shows the protein structure observed from the left side of the model in the left panel. The α helices and β sheets are shown in magenta and orange, respectively. The positions of helix αC, Cys$^{1156}$, and Leu$^{1196}$ are also indicated.

Structure-Function Relationships Between Novel ALK Mutations and Resistance to ALK Tyrosine Kinase Inhibitors FIG. 5 shows the positions of Cys1156 and Leu1196 in a three-dimensional structural model of the kinase domain of ALK based on the crystal structure of a related kinase, the insulin receptor. The former residue is positioned adjacent to the amino-terminus of the predicted helix αC as well as close to the upper lid of the ATP-binding pocket. No activating mutations have been reported at this position in other tyrosine kinases. Leu1196 of ALK corresponds to Thr315 of ABL1 and Thr790 of EGFR, each of which is the site of the most frequent acquired mutations that confer resistance to TKIs in these kinases (Deininger, M. et al. (2005) Blood 105:2640-2653; Linardou, H. et al. (2009) Nat. Rev. Clin. Oncol. 6:352-366). This "gatekeeper" site is located at the bottom surface of the ATP-binding pocket (FIG. 5), and the presence of an amino acid with a bulky side chain at this position is known to interfere with the binding of many TKIs (Shah, N. P. et al. (2002) Cancer Cell 2:117-125; Tsao, M. S. et al. (2005) N. Engl. J. Med. 353:133-144).

Thus, two de novo mutations within the kinase domain of EML4-ALK that confer resistance to multiple ALK inhibitors were identified. Given that no EML4-ALK cDNAs were observed harboring both mutations, it is believed that each mutation developed independently in distinct subclones of the tumor.

Without being bound by theory, given that cDNAs prepared from sputum of the patient before treatment did not contain nucleotide changes corresponding to the C1156Y or L1196M mutations, it is likely that the tumor subclones acquired the mutations de novo during treatment with PF-02341066. However, because pleural effusion could not be examined before treatment, the possibility that tumor cells harboring the C1156Y or L1196M mutants were already present in pleural effusion on initial admission of the patient cannot be completely excluded. If this were the case, the tumor might have acquired other, as yet unknown mutations during the 5-month period of treatment with PF-02341066 that allowed its subsequent rapid growth. However, the subclones of tumor cells with the C1156Y or L1196M mutations should have been refractory to the initial treatment and should have expanded during the treatment course. On the contrary, there were no signs of tumor expansion in the patient for at least 5 months, indicating that the C1156Y and L1196M mutations developed during treatment with PF-02341066. This notion is further supported by the fact that the T790M mutation of EGFR that confers resistance to gefitinib or erlotinib is frequently detected in patients previously treated with TKIs but rarely found in untreated individuals (Pao, W. et al. (2005) PLoS Med. 2:e73).

Amino acid substitutions at the gatekeeper position of several tyrosine kinases have been detected in tumors treated with TKIs (Kobayashi, S. et al. (2005) N. Engl. J. Med. 352:786-792; Pao, W. et al. (2005) PLoS Med. 2:e73; Shah, N. P. et al. (2002) Cancer Cell 2:117-125; Cools, J. et al. (2003) N. Engl. J. Med. 348:1201-1214; Tamborini, E. et al. (2004) Gastroenterology 127:294-299). Whereas no mutations at this site have previously been reported for EML4-ALK or ALK, the effects of various artificial amino acid substitutions at the gatekeeper position of NPM-ALK, another fusion-type oncokinase for ALK, were recently examined (Lu, L. et al. (2009) Biochemistry 48:3600-3609). Consistent with the present analysis of tumor cells in vivo, introduction of Met at this position was found to render NPM-ALK most resistant to multiple ALK inhibitors.

In contrast to gatekeeper substitutions, activating mutations at the position immediately amino-terminal to the αC helix (Cys1156 in ALK) have not been reported for other tyrosine kinases. Whereas a Thr→Ile change at the corresponding position of EGFR was described in one NSCLC case, its relevance to drug sensitivity was not examined (Tsao, M. S. et al. (2005) N. Engl. J. Med. 353:133-144). The importance of helix αC for allosteric regulation of enzymatic activity has been demonstrated for serine-threonine kinases (Hindie, V. et al. (2009) Nat. Chem. Biol. 5:758-764). A change at Cys1156 of ALK might therefore interfere allosterically with TKI binding, or Cys1156 might be directly involved in the physical interaction between the kinase domain and TKIs.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method for identifying a subject who has cancer or who is at risk for developing cancer as having an increased risk of unresponsiveness to treatment with an ALK inhibitor, comprising:
   collecting a sample from a subject who has cancer or who is at risk for developing cancer; and
   detecting in said sample the presence of a mutant ALK polynucleotide molecule comprising a C4493A ALK polynucleotide mutation by contacting nucleic acids from the sample with a nucleic acid probe comprising a nucleic acid sequence complementary to the C4493A ALK polynucleotide mutation and further comprising a detectable label, wherein the probe is capable of hybridizing to the mutant ALK polynucleotide in 6× sodium chloride/sodium citrate (SSC) at about 45° C., followed by one or more washes in 0.2×SSC, 0.1% SDS at 50-65° C.

2. The method of claim 1, wherein the subject has not previously been treated with an ALK inhibitor, or has been previously treated with an ALK inhibitor and has developed at least partial resistance to the ALK inhibitor.

3. The method of claim 1, wherein the cancer is selected from the group consisting of anaplastic large cell lymphoma, neuroblastoma, breast cancer, colorectal cancer, inflammatory myofibroblastic tumors, and non-small cell lung cancers.

4. The method of claim 2, wherein the subject has been previously treated with an ALK inhibitor and has developed at least partial resistance to the ALK inhibitor; and the ALK inhibitor is selected from the group consisting of PF-02341066, PDD, 2-methyl-11-(2-methylpropyl)-4-oxo-4,5,6,11,12,13-hexahydro-2H-indazolo[5,4-a]pyrrolo[3,4-c]

carbazol-8-yl[4-(dimethylamino)benzyl]carbamate, (1S,2S,3R,4R)-3-({5-chloro-2-[(1-ethyl-2,3,4,5-tetrahydro-6-methoxy-2-oxo-1H-1-benzazepin-7-yl)amino]-4-pyrimidinyl}amino)bicyclo[2.2.1]hept-5-ene-2-carboxamide, and NVP-TAE684.

5. The method of claim 1, wherein the sample is selected from the group consisting of sputum, bronchoalveolar lavage, pleural effusion, tissue, whole blood, serum, plasma, buccal scrape, saliva, cerebrospinal fluid, urine, stool, circulating tumor cells, circulating nucleic acids, and bone marrow.

6. The method of claim 5, wherein the sample is tissue; and the tissue is a tumor or cancer tissue.

7. The method of claim 1, wherein the sample comprises cells.

8. The method of claim 1, wherein a polymerase chain reaction is performed on the nucleic acids from the sample.

9. The method of claim 1, wherein the ALK mutation is assessed at a first point in time and at least one subsequent point in time.

10. The method of claim 1, wherein the sample comprises germline or somatic genomic DNA.

11. The method of claim 1, wherein the detectable label is a radioisotope, a fluorescent compound, an enzyme, or an enzyme cofactor.

12. The method of claim 1, wherein the nucleic acid probe is a molecular beacon.

13. The method of claim 1, further comprising detecting the presence of a mutant ALK polynucleotide molecule comprising a G4374A ALK polynucleotide mutation by contacting nucleic acids from the sample with a nucleic acid probe comprising a nucleic acid sequence complementary to the G4374A ALK polynucleotide mutation and further comprising a detectable label, wherein the probe is capable of hybridizing to the mutant ALK polynucleotide comprising the G4374A ALK polynucleotide mutation in 6× sodium chloride/sodium citrate (SSC) at about 45° C., followed by one or more washes in 0.2×SSC, 0.1% SDS at 50-65° C.

* * * * *

SEQUENCE LISTING

<160> NUMBER OF SEQ ID NOS: 40

<210> SEQ ID NO 1
<211> LENGTH: 6222
<212> TYPE: DNA
<213> ORGANISM: Homo sapiens

<400> SEQUENCE: 1

```
gggggcggca gcggtggtag cagctggtac ctcccgccgc ctctgttcgg agggtcgcgg      60
ggcaccgagg tgctttccgg ccgccctctg gtcggccacc caaagccgcg ggcgctgatg     120
atgggtgagg aggggggcggc aagatttcgg gcgcccctgc cctgaacgcc ctcagctgct     180
gccgccgggg ccgctccagt gcctgcgaac tctgaggagc cgaggcgccg gtgagagcaa     240
ggacgctgca aacttgcgca gcgcggggc tgggattcac gcccagaagt tcagcaggca     300
gacagtccga agccttcccg cagcggagag atagcttgag ggtgcgcaag acggcagcct     360
ccgccctcgg ttcccgccca gaccgggcag aagagcttgg aggagccaaa aggaacgcaa     420
aaggcggcca ggacagcgtg cagcagctgg gagccgccgt tctcagcctt aaaagttgca     480
gagattggag gctgccccga gaggggacag accccagctc cgactgcggg gggcaggaga     540
ggacggtacc caactgccac ctcccttcaa ccatagtagt tcctctgtac cgagcgcagc     600
gagctacaga cggggggcgcg gcactcggcg cggagagcgg gaggctcaag gtcccagcca     660
gtgagcccag tgtgcttgag tgtctctgga ctcgcccctg agcttccagg tctgtttcat     720
ttagactcct gctcgcctcc gtgcagttgg gggaaagcaa gagacttgcg cgcacgcaca     780
gtcctctgga gatcaggtgg aaggagccgc tgggtaccaa ggactgttca gagcctcttc     840
ccatctcggg gagagcgaag ggtgaggctg ggcccggaga gcagtgtaaa cggcctcctc     900
cggcgggatg ggagccatcg ggctcctgtg gctcctgccg ctgctgcttt ccacggcagc     960
tgtgggctcc gggatgggga ccggccagcg cgcgggctcc ccagctgcgg ggccgccgct    1020
gcagccccgg gagccactca gctactcgcg cctgcagagg aagagtctgg cagttgactt    1080
cgtggtgccc tcgctcttcc gtgtctacgc ccgggaccta ctgctgccac catcctcctc    1140
ggagctgaag gctggcaggc ccgaggcccg cggctcgcta gctctggact gcgccccgct    1200
gctcaggttg ctggggccgg cgccgggggt ctcctggacc gccggttcac cagcccccggc    1260 agaggcccgg acgctgtcca gggtgctgaa gggcggctcc gtgcgcaagc tccggcgtgc    1320
caagcagttg gtgctggagc tgggcgagga ggcgatcttg gagggttgcg tcgggccccc    1380
cggggaggcg gctgtgggc tgctccagtt caatctcagc gagctgttca gttggtggat    1440
tcgccaaggc gaagggcgac tgaggatccg cctgatgccc gagaagaagg cgtcggaagt    1500
gggcagagag ggaaggctgt ccgcggcaat tgcgcctcc cagccccgcc ttctcttcca    1560
gatcttcggg actggtcata gctccttgga atcaccaaca aacatgcctt ctccttctcc    1620
tgattatttt acatggaatc tcacctggat aatgaaagac tccttcccttt tcctgtctca    1680 tcgcagccga tatggtctgg agtgcagctt tgacttcccc tgtgagctgg agtattcccc    1740
tccactgcat gacctcagga accagagctg gtcctggcgc cgcatcccct ccgaggaggc    1800
```

```
ctcccagatg gacttgctgg atgggcctgg ggcagagcgt tctaaggaga tgcccagagg   1860
ctcctttctc cttctcaaca cctcagctga ctccaagcac accatcctga gtccgtggat   1920
gaggagcagc agtgagcact gcacactggc cgtctcggtg cacaggcacc tgcagccctc   1980
tggaaggtac attgcccagc tgctgcccca caacgaggct gcaagagaga tcctcctgat   2040
gcccactcca gggaagcatg gttggacagt gctccaggga agaatcgggc gtccagacaa   2100
cccatttcga gtggccctgg aatacatctc cagtggaaac cgcagcttgt ctgcagtgga   2160
cttctttgcc ctgaagaact gcagtgaagg aacatcccca ggctccaaga tggccctgca   2220
gagctccttc acttgttgga atgggacagt cctccagctt gggcaggcct gtgacttcca   2280
ccaggactgt gcccagggag aagatgagag ccagatgtgc cggaaactgc ctgtgggttt   2340
ttactgcaac tttgaagatg gcttctgtgg ctggacccaa ggcacactgt caccccacac   2400
tcctcaatgg caggtcagga ccctaaagga tgcccggttc caggaccacc aagaccatgc   2460
tctattgctc agtaccactg atgtccccgc ttctgaaagt gctacagtga ccagtgctac   2520
gtttcctgca ccgatcaaga gctctccatg tgagctccga atgtcctggc tcattcgtgg   2580
agtcttgagg ggaaacgtgt ccttggtgct agtggagaac aaaaccggga aggagcaagg   2640
caggatggtc tggcatgtcg ccgcctatga aggcttgagc ctgtggcagt ggatggtgtt   2700
gcctctcctc gatgtgtctg acaggttctg gctgcagatg gtcgcatggt ggggacaagg   2760
atccagagcc atcgtggctt ttgacaatat ctccatcagc ctggactgct acctcaccat   2820
tagcggagag gacaagatcc tgcagaatac agcacccaaa tcaagaaacc tgtttgagag   2880
aaacccaaac aaggagctga acccggggga aaattcacca agacagaccc ccatctttga   2940
ccctacagtt cattggctgt tcaccacatg tgggggccagc gggccccatg gccccaccca   3000
ggcacagtgc aacaacgcct accagaactc caacctgagc gtggaggtgg ggagcgaggg   3060
ccccctgaaa ggcatccaga tctgaaggt gccagccacc gacacctaca gcatctcggg   3120
ctacggagct gctggcggga aaggcgggaa gaacaccatg atgcggtccc acggcgtgtc   3180
tgtgctgggc atcttcaacc tggagaagga tgacatgctg tacatcctgg ttgggcagca   3240
gggagaggac gcctgcccca gtacaaacca gttaatccag aaagtctgca ttggagagaa   3300
caatgtgata gaagaagaaa tccgtgtgaa cagaagcgtg catgagtggg caggaggcgg   3360
aggaggaggg ggtggagcca cctacgtatt taagatgaag gatggagtgc cggtgcccct   3420
gatcattgca gccggaggtg gtggcagggc ctacggggcc aagacagaca cgttccaccc   3480
agagagactg gagaataact cctcggttct agggctaaac ggcaattccg gagccgcagg   3540
tggtggaggt ggctggaatg ataacacttc cttgctctgg gccggaaaat ctttgcagga   3600
gggtgccacc ggaggacatt cctgccccca ggccatgaag aagtgggggt gggagacaag   3660
aggggggttc ggaggggtg gaggggggtg ctcctcaggt ggaggaggcg gaggatatat   3720
aggcggcaat gcagcctcaa acaatgaccc cgaaatggat ggggaagatg gggtttcctt   3780
catcagtcca ctgggcatcc tgtacacccc agctttaaaa gtgatggaag ccacggggga   3840
agtgaatatt aagcattatc taaactgcag tcactgtgag gtagacgaat gtcacatgga   3900
ccctgaaagc cacaaggtca tctgcttctg tgaccacggg acggtgctgg ctgaggatgg   3960
cgtctcctgc attgtgtcac ccaccccgga gccacacctg ccactctcgc tgatcctctc   4020
tgtggtgacc tctgccctcg tggccgccct ggtcctggct ttctccggca tcatgattgt   4080
gtaccgccgg aagcaccagg agctgcaagc catgcagatg gagctgcaga gccctgagta   4140
```

```
caagctgagc aagctccgca cctcgaccat catgaccgac tacaaccccca actactgctt    4200 tgctggcaag acctcctcca tcagtgacct gaaggaggtg ccgcggaaaa acatcaccct    4260
cattcggggt ctgggccatg gcgcctttgg ggaggtgtat gaaggccagg tgtccggaat    4320
gcccaacgac ccaagccccc tgcaagtggc tgtgaagacg ctgcctgaag tgtgctctga    4380
acaggacgaa ctggatttcc tcatggaagc cctgatcatc agcaaattca accaccagaa    4440
cattgttcgc tgcattgggg tgagcctgca atccctgccc cggttcatcc tgctggagct    4500
catggcgggg ggagacctca agtccttcct ccgagagacc cgccctcgcc cgagccagcc    4560
ctcctccctg gccatgctgg accttctgca cgtggctcgg acattgcct gtggctgtca    4620 gtatttggag gaaaaccact tcatccaccg agacattgct gccagaaact gcctcttgac    4680
ctgtccaggc cctggaagag tggccaagat tggagacttc gggatggccc gagacatcta    4740
cagggcgagc tactatagaa agggaggctg tgccatgctg ccagttaagt ggatgccccc    4800
agaggccttc atggaaggaa tattcacttc taaaacagac acatggtcct ttggagtgct    4860
gctatgggaa atctttttctc ttggatatat gccataccc agcaaaagca accaggaagt    4920
tctggagttt gtcaccagtg gaggccggat ggacccaccc aagaactgcc ctgggcctgt    4980
ataccggata atgactcagt gctggcaaca tcagcctgaa gacaggccca actttgccat    5040
cattttggag aggattgaat actgcaccca ggacccggat gtaatcaaca ccgctttgcc    5100
gatagaatat ggtccacttg tggaagagga agagaaagtg cctgtgaggc ccaaggaccc    5160
tgagggggtt cctcctctcc tggtctctca acaggcaaaa cgggaggagg agcgcagccc    5220
agctgcccca ccacctctgc ctaccacctc ctctggcaag gctgcaaaga acccacagc    5280 tgcagagatc tctgttcgag tccctagagg gccggccgtg aaggggggac acgtgaatat    5340
ggcattctct cagtccaacc ctccttcgga gttgcacaag gtccacggat ccagaaacaa    5400
gcccaccagc ttgtggaacc caacgtacgg ctcctggttt acagagaaac ccaccaaaaa    5460
gaataatcct atagcaaaga aggagccaca cgacaggggt aacctggggc tggagggaag    5520
ctgtactgtc ccacctaacg ttgcaactgg gagacttccg ggggcctcac tgctcctaga    5580
gccctcttcg ctgactgcca atatgaagga ggtacctctg ttcaggctac gtcacttccc    5640
ttgtgggaat gtcaattacg gctaccagca acagggcttg cccttagaag ccgctactgc    5700
ccctggagct ggtcattacg aggataccat tctgaaaagc aagaatagca tgaaccagcc    5760
tgggccctga gctcggtcgc acactcactt ctcttccttg ggatccctaa gaccgtggag    5820
gagagagagg caatggctcc ttcacaaacc agagaccaaa tgtcacgttt tgttttgtgc    5880
caacctattt tgaagtacca ccaaaaaagc tgtatttga aaatgcttta gaaaggtttt    5940
gagcatgggt tcatcctatt ctttcgaaag aagaaaatat cataaaaatg agtgataaat    6000
acaaggccca gatgtggttg cataaggttt ttatgcatgt ttgttgtata cttccttatg    6060
cttctttcaa attgtgtgtg ctctgcttca atgtagtcag aattagctgc ttctatgttt    6120
catagttggg gtcatagatg tttccttgcc ttgttgatgt ggacatgagc catttgaggg    6180
gagagggaac ggaaataaag gagttatttg taatgactaa aa                       6222
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 2
ggtaagaagt ggctcactct tgag                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cacaacaact gcagcaaaga ctgg                                          24

<210> SEQ ID NO 4
<211> LENGTH: 1620
<212> TYPE: PRT
<213> ORGANISM: Homo sapiens

<400> SEQUENCE: 4
```

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

```
Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
        675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
```

```
            705                 710                 715                 720
        Lys Gly Ile Gln Ile Trp Lys Val Pro Ala Thr Asp Thr Tyr Ser Ile
                        725                 730                 735

Ser Gly Tyr Gly Ala Ala Gly Lys Gly Gly Lys Asn Thr Met Met
                        740                 745                 750

Arg Ser His Gly Val Ser Val Leu Gly Ile Phe Asn Leu Glu Lys Asp
                        755                 760                 765

Asp Met Leu Tyr Ile Leu Val Gly Gln Gln Gly Glu Asp Ala Cys Pro
                        770                 775                 780

Ser Thr Asn Gln Leu Ile Gln Lys Val Cys Ile Gly Glu Asn Asn Val
        785                 790                 795                 800

Ile Glu Glu Glu Ile Arg Val Asn Arg Ser Val His Glu Trp Ala Gly
                        805                 810                 815

Gly Gly Gly Gly Gly Gly Ala Thr Tyr Val Phe Lys Met Lys Asp
                        820                 825                 830

Gly Val Pro Val Pro Leu Ile Ile Ala Ala Gly Gly Gly Arg Ala
                        835                 840                 845

Tyr Gly Ala Lys Thr Asp Thr Phe His Pro Glu Arg Leu Glu Asn Asn
                        850                 855                 860

Ser Ser Val Leu Gly Leu Asn Gly Asn Ser Gly Ala Ala Gly Gly
        865                 870                 875                 880

Gly Gly Trp Asn Asp Asn Thr Ser Leu Leu Trp Ala Gly Lys Ser Leu
                        885                 890                 895

Gln Glu Gly Ala Thr Gly Gly His Ser Cys Pro Gln Ala Met Lys Lys
                        900                 905                 910

Trp Gly Trp Glu Thr Arg Gly Phe Gly Gly Gly Gly Gly Cys
                        915                 920                 925

Ser Ser Gly Gly Gly Gly Gly Tyr Ile Gly Gly Asn Ala Ala Ser
                        930                 935                 940

Asn Asn Asp Pro Glu Met Asp Gly Glu Asp Gly Val Ser Phe Ile Ser
        945                 950                 955                 960

Pro Leu Gly Ile Leu Tyr Thr Pro Ala Leu Lys Val Met Glu Gly His
                        965                 970                 975

Gly Glu Val Asn Ile Lys His Tyr Leu Asn Cys Ser His Cys Glu Val
                        980                 985                 990

Asp Glu Cys His Met Asp Pro Glu  Ser His Lys Val Ile  Cys Phe Cys
                        995                 1000                1005

Asp His  Gly Thr Val Leu Ala  Glu Asp Gly Val Ser  Cys Ile Val
                1010                1015                1020

Ser Pro  Thr Pro Glu Pro His  Leu Pro Leu Ser Leu  Ile Leu Ser
                1025                1030                1035

Val Val  Thr Ser Ala Leu Val  Ala Ala Leu Val Leu  Ala Phe Ser
                1040                1045                1050

Gly Ile  Met Ile Val Tyr Arg  Arg Lys His Gln Glu  Leu Gln Ala
                1055                1060                1065

Met Gln  Met Glu Leu Gln Ser  Pro Glu Tyr Lys Leu  Ser Lys Leu
                1070                1075                1080

Arg Thr  Ser Thr Ile Met Thr  Asp Tyr Asn Pro Asn  Tyr Cys Phe
                1085                1090                1095

Ala Gly  Lys Thr Ser Ser Ile  Ser Asp Leu Lys Glu  Val Pro Arg
                1100                1105                1110

Lys Asn  Ile Thr Leu Ile Arg  Gly Leu Gly His Gly  Ala Phe Gly
                1115                1120                1125
```

```
Glu Val Tyr Glu Gly Gln Val Ser Gly Met Pro Asn Asp Pro Ser
    1130                1135                1140

Pro Leu Gln Val Ala Val Lys Thr Leu Pro Glu Val Cys Ser Glu
    1145                1150                1155

Gln Asp Glu Leu Asp Phe Leu Met Glu Ala Leu Ile Ile Ser Lys
    1160                1165                1170

Phe Asn His Gln Asn Ile Val Arg Cys Ile Gly Val Ser Leu Gln
    1175                1180                1185

Ser Leu Pro Arg Phe Ile Leu Leu Glu Leu Met Ala Gly Gly Asp
    1190                1195                1200

Leu Lys Ser Phe Leu Arg Glu Thr Arg Pro Arg Pro Ser Gln Pro
    1205                1210                1215

Ser Ser Leu Ala Met Leu Asp Leu Leu His Val Ala Arg Asp Ile
    1220                1225                1230

Ala Cys Gly Cys Gln Tyr Leu Glu Glu Asn His Phe Ile His Arg
    1235                1240                1245

Asp Ile Ala Ala Arg Asn Cys Leu Leu Thr Cys Pro Gly Pro Gly
    1250                1255                1260

Arg Val Ala Lys Ile Gly Asp Phe Gly Met Ala Arg Asp Ile Tyr
    1265                1270                1275

Arg Ala Ser Tyr Tyr Arg Lys Gly Gly Cys Ala Met Leu Pro Val
    1280                1285                1290

Lys Trp Met Pro Pro Glu Ala Phe Met Glu Gly Ile Phe Thr Ser
    1295                1300                1305

Lys Thr Asp Thr Trp Ser Phe Gly Val Leu Leu Trp Glu Ile Phe
    1310                1315                1320

Ser Leu Gly Tyr Met Pro Tyr Pro Ser Lys Ser Asn Gln Glu Val
    1325                1330                1335

Leu Glu Phe Val Thr Ser Gly Gly Arg Met Asp Pro Pro Lys Asn
    1340                1345                1350

Cys Pro Gly Pro Val Tyr Arg Ile Met Thr Gln Cys Trp Gln His
    1355                1360                1365

Gln Pro Glu Asp Arg Pro Asn Phe Ala Ile Ile Leu Glu Arg Ile
    1370                1375                1380

Glu Tyr Cys Thr Gln Asp Pro Asp Val Ile Asn Thr Ala Leu Pro
    1385                1390                1395

Ile Glu Tyr Gly Pro Leu Val Glu Glu Glu Lys Val Pro Val
    1400                1405                1410

Arg Pro Lys Asp Pro Glu Gly Val Pro Pro Leu Leu Val Ser Gln
    1415                1420                1425

Gln Ala Lys Arg Glu Glu Glu Arg Ser Pro Ala Ala Pro Pro Pro
    1430                1435                1440

Leu Pro Thr Thr Ser Ser Gly Lys Ala Ala Lys Lys Pro Thr Ala
    1445                1450                1455

Ala Glu Ile Ser Val Arg Val Pro Arg Gly Pro Ala Val Glu Gly
    1460                1465                1470

Gly His Val Asn Met Ala Phe Ser Gln Ser Asn Pro Pro Ser Glu
    1475                1480                1485

Leu His Lys Val His Gly Ser Arg Asn Lys Pro Thr Ser Leu Trp
    1490                1495                1500

Asn Pro Thr Tyr Gly Ser Trp Phe Thr Glu Lys Pro Thr Lys Lys
    1505                1510                1515
```

-continued

| Asn | Asn | Pro | Ile | Ala | Lys | Lys | Glu | Pro | His | Asp | Arg | Gly | Asn | Leu |
| --- | --- | --- | --- | --- | --- | --- | --- | --- | --- | --- | --- | --- | --- | --- |
| | 1520 | | | | 1525 | | | | 1530 | | | | | |

| Gly | Leu | Glu | Gly | Ser | Cys | Thr | Val | Pro | Pro | Asn | Val | Ala | Thr | Gly |
| --- | --- | --- | --- | --- | --- | --- | --- | --- | --- | --- | --- | --- | --- | --- |
| 1535 | | | | | 1540 | | | | | 1545 | | | | |

| Arg | Leu | Pro | Gly | Ala | Ser | Leu | Leu | Leu | Glu | Pro | Ser | Ser | Leu | Thr |
| --- | --- | --- | --- | --- | --- | --- | --- | --- | --- | --- | --- | --- | --- | --- |
| 1550 | | | | | 1555 | | | | | 1560 | | | | |

| Ala | Asn | Met | Lys | Glu | Val | Pro | Leu | Phe | Arg | Leu | Arg | His | Phe | Pro |
| --- | --- | --- | --- | --- | --- | --- | --- | --- | --- | --- | --- | --- | --- | --- |
| 1565 | | | | | 1570 | | | | | 1575 | | | | |

| Cys | Gly | Asn | Val | Asn | Tyr | Gly | Tyr | Gln | Gln | Gln | Gly | Leu | Pro | Leu |
| --- | --- | --- | --- | --- | --- | --- | --- | --- | --- | --- | --- | --- | --- | --- |
| 1580 | | | | | 1585 | | | | | 1590 | | | | |

| Glu | Ala | Ala | Thr | Ala | Pro | Gly | Ala | Gly | His | Tyr | Glu | Asp | Thr | Ile |
| --- | --- | --- | --- | --- | --- | --- | --- | --- | --- | --- | --- | --- | --- | --- |
| 1595 | | | | | 1600 | | | | | 1605 | | | | |

| Leu | Lys | Ser | Lys | Asn | Ser | Met | Asn | Gln | Pro | Gly | Pro |
| --- | --- | --- | --- | --- | --- | --- | --- | --- | --- | --- | --- |
| 1610 | | | | | 1615 | | | | | 1620 | |

<210> SEQ ID NO 5
<211> LENGTH: 3926
<212> TYPE: DNA
<213> ORGANISM: Homo sapiens

<400> SEQUENCE: 5

```
ggcggcgcgg cgcggcgctc gcggctgctg cctgggaggg aggccgggca ggcggctgag      60
cggcgcggct ctcaacgtga cggggaagtg gttcgggcgg ccgcggctta ctaccccagg     120
gcgaacggac ggacgacgga ggcgggagcc ggtagccgag ccgggcgacc tagagaacga     180
gcgggtcagg ctcagcgtcg gccactctgt cggtccgctg aatgaagtgc ccgcccctct     240
gagcccggag cccggcgctt tccccgcaag atggacggtt tcgccggcag tctcgatgat     300
agtatttctg ctgcaagtac ttctgatgtt caagatcgcc tgtcagctct tgagtcacga     360
gttcagcaac aagaagatga aatcactgtg ctaaaggcgg ctttggctga tgttttgagg     420
cgtcttgcaa tctctgaaga tcatgtggcc tcagtgaaaa aatcagtctc aagtaaaggc     480
caaccaagcc ctcgagcagt tattcccatg tcctgtataa ccaatggaag tggtgcaaac     540
agaaaaccaa gtcataccag tgctgtctca attgcaggaa agaaactct ttcatctgct     600
gctaaaagtg gtacagaaaa aaagaaagaa aaaccacaag gacagagaga aaaaaaagag     660
gaatctcatt ctaatgatca aagtccacaa attcgagcat caccttctcc ccagccctct     720
tcacaacctc tccaaataca cagacaaact ccagaaagca agaatgctac tcccaccaaa     780
agcataaaac gaccatcacc agctgaaaag tcacataatt cttgggaaaa ttcagatgat     840
agccgtaata aattgtcgaa aataccttca cacccaaat taataccaaa agttaccaaa     900
actgcagaca agcataaaga tgtcatcatc aaccaagaag gagaatatat taaaatgttt     960
atgcgcggtc ggccaattac catgttcatt ccttccgatg ttgacaacta tgatgacatc    1020
agaacggaac tgcctcctga gaagctcaaa ctggagtggg catatggtta tcgaggaaag    1080
gactgtagag ctaatgttta ccttcttccg accggggaaa tagtttattt cattgcatca    1140
gtagtagtac tatttaatta tgaggagaga actcagcgac actacctggg ccatacagac    1200
tgtgtgaaat gccttgctat acatcctgac aaaattagga ttgcaactgg acagatagct    1260
ggcgtggata agatggaag gcctctacaa ccccacgtca gagtgtggga ttctgttact    1320
ctatccacac tgcagattat tggacttggc acttttgagc gtggagtagg atgcctggat    1380
ttttcaaaag cagattcagg tgttcattta tgtgttattg atgactccaa tgagcatatg    1440
cttactgtat gggactggca gaagaaagca aaggagcag aaataaagac aacaaatgaa    1500
```

```
gttgttttgg ctgtggagtt tcacccaaca gatgcaaata ccataattac atgcggtaaa    1560
tctcatattt tcttctggac ctggagcggc aattcactaa caagaaaaca gggaattttt    1620
gggaaatatg aaaagccaaa atttgtgcag tgtttagcat tcttggggaa tggagatgtt    1680
cttactggag actcaggtgg agtcatgctt atatggagca aaactactgt agagcccaca    1740
cctgggaaag gacctaaagt gtaccgccgg aagcaccagg agctgcaagc catgcagatg    1800
gagctgcaga gccctgagta caagctgagc aagctccgca cctcgaccat catgaccgac    1860
tacaacccca actactgctt tgctggcaag acctcctcca tcagtgacct gaaggaggtg    1920
ccgcggaaaa acatcaccct cattcggggt ctgggccatg agccttttgg ggaggtgtat    1980
gaaggccagg tgtccggaat gcccaacgac ccaagccccc tgcaagtggc tgtgaagacg    2040
ctgcctgaag tgtgctctga acaggacgaa ctggatttcc tcatggaagc cctgatcatc    2100
agcaaattca accaccagaa cattgttcgc tgcattgggg tgagcctgca atccctgccc    2160
cggttcatcc tgctggagct catggcgggg ggagacctca gtccttcct ccgagagacc    2220
cgccctcgcc cgagccagcc ctcctccctg gccatgctgg accttctgca cgtggctcgg    2280
gacattgcct gtggctgtca gtatttggag gaaaaccact tcatccaccg agacattgct    2340
gccagaaact gcctcttgac ctgtccaggc cctggaagag tggccaagat ggagacttc    2400
gggatggccc gagacatcta cagggcgagc tactatagaa agggaggctg tgccatgctg    2460
ccagttaagt ggatgccccc agaggccttc atggaaggaa tattcacttc taaaacagac    2520
acatggtcct ttggagtgct gctatgggaa atctttttctc ttggatatat gccatacccc    2580
agcaaaagca accaggaagt tctggagttt gtcaccagtg gaggccggat ggacccaccc    2640
aagaactgcc ctgggcctgt ataccggata tgactcagt gctggcaaca tcagcctgaa    2700
gacaggccca actttgccat cattttggag aggattgaat actgcaccca ggacccggat    2760
gtaatcaaca ccgctttgcc gatagaatat ggtccacttg tggaagagga agagaaagtg    2820
cctgtgaggc ccaaggaccc tgaggggggtt cctcctctcc tggtctctca acaggcaaaa    2880
cgggaggagg agcgcagccc agctgccccca ccacctctgc ctaccacctc ctctggcaag    2940
gctgcaaaga aacccacagc tgcagaggtc tctgttcgag tccctagagg gccggccgtg    3000
gaagggggac acgtgaatat ggcattctct cagtccaacc ctccttcgga gttgcacagg    3060
gtccacggat ccagaaacaa gcccaccagc ttgtggaacc caacgtacgg ctcctggttt    3120
acagagaaac ccaccaaaaa gaataatcct atagcaaaga aggagccaca cgagaggggt    3180
aacctggggc tggagggaag ctgtactgtc ccacctaacg ttgcaactgg gagacttccg    3240
ggggcctcac tgctcctaga gccctcttcg ctgactgcca atatgaagga ggtacctctg    3300
ttcaggctac gtcacttccc ttgtgggaat gtcaattacg gctaccagca acagggcttg    3360
cccttagaag ccgctactgc ccctggagct ggtcattacg aggataccat tctgaaaagc    3420
aagaatagca tgaaccagcc tgggccctga gctcggtcac acactcactt ctcttccttg    3480
ggatccctaa gaccgtggag gagagagagg caatcaatgg ctccttcaca aaccagagac    3540
caaatgtcac gttttgtttt gtgccaacct attttgaagt accaccaaaa aagctgtatt    3600
ttgaaaatgc tttagaaagg ttttgagcat gggttcatcc tattctttcg aaagaagaaa    3660
atatcataaa aatgagtgat aaatacaagg cccagatgtg gttgcataag gtttttatgc    3720
atgtttgttg tatacttcct tatgcttctt ttaaattgtg tgtgctctgc ttcaatgtag    3780
tcagaattag ctgcttctat gtttcatagt tggggtcata gatgtttcct tgccttgttg    3840
atgtggacat gagccatttg aggggagagg gaacggaaat aaaggagtta tttgtaatga    3900
```
aaaaaaaaaa aaaaaaaaaa aaaaaa                                                3926

<210> SEQ ID NO 6
<211> LENGTH: 1059
<212> TYPE: PRT
<213> ORGANISM: Homo sapiens

<400> SEQUENCE: 6

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Val Leu Phe Asn Tyr Glu Glu Arg Thr Gln Arg His
    290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

```
Leu Asp Phe Ser Lys Ala Asp Ser Gly Val His Leu Cys Val Ile Asp
    370                 375                 380
Asp Ser Asn Glu His Met Leu Thr Val Trp Asp Trp Gln Lys Lys Ala
385                 390                 395                 400
Lys Gly Ala Glu Ile Lys Thr Thr Asn Glu Val Val Leu Ala Val Glu
                    405                 410                 415
Phe His Pro Thr Asp Ala Asn Thr Ile Ile Thr Cys Gly Lys Ser His
                420                 425                 430
Ile Phe Phe Trp Thr Trp Ser Gly Asn Ser Leu Thr Arg Lys Gln Gly
            435                 440                 445
Ile Phe Gly Lys Tyr Glu Lys Pro Lys Phe Val Gln Cys Leu Ala Phe
450                 455                 460
Leu Gly Asn Gly Asp Val Leu Thr Gly Asp Ser Gly Gly Val Met Leu
465                 470                 475                 480
Ile Trp Ser Lys Thr Thr Val Glu Pro Thr Pro Gly Lys Gly Pro Lys
                485                 490                 495
Val Tyr Arg Arg Lys His Gln Glu Leu Gln Ala Met Gln Met Glu Leu
                500                 505                 510
Gln Ser Pro Glu Tyr Lys Leu Ser Lys Leu Arg Thr Ser Thr Ile Met
            515                 520                 525
Thr Asp Tyr Asn Pro Asn Tyr Cys Phe Ala Gly Lys Thr Ser Ser Ile
530                 535                 540
Ser Asp Leu Lys Glu Val Pro Arg Lys Asn Ile Thr Leu Ile Arg Gly
545                 550                 555                 560
Leu Gly His Gly Ala Phe Gly Glu Val Tyr Glu Gly Gln Val Ser Gly
                565                 570                 575
Met Pro Asn Asp Pro Ser Pro Leu Gln Val Ala Val Lys Thr Leu Pro
                580                 585                 590
Glu Val Cys Ser Glu Gln Asp Glu Leu Asp Phe Leu Met Glu Ala Leu
            595                 600                 605
Ile Ile Ser Lys Phe Asn His Gln Asn Ile Val Arg Cys Ile Gly Val
610                 615                 620
Ser Leu Gln Ser Leu Pro Arg Phe Ile Leu Leu Glu Leu Met Ala Gly
625                 630                 635                 640
Gly Asp Leu Lys Ser Phe Leu Arg Glu Thr Arg Pro Arg Pro Ser Gln
                645                 650                 655
Pro Ser Ser Leu Ala Met Leu Asp Leu Leu His Val Ala Arg Asp Ile
                660                 665                 670
Ala Cys Gly Cys Gln Tyr Leu Glu Glu Asn His Phe Ile His Arg Asp
            675                 680                 685
Ile Ala Ala Arg Asn Cys Leu Leu Thr Cys Pro Gly Pro Gly Arg Val
690                 695                 700
Ala Lys Ile Gly Asp Phe Gly Met Ala Arg Asp Ile Tyr Arg Ala Ser
705                 710                 715                 720
Tyr Tyr Arg Lys Gly Gly Cys Ala Met Leu Pro Val Lys Trp Met Pro
                725                 730                 735
Pro Glu Ala Phe Met Glu Gly Ile Phe Thr Ser Lys Thr Asp Thr Trp
                740                 745                 750
Ser Phe Gly Val Leu Leu Trp Glu Ile Phe Ser Leu Gly Tyr Met Pro
            755                 760                 765
Tyr Pro Ser Lys Ser Asn Gln Glu Val Leu Glu Phe Val Thr Ser Gly
770                 775                 780
```

```
Gly Arg Met Asp Pro Lys Asn Cys Pro Gly Pro Val Tyr Arg Ile
785                 790                 795                 800

Met Thr Gln Cys Trp Gln His Gln Pro Glu Asp Arg Pro Asn Phe Ala
            805                 810                 815

Ile Ile Leu Glu Arg Ile Glu Tyr Cys Thr Gln Asp Pro Asp Val Ile
            820                 825                 830

Asn Thr Ala Leu Pro Ile Glu Tyr Gly Pro Leu Val Glu Glu Glu
            835                 840                 845

Lys Val Pro Val Arg Pro Lys Asp Pro Glu Gly Val Pro Pro Leu Leu
850                 855                 860

Val Ser Gln Gln Ala Lys Arg Glu Glu Glu Arg Ser Pro Ala Ala Pro
865                 870                 875                 880

Pro Pro Leu Pro Thr Thr Ser Ser Gly Lys Ala Ala Lys Lys Pro Thr
            885                 890                 895

Ala Ala Glu Val Ser Val Arg Val Pro Arg Gly Pro Ala Val Glu Gly
                900                 905                 910

Gly His Val Asn Met Ala Phe Ser Gln Ser Asn Pro Pro Ser Glu Leu
            915                 920                 925

His Arg Val His Gly Ser Arg Asn Lys Pro Thr Ser Leu Trp Asn Pro
930                 935                 940

Thr Tyr Gly Ser Trp Phe Thr Glu Lys Pro Thr Lys Lys Asn Asn Pro
945                 950                 955                 960

Ile Ala Lys Lys Glu Pro His Glu Arg Gly Asn Leu Gly Leu Glu Gly
                965                 970                 975

Ser Cys Thr Val Pro Pro Asn Val Ala Thr Gly Arg Leu Pro Gly Ala
            980                 985                 990

Ser Leu Leu Leu Glu Pro Ser Ser  Leu Thr Ala Asn Met  Lys Glu Val
            995                 1000                1005

Pro Leu Phe Arg Leu Arg His  Phe Pro Cys Gly Asn  Val Asn Tyr
    1010                1015                1020

Gly Tyr Gln Gln Gln Gly Leu  Pro Leu Glu Ala Ala  Thr Ala Pro
    1025                1030                1035

Gly Ala Gly His Tyr Glu Asp  Thr Ile Leu Lys Ser  Lys Asn Ser
    1040                1045                1050

Met Asn  Gln Pro Gly Pro
    1055

<210> SEQ ID NO 7
<211> LENGTH: 4679
<212> TYPE: DNA
<213> ORGANISM: Homo sapiens

<400> SEQUENCE: 7
ggcggcgcgg cgcggcgctc gcggctgctg cctgggaggg aggccgggca ggcggctgag    60
cggcgcggct ctcaacgtga cggggaagtg gttcgggcgg ccgcggctta ctaccccagg   120
gcgaacggac ggacgacgga ggcgggagcc ggtagccgag ccgggcgacc tagagaacga   180
gcgggtcagg ctcagcgtcg gccactctgt cggtccgctg aatgaagtgc cgcccctct    240 gagcccggag cccggcgctt tccccgcaag atggacggtt cgccggcag tctcgatgat    300 agtatttctg ctgcaagtac ttctgatgtt caagatcgcc tgtcagctct tgagtcacga    360
gttcagcaac aagaagatga atcactgtg ctaaaggcgg cttggctga tgttttgagg    420 cgtcttgcaa tctctgaaga tcatgtggcc tcagtgaaaa aatcagtctc aagtaaaggc    480
caaccaagcc ctcgagcagt tattcccatg tcctgtataa ccaatggaag tggtgcaaac    540
```

```
agaaaaccaa gtcataccag tgctgtctca attgcaggaa aagaaactct ttcatctgct    600
gctaaaagtg gtacagaaaa aaagaaagaa aaaccacaag gacagagaga aaaaaaagag    660
gaatctcatt ctaatgatca aagtccacaa attcgagcat caccttctcc ccagccctct    720
tcacaacctc tccaaataca cagacaaact ccagaaagca agaatgctac tcccaccaaa    780
agcataaaac gaccatcacc agctgaaaag tcacataatt cttgggaaaa ttcagatgat    840
agccgtaata aattgtcgaa ataccttca acacccaaat taataccaaa agttaccaaa    900
actgcagaca agcataaaga tgtcatcatc aaccaagaag gagaatatat taaaatgttt    960
atgcgcggtc ggccaattac catgttcatt ccttccgatg ttgacaacta tgatgacatc   1020
agaacggaac tgcctcctga gaagctcaaa ctggagtggg catatggtta tcgaggaaag   1080
gactgtagag ctaatgttta ccttcttccg accggggaaa tagtttattt cattgcatca   1140
gtagtagtac tatttaatta tgaggagaga actcagcgac actacctggg ccatacagac   1200
tgtgtgaaat gccttgctat acatcctgac aaaattagga ttgcaactgg acagatagct   1260
ggcgtggata agatggaag gcctctacaa ccccacgtca gagtgtggga ttctgttact   1320
ctatccacac tgcagattat tggacttggc acttttgagc gtggagtagg atgcctggat   1380
ttttcaaaag cagattcagg tgttcattta tgtgttattg atgactccaa tgagcatatg   1440
cttactgtat gggactggca gaagaaagca aaggagcag aaataaagac aacaaatgaa   1500
gttgttttgg ctgtggagtt tcacccaaca gatgcaaata ccataattac atgcggtaaa   1560
tctcatattt tcttctggac ctggagcggc aattcactaa caagaaaaca gggaattttt   1620
gggaaatatg aaaagccaaa atttgtgcag tgtttagcat tcttggggaa tggagatgtt   1680
cttactggag actcaggtgg agtcatgctt atatggagca aaactactgt agagcccaca   1740
cctgggaaag gacctaaagg tgtatatcaa atcagcaaac aaatcaaagc tcatgatggc   1800
agtgtgttca cactttgtca gatgagaaat gggatgttat taactggagg agggaaagac   1860
agaaaaataa ttctgtggga tcatgatctg aatcctgaaa gagaaataga ggttcctgat   1920
cagtatggca aatcagagc tgtagcagaa ggaaaggcag atcaattttt agtaggcaca   1980
tcacgaaact ttatttacg aggaacattt aatgatggct tccaaataga agtacagggt   2040
catacagatg agctttgggg tcttgccaca catcccttca agatttgct cttgacatgt   2100 gctcaggaca ggcaggtgtg cctgtggaac tcaatggaac acaggctgga atggaccagg   2160
ctggtagatg aaccaggaca ctgtgcagat tttcatccaa gtggcacagt ggtggccata   2220
ggaacgcact caggcaggtg gtttgttctg gatgcagaaa ccagagatct agtttctatc   2280
cacacagacg ggaatgaaca gctctctgtg atgcgctact caatagatgg taccttcctg   2340
gctgtaggat ctcatgacaa ctttatttac ctctatgtag tctctgaaaa tggaagaaaa   2400
tatagcagat atggaaggtg cactggacat tccagctaca tcacacacct tgactggtcc   2460
ccagacaaca agtatataat gtctaactcg ggagactatg aaatattgta cttgtaccgc   2520
cggaagcacc aggagctgca agccatgcag atggagctgc agagccctga gtacaagctg   2580
agcaagctcc gcacctcgac catcatgacc gactacaacc ccaactactg ctttgctggc   2640
aagacctcct ccatcagtga cctgaaggag gtgccgcgga aaacatcac cctcattcgg   2700 ggtctgggcc atggagcctt tggggaggtg tatgaaggcc aggtgtccgg aatgcccaac   2760
gacccaagcc ccctgcaagt ggctgtgaag acgctgcctg aagtgtgctc tgaacaggac   2820
gaactggatt tcctcatgga agccctgatc atcagcaaat tcaaccacca gaacattgtt   2880
```

```
cgctgcattg gggtgagcct gcaatccctg cccoggttca tcctgctgga gctcatggcg    2940
ggggagacc  tcaagtcctt cctccgagag acccgccctc gcccgagcca gccctcctcc    3000
ctggccatgc tggaccttct gcacgtggct cgggacattg cctgtggctg tcagtatttg    3060
gaggaaaacc acttcatcca ccgagacatt gctgccagaa actgcctctt gacctgtcca    3120
ggccctggaa gagtggccaa gattggagac ttcgggatgg cccgagacat ctacagggcg    3180
agctactata gaaagggagg ctgtgccatg ctgccagtta agtggatgcc cccagaggcc    3240
ttcatggaag gaatattcac ttctaaaaca gacacatggt cctttggagt gctgctatgg    3300
gaaatctttt ctcttggata tatgccatac cccagcaaaa gcaaccagga agttctggag    3360
tttgtcacca gtggaggccg gatggaccca cccaagaact gccctgggcc tgtataccgg    3420
ataatgactc agtgctggca acatcagcct gaagacaggc ccaactttgc catcattttg    3480
gagaggattg aatactgcac ccaggacccg gatgtaatca acaccgcttt gccgatagaa    3540
tatggtccac ttgtggaaga ggaagagaaa gtgcctgtga ggcccaagga ccctgagggg    3600
gttcctcctc tcctggtctc tcaacaggca aaacgggagg aggagcgcag cccagctgcc    3660
ccaccacctc tgcctaccac ctcctctggc aaggctgcaa agaaacccac agctgcagag    3720
gtctctgttc gagtccctag agggccggcc gtggaagggg acacgtgaa tatggcattc     3780
tctcagtcca accctccttc ggagttgcac agggtccacg gatccagaaa caagcccacc    3840
agcttgtgga acccaacgta cggctcctgg tttacagaga aacccaccaa aaagaataat    3900
cctatagcaa agaaggagcc acacgagagg ggtaacctgg ggctggaggg aagctgtact    3960
gtcccaccta acgttgcaac tgggagactt ccggggggcct cactgctcct agagccctct    4020
tcgctgactg ccaatatgaa ggaggtacct ctgttcaggc tacgtcactt cccttgtggg    4080
aatgtcaatt acggctacca gcaacagggc ttgcccttag aagccgctac tgcccctgga    4140
gctggtcatt acgaggatac cattctgaaa agcaagaata gcatgaacca gcctgggccc    4200
tgagctcggt cacacactca cttctcttcc ttgggatccc taagaccgtg gaggagagag    4260
aggcaatcaa tggctccttc acaaaccaga gaccaaatgt cacgttttgt tttgtgccaa    4320
cctattttga agtaccacca aaaaagctgt attttgaaaa tgctttagaa aggttttgag    4380
catgggttca tcctattctt tcgaaagaag aaaatatcat aaaaatgagt gataaataca    4440
aggcccagat gtggttgcat aaggttttta tgcatgtttg ttgtatactt ccttatgctt    4500
cttttaaatt gtgtgtgctc tgcttcaatg tagtcagaat tagctgcttc tatgtttcat    4560
agttggggtc atagatgttt ccttgccttg ttgatgtgga catgagccat ttgaggggag    4620
agggaacgga aataaggag ttatttgtaa tgaaaaaaaa aaaaaaaaa aaaaaaaaa       4679
```

<210> SEQ ID NO 8
<211> LENGTH: 1310
<212> TYPE: PRT
<213> ORGANISM: Homo sapiens

<400> SEQUENCE: 8

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60
```

-continued

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Asn Gln Glu Gly
210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Leu Phe Asn Tyr Glu Glu Arg Thr Gln Arg His
290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

Leu Asp Phe Ser Lys Ala Asp Ser Gly Val His Leu Cys Val Ile Asp
370                 375                 380

Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
            420                 425                 430

Ile Phe Phe Trp Thr Trp Ser Gly Asn Ser Leu Thr Arg Lys Gln Gly
        435                 440                 445

Ile Phe Gly Lys Tyr Glu Lys Pro Lys Phe Val Gln Cys Leu Ala Phe
450                 455                 460

Leu Gly Asn Gly Asp Val Leu Thr Gly Asp Ser Gly Gly Val Met Leu
465                 470                 475                 480

-continued

```
Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
            500                 505                 510

Phe Thr Leu Cys Gln Met Arg Asn Gly Met Leu Leu Thr Gly Gly Gly
            515                 520                 525

Lys Asp Arg Lys Ile Ile Leu Trp Asp His Asp Leu Asn Pro Glu Arg
            530                 535                 540

Glu Ile Glu Val Pro Asp Gln Tyr Gly Thr Ile Arg Ala Val Ala Glu
545                 550                 555                 560

Gly Lys Ala Asp Gln Phe Leu Val Gly Thr Ser Arg Asn Phe Ile Leu
                565                 570                 575

Arg Gly Thr Phe Asn Asp Gly Phe Gln Ile Glu Val Gln Gly His Thr
            580                 585                 590

Asp Glu Leu Trp Gly Leu Ala Thr His Pro Phe Lys Asp Leu Leu Leu
            595                 600                 605

Thr Cys Ala Gln Asp Arg Gln Val Cys Leu Trp Asn Ser Met Glu His
            610                 615                 620

Arg Leu Glu Trp Thr Arg Leu Val Asp Glu Pro Gly His Cys Ala Asp
625                 630                 635                 640

Phe His Pro Ser Gly Thr Val Val Ala Ile Gly Thr His Ser Gly Arg
                645                 650                 655

Trp Phe Val Leu Asp Ala Glu Thr Arg Asp Leu Val Ser Ile His Thr
            660                 665                 670

Asp Gly Asn Glu Gln Leu Ser Val Met Arg Tyr Ser Ile Asp Gly Thr
            675                 680                 685

Phe Leu Ala Val Gly Ser His Asp Asn Phe Ile Tyr Leu Tyr Val Val
            690                 695                 700

Ser Glu Asn Gly Arg Lys Tyr Ser Arg Tyr Gly Arg Cys Thr Gly His
705                 710                 715                 720

Ser Ser Tyr Ile Thr His Leu Asp Trp Ser Pro Asp Asn Lys Tyr Ile
                725                 730                 735

Met Ser Asn Ser Gly Asp Tyr Glu Ile Leu Tyr Leu Tyr Arg Arg Lys
            740                 745                 750

His Gln Glu Leu Gln Ala Met Gln Met Glu Leu Gln Ser Pro Glu Tyr
            755                 760                 765

Lys Leu Ser Lys Leu Arg Thr Ser Thr Ile Met Thr Asp Tyr Asn Pro
            770                 775                 780

Asn Tyr Cys Phe Ala Gly Lys Thr Ser Ser Ile Ser Asp Leu Lys Glu
785                 790                 795                 800

Val Pro Arg Lys Asn Ile Thr Leu Ile Arg Gly Leu His Gly Ala
                805                 810                 815

Phe Gly Glu Val Tyr Glu Gly Gln Val Ser Gly Met Pro Asn Asp Pro
            820                 825                 830

Ser Pro Leu Gln Val Ala Val Lys Thr Leu Pro Glu Val Cys Ser Glu
            835                 840                 845

Gln Asp Glu Leu Asp Phe Leu Met Glu Ala Leu Ile Ile Ser Lys Phe
850                 855                 860

Asn His Gln Asn Ile Val Arg Cys Ile Gly Val Ser Leu Gln Ser Leu
865                 870                 875                 880

Pro Arg Phe Ile Leu Leu Glu Leu Met Ala Gly Gly Asp Leu Lys Ser
                885                 890                 895

Phe Leu Arg Glu Thr Arg Pro Arg Pro Ser Gln Pro Ser Ser Leu Ala
```

```
                    900               905                910
Met Leu Asp Leu Leu His Val Ala Arg Asp Ile Ala Cys Gly Cys Gln
            915                 920                 925
Tyr Leu Glu Asn His Phe Ile His Arg Asp Ile Ala Ala Arg Asn
            930                 935                 940
Cys Leu Leu Thr Cys Pro Gly Pro Gly Arg Val Ala Lys Ile Gly Asp
945                 950                 955                 960
Phe Gly Met Ala Arg Asp Ile Tyr Arg Ala Ser Tyr Tyr Arg Lys Gly
                965                 970                 975
Gly Cys Ala Met Leu Pro Val Lys Trp Met Pro Pro Glu Ala Phe Met
                980                 985                 990
Glu Gly Ile Phe Thr Ser Lys Thr Asp Thr Trp Ser Phe Gly Val Leu
            995                1000                1005
Leu Trp Glu Ile Phe Ser Leu Gly Tyr Met Pro Tyr Pro Ser Lys
        1010                1015                1020
Ser Asn Gln Glu Val Leu Glu Phe Val Thr Ser Gly Gly Arg Met
        1025                1030                1035
Asp Pro Pro Lys Asn Cys Pro Gly Pro Val Tyr Arg Ile Met Thr
        1040                1045                1050
Gln Cys Trp Gln His Gln Pro Glu Asp Arg Pro Asn Phe Ala Ile
        1055                1060                1065
Ile Leu Glu Arg Ile Glu Tyr Cys Thr Gln Asp Pro Asp Val Ile
        1070                1075                1080
Asn Thr Ala Leu Pro Ile Glu Tyr Gly Pro Leu Val Glu Glu Glu
        1085                1090                1095
Glu Lys Val Pro Val Arg Pro Lys Asp Pro Glu Gly Val Pro Pro
        1100                1105                1110
Leu Leu Val Ser Gln Gln Ala Lys Arg Glu Glu Glu Arg Ser Pro
        1115                1120                1125
Ala Ala Pro Pro Pro Leu Pro Thr Thr Ser Ser Gly Lys Ala Ala
        1130                1135                1140
Lys Lys Pro Thr Ala Ala Glu Val Ser Val Arg Val Pro Arg Gly
        1145                1150                1155
Pro Ala Val Glu Gly Gly His Val Asn Met Ala Phe Ser Gln Ser
        1160                1165                1170
Asn Pro Pro Ser Glu Leu His Arg Val His Gly Ser Arg Asn Lys
        1175                1180                1185
Pro Thr Ser Leu Trp Asn Pro Thr Tyr Gly Ser Trp Phe Thr Glu
        1190                1195                1200
Lys Pro Thr Lys Lys Asn Asn Pro Ile Ala Lys Lys Glu Pro His
        1205                1210                1215
Glu Arg Gly Asn Leu Gly Leu Glu Gly Ser Cys Thr Val Pro Pro
        1220                1225                1230
Asn Val Ala Thr Gly Arg Leu Pro Gly Ala Ser Leu Leu Leu Glu
        1235                1240                1245
Pro Ser Ser Leu Thr Ala Asn Met Lys Glu Val Pro Leu Phe Arg
        1250                1255                1260
Leu Arg His Phe Pro Cys Gly Asn Val Asn Tyr Gly Tyr Gln Gln
        1265                1270                1275
Gln Gly Leu Pro Leu Glu Ala Ala Thr Ala Pro Gly Ala Gly His
        1280                1285                1290
Tyr Glu Asp Thr Ile Leu Lys Ser Lys Asn Ser Met Asn Gln Pro
        1295                1300                1305
```

Gly Pro
    1310

<210> SEQ ID NO 9
<211> LENGTH: 2473
<212> TYPE: DNA
<213> ORGANISM: Homo sapiens

<400> SEQUENCE: 9

| | | | | | |
|---|---|---|---|---|---|
| actctgtcgg | tccgctgaat | gaagtgcccg | cccctctaag | cccggagccc | ggcgctttcc | 60 |
| ccgcaagatg | gacggtttcg | ccggcagtct | cgatgatagt | atttctgctg | caagtacttc | 120 |
| tgatgttcaa | gatcgcctgt | cagctcttga | gtcacgagtt | cagcaacaag | aagatgaaat | 180 |
| cactgtgcta | aaggcggctt | tggctgatgt | tttgaggcgt | cttgcaatct | ctgaagatca | 240 |
| tgtggcctca | gtgaaaaaat | cagtctcaag | taaaggccaa | ccaagccctc | gagcagttat | 300 |
| tcccatgtcc | tgtataacca | atggaagtgg | tgcaaacaga | aaaccaagtc | ataccagtgc | 360 |
| tgtctcaatt | gcaggaaaag | aaactctttc | atctgctgct | aaaagtggta | cagaaaaaaa | 420 |
| gaaagaaaaa | ccacaaggac | agagagaaaa | aaaagaggaa | tctcattcta | atgatcaaag | 480 |
| tccacaaatt | cgagcatcac | cttctcccca | gccctcttca | aacctctccc | aaatacacag | 540 |
| acaaactcca | gaaagcaaga | atgctactcc | caccaaaagc | ataaaacgac | catcaccagc | 600 |
| tgaaaagtca | cataattctt | gggaaaattc | agatgatagc | cgtaataaat | tgtcgaaaat | 660 |
| accttcaaca | cccaaattaa | taccaaaagt | taccaaaact | gcagacaagc | ataaagatgt | 720 |
| catcatcaac | caagtgtacc | gccggaagca | ccaggagctg | caagccatgc | agatggagct | 780 |
| gcagagccct | gagtacaagc | tgagcaagct | ccgcacctcg | accatcatga | ccgactacaa | 840 |
| ccccaactac | tgctttgctg | gcaagacctc | ctccatcagt | gacctgaagg | aggtgccgcg | 900 |
| gaaaaacatc | accctcattc | ggggtctggg | ccatggagcc | tttgggagg | tgtatgaagg | 960 |
| ccaggtgtcc | ggaatgccca | acgacccaag | cccctgcaa | gtggctgtga | agacgctgcc | 1020 |
| tgaagtgtgc | tctgaacagg | acgaactgga | tttcctcatg | gaagccctga | tcatcagcaa | 1080 |
| attcaaccac | cagaacattg | ttcgctgcat | tggggtgagc | ctgcaatccc | tgccccggtt | 1140 |
| catcctgctg | gagctcatgg | cgggggga | cctcaagtcc | ttcctccgag | agacccgccc | 1200 |
| tcgcccgagc | cagccctcct | ccctggccat | gctggacctt | ctgcacgtgg | ctcgggacat | 1260 |
| tgcctgtggc | tgtcagtatt | tggaggaaaa | ccacttcatc | caccgagaca | ttgctgccag | 1320 |
| aaactgcctc | ttgacctgtc | caggccctgg | aagagtggcc | aagattggag | acttcgggat | 1380 |
| ggcccgagac | atctacaggg | cgagctacta | tagaaaggga | ggctgtgcca | tgctgccagt | 1440 |
| taagtggatg | cccccagagg | ccttcatgga | aggaatattc | acttctaaaa | cagacacatg | 1500 |
| gtcctttgga | gtgctgctat | gggaaatctt | ttctcttgga | tatatgccat | accccagcaa | 1560 |
| aagcaaccag | gaagttctgg | agtttgtcac | cagtggaggc | cggatggacc | cacccaagaa | 1620 |
| ctgccctggg | cctgtatacc | ggataatgac | tcagtgctgg | caacatcagc | ctgaagacag | 1680 |
| gcccaacttt | gccatcattt | tggagaggat | tgaatactgc | acccaggacc | cggatgtaat | 1740 |
| caacaccgct | tgccgatag | aatatggtcc | acttgtggaa | gaggaagaga | agtgcctgt | 1800 |
| gaggcccaag | gaccctgagg | gggttcctcc | tctcctggtc | tctcaacagg | caaaacggga | 1860 |
| ggaggagcgc | agcccagctg | ccccaccacc | tctgcctacc | acctcctctg | caaggctgc | 1920 |
| aaagaaaccc | acagctgcag | aggtctctgt | tcgagtccct | agaggccgg | ccgtggaagg | 1980 |
| gggacacgtg | aatatggcat | tctctcagtc | caaccctcct | tcggagttgc | acagggtcca | 2040 |

-continued

```
cggatccaga acaagccca ccagcttgtg aacccaacg tacggctcct ggtttacaga    2100
gaaacccacc aaaagaata atcctatagc aagaaggag ccacacgaga ggggtaacct    2160
ggggctggag ggaagctgta ctgtcccacc taacgttgca actgggagac ttccgggggc    2220
ctcactgctc ctagagccct cttcgctgac tgccaatatg aaggaggtac ctctgttcag    2280
gctacgtcac ttcccttgtg ggaatgtcaa ttacggctac cagcaacagg gcttgccctt    2340
agaagccgct actgccctg agctggtca ttacgaggat accattctga aaagcaagaa    2400
tagcatgaac cagcctgggc cctgagctcg gtcgcacact cacttctctt ccttgggatc    2460
cctaagaccg tgg                                                      2473
```

<210> SEQ ID NO 10
<211> LENGTH: 785
<212> TYPE: PRT
<213> ORGANISM: Homo sapiens

<400> SEQUENCE: 10

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Val Tyr
    210                 215                 220

Arg Arg Lys His Gln Glu Leu Gln Ala Met Gln Met Glu Leu Gln Ser
225                 230                 235                 240

Pro Glu Tyr Lys Leu Ser Lys Leu Arg Thr Ser Thr Ile Met Thr Asp
                245                 250                 255

Tyr Asn Pro Asn Tyr Cys Phe Ala Gly Lys Thr Ser Ser Ile Ser Asp
            260                 265                 270

Leu Lys Glu Val Pro Arg Lys Asn Ile Thr Leu Ile Arg Gly Leu Gly
        275                 280                 285
```

-continued

```
His Gly Ala Phe Gly Glu Val Tyr Glu Gly Gln Val Ser Gly Met Pro
290                 295                 300

Asn Asp Pro Ser Pro Leu Gln Val Ala Val Lys Thr Leu Pro Glu Val
305                 310                 315                 320

Cys Ser Glu Gln Asp Glu Leu Asp Phe Leu Met Glu Ala Leu Ile Ile
                    325                 330                 335

Ser Lys Phe Asn His Gln Asn Ile Val Arg Cys Ile Gly Val Ser Leu
                340                 345                 350

Gln Ser Leu Pro Arg Phe Ile Leu Leu Glu Leu Met Ala Gly Gly Asp
            355                 360                 365

Leu Lys Ser Phe Leu Arg Glu Thr Arg Pro Arg Pro Ser Gln Pro Ser
370                 375                 380

Ser Leu Ala Met Leu Asp Leu Leu His Val Ala Arg Asp Ile Ala Cys
385                 390                 395                 400

Gly Cys Gln Tyr Leu Glu Glu Asn His Phe Ile His Arg Asp Ile Ala
                    405                 410                 415

Ala Arg Asn Cys Leu Leu Thr Cys Pro Gly Pro Gly Arg Val Ala Lys
                420                 425                 430

Ile Gly Asp Phe Gly Met Ala Arg Asp Ile Tyr Arg Ala Ser Tyr Tyr
            435                 440                 445

Arg Lys Gly Gly Cys Ala Met Leu Pro Val Lys Trp Met Pro Pro Glu
450                 455                 460

Ala Phe Met Glu Gly Ile Phe Thr Ser Lys Thr Asp Thr Trp Ser Phe
465                 470                 475                 480

Gly Val Leu Leu Trp Glu Ile Phe Ser Leu Gly Tyr Met Pro Tyr Pro
                    485                 490                 495

Ser Lys Ser Asn Gln Glu Val Leu Glu Phe Val Thr Ser Gly Gly Arg
                500                 505                 510

Met Asp Pro Pro Lys Asn Cys Pro Gly Pro Val Tyr Arg Ile Met Thr
            515                 520                 525

Gln Cys Trp Gln His Gln Pro Glu Asp Arg Pro Asn Phe Ala Ile Ile
530                 535                 540

Leu Glu Arg Ile Glu Tyr Cys Thr Gln Asp Pro Asp Val Ile Asn Thr
545                 550                 555                 560

Ala Leu Pro Ile Glu Tyr Gly Pro Leu Val Glu Glu Glu Lys Val
                    565                 570                 575

Pro Val Arg Pro Lys Asp Pro Glu Gly Val Pro Pro Leu Leu Val Ser
                580                 585                 590

Gln Gln Ala Lys Arg Glu Glu Arg Ser Pro Ala Ala Pro Pro Pro
            595                 600                 605

Leu Pro Thr Thr Ser Ser Gly Lys Ala Ala Lys Lys Pro Thr Ala Ala
610                 615                 620

Glu Val Ser Val Arg Val Pro Arg Gly Pro Ala Val Glu Gly Gly His
625                 630                 635                 640

Val Asn Met Ala Phe Ser Gln Ser Asn Pro Pro Ser Glu Leu His Arg
                    645                 650                 655

Val His Gly Ser Arg Asn Lys Pro Thr Ser Leu Trp Asn Pro Thr Tyr
                660                 665                 670

Gly Ser Trp Phe Thr Glu Lys Pro Thr Lys Asn Asn Pro Ile Ala
            675                 680                 685

Lys Lys Glu Pro His Glu Arg Gly Asn Leu Gly Leu Glu Gly Ser Cys
690                 695                 700

Thr Val Pro Pro Asn Val Ala Thr Gly Arg Leu Pro Gly Ala Ser Leu
```

```
                705                 710                 715                 720
Leu Leu Glu Pro Ser Ser Leu Thr Ala Asn Met Lys Glu Val Pro Leu
                    725                 730                 735

Phe Arg Leu Arg His Phe Pro Cys Gly Asn Val Asn Tyr Gly Tyr Gln
            740                 745                 750

Gln Gln Gly Leu Pro Leu Glu Ala Ala Thr Ala Pro Gly Ala Gly His
        755                 760                 765

Tyr Glu Asp Thr Ile Leu Lys Ser Lys Asn Ser Met Asn Gln Pro Gly
    770                 775                 780

Pro
785

<210> SEQ ID NO 11
<211> LENGTH: 2506
<212> TYPE: DNA
<213> ORGANISM: Homo sapiens

<400> SEQUENCE: 11
actctgtcgg tccgctgaat gaagtgcccg cccctctaag cccggagccc ggcgctttcc        60
ccgcaagatg gacggtttcg ccggcagtct cgatgatagt atttctgctg caagtacttc       120
tgatgttcaa gatcgcctgt cagctcttga gtcacgagtt cagcaacaag aagatgaaat       180
cactgtgcta aaggcggctt tggctgatgt tttgaggcgt cttgcaatct ctgaagatca       240
tgtggcctca gtgaaaaaat cagtctcaag taaaggccaa ccaagccctc gagcagttat       300
tcccatgtcc tgtataacca atggaagtgg tgcaaacaga aaccaagtc ataccagtgc        360 tgtctcaatt gcaggaaaag aaactctttc atctgctgct aaaagtggta cagaaaaaaa       420
gaaagaaaaa ccacaaggac agagagaaaa aaagaggaa tctcattcta atgatcaaag        480
tccacaaatt cgagcatcac cttctcccca gccctcttca caacctctcc aaatacacag       540
acaaactcca gaaagcaaga atgctactcc caccaaaagc ataaaacgac catcaccagc       600
tgaaaagtca cataattctt gggaaaattc agatgatagc cgtaataaat tgtcgaaaat       660
accttcaaca cccaaattaa taccaaaagt taccaaaact gcagacaagc ataaagatgt       720
catcatcaac caagcaaaaa tgtcaactcg cgaaaaaaac agccaagtgt accgccggaa       780
gcaccaggag ctgcaagcca tgcagatgga gctgcagagc cctgagtaca agctgagcaa       840
gctccgcacc tcgaccatca tgaccgacta caacccacaa ctgctttg ctggcaagac         900 ctcctccatc agtgacctga aggaggtgcc gcggaaaaac atcaccctca ttcgggtct        960 gggccatgga gcctttgggg aggtgtatga aggccaggtg tccggaatgc caacgaccc       1020 aagccccctg caagtggctg tgaagacgct gcctgaagtg tgctctgaac aggacgaact      1080
ggatttcctc atggaagccc tgatcatcag caaattcaac caccagaaca ttgttcgctg      1140
cattggggtg agcctgcaat ccctgccccg gttcatcctg ctggagctca tggcggggg       1200 agacctcaag tccttcctcc gagacccgc cctcgcccg agccagccct cctccctggc        1260
catgctggac cttctgcacg tggctcggga cattgcctgt ggctgtcagt atttggagga      1320
aaaccacttc atccaccgag acattgctgc cagaaactgc ctcttgacct gtccaggccc     1380
tggaagagtg gccaagattg agacttcgg gatggcccga cacatctaca gggcgagcta      1440
ctatagaaag ggaggctgtg ccatgctgcc agttaagtgg atgccccag aggccttcat       1500 ggaaggaata ttcacttcta aaacagacac atggtccttt ggagtgctgc tatgggaaat     1560
cttttctctt ggatatatgc cataccccag caaaagcaac caggaagttc tggagttgt      1620
```

```
caccagtgga ggccggatgg acccacccaa gaactgccct gggcctgtat accggataat   1680
gactcagtgc tggcaacatc agcctgaaga caggcccaac tttgccatca ttttggagag   1740
gattgaatac tgcacccagg acccggatgt aatcaacacc gctttgccga tagaatatgg   1800
tccacttgtg gaagaggaag agaaagtgcc tgtgaggccc aaggaccctg agggggttcc   1860
tcctctcctg gtctctcaac aggcaaaacg ggaggaggag cgcagcccag ctgccccacc   1920
acctctgcct accacctcct ctggcaaggc tgcaaagaaa cccacagctg cagaggtctc   1980
tgttcgagtc cctagagggc cggccgtgga aggggacac gtgaatatgg cattctctca   2040
gtccaaccct ccttcggagt tgcacagggt ccacggatcc agaaacaagc ccaccagctt   2100
gtggaaccca acgtacggct cctggtttac agagaaaccc accaaaaaga ataatcctat   2160
agcaaagaag gagccacacg agaggggtaa cctggggctg gagggaagct gtactgtccc   2220
acctaacgtt gcaactggga gacttccggg ggcctcactg ctcctagagc cctcttcgct   2280
gactgccaat atgaaggagg tacctctgtt caggctacgt cacttcccctt gtgggaatgt   2340 caattacggc taccagcaac agggcttgcc cttagaagcc gctactgccc ctggagctgg   2400
tcattacgag gataccattc tgaaaagcaa gaatagcatg aaccagcctg ggccctgagc   2460
tcggtcgcac actcacttct cttccttggg atccctaaga ccgtgg             2506

<210> SEQ ID NO 12
<211> LENGTH: 796
<212> TYPE: PRT
<213> ORGANISM: Homo sapiens

<400> SEQUENCE: 12

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
                20                  25                  30

Gln Gln Glu Asp Glu Ile Thr Val Leu Lys Ala Ala Leu Ala Asp Val
            35                  40                  45

Leu Arg Arg Leu Ala Ile Ser Glu Asp His Val Ala Ser Val Lys Lys
        50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
                100                 105                 110

Ser Gly Thr Glu Lys Lys Lys Glu Lys Pro Gln Gly Gln Arg Glu Lys
            115                 120                 125

Lys Glu Glu Ser His Ser Asn Asp Gln Ser Pro Gln Ile Arg Ala Ser
        130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Ser Arg
                180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Ala Lys
    210                 215                 220
```

```
-continued

Met Ser Thr Arg Glu Lys Asn Ser Gln Val Tyr Arg Lys His Gln
225                 230                 235                 240

Glu Leu Gln Ala Met Gln Met Glu Leu Gln Ser Pro Glu Tyr Lys Leu
            245                 250                 255

Ser Lys Leu Arg Thr Ser Thr Ile Met Thr Asp Tyr Asn Pro Asn Tyr
            260                 265                 270

Cys Phe Ala Gly Lys Thr Ser Ser Ile Ser Asp Leu Lys Glu Val Pro
            275                 280                 285

Arg Lys Asn Ile Thr Leu Ile Arg Gly Leu Gly His Gly Ala Phe Gly
290                 295                 300

Glu Val Tyr Glu Gly Gln Val Ser Gly Met Pro Asn Asp Pro Ser Pro
305                 310                 315                 320

Leu Gln Val Ala Val Lys Thr Leu Pro Glu Val Cys Ser Glu Gln Asp
            325                 330                 335

Glu Leu Asp Phe Leu Met Glu Ala Leu Ile Ile Ser Lys Phe Asn His
            340                 345                 350

Gln Asn Ile Val Arg Cys Ile Gly Val Ser Leu Gln Ser Leu Pro Arg
            355                 360                 365

Phe Ile Leu Leu Glu Leu Met Ala Gly Gly Asp Leu Lys Ser Phe Leu
370                 375                 380

Arg Glu Thr Arg Pro Arg Pro Ser Gln Pro Ser Ser Leu Ala Met Leu
385                 390                 395                 400

Asp Leu Leu His Val Ala Arg Asp Ile Ala Cys Gly Cys Gln Tyr Leu
            405                 410                 415

Glu Glu Asn His Phe Ile His Arg Asp Ile Ala Ala Arg Asn Cys Leu
            420                 425                 430

Leu Thr Cys Pro Gly Pro Gly Arg Val Ala Lys Ile Gly Asp Phe Gly
            435                 440                 445

Met Ala Arg Asp Ile Tyr Arg Ala Ser Tyr Tyr Arg Lys Gly Gly Cys
450                 455                 460

Ala Met Leu Pro Val Lys Trp Met Pro Pro Glu Ala Phe Met Glu Gly
465                 470                 475                 480

Ile Phe Thr Ser Lys Thr Asp Thr Trp Ser Phe Gly Val Leu Leu Trp
            485                 490                 495

Glu Ile Phe Ser Leu Gly Tyr Met Pro Tyr Pro Ser Lys Ser Asn Gln
            500                 505                 510

Glu Val Leu Glu Phe Val Thr Ser Gly Gly Arg Met Asp Pro Pro Lys
            515                 520                 525

Asn Cys Pro Gly Pro Val Tyr Arg Ile Met Thr Gln Cys Trp Gln His
            530                 535                 540

Gln Pro Glu Asp Arg Pro Asn Phe Ala Ile Ile Leu Glu Arg Ile Glu
545                 550                 555                 560

Tyr Cys Thr Gln Asp Pro Asp Val Ile Asn Thr Ala Leu Pro Ile Glu
            565                 570                 575

Tyr Gly Pro Leu Val Glu Glu Glu Lys Val Pro Val Arg Pro Lys
            580                 585                 590

Asp Pro Glu Gly Val Pro Pro Leu Leu Val Ser Gln Gln Ala Lys Arg
            595                 600                 605

Glu Glu Glu Arg Ser Pro Ala Ala Pro Pro Pro Leu Pro Thr Thr Ser
            610                 615                 620

Ser Gly Lys Ala Ala Lys Lys Pro Thr Ala Ala Glu Val Ser Val Arg
625                 630                 635                 640
```

| | | | | | | | | | | | |
|---|---|---|---|---|---|---|---|---|---|---|---|
|Val|Pro|Arg|Gly|Pro|Ala|Val|Glu|Gly|Gly|His|Val|Asn|Met|Ala|Phe|
| | | |645| | | |650| | | |655|

Val Pro Arg Gly Pro Ala Val Glu Gly Gly His Val Asn Met Ala Phe
            645                 650                 655

Ser Gln Ser Asn Pro Pro Ser Glu Leu His Arg Val His Gly Ser Arg
            660                 665                 670

Asn Lys Pro Thr Ser Leu Trp Asn Pro Thr Tyr Gly Ser Trp Phe Thr
            675                 680                 685

Glu Lys Pro Thr Lys Lys Asn Asn Pro Ile Ala Lys Lys Glu Pro His
            690                 695                 700

Glu Arg Gly Asn Leu Gly Leu Glu Gly Ser Cys Thr Val Pro Pro Asn
705                 710                 715                 720

Val Ala Thr Gly Arg Leu Pro Gly Ala Ser Leu Leu Leu Glu Pro Ser
            725                 730                 735

Ser Leu Thr Ala Asn Met Lys Glu Val Pro Leu Phe Arg Leu Arg His
            740                 745                 750

Phe Pro Cys Gly Asn Val Asn Tyr Gly Tyr Gln Gln Gln Gly Leu Pro
            755                 760                 765

Leu Glu Ala Ala Thr Ala Pro Gly Ala Gly His Tyr Glu Asp Thr Ile
            770                 775                 780

Leu Lys Ser Lys Asn Ser Met Asn Gln Pro Gly Pro
785                 790                 795

<210> SEQ ID NO 13
<211> LENGTH: 3409
<212> TYPE: DNA
<213> ORGANISM: Homo sapiens

<400> SEQUENCE: 13

```
actctgtcgg tccgctgaat gaagtgcccg cccctctaag cccggagccc ggcgctttcc      60
ccgcaagatg gacggtttcg ccggcagtct cgatgtatgt atttctgctg caagtacttc     120
tgatgttcaa gatcgcctgt cagctcttga gtcacgagtt cagcaacaag aagatgaaat     180
cactgtgcta aaggcggctt tggctgatgt tttgaggcgt cttgcaatct ctgaagatca     240
tgtggcctca gtgaaaaaat cagtctcaag taaaggccaa ccaagccctc gagcagttat     300
tcccatgtcc tgtataacca atggaagtgg tgcaaacaga aaaccaagtc ataccagtgc     360
tgtctcaatt gcaggaaaag aaactctttc atctgctgct aaaagtggta cagaaaaaaa     420
gaaagaaaaa ccacaaggac agagagaaaa aaaagaggaa tctcattcta atgatcaaag     480
tccacaaatt cgagcatcac cttctcccca gccctcttca caacctctcc aaatacacag     540
acaaactcca gaaagcaaga atgctactcc caccaaaagc ataaaacgac catcaccagc     600
tgaaaagtca cataattctt gggaaaattc agatgatagc cgtaataaat tgtcgaaaat     660
accttcaaca cccaaattaa taccaaaagt taccaaaact gcagacaagc ataaagatgt     720
catcatcaac caagaaggag aatatattaa aatgtttatg cgcggtcggc caattaccat     780
gttcattcct tccgatgttg acaactatga tgacatcaga acggaactgc ctccgagaa     840
gctcaaactg gagtgggcat atggttatcg aggaaaggac tgtagagcta atgtttacct     900
tcttccgacc ggggaaatag tttatttcat tgcatcagta gtagtactat ttaattatga     960
ggagagaact cagcgacact acctgggcca tacagactgt gtgaaatgcc ttgctataca    1020
tcctgacaaa attaggattg caactggaca gatagctggc gtggataaag atggaaggcc    1080
tctacaaccc cacgtcagag tgtgggattc tgttactcta tccacactgc agattattgg    1140
acttggcact tttgagcgtg gagtaggatg cctggatttt tcaaaagcag attcaggtgt    1200
tcatttatgt gttattgatg actccaatga gcatatgctt actgtatggg actggcagag    1260
```

```
gaaagcaaaa ggagcagaaa taaagacaac aaatgaagtt gttttggctg tggagtttca    1320
cccaacagat gcaaatacca taattacatg cggtaaatct catattttct tctggacctg    1380
gagcggcaat tcactaacaa gaaaacaggg aattttggg aaatatgaaa agccaaaatt    1440
tgtgcagtgt ttagcattct tggggaatgg agatgttctt actggagact caggtggagt    1500
catgcttata tggagcaaaa ctactgtaga gcccacacct gggaaggac ctaaaggtgt    1560
atatcaaatc agcaaacaaa tcaaagctca tgatggcagt gtgttcacac tttgtcagat    1620
gagaaatggg atgttattaa ctggaggagg gaaagacaga aaaataattc tgtgggatca    1680
tgatctgaat cctgaaagag aaatagagat atgctggatg agccctgagt acaagctgag    1740
caagctccgc acctcgacca tcatgaccga ctacaacccc aactactgct tgctggcaa    1800
gacctcctcc atcagtgacc tgaaggaggt gccgcggaaa aacatcaccc tcattcgggg    1860
tctgggccat ggagcctttg ggaggtgta tgaaggccag gtgtccggaa tgcccaacga    1920
cccaagcccc ctgcaagtgg ctgtgaagac gctgcctgaa gtgtgctctg aacaggacga    1980
actggatttc ctcatggaag ccctgatcat cagcaaattc aaccaccaga acattgttcg    2040
ctgcattggg gtgagcctgc aatccctgcc ccggttcatc ctgctggagc tcatggcggg    2100
gggagacctc aagtccttcc tccgagagac ccgccctcgc ccgagccagc cctcctccct    2160
ggccatgctg gaccttctgc acgtggctcg ggacattgcc tgtggctgtc agtatttgga    2220
ggaaaaccac ttcatccacc gagacattgc tgccagaaac tgcctcttga cctgtccagg    2280
ccctggaaga gtggccaaga ttggagactt cgggatggcc cgagacatct acagggcgag    2340
ctactataga aagggaggct gtgccatgct gccagttaag tggatgcccc cagaggcctt    2400
catgaagga atattcactt ctaaaacaga cacatggtcc tttggagtgc tgctatggga    2460
aatcttttct cttggatata tgccataccc cagcaaaagc aaccaagaag ttctggagtt    2520
tgtcaccagt ggaggccgga tggacccacc caagaactgc cctgggcctg tataccggat    2580
aatgactcag tgctggcaac atcagcctga agacaggccc aactttgcca tcattttgga    2640
gaggattgaa tactgcaccc aggacccgga tgtaatcaac accgctttgc cgatagaata    2700
tggtccactt gtgaagagg aagagaaagt gcctgtgagg cccaaggacc ctgagggggt    2760
tcctcctctc ctggtctctc aacaggcaaa acgggaggag gagcgcagcc cagctgcccc    2820
accacctctg cctaccacct cctctggcaa ggctgcaaag aaacccacag ctgcagaggt    2880
ctctgttcga gtccctagag ggccggccgt ggaaggggga cacgtgaata tggcattctc    2940
tcagtccaac cctccttcgg agttgcacag ggtccacgtg tccagaaaca gcccaccag    3000
cttgtggaac ccaacgtacg gctcctggtt tacagagaaa cccaccaaaa agaataatcc    3060
tatagcaaag aaggagccac acgagagggg taacctgggg ctggagggaa gctgtactgt    3120
cccacctaac gttgcaactg ggagacttcc gggggcctca ctgctcctag agccctcttc    3180
gctgactgcc aatatgaagg aggtacctct gttcaggcta cgtcacttcc cttgtgggaa    3240
tgtcaattac ggctaccagc aacagggctt gcccttagaa gccgctactg ccctggagc    3300
tggtcattac gaggatacca ttctgaaaag caagaatagc atgaaccagc tgggccctg    3360
agctcggtcg cacactcact tctcttcctt gggatcccta agaccgtgg              3409
```

<210> SEQ ID NO 14
<211> LENGTH: 1097
<212> TYPE: PRT
<213> ORGANISM: Homo sapiens

```
<400> SEQUENCE: 14

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Leu Phe Asn Tyr Glu Glu Arg Thr Gln Arg His
    290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

Leu Asp Phe Ser Lys Ala Asp Ser Gly Val His Leu Cys Val Ile Asp
    370                 375                 380

Asp Ser Asn Glu His Met Leu Thr Val Trp Asp Trp Gln Arg Lys Ala
385                 390                 395                 400

Lys Gly Ala Glu Ile Lys Thr Thr Asn Glu Val Val Leu Ala Val Glu
                405                 410                 415
```

```
Phe His Pro Thr Asp Ala Asn Thr Ile Ile Thr Cys Gly Lys Ser His
            420                 425                 430

Ile Phe Phe Trp Thr Trp Ser Gly Asn Ser Leu Thr Arg Lys Gln Gly
            435                 440                 445

Ile Phe Gly Lys Tyr Glu Lys Pro Lys Phe Val Gln Cys Leu Ala Phe
            450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
            485                 490                 495

Gly Val Tyr Gln Ile Ser Lys Gln Ile Lys Ala His Asp Gly Ser Val
            500                 505                 510

Phe Thr Leu Cys Gln Met Arg Asn Gly Met Leu Leu Thr Gly Gly Gly
            515                 520                 525

Lys Asp Arg Lys Ile Ile Leu Trp Asp His Asp Leu Asn Pro Glu Arg
530                 535                 540

Glu Ile Glu Ile Cys Trp Met Ser Pro Glu Tyr Lys Leu Ser Lys Leu
545                 550                 555                 560

Arg Thr Ser Thr Ile Met Thr Asp Tyr Asn Pro Asn Tyr Cys Phe Ala
            565                 570                 575

Gly Lys Thr Ser Ser Ile Ser Asp Leu Lys Glu Val Pro Arg Lys Asn
            580                 585                 590

Ile Thr Leu Ile Arg Gly Leu Gly His Gly Ala Phe Gly Glu Val Tyr
            595                 600                 605

Glu Gly Gln Val Ser Gly Met Pro Asn Asp Pro Ser Pro Leu Gln Val
            610                 615                 620

Ala Val Lys Thr Leu Pro Glu Val Cys Ser Glu Gln Asp Glu Leu Asp
625                 630                 635                 640

Phe Leu Met Glu Ala Leu Ile Ile Ser Lys Phe Asn His Gln Asn Ile
            645                 650                 655

Val Arg Cys Ile Gly Val Ser Leu Gln Ser Leu Pro Arg Phe Ile Leu
            660                 665                 670

Leu Glu Leu Met Ala Gly Gly Asp Leu Lys Ser Phe Leu Arg Glu Thr
            675                 680                 685

Arg Pro Arg Pro Ser Gln Pro Ser Ser Leu Ala Met Leu Asp Leu Leu
            690                 695                 700

His Val Ala Arg Asp Ile Ala Cys Gly Cys Gln Tyr Leu Glu Glu Asn
705                 710                 715                 720

His Phe Ile His Arg Asp Ile Ala Ala Arg Asn Cys Leu Leu Thr Cys
            725                 730                 735

Pro Gly Pro Gly Arg Val Ala Lys Ile Gly Asp Phe Gly Met Ala Arg
            740                 745                 750

Asp Ile Tyr Arg Ala Ser Tyr Tyr Arg Lys Gly Gly Cys Ala Met Leu
            755                 760                 765

Pro Val Lys Trp Met Pro Pro Glu Ala Phe Met Glu Gly Ile Phe Thr
            770                 775                 780

Ser Lys Thr Asp Thr Trp Ser Phe Gly Val Leu Leu Trp Glu Ile Phe
785                 790                 795                 800

Ser Leu Gly Tyr Met Pro Tyr Pro Ser Lys Ser Asn Gln Glu Val Leu
            805                 810                 815

Glu Phe Val Thr Ser Gly Gly Arg Met Asp Pro Pro Lys Asn Cys Pro
            820                 825                 830
```

Gly Pro Val Tyr Arg Ile Met Thr Gln Cys Trp Gln His Gln Pro Glu
835                 840                 845

Asp Arg Pro Asn Phe Ala Ile Ile Leu Glu Arg Ile Glu Tyr Cys Thr
850                 855                 860

Gln Asp Pro Asp Val Ile Asn Thr Ala Leu Pro Ile Glu Tyr Gly Pro
865                 870                 875                 880

Leu Val Glu Glu Glu Lys Val Pro Val Arg Pro Lys Asp Pro Glu
            885                 890                 895

Gly Val Pro Pro Leu Leu Val Ser Gln Ala Lys Arg Glu Glu
            900                 905                 910

Arg Ser Pro Ala Ala Pro Pro Pro Leu Pro Thr Thr Ser Ser Gly Lys
915                 920                 925

Ala Ala Lys Lys Pro Thr Ala Ala Glu Val Ser Val Arg Val Pro Arg
930                 935                 940

Gly Pro Ala Val Glu Gly Gly His Val Asn Met Ala Phe Ser Gln Ser
945                 950                 955                 960

Asn Pro Pro Ser Glu Leu His Arg Val His Gly Ser Arg Asn Lys Pro
            965                 970                 975

Thr Ser Leu Trp Asn Pro Thr Tyr Gly Ser Trp Phe Thr Glu Lys Pro
            980                 985                 990

Thr Lys Lys Asn Asn Pro Ile Ala  Lys Lys Glu Pro His  Glu Arg Gly
            995                 1000                1005

Asn Leu  Gly Leu Glu Gly Ser  Cys Thr Val Pro Pro  Asn Val Ala
         1010                1015                1020

Thr Gly  Arg Leu Pro Gly Ala  Ser Leu Leu Glu  Pro Ser Ser
         1025                1030                1035

Leu Thr  Ala Asn Met Lys Glu  Val Pro Leu Phe Arg  Leu Arg His
         1040                1045                1050

Phe Pro  Cys Gly Asn Val Asn  Tyr Gly Tyr Gln Gln  Gln Gly Leu
         1055                1060                1065

Pro Leu  Glu Ala Ala Thr Ala  Pro Gly Ala Gly His  Tyr Glu Asp
         1070                1075                1080

Thr Ile  Leu Lys Ser Lys Asn  Ser Met Asn Gln Pro  Gly Pro
         1085                1090                1095

<210> SEQ ID NO 15
<211> LENGTH: 2014
<212> TYPE: DNA
<213> ORGANISM: Homo sapiens

<400> SEQUENCE: 15
actctgtcgg tccgctgaat gaagtgcccg cccctctaag cccggagccc ggcgctttcc      60
ccgcaagatg gacggtttcg ccggcagtct cgatgtatgt atttctgctg caagtacttc     120
tgatgttcaa gatcgcctgt cagctcttga gtcacgagtt cagcaacaag aagatgaaat     180
cactgtgcta aaggcggctt tggctgatgt tttgaggcgt cttgcaatct ctgaagatca     240
tgtggcctca gtgaaaaaat cagtctcaag taaagtgtac cgccggaagc accaggagct     300
gcaagccatg cagatggagc tgcagagccc tgagtacaag ctgagcaagc tccgcacctc     360
gaccatcatg accgactaca cccccaacta ctgctttgct ggcaagacct cctccatcag     420
tgacctgaag gaggtgccgc ggaaaaacat cccctcatt cggggtctgg ccatggagc      480 ctttggggag gtgtatgaag ccaggtgtc cggaatgccc aacgacccaa gcccctgca      540 agtggctgtg aagacgctgc ctgaagtgtg ctctgaacag gacgaactgg atttcctcat     600

```
ggaagccctg atcatcagca aattcaacca ccagaacatt gttcgctgca ttggggtgag    660
cctgcaatcc ctgccccggt tcatcctgct ggagctcatg gcgggggag acctcaagtc    720
cttcctccga gagacccgcc ctcgcccgag ccagccctcc tccctggcca tgctggacct    780
tctgcacgtg gctcgggaca ttgcctgtgg ctgtcagtat ttggaggaaa accacttcat    840
ccaccgagac attgctgcca gaaactgcct cttgacctgt ccaggccctg aagagtggc    900
caagattgga gacttcggga tggcccgaga catctacagg gcgagctact atagaaaggg    960
aggctgtgcc atgctgccag ttaagtggat gccccagag gccttcatgg aaggaatatt   1020
cacttctaaa acagacacat ggtcctttgg agtgctgcta tgggaaatct tttctcttgg   1080
atatatgcca taccccagca aaagcaacca ggaagttctg gagtttgtca ccagtggagg   1140
ccggatggac ccaccccaaga actgccctgg gcctgtatac cggataatga ctcagtgctg   1200
gcaacatcag cctgaagaca ggcccaactt tgccatcatt ttggagagga ttgaatactg   1260
cacccaggac ccggatgtaa tcaacaccgc tttgccgata gaatatggtc acttgtgga   1320
agaggaagag aaagtgcctg tgaggcccaa ggaccctgag ggggttcctc ctctcctggt   1380
ctctcaacag gcaaaacggg aggaggagcg cagcccagct gccccaccac ctctgcctac   1440
cacctcctct ggcaaggctg caaagaaacc cacagctgca gaggtctctg ttcgagtccc   1500
tagagggccg gccgtggaag ggggacacgt gaatatggca ttctctcagt ccaaccctcc   1560
ttcggagttg cacagggtcc acggatccag aaacaagccc accagcttgt ggaacccaac   1620
gtacggctcc tggtttacag agaaacccac caaaaagaat aatcctatag caagaagga   1680
gccacacgag aggggtaacc tggggctgga gggaagctgt actgtcccac taacgttgc   1740
aactgggaga cttccggggg cctcactgct cctagagccc tcttcgctga ctgccaatat   1800
gaaggaggta cctctgttca ggctacgtca cttcccttgt gggaatgtca attacggcta   1860
ccagcaacag gcttgccct tagaagccgc tactgcccct ggagctggtc attacgagga   1920
taccattctg aaaagcaaga atagcatgaa ccagcctggg ccctgagctc ggtcgcacac   1980
tcacttctct tccttgggat ccctaagacc gtgg                                2014
```

<210> SEQ ID NO 16
<211> LENGTH: 632
<212> TYPE: PRT
<213> ORGANISM: Homo sapiens

<400> SEQUENCE: 16

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Val Tyr Arg Arg Lys His Gln Glu Leu Gln Ala
65                  70                  75                  80

Met Gln Met Glu Leu Gln Ser Pro Glu Tyr Lys Leu Ser Lys Leu Arg
                85                  90                  95

Thr Ser Thr Ile Met Thr Asp Tyr Asn Pro Asn Tyr Cys Phe Ala Gly
            100                 105                 110

Lys Thr Ser Ser Ile Ser Asp Leu Lys Glu Val Pro Arg Lys Asn Ile
        115                 120                 125
```

```
Thr Leu Ile Arg Gly Leu Gly His Gly Ala Phe Gly Glu Val Tyr Glu
        130                 135                 140

Gly Gln Val Ser Gly Met Pro Asn Asp Pro Ser Pro Leu Gln Val Ala
145                 150                 155                 160

Val Lys Thr Leu Pro Glu Val Cys Ser Glu Gln Asp Glu Leu Asp Phe
                165                 170                 175

Leu Met Glu Ala Leu Ile Ile Ser Lys Phe Asn His Gln Asn Ile Val
                180                 185                 190

Arg Cys Ile Gly Val Ser Leu Gln Ser Leu Pro Arg Phe Ile Leu Leu
        195                 200                 205

Glu Leu Met Ala Gly Gly Asp Leu Lys Ser Phe Leu Arg Glu Thr Arg
210                 215                 220

Pro Arg Pro Ser Gln Pro Ser Ser Leu Ala Met Leu Asp Leu Leu His
225                 230                 235                 240

Val Ala Arg Asp Ile Ala Cys Gly Cys Gln Tyr Leu Glu Glu Asn His
                245                 250                 255

Phe Ile His Arg Asp Ile Ala Ala Arg Asn Cys Leu Leu Thr Cys Pro
                260                 265                 270

Gly Pro Gly Arg Val Ala Lys Ile Gly Asp Phe Gly Met Ala Arg Asp
        275                 280                 285

Ile Tyr Arg Ala Ser Tyr Tyr Arg Lys Gly Gly Cys Ala Met Leu Pro
290                 295                 300

Val Lys Trp Met Pro Pro Glu Ala Phe Met Glu Gly Ile Phe Thr Ser
305                 310                 315                 320

Lys Thr Asp Thr Trp Ser Phe Gly Val Leu Leu Trp Glu Ile Phe Ser
                325                 330                 335

Leu Gly Tyr Met Pro Tyr Pro Ser Lys Ser Asn Gln Glu Val Leu Glu
                340                 345                 350

Phe Val Thr Ser Gly Gly Arg Met Asp Pro Pro Lys Asn Cys Pro Gly
        355                 360                 365

Pro Val Tyr Arg Ile Met Thr Gln Cys Trp Gln His Gln Pro Glu Asp
370                 375                 380

Arg Pro Asn Phe Ala Ile Ile Leu Glu Arg Ile Glu Tyr Cys Thr Gln
385                 390                 395                 400

Asp Pro Asp Val Ile Asn Thr Ala Leu Pro Ile Glu Tyr Gly Pro Leu
                405                 410                 415

Val Glu Glu Glu Lys Val Pro Val Arg Pro Lys Asp Pro Glu Gly
                420                 425                 430

Val Pro Pro Leu Leu Val Ser Gln Gln Ala Lys Arg Glu Glu Arg
                435                 440                 445

Ser Pro Ala Ala Pro Pro Pro Leu Pro Thr Thr Ser Ser Gly Lys Ala
450                 455                 460

Ala Lys Lys Pro Thr Ala Ala Glu Val Ser Val Arg Val Pro Arg Gly
465                 470                 475                 480

Pro Ala Val Glu Gly Gly His Val Asn Met Ala Phe Ser Gln Ser Asn
                485                 490                 495

Pro Pro Ser Glu Leu His Arg Val His Gly Ser Arg Asn Lys Pro Thr
                500                 505                 510

Ser Leu Trp Asn Pro Thr Tyr Gly Ser Trp Phe Thr Glu Lys Pro Thr
                515                 520                 525

Lys Lys Asn Asn Pro Ile Ala Lys Lys Glu Pro His Glu Arg Gly Asn
530                 535                 540
```

```
Leu Gly Leu Glu Gly Ser Cys Thr Val Pro Pro Asn Val Ala Thr Gly
545                 550                 555                 560

Arg Leu Pro Gly Ala Ser Leu Leu Leu Glu Pro Ser Ser Leu Thr Ala
                565                 570                 575

Asn Met Lys Glu Val Pro Leu Phe Arg Leu Arg His Phe Pro Cys Gly
            580                 585                 590

Asn Val Asn Tyr Gly Tyr Gln Gln Gln Gly Leu Pro Leu Glu Ala Ala
        595                 600                 605

Thr Ala Pro Gly Ala Gly His Tyr Glu Asp Thr Ile Leu Lys Ser Lys
    610                 615                 620

Asn Ser Met Asn Gln Pro Gly Pro
625                 630

<210> SEQ ID NO 17
<211> LENGTH: 2131
<212> TYPE: DNA
<213> ORGANISM: Homo sapiens

<400> SEQUENCE: 17
actctgtcgg tccgctgaat gaagtgcccg cccctctaag cccggagccc ggcgctttcc      60
ccgcaagatg gacggtttcg ccggcagtct cgatgatagt atttctgctg caagtacttc     120
tgatgttcaa gatcgcctgt cagctcttga gtcacgagtt cagcaacaag aagatgaaat     180
cactgtgcta aaggcggctt tggctgatgt tttgaggcgt cttgcaatct ctgaagatca     240
tgtggcctca gtgaaaaaat cagtctcaag taaaggttca gagctcaggg gaggatatgg     300
agatccaggg aggcttcctg taggaagtgg cctgtgtagt gcttcaaggg ccaggctgcc     360
aggccatgtt gcagctgacc acccacctgc agtgtaccgc cggaagcacc aggagctgca     420
agccatgcag atggagctgc agagccctga gtacaagctg agcaagctcc gcacctcgac     480
catcatgacc gactacaacc ccaactactg ctttgctggc aagacctcct ccatcagtga     540
cctgaaggag gtgccgcgga aaacatcac cctcattcgg gtctgggcc atggagcctt       600
tggggaggtg tatgaaggcc aggtgtccgg aatgcccaac gacccaagcc cctgcaagt       660
ggctgtgaag acgctgcctg aagtgtgctc tgaacaggac gaactggatt cctcatgga       720
agccctgatc atcagcaaat tcaaccacca gaacattgtt cgctgcattg ggtgagcct       780
gcaatccctg ccccggttca tcctgctgga gctcatggcg gggggagacc tcaagtcctt      840
cctccgagag acccgccctc gcccgagcca gccctcctcc ctggccatgc tggaccttct      900
gcacgtggct cgggacattg cctgtggctg tcagtatttg gaggaaaacc acttcatcca      960
ccgagacatt gctgccagaa actgcctctt gacctgtcca ggccctggaa gagtggccaa     1020
gattggagac ttcgggatgg cccgagacat ctacagggcg agctactata gaaagggagg     1080
ctgtgccatg ctgccagtta agtggatgcc cccagaggcc ttcatggaag gaatattcac     1140
ttctaaaaca gacacatggt cctttggagt gctgctatgg gaaatctttt ctcttggata     1200
tatgccatac cccagcaaaa gcaaccagga agttctggag tttgtcacca gtggaggccg     1260
gatggaccca cccaagaact gccctgggcc tgtataccgg ataatgactc agtgctggca     1320
acatcagcct gaagacaggc caactttgc catcattttg gagaggattg aatactgcac      1380
ccaggacccg gatgtaatca acaccgcttt gccgatagaa tatggtccac ttgtggaaga     1440
ggaagagaaa gtgcctgtga ggcccaagga ccctgagggg gttcctcctc tcctggtctc     1500
tcaacaggca aaacgggagg aggagcgcag cccagctgcc ccaccactc tgcctaccac      1560
ctcctctggc aaggctgcaa agaaacccac agctgcagag gtctctgttc gagtccctag     1620
```

-continued

```
agggccggcc gtggaagggg gacacgtgaa tatggcattc tctcagtcca accctccttc    1680
ggagttgcac agggtccacg gatccagaaa caagcccacc agcttgtgga acccaacgta    1740
cggctcctgg tttacagaga aacccaccaa aagaataat cctatagcaa agaaggagcc     1800
acacgagagg ggtaacctgg ggctggaggg aagctgtact gtcccaccta acgttgcaac    1860
tgggagactt ccgggggcct cactgctcct agagccctct tcgctgactg ccaatatgaa    1920
ggaggtacct ctgttcaggc tacgtcactt cccttgtggg aatgtcaatt acggctacca    1980
gcaacagggc ttgcccttag aagccgctac tgcccctgga gctggtcatt acgaggatac    2040
cattctgaaa agcaagaata gcatgaacca gcctgggccc tgagctcggt cgcacactca    2100
cttctcttcc ttgggatccc taagaccgtg g                                  2131
```

<210> SEQ ID NO 18
<211> LENGTH: 671
<212> TYPE: PRT
<213> ORGANISM: Homo sapiens

<400> SEQUENCE: 18

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Ser Glu Leu Arg Gly Gly Tyr Gly Asp Pro
65                  70                  75                  80

Gly Arg Leu Pro Val Gly Ser Gly Leu Cys Ser Ala Ser Arg Ala Arg
                85                  90                  95

Leu Pro Gly His Val Ala Ala Asp His Pro Pro Ala Val Tyr Arg Arg
            100                 105                 110

Lys His Gln Glu Leu Gln Ala Met Gln Met Glu Leu Gln Ser Pro Glu
        115                 120                 125

Tyr Lys Leu Ser Lys Leu Arg Thr Ser Thr Ile Met Thr Asp Tyr Asn
    130                 135                 140

Pro Asn Tyr Cys Phe Ala Gly Lys Thr Ser Ser Ile Ser Asp Leu Lys
145                 150                 155                 160

Glu Val Pro Arg Lys Asn Ile Thr Leu Ile Arg Gly Leu Gly His Gly
                165                 170                 175

Ala Phe Gly Glu Val Tyr Glu Gly Gln Val Ser Gly Met Pro Asn Asp
            180                 185                 190

Pro Ser Pro Leu Gln Val Ala Val Lys Thr Leu Pro Glu Val Cys Ser
        195                 200                 205

Glu Gln Asp Glu Leu Asp Phe Leu Met Glu Ala Leu Ile Ile Ser Lys
    210                 215                 220

Phe Asn His Gln Asn Ile Val Arg Cys Ile Gly Val Ser Leu Gln Ser
225                 230                 235                 240

Leu Pro Arg Phe Ile Leu Leu Glu Leu Met Ala Gly Gly Asp Leu Lys
                245                 250                 255

Ser Phe Leu Arg Glu Thr Arg Pro Arg Pro Ser Gln Pro Ser Ser Leu
            260                 265                 270

Ala Met Leu Asp Leu Leu His Val Ala Arg Asp Ile Ala Cys Gly Cys
```

275                 280                 285
Gln Tyr Leu Glu Glu Asn His Phe Ile His Arg Asp Ile Ala Ala Arg
290                 295                 300
Asn Cys Leu Leu Thr Cys Pro Gly Pro Gly Arg Val Ala Lys Ile Gly
305                 310                 315                 320
Asp Phe Gly Met Ala Arg Asp Ile Tyr Arg Ala Ser Tyr Tyr Arg Lys
                325                 330                 335
Gly Gly Cys Ala Met Leu Pro Val Lys Trp Met Pro Pro Glu Ala Phe
            340                 345                 350
Met Glu Gly Ile Phe Thr Ser Lys Thr Asp Thr Trp Ser Phe Gly Val
        355                 360                 365
Leu Leu Trp Glu Ile Phe Ser Leu Gly Tyr Met Pro Tyr Pro Ser Lys
    370                 375                 380
Ser Asn Gln Glu Val Leu Glu Phe Val Thr Ser Gly Gly Arg Met Asp
385                 390                 395                 400
Pro Pro Lys Asn Cys Pro Gly Pro Val Tyr Arg Ile Met Thr Gln Cys
                405                 410                 415
Trp Gln His Gln Pro Glu Asp Arg Pro Asn Phe Ala Ile Ile Leu Glu
            420                 425                 430
Arg Ile Glu Tyr Cys Thr Gln Asp Pro Asp Val Ile Asn Thr Ala Leu
        435                 440                 445
Pro Ile Glu Tyr Gly Pro Leu Val Glu Glu Glu Lys Val Pro Val
    450                 455                 460
Arg Pro Lys Asp Pro Glu Gly Val Pro Pro Leu Leu Val Ser Gln Gln
465                 470                 475                 480
Ala Lys Arg Glu Glu Glu Arg Ser Pro Ala Ala Pro Pro Pro Leu Pro
                485                 490                 495
Thr Thr Ser Ser Gly Lys Ala Ala Lys Lys Pro Thr Ala Ala Glu Val
            500                 505                 510
Ser Val Arg Val Pro Arg Gly Pro Ala Val Glu Gly Gly His Val Asn
        515                 520                 525
Met Ala Phe Ser Gln Ser Asn Pro Pro Ser Glu Leu His Arg Val His
    530                 535                 540
Gly Ser Arg Asn Lys Pro Thr Ser Leu Trp Asn Pro Thr Tyr Gly Ser
545                 550                 555                 560
Trp Phe Thr Glu Lys Pro Thr Lys Lys Asn Asn Pro Ile Ala Lys Lys
                565                 570                 575
Glu Pro His Glu Arg Gly Asn Leu Gly Leu Glu Gly Ser Cys Thr Val
            580                 585                 590
Pro Pro Asn Val Ala Thr Gly Arg Leu Pro Gly Ala Ser Leu Leu Leu
        595                 600                 605
Glu Pro Ser Ser Leu Thr Ala Asn Met Lys Glu Val Pro Leu Phe Arg
    610                 615                 620
Leu Arg His Phe Pro Cys Gly Asn Val Asn Tyr Gly Tyr Gln Gln Gln
625                 630                 635                 640
Gly Leu Pro Leu Glu Ala Ala Thr Ala Pro Gly Ala Gly His Tyr Glu
                645                 650                 655
Asp Thr Ile Leu Lys Ser Lys Asn Ser Met Asn Gln Pro Gly Pro
            660                 665                 670

<210> SEQ ID NO 19
<211> LENGTH: 3365
<212> TYPE: DNA
<213> ORGANISM: Homo sapiens

<400> SEQUENCE: 19

```
tactctgtcg gtccgctgaa tgaagtgccc gccccctctaa gcccggagcc cggcgctttc      60
cccgcaagat ggacggtttc gccggcagtc tcgatgatag tatttctgct gcaagtactt     120
ctgatgttca agatcgcctg tcagctcttg agtcacgagt tcagcaacaa gaagatgaaa     180
tcactgtgct aaaggcggct ttggctgatg ttttgaggcg tcttgcaatc tctgaagatc     240
atgtggcctc agtgaaaaaa tcagtctcaa gtaaaggcca accaagccct cgagcagtta     300
ttcccatgtc ctgtataacc aatggaagtg gtgcaaacag aaaaccaagt cataccagtg     360
ctgtctcaat tgcaggaaaa gaaactctt  catctgctgc taaaagtggt acagaaaaaa     420
agaaagaaaa accacaagga cagagagaaa aaaagagga  atctcattct aatgatcaaa     480
gtccacaaat tcgagcatca ccttctcccc agccctcttc acaacctctc caaatacaca     540
gacaaactcc agaaagcaag aatgctactc ccaccaaaag cataaaacga ccatcaccag     600
ctgaaaagtc acataattct tgggaaaatt cagatgatag ccgtaataaa ttgtcgaaaa     660
taccttcaac acccaaatta ataccaaaag ttaccaaaac tgcagacaag cataaagatg     720
tcatcatcaa ccaagaagga gaatatatta aaatgtttat gcgcggtcgg ccaattacca     780
tgttcattcc ttccgatgtt gacaactatg atgacatcag aacggaactg cctcctgaga     840
agctcaaact ggagtgggca tatggttatc gaggaaagga ctgtagagct aatgtttacc     900
ttcttccgac cggggaaata gtttatttca ttgcatcagt agtagtacta tttaattatg     960
aggagagaac tcagcgacac tacctgggcc atacagactg tgtgaaatgc cttgctatac    1020
atcctgacaa aattaggatt gcaactggac agatagctgg cgtggataaa gatggaaggc    1080
ctctacaacc ccacgtcaga gtgtgggatt ctgttactct atccacactg cagattattg    1140
gacttggcac ttttgagcgt ggagtaggat gcctggattt ttcaaaagca gattcaggtg    1200
ttcatttatg tgttattgat gactccaatg agcatatgct tactgtatgg gactggcaga    1260
ggaaagcaaa aggagcagaa ataaagacaa caaatgaagt tgtttttggct gtggagtttc    1320
acccaacaga tgcaaatacc ataattcat  gcggtaaatc tcatatttc  ttctggacct    1380
ggagcggcaa ttcactaaca agaaaacagg gaattttgg  gaaatatgaa aagccaaaat    1440
ttgtgcagtg tttagcattc ttggggaatg gagatgttct tactggagac tcaggtggag    1500
tcatgcttat atggagcaaa actactgtag agcccacacc tggaaaagga cctaaaggaa    1560
gtggcctgtg tagtgcttca agggccaggc tgccaggcca tgttgcagct gaccacccac    1620
ctgcagtgta ccgccggaag caccaggagc tgcaagccat gcagatggag ctgcagagcc    1680
ctgagtacaa gctgagcaag ctccgcacct cgaccatcat gaccgactac aaccccaact    1740
actgctttgc tggcaagacc tcctccatca gtgacctgaa ggaggtgccg cggaaaaaca    1800
tcaccctcat tcggggtctg ggccatggag cctttgggga ggtgtatgaa ggccaggtgt    1860
ccggaatgcc caacgaccca agccccctgc aagtggctgt gaagacgctg cctgaagtgt    1920
gctctgaaca ggacgaactg gatttcctca tggaagccct gatcatcagc aaattcaacc    1980
accagaacat tgttcgctgc attggggtga gcctgcaatc cctgcccggg ttcatcctgc    2040
tggagctcat ggcgggggga gacctcaagt ccttcctccg agagacccgc cctcgcccga    2100
gccagccctc ctccctggcc atgctggacc ttctgcacgt ggctcgggac attgcctgtg    2160
gctgtcagta tttggaggaa aaccacttca tccaccgaga cattgctgcc agaaactgcc    2220
tcttgacctg tccaggccct ggaagagtgg ccaagattgg agacttcggg atggcccgag    2280
```

```
acatctacag ggcgagctac tatagaaagg gaggctgtgc catgctgcca gttaagtgga    2340
tgcccccaga ggccttcatg gaaggaatat tcacttctaa aacagacaca tggtcctttg    2400
gagtgctgct atgggaaatc ttttctcttg gatatatgcc ataccccagc aaaagcaacc    2460
aggaagttct ggagtttgtc accagtggag gccggatgga cccacccaag aactgccctg    2520
ggcctgtata ccggataatg actcagtgct ggcaacatca gcctgaagac aggcccaact    2580
ttgccatcat tttggagagg attgaatact gcacccagga cccggatgta atcaacaccg    2640
ctttgccgat agaatatggt ccacttgtgg aagaggaaga gaaagtgcct gtgaggccca    2700
aggaccctga gggggttcct cctctcctgg tctctcaaca ggcaaaacgg gaggaggagc    2760
gcagcccagc tgccccacca cctctgccta ccacctcctc tggcaaggct gcaaagaaac    2820
ccacagctgc agaggtctct gttcgagtcc ctagagggcc ggccgtggaa ggggacacg    2880
tgaatatggc attctctcag tccaacccte cttcggagtt gcacagggtc cacggatcca    2940
gaaacaagcc caccagcttg tggaacccaa cgtacggctc ctggtttaca gagaaaccca    3000
ccaaaaagaa taatcctata gcaaagaagg agccacacga gaggggtaac ctggggctgg    3060
agggaagctg tactgtccca cctaacgttg caactgggag acttccgggg gcctcactgc    3120
tcctagagcc ctcttcgctg actgccaata tgaaggaggt acctctgttc aggctacgtc    3180
acttcccttg tgggaatgtc aattacggct accagcaaca gggcttgccc ttagaagccg    3240
ctactgcccc tggagctggt cattacgagg ataccattct gaaaagcaag aatagcatga    3300
accagcctgg gccctgagct cggtcgcaca ctcacttctc ttccttggga tccctaagac    3360
cgtgg                                                                3365
```

<210> SEQ ID NO 20
<211> LENGTH: 1082
<212> TYPE: PRT
<213> ORGANISM: Homo sapiens

<400> SEQUENCE: 20

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

```
Pro Ala Glu Lys Ser His Asn Ser Trp Asn Ser Asp Asp Ser Arg
            180                 185                 190
Asn Lys Leu Ser Lys Ile Pro Ser Thr Pro Lys Leu Ile Pro Lys Val
    195                 200                 205
Thr Lys Thr Ala Asp Lys His Lys Asp Val Ile Ile Asn Gln Glu Gly
210                 215                 220
Glu Tyr Ile Lys Met Phe Met Arg Gly Arg Pro Ile Thr Met Phe Ile
225                 230                 235                 240
Pro Ser Asp Val Asp Asn Tyr Asp Asp Ile Arg Thr Glu Leu Pro Pro
            245                 250                 255
Glu Lys Leu Lys Leu Glu Trp Ala Tyr Gly Tyr Arg Gly Lys Asp Cys
        260                 265                 270
Arg Ala Asn Val Tyr Leu Leu Pro Thr Gly Glu Ile Val Tyr Phe Ile
    275                 280                 285
Ala Ser Val Val Leu Phe Asn Tyr Glu Glu Arg Thr Gln Arg His
290                 295                 300
Tyr Leu Gly His Thr Asp Cys Val Lys Cys Leu Ala Ile His Pro Asp
305                 310                 315                 320
Lys Ile Arg Ile Ala Thr Gly Gln Ile Ala Gly Val Asp Lys Asp Gly
            325                 330                 335
Arg Pro Leu Gln Pro His Val Arg Val Trp Asp Ser Val Thr Leu Ser
        340                 345                 350
Thr Leu Gln Ile Ile Gly Leu Gly Thr Phe Glu Arg Gly Val Gly Cys
    355                 360                 365
Leu Asp Phe Ser Lys Ala Asp Ser Gly Val His Leu Cys Val Ile Asp
370                 375                 380
Asp Ser Asn Glu His Met Leu Thr Val Trp Asp Trp Gln Arg Lys Ala
385                 390                 395                 400
Lys Gly Ala Glu Ile Lys Thr Thr Asn Glu Val Val Leu Ala Val Glu
            405                 410                 415
Phe His Pro Thr Asp Ala Asn Thr Ile Ile Thr Cys Gly Lys Ser His
        420                 425                 430
Ile Phe Phe Trp Thr Trp Ser Gly Asn Ser Leu Thr Arg Lys Gln Gly
    435                 440                 445
Ile Phe Gly Lys Tyr Glu Lys Pro Lys Phe Val Gln Cys Leu Ala Phe
450                 455                 460
Leu Gly Asn Gly Asp Val Leu Thr Gly Asp Ser Gly Gly Val Met Leu
465                 470                 475                 480
Ile Trp Ser Lys Thr Thr Val Glu Pro Thr Pro Gly Lys Gly Pro Lys
            485                 490                 495
Gly Ser Gly Leu Cys Ser Ala Ser Arg Ala Arg Leu Pro Gly His Val
        500                 505                 510
Ala Ala Asp His Pro Pro Ala Val Tyr Arg Arg Lys His Gln Glu Leu
    515                 520                 525
Gln Ala Met Gln Met Glu Leu Gln Ser Pro Glu Tyr Lys Leu Ser Lys
530                 535                 540
Leu Arg Thr Ser Thr Ile Met Thr Asp Tyr Asn Pro Asn Tyr Cys Phe
545                 550                 555                 560
Ala Gly Lys Thr Ser Ser Ile Ser Asp Leu Lys Glu Val Pro Arg Lys
            565                 570                 575
Asn Ile Thr Leu Ile Arg Gly Leu Gly His Gly Ala Phe Gly Glu Val
        580                 585                 590
Tyr Glu Gly Gln Val Ser Gly Met Pro Asn Asp Pro Ser Pro Leu Gln
```

```
            595                 600                 605
Val Ala Val Lys Thr Leu Pro Glu Val Cys Ser Glu Gln Asp Glu Leu
            610                 615                 620
Asp Phe Leu Met Glu Ala Leu Ile Ile Ser Lys Phe Asn His Gln Asn
625                 630                 635                 640
Ile Val Arg Cys Ile Gly Val Ser Leu Gln Ser Leu Pro Arg Phe Ile
                645                 650                 655
Leu Leu Glu Leu Met Ala Gly Gly Asp Leu Lys Ser Phe Leu Arg Glu
            660                 665                 670
Thr Arg Pro Arg Pro Ser Gln Pro Ser Ser Leu Ala Met Leu Asp Leu
            675                 680                 685
Leu His Val Ala Arg Asp Ile Ala Cys Gly Cys Gln Tyr Leu Glu Glu
            690                 695                 700
Asn His Phe Ile His Arg Asp Ile Ala Ala Arg Asn Cys Leu Leu Thr
705                 710                 715                 720
Cys Pro Gly Pro Gly Arg Val Ala Lys Ile Gly Asp Phe Gly Met Ala
                725                 730                 735
Arg Asp Ile Tyr Arg Ala Ser Tyr Tyr Arg Lys Gly Gly Cys Ala Met
            740                 745                 750
Leu Pro Val Lys Trp Met Pro Glu Ala Phe Met Glu Gly Ile Phe
            755                 760                 765
Thr Ser Lys Thr Asp Thr Trp Ser Phe Gly Val Leu Leu Trp Glu Ile
770                 775                 780
Phe Ser Leu Gly Tyr Met Pro Tyr Pro Ser Lys Ser Asn Gln Glu Val
785                 790                 795                 800
Leu Glu Phe Val Thr Ser Gly Gly Arg Met Asp Pro Pro Lys Asn Cys
                805                 810                 815
Pro Gly Pro Val Tyr Arg Ile Met Thr Gln Cys Trp Gln His Gln Pro
            820                 825                 830
Glu Asp Arg Pro Asn Phe Ala Ile Ile Leu Glu Arg Ile Glu Tyr Cys
            835                 840                 845
Thr Gln Asp Pro Asp Val Ile Asn Thr Ala Leu Pro Ile Glu Tyr Gly
            850                 855                 860
Pro Leu Val Glu Glu Glu Lys Val Pro Val Arg Pro Lys Asp Pro
865                 870                 875                 880
Glu Gly Val Pro Pro Leu Leu Val Ser Gln Gln Ala Lys Arg Glu Glu
                885                 890                 895
Glu Arg Ser Pro Ala Ala Pro Pro Pro Leu Pro Thr Thr Ser Ser Gly
            900                 905                 910
Lys Ala Ala Lys Lys Pro Thr Ala Ala Glu Val Ser Val Arg Val Pro
            915                 920                 925
Arg Gly Pro Ala Val Glu Gly Gly His Val Asn Met Ala Phe Ser Gln
            930                 935                 940
Ser Asn Pro Pro Ser Glu Leu His Arg Val His Gly Ser Arg Asn Lys
945                 950                 955                 960
Pro Thr Ser Leu Trp Asn Pro Thr Tyr Gly Ser Trp Phe Thr Glu Lys
                965                 970                 975
Pro Thr Lys Lys Asn Asn Pro Ile Ala Lys Lys Glu Pro His Glu Arg
            980                 985                 990
Gly Asn Leu Gly Leu Glu Gly Ser Cys Thr Val Pro Pro Asn Val Ala
            995                 1000                1005
Thr Gly Arg Leu Pro Gly Ala Ser Leu Leu Leu Glu Pro Ser Ser
            1010                1015                1020
```

```
Leu Thr Ala Asn Met Lys Glu Val Pro Leu Phe Arg Leu Arg His
    1025            1030                1035

Phe Pro Cys Gly Asn Val Asn Tyr Gly Tyr Gln Gln Gln Gly Leu
    1040            1045                1050

Pro Leu Glu Ala Ala Thr Ala Pro Gly Ala Gly His Tyr Glu Asp
    1055            1060                1065

Thr Ile Leu Lys Ser Lys Asn Ser Met Asn Gln Pro Gly Pro
    1070            1075                1080

<210> SEQ ID NO 21
<211> LENGTH: 3435
<212> TYPE: DNA
<213> ORGANISM: Homo sapiens

<400> SEQUENCE: 21
tactctgtcg gtccgctgaa tgaagtgccc gcccctctaa gcccggagcc cggcgctttc      60
cccgcaagat ggacggtttc gccggcagtc tcgatgatag tatttctgct gcaagtactt     120
ctgatgttca agatcgcctg tcagctcttg agtcacgagt tcagcaacaa gaagatgaaa     180
tcactgtgct aaaggcggct ttggctgatg ttttgaggcg tcttgcaatc tctgaagatc     240
atgtggcctc agtgaaaaaa tcagtctcaa gtaaaggcca accagccct cgagcagtta      300
ttcccatgtc ctgtataacc aatggaagtg gtgcaaacag aaaaccaagt cataccagtg     360
ctgtctcaat tgcaggaaaa gaaactcttt catctgctgc taaaagtggt acagaaaaaa     420
agaaagaaaa accacaagga cagagagaaa aaaagagga atctcattct aatgatcaaa      480
gtccacaaat tcgagcatca ccttctcccc agccctcttc acaacctctc caaatacaca     540
gacaaactcc agaaagcaag aatgctactc ccaccaaaag cataaaacga ccatcaccag     600
ctgaaaagtc acataattct tgggaaaatt cagatgatag ccgtaataaa ttgtcgaaaa     660
taccttcaac acccaaatta ataccaaaag ttaccaaaac tgcagacaag cataaagatg     720
tcatcatcaa ccaagaagga gaatatatta aaatgtttat gcgcggtcgg ccaattacca     780
tgttcattcc ttccgatgtt gacaactatg atgacatcag aacggaactg cctcctgaga     840
agctcaaact ggagtgggca tatggttatc gaggaaagga ctgtagagct aatgtttacc     900
ttcttccgac cggggaaata gtttatttca ttgcatcagt agtagtacta tttaattatg     960
aggagagaac tcagcgacac tacctgggcc atacagactg tgtgaaatgc ttgctatac    1020
atcctgacaa aattaggatt gcaactggac agatagctgg cgtggataaa gatggaaggc    1080
ctctacaacc ccacgtcaga gtgtgggatt ctgttactct atccacactg cagattattg    1140
gacttggcac ttttgagcgt ggagtaggat gcctggattt ttcaaaagca gattcaggtg    1200
ttcatttatg tgttattgat gactccaatg agcatatgct tactgtatgg gactggcaga    1260
ggaaagcaaa aggagcagaa ataaagacaa caaatgaagt tgttttggct gtggagtttc    1320
acccaacaga tgcaaatacc ataattcat gcggtaaatc tcatattttc ttctggacct    1380
ggagcggcaa ttcactaaca agaaaacagg gaattttggg aaatatgaa agccaaaat     1440
ttgtgcagtg tttagcattc ttggggaatg gagatgttct tactggagac tcaggtggag    1500
tcatgcttat atggagcaaa actactgtag agcccacacc tgggaaagga cctaaaggtg    1560
tatatcaaat cagcaaacaa atcaaagctc atgatggcag tgtgttcaca ctttgtcaga    1620
tgagaaatgg gatgttatta actggaggag ggaaagacaa aaaaataatt ctgtgggatc    1680
atgatctgaa tcctgaaaga gaaatagagc accaggagct gcaagccatg cagatggagc    1740
```

```
tgcagagccc tgagtacaag ctgagcaagc tccgcacctc gaccatcatg accgactaca   1800
accccaacta ctgctttgct ggcaagacct cctccatcag tgacctgaag gaggtgccgc   1860
ggaaaaacat caccctcatt cggggtctgg gccatggagc ctttggggag gtgtatgaag   1920
gccaggtgtc cggaatgccc aacgacccaa gccccctgca agtggctgtg aagacgctgc   1980
ctgaagtgtg ctctgaacag gacgaactgg atttcctcat ggaagccctg atcatcagca   2040
aattcaacca ccagaacatt gttcgctgca ttggggtgag cctgcaatcc ctgcccggt    2100 tcatcctgct ggagctcatg gcgggggag acctcaagtc cttcctccga gagacccgcc    2160
ctcgcccgag ccagccctcc tccctggcca tgctggacct tctgcacgtg gctcgggaca   2220
ttgcctgtgg ctgtcagtat ttggaggaaa accacttcat ccaccgagac attgctgcca   2280
gaaactgcct cttgacctgt ccaggccctg aagagtggc caagattgga gacttcggga    2340
tggcccgaga catctacagg gcgagctact atagaaaggg aggctgtgcc atgctgccag   2400
ttaagtggat gccccagag gccttcatgg aaggaatatt cacttctaaa acagacacat    2460
ggtcctttgg agtgctgcta tgggaaatct tttctcttgg atatatgcca taccccagca   2520
aaagcaacca ggaagttctg gagtttgtca ccagtggagg ccggatggac ccacccaaga   2580
actgccctgg gcctgtatac cggataatga ctcagtgctg gcaacatcag cctgaagaca   2640
ggcccaactt tgccatcatt ttggagagga ttgaatactg cacccaggac ccggatgtaa   2700
tcaacaccgc tttgccgata gaatatggtc cacttgtgga agaggaagag aaagtgcctg   2760
tgaggcccaa ggaccctgag ggggttcctc ctctcctggt ctctcaacag gcaaaacggg   2820
aggaggagcg cagcccagct gccccaccac ctctgcctac cacctcctct ggcaaggctg   2880
caaagaaacc cacagctgca gaggtctctg ttcgagtccc tagagggccg gccgtggaag   2940
ggggacacgt gaatatggca ttctctcagt ccaaccctcc ttcggagttg cacaaggtcc   3000
acggatccag aaacaagccc accagcttgt ggaacccaac gtacggctcc tggtttacag   3060
agaaacccac caaaaagaat aatcctatag caaagaagga ccacacgac aggggtaacc    3120 tggggctgga gggaagctgt actgtcccac ctaacgttgc aactgggaga cttccggggg   3180
cctcactgct cctagagccc tcttcgctga ctgccaatat gaaggaggta cctctgttca   3240
ggctacgtca cttcccttgt gggaatgtca attacggcta ccagcaacag gcttgccct    3300 tagaagccgc tactgcccct ggagctggtc attacgagga taccattctg aaaagcaaga   3360
atagcatgaa ccagcctggg ccctgagctc ggtcgcacac tcacttctct tccttgggat   3420
ccctaagacc gtgga                                                    3435
```

<210> SEQ ID NO 22
<211> LENGTH: 1105
<212> TYPE: PRT
<213> ORGANISM: Homo sapiens

<400> SEQUENCE: 22

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
```

```
                65                  70                  75                  80
        Ser Cys Ile Thr Asn Gly Ser Gly Ala Asn Arg Lys Pro Ser His Thr
                            85                  90                  95

Ser Ala Val Ser Ile Ala Gly Lys Glu Thr Leu Ser Ser Ala Ala Lys
                        100                 105                 110

Ser Gly Thr Glu Lys Lys Lys Glu Lys Pro Gln Gly Gln Arg Glu Lys
                        115                 120                 125

Lys Glu Glu Ser His Ser Asn Asp Gln Ser Pro Gln Ile Arg Ala Ser
                    130                 135                 140

Pro Ser Pro Gln Pro Ser Ser Gln Pro Leu Gln Ile His Arg Gln Thr
        145                 150                 155                 160

Pro Glu Ser Lys Asn Ala Thr Pro Thr Lys Ser Ile Lys Arg Pro Ser
                        165                 170                 175

Pro Ala Glu Lys Ser His Asn Ser Trp Glu Asn Ser Asp Asp Ser Arg
                    180                 185                 190

Asn Lys Leu Ser Lys Ile Pro Ser Thr Pro Lys Leu Ile Pro Lys Val
                    195                 200                 205

Thr Lys Thr Ala Asp Lys His Lys Asp Val Ile Ile Asn Gln Glu Gly
        210                 215                 220

Glu Tyr Ile Lys Met Phe Met Arg Gly Arg Pro Ile Thr Met Phe Ile
        225                 230                 235                 240

Pro Ser Asp Val Asp Asn Tyr Asp Asp Ile Arg Thr Glu Leu Pro Pro
                        245                 250                 255

Glu Lys Leu Lys Leu Glu Trp Ala Tyr Gly Tyr Arg Gly Lys Asp Cys
                        260                 265                 270

Arg Ala Asn Val Tyr Leu Leu Pro Thr Gly Glu Ile Val Tyr Phe Ile
                    275                 280                 285

Ala Ser Val Val Val Leu Phe Asn Tyr Glu Glu Arg Thr Gln Arg His
                    290                 295                 300

Tyr Leu Gly His Thr Asp Cys Val Lys Cys Leu Ala Ile His Pro Asp
        305                 310                 315                 320

Lys Ile Arg Ile Ala Thr Gly Gln Ile Ala Gly Val Asp Lys Asp Gly
                        325                 330                 335

Arg Pro Leu Gln Pro His Val Arg Val Trp Asp Ser Val Thr Leu Ser
                    340                 345                 350

Thr Leu Gln Ile Ile Gly Leu Gly Thr Phe Glu Arg Gly Val Gly Cys
                    355                 360                 365

Leu Asp Phe Ser Lys Ala Asp Ser Gly Val His Leu Cys Val Ile Asp
                    370                 375                 380

Asp Ser Asn Glu His Met Leu Thr Val Trp Asp Trp Gln Arg Lys Ala
        385                 390                 395                 400

Lys Gly Ala Glu Ile Lys Thr Thr Asn Glu Val Val Leu Ala Val Glu
                        405                 410                 415

Phe His Pro Thr Asp Ala Asn Thr Ile Ile Thr Cys Gly Lys Ser His
                        420                 425                 430

Ile Phe Phe Trp Thr Trp Ser Gly Asn Ser Leu Thr Arg Lys Gln Gly
                    435                 440                 445

Ile Phe Gly Lys Tyr Glu Lys Pro Lys Phe Val Gln Cys Leu Ala Phe
                    450                 455                 460

Leu Gly Asn Gly Asp Val Leu Thr Gly Asp Ser Gly Gly Val Met Leu
        465                 470                 475                 480

Ile Trp Ser Lys Thr Thr Val Glu Pro Thr Pro Gly Lys Gly Pro Lys
                        485                 490                 495
```

-continued

```
Gly Val Tyr Gln Ile Ser Lys Gln Ile Lys Ala His Asp Gly Ser Val
                500                 505                 510
Phe Thr Leu Cys Gln Met Arg Asn Gly Met Leu Leu Thr Gly Gly Gly
                515                 520                 525
Lys Asp Arg Lys Ile Ile Leu Trp Asp His Asp Leu Asn Pro Glu Arg
                530                 535                 540
Glu Ile Glu His Gln Glu Leu Gln Ala Met Gln Met Glu Leu Gln Ser
545                 550                 555                 560
Pro Glu Tyr Lys Leu Ser Lys Leu Arg Thr Ser Thr Ile Met Thr Asp
                565                 570                 575
Tyr Asn Pro Asn Tyr Cys Phe Ala Gly Lys Thr Ser Ser Ile Ser Asp
                580                 585                 590
Leu Lys Glu Val Pro Arg Lys Asn Ile Thr Leu Ile Arg Gly Leu Gly
                595                 600                 605
His Gly Ala Phe Gly Glu Val Tyr Glu Gly Gln Val Ser Gly Met Pro
                610                 615                 620
Asn Asp Pro Ser Pro Leu Gln Val Ala Val Lys Thr Leu Pro Glu Val
625                 630                 635                 640
Cys Ser Glu Gln Asp Glu Leu Asp Phe Leu Met Glu Ala Leu Ile Ile
                645                 650                 655
Ser Lys Phe Asn His Gln Asn Ile Val Arg Cys Ile Gly Val Ser Leu
                660                 665                 670
Gln Ser Leu Pro Arg Phe Ile Leu Leu Glu Leu Met Ala Gly Gly Asp
                675                 680                 685
Leu Lys Ser Phe Leu Arg Glu Thr Arg Pro Arg Pro Ser Gln Pro Ser
                690                 695                 700
Ser Leu Ala Met Leu Asp Leu Leu His Val Ala Arg Asp Ile Ala Cys
705                 710                 715                 720
Gly Cys Gln Tyr Leu Glu Glu Asn His Phe Ile His Arg Asp Ile Ala
                725                 730                 735
Ala Arg Asn Cys Leu Leu Thr Cys Pro Gly Pro Gly Arg Val Ala Lys
                740                 745                 750
Ile Gly Asp Phe Gly Met Ala Arg Asp Ile Tyr Arg Ala Ser Tyr Tyr
                755                 760                 765
Arg Lys Gly Gly Cys Ala Met Leu Pro Val Lys Trp Met Pro Pro Glu
770                 775                 780
Ala Phe Met Glu Gly Ile Phe Thr Ser Lys Thr Asp Thr Trp Ser Phe
785                 790                 795                 800
Gly Val Leu Leu Trp Glu Ile Phe Ser Leu Gly Tyr Met Pro Tyr Pro
                805                 810                 815
Ser Lys Asn Gln Glu Val Leu Glu Phe Val Thr Ser Gly Gly Arg
                820                 825                 830
Met Asp Pro Pro Lys Asn Cys Pro Gly Pro Val Tyr Arg Ile Met Thr
                835                 840                 845
Gln Cys Trp Gln His Gln Pro Glu Asp Arg Pro Asn Phe Ala Ile Ile
                850                 855                 860
Leu Glu Arg Ile Glu Tyr Cys Thr Gln Asp Pro Asp Val Ile Asn Thr
865                 870                 875                 880
Ala Leu Pro Ile Glu Tyr Gly Pro Leu Val Glu Glu Glu Lys Val
                885                 890                 895
Pro Val Arg Pro Lys Asp Pro Glu Gly Val Pro Pro Leu Leu Val Ser
                900                 905                 910
```

| | | | | | | | | | | |
|---|---|---|---|---|---|---|---|---|---|---|
|Gln|Gln|Ala|Lys|Arg|Glu|Glu|Arg|Ser|Pro|Ala|Pro|Pro|Pro|
| | |915| | | |920| | | |925| | | |

Leu Pro Thr Thr Ser Ser Gly Lys Ala Ala Lys Pro Thr Ala Ala
    930                 935                940

Glu Val Ser Val Arg Val Pro Arg Gly Pro Ala Val Glu Gly His
945                 950                955               960

Val Asn Met Ala Phe Ser Gln Ser Asn Pro Pro Ser Glu Leu His Lys
            965                970              975

Val His Gly Ser Arg Asn Lys Pro Thr Ser Leu Trp Asn Pro Thr Tyr
        980                 985              990

Gly Ser Trp Phe Thr Glu Lys Pro  Thr Lys Lys Asn Asn  Pro Ile Ala
        995               1000            1005

Lys Lys  Glu Pro His Asp Arg  Gly Asn Leu Gly Leu  Glu Gly Ser
  1010                1015                 1020

Cys Thr  Val Pro Pro Asn Val  Ala Thr Gly Arg Leu  Pro Gly Ala
  1025                1030               1035

Ser Leu  Leu Leu Glu Pro Ser  Ser Leu Thr Ala Asn  Met Lys Glu
  1040                1045               1050

Val Pro  Leu Phe Arg Leu Arg  His Phe Pro Cys Gly  Asn Val Asn
  1055                1060               1065

Tyr Gly  Tyr Gln Gln Gln Gly  Leu Pro Leu Glu Ala  Ala Thr Ala
  1070                1075               1080

Pro Gly  Ala Gly His Tyr Glu  Asp Thr Ile Leu Lys  Ser Lys Asn
  1085                1090               1095

Ser Met  Asn Gln Pro Gly Pro
  1100                1105

<210> SEQ ID NO 23
<211> LENGTH: 4479
<212> TYPE: DNA
<213> ORGANISM: Homo sapiens

<400> SEQUENCE: 23

```
tgcgagaaag atggcggacc tggccgagtg caacatcaaa gtgatgtgtc gcttcagacc      60
tctcaacgag tctgaagtga accgcggcga caagtacatc gccaagtttc agggagaaga     120
cacggtcgtg atcgcgtcca agccttatgc atttgatcgg gtgttccagt caagcacatc     180
tcaagagcaa gtgtataatg actgtgcaaa gaagattgtt aaagatgtac ttgaaggata     240
taatggaaca atatttgcat atggacaaac atcctctggg aagacacaca caatggaggg     300
taaacttcat gatccagaag gcatgggaat tattccaaga atagtgcaag atattttaa      360 ttatatttac tccatggatg aaaatttgga atttcatatt aaggtttcat attttgaaat     420
atatttggat aagataaggg acctgttaga tgtttcaaag accaaccttt cagttcatga     480
agacaaaaac cgagttccct atgtaaaggg gtgcacagag cgttttgtat gtagtccaga     540
tgaagttatg gataccatag atgaaggaaa atccaacaga catgtagcag ttacaaatat     600
gaatgaacat agctctagga gtcacagtat atttcttatt aatgtcaaac aagagaacac     660
acaaacggaa caaaagctga gtggaaaact ttatctggtt gatttagctg gtagtgaaaa     720
ggttagtaaa actggagctg aaggtgctgt gctggatgaa gctaaaaaca tcaacaagtc     780
actttctgct cttggaaatg ttatttctgc tttggctgag ggtagtacat atgttccata     840
tcgagatagt aaaatgacaa gaatccttca agattcatta ggtggcaact gtagaaccac     900
tattgtaatt tgctgctctc catcatcata caatgagtct gaaacaaaat ctacactctt     960
```

```
atttggccaa agggccaaaa caattaagaa cacagtttgt gtcaatgtgg agttaactgc    1020
agaacagtgg aaaagaagt atgaaaaga aaagaaaaa aataagatcc tgcggaacac       1080
tattcagtgg cttgaaaatg agctcaacag atggcgtaat ggggagacgg tgcctattga   1140
tgaacagttt gacaaagaga aagccaactt ggaagctttc acagtggata agatattac    1200
tcttaccaat gataaaccag caaccgcaat tggagttata ggaaatttta ctgatgctga   1260
aagaagaaag tgtgaagaag aaattgctaa attatacaaa cagcttgatg acaaggatga   1320
agaaattaac cagcaaagtc aactggtaga gaaactgaag acgcaaatgt ggatcagga    1380
ggagcttttg gcatctacca gaagggatca agacaatatg caagctgagc tgaatcgcct   1440
tcaagcagaa aatgatgcct ctaaagaaga agtgaaagaa gttttacagg ccctagaaga   1500
acttgctgtc aattatgatc agaagtctca ggaagttgaa gacaaaacta aggaatatga   1560
attgcttagt gatgaattga atcagaaatc ggcaacttta gcgagtatag atgctgagct   1620
tcagaaactt aaggaaatga ccaaccacca gaaaaaacga gcagctgaga tgatggcatc   1680
tttactaaaa gaccttgcag aaataggaat tgctgtggga aataatgatg taaagcagcc   1740
tgagggaact ggcatgatag atgaagagtt cactgttgca agactctaca ttagcaaaat   1800
gaagtcagaa gtaaaaacca tggtgaaacg ttgcaagcag ttagaaagca cacaaactga   1860
gagcaacaaa aaaatggaag aaaatgaaaa ggagttagca gcatgtcagc ttcgtatctc   1920
tcaacatgaa gccaaaatca agtcattgac tgaatacctt caaaatgtgg aacaaaagaa   1980
aagacagttg gaggaatctg tcgatgccct cagtgaagaa ctagtccagc ttcgagcaca   2040
agagaaagtc catgaaatgg aaaaggagca cttaaataag gttcagactg caaatgaagt   2100
taagcaagct gttgaacagc agatccagag ccatagagaa actcatcaaa aacagatcag   2160
tagtttgaga gatgaagtag aagcaaaagc aaaacttatt actgatcttc aagaccaaaa   2220
ccagaaaatg atgttagagc aggaacgtct aagagtagaa catgagaagt gaaaagccac   2280
agatcaggaa aagagcagaa aactacatga acttacggtt atgcaagata gacgagaaca   2340
agcaagacaa gacttgaagg gtttggaaga gacagtggca aaagaacttc agactttaca   2400
caacctgcgc aaactctttg ttcaggacct ggctacaaga gttaaaaaga gtgctgagat   2460
tgattctgat gacaccggag gcagcgctgc tcagaagcaa aaaatctcct ttcttgaaaa   2520
taatcttgaa cagctcacta agtgcacaa acagttggta cgtgataatg cagatctccg   2580
ctgtgaactt cctaagttgg aaaagcgact tcgagctaca gctgagagag tgaaagcttt   2640
ggaatcagca ctgaaagaag ctaaagaaaa tgcatctcgt gatcgcaaac gctatcagca   2700
agaagtagat cgcataaagg aagcagtcag gtcaaagaat atggccagaa gagggcattc   2760
tgcacagatt gtgtaccgcc ggaagcacca ggagctgcaa gccatgcaga tggagctgca   2820
gagccctgag tacaagctga gcaagctccg cacctcgacc atcatgaccg actacaaccc   2880
caactactgc tttgctggca agacctcctc catcagtgac ctgaaggagg tgccgcggaa   2940
aaacatcacc ctcattcggg gtctgggcca tggcgccttt ggggaggtgt atgaaggcca   3000
ggtgtccgga atgcccaacg acccaagccc cctgcaagtg gctgtgaaga cgctgcctga   3060
agtgtgctct gaacaggacg aactggattt cctcatggaa gccctgatca tcagcaaatt   3120
caaccaccag aacattgttc gctgcattgg ggtgagcctg caatccctgc ccggttcat    3180
cctgctggag ctcatggcgg ggggagacct caagtccttc ctccgagaga cccgccctcg   3240
cccgagccaa ccctcctccc tggccatgct ggacttctg cacgtgggctc gggacattgc    3300
ctgtggctgt cagtatttgg aggaaaacca cttcatccac cgagacattg ctgccagaaa   3360
```

```
ctgcctcttg acctgtccag gccctggaag agtggccaag attggagact tcgggatggc    3420
ccgagacatc tacagggcga gctactatag aaagggaggc tgtgccatgc tgccagttaa    3480
gtggatgccc ccagaggcct tcatggaagg aatattcact tctaaaacag acacatggtc    3540
ctttggagtg ctgctatggg aaatcttttc tcttggatat atgccatacc ccagcaaaag    3600
caaccaggaa gttctggagt tgtcaccag tggaggccgg atggacccac ccaagaactg     3660
ccctgggcct gtataccgga taatgactca gtgctggcaa catcagcctg aagacaggcc    3720
caactttgcc atcattttgg agaggattga atactgcacc caggacccgg atgtaatcaa    3780
caccgctttg ccgatagaat atggtccact tgtggaagag aaagaaaag tgcctgtgag     3840
gcccaaggac cctgagggg ttcctcctct cctggtctct caacaggcaa acgggagga      3900
ggagcgcagc ccagctgccc caccacctct gcctaccacc tcctctggca aggctgcaaa    3960
gaaacccaca gctgcagagg tctctgttcg agtccctaga gggccggccg tggaagggg     4020
acacgtgaat atggcattct ctcagtccaa ccctccttcg gagttgcaca aggtccacgg    4080
atccagaaac aagcccacca gcttgtggaa cccaacgtac ggctcctggt ttacagagaa    4140
acccaccaaa aagaataatc ctatagcaaa gaaggagcca cacgacaggg gtaacctggg    4200
gctggaggga agctgtactg tcccacctaa cgttgcaact gggagacttc cgggggcctc    4260
actgctccta gagccctctt cgctgactgc aatatgaag gaggtacctc tgttcaggct     4320
acgtcacttc ccttgtggga atgtcaatta cggctaccag caacagggct tgcccttaga    4380
agccgctact gccccctggag ctggtcatta cgaggatacc attctgaaaa gcaagaatag   4440
catgaaccag cctgggccct gagctcggtc gcacactca                          4479
```

<210> SEQ ID NO 24
<211> LENGTH: 1483
<212> TYPE: PRT
<213> ORGANISM: Homo sapiens

<400> SEQUENCE: 24

```
Met Ala Asp Leu Ala Glu Cys Asn Ile Lys Val Met Cys Arg Phe Arg
1               5                   10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Ser Thr Ser Gln Glu Gln Val Tyr Asn Asp
    50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175
```

```
Asp Glu Val Met Asp Thr Ile Asp Glu Gly Lys Ser Asn Arg His Val
            180                 185                 190
Ala Val Thr Asn Met Asn Glu His Ser Ser Arg Ser His Ser Ile Phe
        195                 200                 205
Leu Ile Asn Val Lys Gln Glu Asn Thr Gln Thr Glu Gln Lys Leu Ser
210                 215                 220
Gly Lys Leu Tyr Leu Val Asp Leu Ala Gly Ser Glu Lys Val Ser Lys
225                 230                 235                 240
Thr Gly Ala Glu Gly Ala Val Leu Asp Glu Ala Lys Asn Ile Asn Lys
                245                 250                 255
Ser Leu Ser Ala Leu Gly Asn Val Ile Ser Ala Leu Ala Glu Gly Ser
            260                 265                 270
Thr Tyr Val Pro Tyr Arg Asp Ser Lys Met Thr Arg Ile Leu Gln Asp
        275                 280                 285
Ser Leu Gly Gly Asn Cys Arg Thr Thr Ile Val Ile Cys Cys Ser Pro
    290                 295                 300
Ser Ser Tyr Asn Glu Ser Glu Thr Lys Ser Thr Leu Leu Phe Gly Gln
305                 310                 315                 320
Arg Ala Lys Thr Ile Lys Asn Thr Val Cys Val Asn Val Glu Leu Thr
                325                 330                 335
Ala Glu Gln Trp Lys Lys Lys Tyr Glu Lys Glu Lys Glu Lys Asn Lys
            340                 345                 350
Ile Leu Arg Asn Thr Ile Gln Trp Leu Glu Asn Glu Leu Asn Arg Trp
        355                 360                 365
Arg Asn Gly Glu Thr Val Pro Ile Asp Glu Gln Phe Asp Lys Glu Lys
    370                 375                 380
Ala Asn Leu Glu Ala Phe Thr Val Asp Lys Asp Ile Thr Leu Thr Asn
385                 390                 395                 400
Asp Lys Pro Ala Thr Ala Ile Gly Val Ile Gly Asn Phe Thr Asp Ala
                405                 410                 415
Glu Arg Arg Lys Cys Glu Glu Glu Ile Ala Lys Leu Tyr Lys Gln Leu
            420                 425                 430
Asp Asp Lys Asp Glu Glu Ile Asn Gln Gln Ser Gln Leu Val Glu Lys
        435                 440                 445
Leu Lys Thr Gln Met Leu Asp Gln Glu Glu Leu Leu Ala Ser Thr Arg
    450                 455                 460
Arg Asp Gln Asp Asn Met Gln Ala Glu Leu Asn Arg Leu Gln Ala Glu
465                 470                 475                 480
Asn Asp Ala Ser Lys Glu Glu Val Lys Glu Val Leu Gln Ala Leu Glu
                485                 490                 495
Glu Leu Ala Val Asn Tyr Asp Gln Lys Ser Gln Glu Val Glu Asp Lys
            500                 505                 510
Thr Lys Glu Tyr Glu Leu Leu Ser Asp Glu Leu Asn Gln Lys Ser Ala
        515                 520                 525
Thr Leu Ala Ser Ile Asp Ala Glu Leu Gln Lys Leu Lys Glu Met Thr
    530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
            580                 585                 590
```

Tyr Ile Ser Lys Met Lys Ser Glu Val Lys Thr Met Val Lys Arg Cys
            595                 600                 605

Lys Gln Leu Glu Ser Thr Gln Thr Glu Ser Asn Lys Lys Met Glu Glu
        610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
                645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
        690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
                725                 730                 735

Asn Gln Lys Met Met Leu Glu Gln Glu Arg Leu Arg Val Glu His Glu
            740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
        770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
                805                 810                 815

Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
        835                 840                 845

Leu Val Arg Asp Asn Ala Asp Leu Arg Cys Glu Leu Pro Lys Leu Glu
850                 855                 860

Lys Arg Leu Arg Ala Thr Ala Glu Arg Val Lys Ala Leu Glu Ser Ala
865                 870                 875                 880

Leu Lys Glu Ala Lys Glu Asn Ala Ser Arg Asp Arg Lys Arg Tyr Gln
                885                 890                 895

Gln Glu Val Asp Arg Ile Lys Glu Ala Val Arg Ser Lys Asn Met Ala
            900                 905                 910

Arg Arg Gly His Ser Ala Gln Ile Val Tyr Arg Arg Lys His Gln Glu
        915                 920                 925

Leu Gln Ala Met Gln Met Glu Leu Gln Ser Pro Glu Tyr Lys Leu Ser
        930                 935                 940

Lys Leu Arg Thr Ser Thr Ile Met Thr Asp Tyr Asn Pro Asn Tyr Cys
945                 950                 955                 960

Phe Ala Gly Lys Thr Ser Ser Ile Ser Asp Leu Lys Glu Val Pro Arg
                965                 970                 975

Lys Asn Ile Thr Leu Ile Arg Gly Leu Gly His Gly Ala Phe Gly Glu
            980                 985                 990

Val Tyr Glu Gly Gln Val Ser Gly Met Pro Asn Asp Pro Ser Pro Leu
        995                 1000                1005

Gln Val Ala Val Lys Thr Leu Pro Glu Val Cys Ser Glu Gln Asp

```
            1010                1015                1020

Glu Leu Asp Phe Leu Met Glu Ala Leu Ile Ile Ser Lys Phe Asn
        1025                1030                1035

His Gln Asn Ile Val Arg Cys Ile Gly Val Ser Leu Gln Ser Leu
        1040                1045                1050

Pro Arg Phe Ile Leu Leu Glu Leu Met Ala Gly Gly Asp Leu Lys
        1055                1060                1065

Ser Phe Leu Arg Glu Thr Arg Pro Arg Pro Ser Gln Pro Ser Ser
        1070                1075                1080

Leu Ala Met Leu Asp Leu Leu His Val Ala Arg Asp Ile Ala Cys
        1085                1090                1095

Gly Cys Gln Tyr Leu Glu Glu Asn His Phe Ile His Arg Asp Ile
        1100                1105                1110

Ala Ala Arg Asn Cys Leu Leu Thr Cys Pro Gly Pro Gly Arg Val
        1115                1120                1125

Ala Lys Ile Gly Asp Phe Gly Met Ala Arg Asp Ile Tyr Arg Ala
        1130                1135                1140

Ser Tyr Tyr Arg Lys Gly Gly Cys Ala Met Leu Pro Val Lys Trp
        1145                1150                1155

Met Pro Pro Glu Ala Phe Met Glu Gly Ile Phe Thr Ser Lys Thr
        1160                1165                1170

Asp Thr Trp Ser Phe Gly Val Leu Leu Trp Glu Ile Phe Ser Leu
        1175                1180                1185

Gly Tyr Met Pro Tyr Pro Ser Lys Ser Asn Gln Glu Val Leu Glu
        1190                1195                1200

Phe Val Thr Ser Gly Gly Arg Met Asp Pro Pro Lys Asn Cys Pro
        1205                1210                1215

Gly Pro Val Tyr Arg Ile Met Thr Gln Cys Trp Gln His Gln Pro
        1220                1225                1230

Glu Asp Arg Pro Asn Phe Ala Ile Ile Leu Glu Arg Ile Glu Tyr
        1235                1240                1245

Cys Thr Gln Asp Pro Asp Val Ile Asn Thr Ala Leu Pro Ile Glu
        1250                1255                1260

Tyr Gly Pro Leu Val Glu Glu Glu Lys Val Pro Val Arg Pro
        1265                1270                1275

Lys Asp Pro Glu Gly Val Pro Pro Leu Leu Val Ser Gln Gln Ala
        1280                1285                1290

Lys Arg Glu Glu Glu Arg Ser Pro Ala Ala Pro Pro Pro Leu Pro
        1295                1300                1305

Thr Thr Ser Ser Gly Lys Ala Ala Lys Lys Pro Thr Ala Ala Glu
        1310                1315                1320

Val Ser Val Arg Val Pro Arg Gly Pro Ala Val Glu Gly Gly His
        1325                1330                1335

Val Asn Met Ala Phe Ser Gln Ser Asn Pro Pro Ser Glu Leu His
        1340                1345                1350

Lys Val His Gly Ser Arg Asn Lys Pro Thr Ser Leu Trp Asn Pro
        1355                1360                1365

Thr Tyr Gly Ser Trp Phe Thr Glu Lys Pro Thr Lys Lys Asn Asn
        1370                1375                1380

Pro Ile Ala Lys Lys Glu Pro His Asp Arg Gly Asn Leu Gly Leu
        1385                1390                1395

Glu Gly Ser Cys Thr Val Pro Pro Asn Val Ala Thr Gly Arg Leu
        1400                1405                1410
```

Pro Gly Ala Ser Leu Leu Glu Pro Ser Ser Leu Thr Ala Asn
    1415                1420                1425

Met Lys Glu Val Pro Leu Phe Arg Leu Arg His Phe Pro Cys Gly
    1430                1435                1440

Asn Val Asn Tyr Gly Tyr Gln Gln Gln Gly Leu Pro Leu Glu Ala
    1445                1450                1455

Ala Thr Ala Pro Gly Ala Gly His Tyr Glu Asp Thr Ile Leu Lys
    1460                1465                1470

Ser Lys Asn Ser Met Asn Gln Pro Gly Pro
    1475                1480

<210> SEQ ID NO 25
<211> LENGTH: 2412
<212> TYPE: DNA
<213> ORGANISM: Homo sapiens

<400> SEQUENCE: 25

| | |
|---|---|
| atgaacggac agttggatct aagtgggaag ctaatcatca aagctcaact tggggaggat | 60 |
| attcggcgaa ttcctattca taatgaagat attacttatg atgaattagt gctaatgatg | 120 |
| caacgagttt tcagaggaaa acttctgagt aatgatgaag taacaataaa gtataaagat | 180 |
| gaagatggag atcttataac aattttttgat agttctgacc tttcctttgc aattcagtgc | 240 |
| agtaggatac tgaaactgac attatttgtt aatggccagc caagacccct tgaatcaagt | 300 |
| caggtgaaat atctccgtcg agaactgata gaacttcgaa ataaagtgaa tcgtttattg | 360 |
| gatagcttgg aaccacctgg agaaccagga ccttccacca atattcctga aaatgatact | 420 |
| gtggatggta gggaagaaaa gtctgcttct gattcttctg aaaacagtc tactcaggtt | 480 |
| atggcagcaa gtatgtctgc tttttgatcct ttaaaaaacc aagatgaaat caataaaaat | 540 |
| gttatgtcag cgtttggctt aacagatgat caggtttcag ggccacccag tgctcctgca | 600 |
| gaagatcgtt caggaacacc cgacagcatt gcttcctcct cctcagcagc tcacccacca | 660 |
| ggcgttcagc cacagcagcc accatataca ggagctcaga ctcaagcagg tcagattgaa | 720 |
| gtgtaccgcc ggaagcacca ggagctgcaa gccatgcaga tggagctgca gagccctgag | 780 |
| tacaagctga gcaagctccg cacctcgacc atcatgaccg actacaaccc caactactgc | 840 |
| tttgctggca agacctcctc catcagtgac ctgaaggagg tgccgcggaa aaacatcacc | 900 |
| ctcattcggg gtctgggcca tggcgccttt gggggagggt atgaaggcca ggtgtccgga | 960 |
| atgcccaacg acccaagccc cctgcaagtg gctgtgaaga cgctgcctga agtgtgctct | 1020 |
| gaacaggacg aactggattt cctcatggaa gccctgatca tcagcaaatt caaccaccag | 1080 |
| aacattgttc gctgcattgg ggtgagcctg caatccctgc cccggttcat cctgctggag | 1140 |
| ctcatggcgg ggggagacct caagtccttc ctccgagaga cccgccctcg cccgagccag | 1200 |
| ccctcctccc tggccatgct ggaccttctg cacgtggctc gggacattgc ctgtggctgt | 1260 |
| cagtatttgg aggaaaacca cttcatccac cgagacattc tgccagaaa ctgcctcttg | 1320 |
| acctgtccag gccctggaag agtggccaag attggagact cgggatggc ccgagacatc | 1380 |
| tacagggcga gctactatag aaagggaggc tgtgccatgc tgccagttaa gtggatgccc | 1440 |
| ccagaggcct tcatggaagg aatattcact tctaaaacag acacatggtc ctttggagtg | 1500 |
| ctgctatggg aaatctttc tcttggatat atgccatacc ccagcaaaag caaccaggaa | 1560 |
| gttctggagt ttgtcaccag tggaggccgg atggaccca ccaagaactg ccctgggcct | 1620 |
| gtataccgga taatgactca gtgctggcaa catcagcctg aagacaggcc caactttgcc | 1680 |

-continued

```
atcattttgg agaggattga atactgcacc caggacccgg atgtaatcaa caccgctttg    1740
ccgatagaat atggtccact tgtggaagag gaagagaaag tgcctgtgag gcccaaggac    1800
cctgaggggg ttcctcctct cctggtctct caacaggcaa aacgggagga ggagcgcagc    1860
ccagctgccc caccacctct gcctaccacc tcctctggca aggctgcaaa gaaacccaca    1920
gctgcagagg tctctgttcg agtccctaga gggccggccg tggaagggggg acacgtgaat   1980 atggcattct ctcagtccaa ccctccttcg gagttgcaca aggtccacgg atccagaaac    2040
aagcccacca gcttgtggaa cccaacgtac ggctcctggt ttacagagaa acccaccaaa    2100
aagaataatc ctatagcaaa gaaggagcca cacgacaggg gtaacctggg gctggaggga    2160
agctgtactg tcccacctaa cgttgcaact gggagacttc cgggggcctc actgctccta    2220
gagccctctt cgctgactgc caatatgaag gaggtacctc tgttcaggct acgtcacttc    2280
ccttgtggga atgtcaatta cggctaccag caacagggct gcccttaga agccgctact    2340 gcccctggag ctggtcatta cgaggatacc attctgaaaa gcaagaatag catgaaccag    2400
cctgggccct ga                                                       2412
```

<210> SEQ ID NO 26
<211> LENGTH: 803
<212> TYPE: PRT
<213> ORGANISM: Homo sapiens

<400> SEQUENCE: 26

```
Met Asn Gly Gln Leu Asp Leu Ser Gly Lys Leu Ile Ile Lys Ala Gln
1               5                   10                  15

Leu Gly Glu Asp Ile Arg Arg Ile Pro Ile His Asn Glu Asp Ile Thr
            20                  25                  30

Tyr Asp Glu Leu Val Leu Met Met Gln Arg Val Phe Arg Gly Lys Leu
        35                  40                  45

Leu Ser Asn Asp Glu Val Thr Ile Lys Tyr Lys Asp Glu Asp Gly Asp
    50                  55                  60

Leu Ile Thr Ile Phe Asp Ser Ser Asp Leu Ser Phe Ala Ile Gln Cys
65                  70                  75                  80

Ser Arg Ile Leu Lys Leu Thr Leu Phe Val Asn Gly Gln Pro Arg Pro
                85                  90                  95

Leu Glu Ser Ser Gln Val Lys Tyr Leu Arg Arg Glu Leu Ile Glu Leu
            100                 105                 110

Arg Asn Lys Val Asn Arg Leu Leu Asp Ser Leu Glu Pro Pro Gly Glu
        115                 120                 125

Pro Gly Pro Ser Thr Asn Ile Pro Glu Asn Asp Thr Val Asp Gly Arg
    130                 135                 140

Glu Glu Lys Ser Ala Asp Ser Ser Gly Lys Gln Ser Thr Gln Val
145                 150                 155                 160

Met Ala Ala Ser Met Ser Ala Phe Asp Pro Leu Lys Asn Gln Asp Glu
                165                 170                 175

Ile Asn Lys Asn Val Met Ser Ala Phe Gly Leu Thr Asp Asp Gln Val
            180                 185                 190

Ser Gly Pro Pro Ser Ala Pro Ala Glu Asp Arg Ser Gly Thr Pro Asp
        195                 200                 205

Ser Ile Ala Ser Ser Ser Ala Ala His Pro Pro Gly Val Gln Pro
    210                 215                 220

Gln Gln Pro Pro Tyr Thr Gly Ala Gln Thr Gln Ala Gly Gln Ile Glu
225                 230                 235                 240
```

```
Val Tyr Arg Arg Lys His Gln Glu Leu Gln Ala Met Gln Met Glu Leu
                245                 250                 255

Gln Ser Pro Glu Tyr Lys Leu Ser Lys Leu Arg Thr Ser Thr Ile Met
            260                 265                 270

Thr Asp Tyr Asn Pro Asn Tyr Cys Phe Ala Gly Lys Thr Ser Ser Ile
        275                 280                 285

Ser Asp Leu Lys Glu Val Pro Arg Lys Asn Ile Thr Leu Ile Arg Gly
    290                 295                 300

Leu Gly His Gly Ala Phe Gly Glu Val Tyr Glu Gly Gln Val Ser Gly
305                 310                 315                 320

Met Pro Asn Asp Pro Ser Pro Leu Gln Val Ala Val Lys Thr Leu Pro
                325                 330                 335

Glu Val Cys Ser Glu Gln Asp Glu Leu Asp Phe Leu Met Glu Ala Leu
            340                 345                 350

Ile Ile Ser Lys Phe Asn His Gln Asn Ile Val Arg Cys Ile Gly Val
        355                 360                 365

Ser Leu Gln Ser Leu Pro Arg Phe Ile Leu Leu Glu Leu Met Ala Gly
    370                 375                 380

Gly Asp Leu Lys Ser Phe Leu Arg Glu Thr Arg Pro Arg Pro Ser Gln
385                 390                 395                 400

Pro Ser Ser Leu Ala Met Leu Asp Leu Leu His Val Ala Arg Asp Ile
                405                 410                 415

Ala Cys Gly Cys Gln Tyr Leu Glu Glu Asn His Phe Ile His Arg Asp
            420                 425                 430

Ile Ala Ala Arg Asn Cys Leu Leu Thr Cys Pro Gly Pro Gly Arg Val
        435                 440                 445

Ala Lys Ile Gly Asp Phe Gly Met Ala Arg Asp Ile Tyr Arg Ala Ser
    450                 455                 460

Tyr Tyr Arg Lys Gly Gly Cys Ala Met Leu Pro Val Lys Trp Met Pro
465                 470                 475                 480

Pro Glu Ala Phe Met Glu Gly Ile Phe Thr Ser Lys Thr Asp Thr Trp
                485                 490                 495

Ser Phe Gly Val Leu Leu Trp Glu Ile Phe Ser Leu Gly Tyr Met Pro
            500                 505                 510

Tyr Pro Ser Lys Ser Asn Gln Glu Val Leu Glu Phe Val Thr Ser Gly
        515                 520                 525

Gly Arg Met Asp Pro Pro Lys Asn Cys Pro Gly Pro Val Tyr Arg Ile
    530                 535                 540

Met Thr Gln Cys Trp Gln His Gln Pro Glu Asp Arg Pro Asn Phe Ala
545                 550                 555                 560

Ile Ile Leu Glu Arg Ile Glu Tyr Cys Thr Gln Asp Pro Asp Val Ile
                565                 570                 575

Asn Thr Ala Leu Pro Ile Glu Tyr Gly Pro Leu Val Glu Glu Glu Glu
            580                 585                 590

Lys Val Pro Val Arg Pro Lys Asp Pro Glu Gly Val Pro Pro Leu Leu
        595                 600                 605

Val Ser Gln Gln Ala Lys Arg Glu Glu Glu Arg Ser Pro Ala Ala Pro
    610                 615                 620

Pro Pro Leu Pro Thr Thr Ser Ser Gly Lys Ala Ala Lys Lys Pro Thr
625                 630                 635                 640

Ala Ala Glu Val Ser Val Arg Val Pro Arg Gly Pro Ala Val Glu Gly
                645                 650                 655
```

```
Gly His Val Asn Met Ala Phe Ser Gln Ser Asn Pro Pro Ser Glu Leu
            660                 665                 670

His Lys Val His Gly Ser Arg Asn Lys Pro Thr Ser Leu Trp Asn Pro
        675                 680                 685

Thr Tyr Gly Ser Trp Phe Thr Glu Lys Pro Thr Lys Lys Asn Asn Pro
    690                 695                 700

Ile Ala Lys Lys Glu Pro His Asp Arg Gly Asn Leu Gly Leu Glu Gly
705                 710                 715                 720

Ser Cys Thr Val Pro Pro Asn Val Ala Thr Gly Arg Leu Pro Gly Ala
                725                 730                 735

Ser Leu Leu Leu Glu Pro Ser Ser Leu Thr Ala Asn Met Lys Glu Val
            740                 745                 750

Pro Leu Phe Arg Leu Arg His Phe Pro Cys Gly Asn Val Asn Tyr Gly
        755                 760                 765

Tyr Gln Gln Gln Gly Leu Pro Leu Glu Ala Ala Thr Ala Pro Gly Ala
    770                 775                 780

Gly His Tyr Glu Asp Thr Ile Leu Lys Ser Lys Asn Ser Met Asn Gln
785                 790                 795                 800

Pro Gly Pro

<210> SEQ ID NO 27
<211> LENGTH: 2779
<212> TYPE: DNA
<213> ORGANISM: Homo sapiens

<400> SEQUENCE: 27
cctccgcaag ccgtctttct ctagagttgt atatatagaa catcctggag tccaccatga      60
acggacagtt ggatctaagt gggaagctaa tcatcaaagc tcaacttggg gaggatattc     120
ggcgaattcc tattcataat gaagatatta cttatgatga attagtgcta atgatgcaac     180
gagttttcag aggaaaactt ctgagtaatg atgaagtaac aataaagtat aaagatgaag     240
atggagatct tataacaatt tttgatagtt ctgacctttc ctttgcaatt cagtgcagta     300
ggatactgaa actgacatta tttgttaatg ccagccaag accccttgaa tcaagtcagg      360
tgaaatatct ccgtcgagaa ctgatagaac ttcgaaataa agtgaatcgt ttattggata     420
gcttggaacc acctggagaa ccaggacctt ccaccaatat tcctgaaaat gatactgtgg     480
atggtaggga agaaaagtct gcttctgatt cttctggaaa acagtctact caggttatgg     540
cagcaagtat gtctgctttt gatccttaa aaaccaaga tgaaatcaat aaaaatgtta       600
tgtcagcgtt tggcttaaca gatgatcagg tttcagtgta ccgccggaag caccaggagc     660
tgcaagccat gcagatggag ctgcagagcc tgagtacaa gctgagcaag ctccgcacct      720
cgaccatcat gaccgactac aaccccaact actgctttgc tggcaagacc tcctccatca     780
gtgacctgaa ggaggtgccg cggaaaaaca tcaccctcat tcgggtctg ggccatggcg      840 cctttgggga ggtgtatgaa ggccaggtgt ccggaatgcc caacgaccca gccccctgc      900 aagtggctgt gaagacgctg cctgaagtgt gctctgaaca ggacgaactg gatttcctca     960
tggaagccct gatcatcagc aaattcaacc accagaacat tgttcgctgc attggggtga    1020
gcctgcaatc cctgccccgg ttcatcctgc tggagctcat ggcgggggga gacctcaagt    1080
ccttcctccg agagacccgc cctcgcccga gccagccctc ctccctggcc atgctggacc    1140
ttctgcacgt ggctcgggac attgcctgtg ctgtcagta tttggaggaa aaccacttca    1200
tccaccgaga cattgctgcc agaaactgcc tcttgacctg tccaggccct ggaagagtgg    1260
```

```
ccaagattgg agacttcggg atggcccgag acatctacag ggcgagctac tatagaaagg    1320
gaggctgtgc catgctgcca gttaagtgga tgcccccaga ggccttcatg gaaggaatat    1380
tcacttctaa aacagacaca tggtcctttg gagtgctgct atgggaaatc tttctcttg     1440
gatatatgcc atacccccagc aaaagcaacc aggaagttct ggagtttgtc ccagtggag    1500
gccggatgga cccacccaag aactgccctg gcctgtata ccggataatg actcagtgct    1560
ggcaacatca gcctgaagac aggcccaact ttgccatcat tttggagagg attgaatact    1620
gcacccagga cccggatgta atcaacaccg ctttgccgat agaatatggt ccacttgtgg    1680
aagaggaaga gaaagtgcct gtgaggccca aggaccctga gggggttcct cctctcctgg    1740
tctctcaaca ggcaaaacgg gaggaggagc gcagcccagc tgccccacca cctctgccta    1800
ccacctcctc tggcaaggct gcaaagaaac ccacagctgc agaggtctct gttcgagtcc    1860
ctagagggcc ggccgtggaa gggggacacg tgaatatggc attctctcag tccaaccctc    1920
cttcggagtt gcacaaggtc cacggatcca gaaacaagcc caccagcttg tggaacccaa    1980
cgtacggctc ctggtttaca gagaaaccca ccaaaaagaa taatcctata gcaaagaagg    2040
agccacacga caggggtaac ctggggctgg agggaagctg tactgtccca cctaacgttg    2100
caactgggag acttccgggg gcctcactgc tcctagagcc ctcttcgctg actgccaata    2160
tgaaggaggt acctctgttc aggctacgtc acttcccttg tgggaatgtc aattacggct    2220
accagcaaca gggcttgccc ttagaagccg ctactgcccc tggagctggt cattacgagg    2280
ataccattct gaaaagcaag aatagcatga accagcctgg gccctgagct cggtcgcaca    2340
ctcacttctc ttccttggga tccctaagac cgtggaggag agagaggcaa tggctccttc    2400
acaaaccaga gaccaaatgt cacgttttgt tttgtgccaa cctatttga agtaccacca     2460
aaaaagctgt attttgaaaa tgctttagaa aggttttgag catgggttca tcctattctt    2520
tcgaaagaag aaaatatcat aaaaatgagt gataaataca aggcccagat gtggttgcat    2580
aaggtttta tgcatgtttg ttgtatactt ccttatgctt cttttaaatt gtgtgtgctc      2640
tgcttcaatg tagtcagaat tagctgcttc tatgtttcat agttggggtc atagatgttt    2700
ccttgccttg ttgatgtgga catgagccat ttgaggggag agggaacgga aataaggag     2760
ttatttgtaa tgactaaaa                                                 2779
```

<210> SEQ ID NO 28
<211> LENGTH: 756
<212> TYPE: PRT
<213> ORGANISM: Homo sapiens

<400> SEQUENCE: 28

Met Asn Gly Gln Leu Asp Leu Ser Gly Lys Leu Ile Ile Lys Ala Gln
1               5                   10                  15

Leu Gly Glu Asp Ile Arg Arg Ile Pro Ile His Asn Glu Asp Ile Thr
            20                  25                  30

Tyr Asp Glu Leu Val Leu Met Met Gln Arg Val Phe Arg Gly Lys Leu
        35                  40                  45

Leu Ser Asn Asp Glu Val Thr Ile Lys Tyr Lys Asp Glu Asp Gly Asp
    50                  55                  60

Leu Ile Thr Ile Phe Asp Ser Ser Asp Leu Ser Phe Ala Ile Gln Cys
65                  70                  75                  80

Ser Arg Ile Leu Lys Leu Thr Leu Phe Val Asn Gly Gln Pro Arg Pro
                85                  90                  95

Leu Glu Ser Ser Gln Val Lys Tyr Leu Arg Arg Glu Leu Ile Glu Leu

```
                 100                 105                 110
Arg Asn Lys Val Asn Arg Leu Leu Asp Ser Leu Glu Pro Pro Gly Glu
            115                 120                 125

Pro Gly Pro Ser Thr Asn Ile Pro Glu Asn Asp Thr Val Asp Gly Arg
        130                 135                 140

Glu Glu Lys Ser Ala Ser Asp Ser Ser Gly Lys Gln Ser Thr Gln Val
145                 150                 155                 160

Met Ala Ala Ser Met Ser Ala Phe Asp Pro Leu Lys Asn Gln Asp Glu
            165                 170                 175

Ile Asn Lys Asn Val Met Ser Ala Phe Gly Leu Thr Asp Asp Gln Val
            180                 185                 190

Ser Val Tyr Arg Arg Lys His Gln Glu Leu Gln Ala Met Gln Met Glu
        195                 200                 205

Leu Gln Ser Pro Glu Tyr Lys Leu Ser Lys Leu Arg Thr Ser Thr Ile
        210                 215                 220

Met Thr Asp Tyr Asn Pro Asn Tyr Cys Phe Ala Gly Lys Thr Ser Ser
225                 230                 235                 240

Ile Ser Asp Leu Lys Glu Val Pro Arg Lys Asn Ile Thr Leu Ile Arg
            245                 250                 255

Gly Leu Gly His Gly Ala Phe Gly Glu Val Tyr Glu Gly Gln Val Ser
            260                 265                 270

Gly Met Pro Asn Asp Pro Ser Pro Leu Gln Val Ala Val Lys Thr Leu
            275                 280                 285

Pro Glu Val Cys Ser Glu Gln Asp Glu Leu Asp Phe Leu Met Glu Ala
            290                 295                 300

Leu Ile Ile Ser Lys Phe Asn His Gln Asn Ile Val Arg Cys Ile Gly
305                 310                 315                 320

Val Ser Leu Gln Ser Leu Pro Arg Phe Ile Leu Leu Glu Leu Met Ala
            325                 330                 335

Gly Gly Asp Leu Lys Ser Phe Leu Arg Glu Thr Arg Pro Arg Pro Ser
            340                 345                 350

Gln Pro Ser Ser Leu Ala Met Leu Asp Leu Leu His Val Ala Arg Asp
            355                 360                 365

Ile Ala Cys Gly Cys Gln Tyr Leu Glu Glu Asn His Phe Ile His Arg
            370                 375                 380

Asp Ile Ala Ala Arg Asn Cys Leu Leu Thr Cys Pro Gly Pro Gly Arg
385                 390                 395                 400

Val Ala Lys Ile Gly Asp Phe Gly Met Ala Arg Asp Ile Tyr Arg Ala
            405                 410                 415

Ser Tyr Tyr Arg Lys Gly Gly Cys Ala Met Leu Pro Val Lys Trp Met
            420                 425                 430

Pro Pro Glu Ala Phe Met Glu Gly Ile Phe Thr Ser Lys Thr Asp Thr
            435                 440                 445

Trp Ser Phe Gly Val Leu Leu Trp Glu Ile Phe Ser Leu Gly Tyr Met
            450                 455                 460

Pro Tyr Pro Ser Lys Ser Asn Gln Glu Val Leu Glu Phe Val Thr Ser
465                 470                 475                 480

Gly Gly Arg Met Asp Pro Pro Lys Asn Cys Pro Gly Pro Val Tyr Arg
            485                 490                 495

Ile Met Thr Gln Cys Trp Gln His Gln Pro Glu Asp Arg Pro Asn Phe
            500                 505                 510

Ala Ile Ile Leu Glu Arg Ile Glu Tyr Cys Thr Gln Asp Pro Asp Val
            515                 520                 525
```

```
Ile Asn Thr Ala Leu Pro Ile Glu Tyr Gly Pro Leu Val Glu Glu Glu
        530                 535                 540

Glu Lys Val Pro Val Arg Pro Lys Asp Pro Glu Gly Val Pro Pro Leu
545                 550                 555                 560

Leu Val Ser Gln Gln Ala Lys Arg Glu Glu Arg Ser Pro Ala Ala
                565                 570                 575

Pro Pro Pro Leu Pro Thr Thr Ser Ser Gly Lys Ala Ala Lys Lys Pro
            580                 585                 590

Thr Ala Ala Glu Val Ser Val Arg Val Pro Arg Gly Pro Ala Val Glu
                595                 600                 605

Gly Gly His Val Asn Met Ala Phe Ser Gln Ser Asn Pro Pro Ser Glu
        610                 615                 620

Leu His Lys Val His Gly Ser Arg Asn Lys Pro Thr Ser Leu Trp Asn
625                 630                 635                 640

Pro Thr Tyr Gly Ser Trp Phe Thr Glu Lys Pro Thr Lys Lys Asn Asn
                645                 650                 655

Pro Ile Ala Lys Lys Glu Pro His Asp Arg Gly Asn Leu Gly Leu Glu
                660                 665                 670

Gly Ser Cys Thr Val Pro Pro Asn Val Ala Thr Gly Arg Leu Pro Gly
            675                 680                 685

Ala Ser Leu Leu Leu Glu Pro Ser Ser Leu Thr Ala Asn Met Lys Glu
        690                 695                 700

Val Pro Leu Phe Arg Leu Arg His Phe Pro Cys Gly Asn Val Asn Tyr
705                 710                 715                 720

Gly Tyr Gln Gln Gln Gly Leu Pro Leu Glu Ala Ala Thr Ala Pro Gly
                725                 730                 735

Ala Gly His Tyr Glu Asp Thr Ile Leu Lys Ser Lys Asn Ser Met Asn
            740                 745                 750

Gln Pro Gly Pro
        755
```

<210> SEQ ID NO 29
<211> LENGTH: 2614
<212> TYPE: DNA
<213> ORGANISM: Homo sapiens

<400> SEQUENCE: 29

```
cctccgcaag ccgtctttct ctagagttgt atatatagaa catcctggag tccaccatga      60
acggacagtt ggatctaagt gggaagctaa tcatcaaagc tcaacttggg gaggatattc     120
ggcgaattcc tattcataat gaagatatta cttatgatga attagtgcta atgatgcaac     180
gagttttcag aggaaaactt ctgagtaatg atgaagtaac aataaagtat aaagatgaag     240
atggagatct tataacaatt tttgatagtt ctgacctttc ctttgcaatt cagtgcagta     300
ggatactgaa actgacatta tttgttaatg ccagccaag accccttgaa tcaagtcagg      360
tgaaatatct ccgtcgagaa ctgatagaac ttcgaaataa agtgaatcgt ttattggata     420
gcttggaacc acctggagaa ccaggaccct tccaccatat tcctgaaaat gtgtaccgcc     480
ggaagcacca ggagctgcaa gccatgcaga tggagctgca gagccctgag tacaagctga     540
gcaagctccg cacctcgacc atcatgaccg actacaaccc caactactgc tttgctggca     600
agacctcctc catcagtgac ctgaaggagt gccgcggaa aaacatcacc ctcattcggg      660
gtctgggcca tggcgccttt ggggaggtgt atgaaggcca ggtgtccgga atgcccaacg     720
acccaagccc cctgcaagtg gctgtgaaga cgctgcctga agtgctctct gaacaggacg     780
```

```
aactggattt cctcatggaa gccctgatca tcagcaaatt caaccaccag aacattgttc    840
gctgcattgg ggtgagcctg caatccctgc cccggttcat cctgctggag ctcatggcgg    900
ggggagacct caagtccttc ctccgagaga cccgccctcg cccgagccag ccctcctccc    960
tggccatgct ggaccttctg cacgtggctc gggacattgc ctgtggctgt cagtatttgg   1020
aggaaaacca cttcatccac cgagacattg ctgccagaaa ctgcctcttg acctgtccag   1080
gccctggaag agtggccaag attggagact cgggatggc ccgagacatc tacagggcga   1140
gctactatag aaagggaggc tgtgccatgc tgccagttaa gtggatgccc ccagaggcct   1200
tcatggaagg aatattcact tctaaaacag acacatggtc ctttggagtg ctgctatggg   1260
aaatcttttc tcttggatat atgccatacc ccagcaaaag caaccaggaa gttctggagt   1320
ttgtcaccag tggaggccgg atggacccac ccaagaactg ccctgggcct gtataccgga   1380
taatgactca gtgctggcaa catcagcctg aagacaggcc caactttgcc atcattttgg   1440
agaggattga atactgcacc caggacccgg atgtaatcaa caccgctttg ccgatagaat   1500
atggtccact tgtggaagag gaagagaaag tgcctgtgag gcccaaggac cctgaggggg   1560
ttcctcctct cctggtctct caacaggcaa acgggaggag ggagcgcagc ccagctgccc   1620
caccacctct gcctaccacc tcctctggca aggctgcaaa gaaacccaca gctgcagagg   1680
tctctgttcg agtccctaga gggccggccg tggaaggggg acacgtgaat atggcattct   1740
ctcagtccaa ccctccttcg gagttgcaca aggtccacgg atccagaaac aagcccacca   1800
gcttgtggaa cccaacgtac ggctcctggt ttacagagaa acccaccaaa agaataatc   1860
ctatagcaaa gaaggagcca cacgacaggg gtaacctggg gctggaggga agctgtactg   1920
tcccacctaa cgttgcaact gggagacttc cgggggcctc actgctccta gagccctctt   1980
cgctgactgc caatatgaag gaggtacctc tgttcaggct acgtcacttc ccttgtggga   2040
atgtcaatta cggctaccag caacagggct gcccttaga gccgctact gcccctggag   2100
ctggtcatta cgaggatacc attctgaaaa gcaagaatag catgaaccag cctgggccct   2160
gagctcggtc gcacactcac ttctcttcct tgggatccct aagaccgtgg aggagagaga   2220
ggcaatggct ccttcacaaa ccagagacca aatgtcacgt tttgttttgt gccaacctat   2280
tttgaagtac caccaaaaaa gctgtatttt gaaaatgctt tagaaaggtt ttgagcatgg   2340
gttcatccta ttctttcgaa agaagaaaat atcataaaaa tgagtgataa atacaaggcc   2400
cagatgtggt tgcataaggt ttttatgcat gtttgttgta tacttcctta tgcttctttt   2460
aaattgtgtg tgctctgctt caatgtagtc agaattagct gcttctatgt ttcatagttg   2520
gggtcataga tgtttccttg ccttgttgat gtggacatga gccatttgag gggagaggga   2580
acggaaataa aggagttatt tgtaatgact aaaa                              2614

<210> SEQ ID NO 30
<211> LENGTH: 701
<212> TYPE: PRT
<213> ORGANISM: Homo sapiens

<400> SEQUENCE: 30

Met Asn Gly Gln Leu Asp Leu Ser Gly Lys Leu Ile Ile Lys Ala Gln
1               5                   10                  15

Leu Gly Glu Asp Ile Arg Arg Ile Pro Ile His Asn Glu Asp Ile Thr
                20                  25                  30

Tyr Asp Glu Leu Val Leu Met Met Gln Arg Val Phe Arg Gly Lys Leu
            35                  40                  45
```

```
Leu Ser Asn Asp Glu Val Thr Ile Lys Tyr Lys Asp Glu Asp Gly Asp
    50                  55                  60

Leu Ile Thr Ile Phe Asp Ser Ser Asp Leu Ser Phe Ala Ile Gln Cys
65                  70                  75                  80

Ser Arg Ile Leu Lys Leu Thr Leu Phe Val Asn Gly Gln Pro Arg Pro
                85                  90                  95

Leu Glu Ser Ser Gln Val Lys Tyr Leu Arg Arg Glu Leu Ile Glu Leu
            100                 105                 110

Arg Asn Lys Val Asn Arg Leu Leu Asp Ser Leu Glu Pro Pro Gly Glu
        115                 120                 125

Pro Gly Pro Ser Thr Asn Ile Pro Glu Asn Val Tyr Arg Arg Lys His
    130                 135                 140

Gln Glu Leu Gln Ala Met Gln Met Glu Leu Gln Ser Pro Glu Tyr Lys
145                 150                 155                 160

Leu Ser Lys Leu Arg Thr Ser Thr Ile Met Thr Asp Tyr Asn Pro Asn
                165                 170                 175

Tyr Cys Phe Ala Gly Lys Thr Ser Ser Ile Ser Asp Leu Lys Glu Val
            180                 185                 190

Pro Arg Lys Asn Ile Thr Leu Ile Arg Gly Leu Gly His Gly Ala Phe
        195                 200                 205

Gly Glu Val Tyr Glu Gly Gln Val Ser Gly Met Pro Asn Asp Pro Ser
    210                 215                 220

Pro Leu Gln Val Ala Val Lys Thr Leu Pro Glu Val Cys Ser Glu Gln
225                 230                 235                 240

Asp Glu Leu Asp Phe Leu Met Glu Ala Leu Ile Ile Ser Lys Phe Asn
                245                 250                 255

His Gln Asn Ile Val Arg Cys Ile Gly Val Ser Leu Gln Ser Leu Pro
            260                 265                 270

Arg Phe Ile Leu Leu Glu Leu Met Ala Gly Gly Asp Leu Lys Ser Phe
        275                 280                 285

Leu Arg Glu Thr Arg Pro Arg Pro Ser Gln Pro Ser Ser Leu Ala Met
    290                 295                 300

Leu Asp Leu Leu His Val Ala Arg Asp Ile Ala Cys Gly Cys Gln Tyr
305                 310                 315                 320

Leu Glu Glu Asn His Phe Ile His Arg Asp Ile Ala Ala Arg Asn Cys
                325                 330                 335

Leu Leu Thr Cys Pro Gly Pro Gly Arg Val Ala Lys Ile Gly Asp Phe
            340                 345                 350

Gly Met Ala Arg Asp Ile Tyr Arg Ala Ser Tyr Tyr Arg Lys Gly Gly
        355                 360                 365

Cys Ala Met Leu Pro Val Lys Trp Met Pro Pro Glu Ala Phe Met Glu
    370                 375                 380

Gly Ile Phe Thr Ser Lys Thr Asp Thr Trp Ser Phe Gly Val Leu Leu
385                 390                 395                 400

Trp Glu Ile Phe Ser Leu Gly Tyr Met Pro Tyr Pro Ser Lys Ser Asn
                405                 410                 415

Gln Glu Val Leu Glu Phe Val Thr Ser Gly Gly Arg Met Asp Pro Pro
            420                 425                 430

Lys Asn Cys Pro Gly Pro Val Tyr Arg Ile Met Thr Gln Cys Trp Gln
        435                 440                 445

His Gln Pro Glu Asp Arg Pro Asn Phe Ala Ile Ile Leu Glu Arg Ile
    450                 455                 460
```

```
Glu Tyr Cys Thr Gln Asp Pro Asp Val Ile Asn Thr Ala Leu Pro Ile
465                 470                 475                 480

Glu Tyr Gly Pro Leu Val Glu Glu Glu Lys Val Pro Val Arg Pro
        485                 490                 495

Lys Asp Pro Glu Gly Val Pro Pro Leu Leu Val Ser Gln Gln Ala Lys
            500                 505                 510

Arg Glu Glu Glu Arg Ser Pro Ala Ala Pro Pro Leu Pro Thr Thr
        515                 520                 525

Ser Ser Gly Lys Ala Ala Lys Lys Pro Thr Ala Ala Glu Val Ser Val
530                 535                 540

Arg Val Pro Arg Gly Pro Ala Val Glu Gly Gly His Val Asn Met Ala
545                 550                 555                 560

Phe Ser Gln Ser Asn Pro Pro Ser Glu Leu His Lys Val His Gly Ser
                565                 570                 575

Arg Asn Lys Pro Thr Ser Leu Trp Asn Pro Thr Tyr Gly Ser Trp Phe
            580                 585                 590

Thr Glu Lys Pro Thr Lys Asn Asn Pro Ile Ala Lys Lys Glu Pro
        595                 600                 605

His Asp Arg Gly Asn Leu Gly Leu Glu Gly Ser Cys Thr Val Pro Pro
610                 615                 620

Asn Val Ala Thr Gly Arg Leu Pro Gly Ala Ser Leu Leu Leu Glu Pro
625                 630                 635                 640

Ser Ser Leu Thr Ala Asn Met Lys Glu Val Pro Leu Phe Arg Leu Arg
                645                 650                 655

His Phe Pro Cys Gly Asn Val Asn Tyr Gly Tyr Gln Gln Gln Gly Leu
            660                 665                 670

Pro Leu Glu Ala Ala Thr Ala Pro Gly Ala Gly His Tyr Glu Asp Thr
            675                 680                 685

Ile Leu Lys Ser Lys Asn Ser Met Asn Gln Pro Gly Pro
            690                 695                 700

<210> SEQ ID NO 31
<211> LENGTH: 1607
<212> TYPE: DNA
<213> ORGANISM: Homo sapiens

<400> SEQUENCE: 31
aactccgctg cctttgccgc caccatgccc aaaacgatca gtgtgcgtgt gaccaccatg      60
gatgcagagc tggagtttgc catccagccc aacaccaccg ggaagcagct atttgaccag     120
gtggtgaaaa ctattggctt gagggaagtt tggttctttg gtctgcagta ccaggacact     180
aaaggtttct ccacctggct gaaactcaat aagaaggtga ctgcccagga tgtgcggaag     240
gaaagccccc tgctctttaa gttccgtgcc aagttctacc tgaggatgt gtccgaggaa      300 ttgattcagg acatcactca gcgcctgttc tttctgcaag tgaaagaggg cattctcaat     360
gatgatattt actgcccgcc tgagaccgct gtgctgctgg cctcgtatgc tgtccagtct     420
aagtatggcg acttcaataa ggaagtgcat aagtctggct acctggccgg agacaagttg     480
ctcccgcaga gagtcctgga acagcacaaa ctcaacaagg accagtggga ggagcggatc     540
caggtgtggc atgaggaaca ccgtggcatg ctcagggagg atgctgtcct ggaatatctg     600
aagattgctc aagatctgga gatgtatggt gtgaactact cagcatcaa gaacaagaaa      660 ggctcagagc tgtggctggg ggtggatgcc ctgggtctca acatctatga gcagaatgac     720
agactaactc ccaagatagg cttcccctgg agtgaaatca ggaacatctc tttcaatgat     780
```

```
aagaaatttg tcatcaagcc cattgacaaa aaagccccgg acttcgtctt ctatgctccc    840
cggctgcgga ttaacaagcg gatcttggcc ttgtgcatgg ggaaccatga actatacatg    900
cgccgtcgca agcctgatac cattgaggtg cagcagatga aggcacaggc ccgggaggag    960
aagcaccaga agcagatgga gcgtgctatg ctggaaaatg agaagaagaa gcgtgaaatg   1020
gcagagaagg agaaagagaa gattgaacgg gagaaggagg agctgatgga gaggctgaag   1080
cagatcgagg aacagactaa gaaggctcag caagaactgg aagaacagac ccgtagggct   1140
ctggaacttg agcaggaacg gaagcgtgcc cagagcgagg ctgaaaagct ggccaaggag   1200
cgtcaagaag ctgaagaggc caaggaggcc ttgctgcagg cctcccggga ccagaaaaag   1260
actcaggaac agctggcctt ggaaatggca gagctgacag ctcgaatctc ccagctggag   1320
atggcccgac agaagaagga gagtgaggct gtggagtggc agcagaagca ggagctgcaa   1380
gccatgcaga tggagctgca gagccctgag tacaagctga gcaagctccg cacctcgacc   1440
atcatgaccg actacaaccc caactactgc tttgctggca agacctcctc catcagtgac   1500
ctgaaggagg tgccgcggaa aaacatcacc ctcattcggg gtctgggcca tggcgccttt   1560
ggggaggtgt atgaaggcca ggtgtccgga atgcccaacg acccaag                 1607
```

<210> SEQ ID NO 32  
<211> LENGTH: 527  
<212> TYPE: PRT  
<213> ORGANISM: Homo sapiens

<400> SEQUENCE: 32

```
Met Pro Lys Thr Ile Ser Val Arg Val Thr Thr Met Asp Ala Glu Leu
1               5                  10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
```

```
                225                 230                 235                 240
        Pro Trp Ser Glu Ile Arg Asn Ile Ser Phe Asn Asp Lys Lys Phe Val
                        245                 250                 255
        Ile Lys Pro Ile Asp Lys Lys Ala Pro Asp Phe Val Phe Tyr Ala Pro
                        260                 265                 270
        Arg Leu Arg Ile Asn Lys Arg Ile Leu Ala Leu Cys Met Gly Asn His
                        275                 280                 285
        Glu Leu Tyr Met Arg Arg Lys Pro Asp Thr Ile Glu Val Gln Gln
                        290                 295                 300
        Met Lys Ala Gln Ala Arg Glu Glu Lys His Gln Lys Gln Met Glu Arg
        305                 310                 315                 320
        Ala Met Leu Glu Asn Glu Lys Lys Arg Glu Met Ala Glu Lys Glu
                        325                 330                 335
        Lys Glu Lys Ile Glu Arg Glu Lys Glu Glu Leu Met Glu Arg Leu Lys
                        340                 345                 350
        Gln Ile Glu Glu Gln Thr Lys Lys Ala Gln Gln Glu Leu Glu Gln
                        355                 360                 365
        Thr Arg Arg Ala Leu Glu Leu Glu Gln Glu Arg Lys Arg Ala Gln Ser
                        370                 375                 380
        Glu Ala Glu Lys Leu Ala Lys Glu Arg Gln Glu Ala Glu Ala Lys
        385                 390                 395                 400
        Glu Ala Leu Leu Gln Ala Ser Arg Asp Gln Lys Lys Thr Gln Glu Gln
                        405                 410                 415
        Leu Ala Leu Glu Met Ala Glu Leu Thr Ala Arg Ile Ser Gln Leu Glu
                        420                 425                 430
        Met Ala Arg Gln Lys Lys Glu Ser Glu Ala Val Glu Trp Gln Gln Lys
                        435                 440                 445
        Gln Glu Leu Gln Ala Met Gln Met Glu Leu Gln Ser Pro Glu Tyr Lys
                        450                 455                 460
        Leu Ser Lys Leu Arg Thr Ser Thr Ile Met Thr Asp Tyr Asn Pro Asn
        465                 470                 475                 480
        Tyr Cys Phe Ala Gly Lys Thr Ser Ser Ile Ser Asp Leu Lys Glu Val
                        485                 490                 495
        Pro Arg Lys Asn Ile Thr Leu Ile Arg Gly Leu Gly His Gly Ala Phe
                        500                 505                 510
        Gly Glu Val Tyr Glu Gly Gln Val Ser Gly Met Pro Asn Asp Pro
                        515                 520                 525

<210> SEQ ID NO 33
<211> LENGTH: 426
<212> TYPE: DNA
<213> ORGANISM: Homo sapiens

<400> SEQUENCE: 33
cgagaagttg agggagaaag gcgggcccgg gaacaggctg aggctgaggt ggcctccttg      60
aaccgtagga tccagctggt tgaagaagag ctggaccgtg ctcaggagcg tgcggaggtg     120
tctgaactaa aatgtggtga cctggaagaa gaactcaaga atgttactaa caatctgaaa     180
tctctggagg ctgcatctga aaagtattct gaaaaggagg acaaatatga agaagaaatt     240
aaacttctgt ctgacaaact gaaagaggct gagacccgtg ctgaatttgc agagagaacg     300
gttgcaaaac tggaaaagac aattgatgac ctggaagtgt acctccggaa gcaccaagag     360
ctgcaagcca tgcagatgga gctgcagagc cctgagtaca agctgagcaa gctccgcacc     420
ctcgac                                                               426
```

```
<210> SEQ ID NO 34
<211> LENGTH: 142
<212> TYPE: PRT
<213> ORGANISM: Homo sapiens

<400> SEQUENCE: 34

Arg Glu Val Glu Gly Glu Arg Ala Arg Glu Gln Ala Glu Ala Glu
1               5                   10                  15

Val Ala Ser Leu Asn Arg Arg Ile Gln Leu Val Glu Glu Leu Asp
            20                  25                  30

Arg Ala Gln Glu Arg Ala Glu Val Ser Glu Leu Lys Cys Gly Asp Leu
        35                  40                  45

Glu Glu Glu Leu Lys Asn Val Thr Asn Asn Leu Lys Ser Leu Glu Ala
    50                  55                  60

Ala Ser Glu Lys Tyr Ser Gln Lys Glu Asp Lys Tyr Glu Glu Glu Ile
65                  70                  75                  80

Lys Leu Leu Ser Asp Lys Leu Lys Glu Ala Glu Thr Arg Ala Glu Phe
                85                  90                  95

Ala Glu Arg Thr Val Ala Lys Leu Glu Lys Thr Ile Asp Asp Leu Glu
            100                 105                 110

Val Tyr Leu Arg Lys His Gln Glu Leu Gln Ala Met Gln Met Glu Leu
        115                 120                 125

Gln Ser Pro Glu Tyr Lys Leu Ser Lys Leu Arg Thr Leu Asp
    130                 135                 140

<210> SEQ ID NO 35
<211> LENGTH: 308
<212> TYPE: DNA
<213> ORGANISM: Homo sapiens

<400> SEQUENCE: 35
ctggcagagt cccgttgccg agagatggat gagcagatta gactgatgga ccagaacctg     60
aagtgtctga gtgctgctga agaaaagtac tctcaaaaag aagataaata tgaggaagaa    120
atcaagattc ttactgataa actcaaggag gcagagaccc gtgctgaatt tgcagagaga    180
acggttgcaa aactggaaaa gacaattgat gacctggaag tgtaccgccg gaagcaccag    240
gagctgcaag ccatgcagat ggagctgcag agccctgagt acaagctgag caagctccgc    300
acctcgac                                                             308

<210> SEQ ID NO 36
<211> LENGTH: 103
<212> TYPE: PRT
<213> ORGANISM: Homo sapiens

<400> SEQUENCE: 36

Leu Ala Glu Ser Arg Cys Arg Glu Met Asp Glu Gln Ile Arg Leu Met
1               5                   10                  15

Asp Gln Asn Leu Lys Cys Leu Ser Ala Ala Glu Glu Lys Tyr Ser Gln
            20                  25                  30

Lys Glu Asp Lys Tyr Glu Glu Glu Ile Lys Ile Leu Thr Asp Lys Leu
        35                  40                  45

Lys Glu Ala Glu Thr Arg Ala Glu Phe Ala Glu Arg Thr Val Ala Lys
    50                  55                  60

Leu Glu Lys Thr Ile Asp Asp Leu Glu Val Tyr Arg Arg Lys His Gln
65                  70                  75                  80
```

```
Glu Leu Gln Ala Met Gln Met Glu Leu Gln Ser Pro Glu Tyr Lys Leu
             85                  90                  95

Ser Lys Leu Arg Thr Ser Thr
            100

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tacaacccca actactgctt tgct                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aggcactttc tcttcctctt ccac                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccacacctgg gaaaggacct aaag                                              24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cctccaaata ctgacagcca cagg                                              24
```